(12) United States Patent
Walker et al.

(10) Patent No.: US 6,767,895 B2
(45) Date of Patent: Jul. 27, 2004

(54) I-SUPERFAMILY CONOTOXINS

(75) Inventors: Craig S. Walker, Salt Lake City, UT (US); Reshma Shetty, Salt Lake City, UT (US); Elsie C. Jimenez, Quezon (PH); J. Michael McIntosh, Salt Lake City, UT (US); Baldomero M. Olivera, Salt Lake City, UT (US); Maren Watkins, Salt Lake City, UT (US); Robert M. Jones, Salt Lake City, UT (US); Gregory S. Shen, Salt Lake City, UT (US)

(73) Assignees: Cognetix, Inc., Salt Lake City, UT (US); University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/894,882

(22) Filed: Jun. 29, 2001

(65) Prior Publication Data

US 2002/0102607 A1 Aug. 1, 2002

Related U.S. Application Data

(60) Provisional application No. 60/264,256, filed on Jan. 29, 2001, provisional application No. 60/247,714, filed on Nov. 14, 2000, provisional application No. 60/246,581, filed on Nov. 8, 2000, provisional application No. 60/243,410, filed on Oct. 27, 2000, and provisional application No. 60/304,166, filed on Jun. 30, 2000, now abandoned.

(51) Int. Cl.$^7$ .................. A61K 38/16; C07K 14/435
(52) U.S. Cl. .................. 514/12; 514/2; 530/300; 530/324
(58) Field of Search .................. 530/300, 324; 512/2, 12, 325, 326

(56) References Cited

U.S. PATENT DOCUMENTS 5,432,155 A    7/1995   Olivera et al. ............. 514/12

OTHER PUBLICATIONS

McIntosh et al. Conus peptides as probes for ion channels. <Methods in Enzymology 294:605–624 (1999).*

Yokoshiki, H. et al., "ATP–sensitive K+ channels in pancreatic, cardiac, and vascular smooth muscle cells," *Am J Physiology*, 1998, 274:C25–C37.

* cited by examiner

*Primary Examiner*—Gabriele Bugaisky
(74) *Attorney, Agent, or Firm*—Rothwell Figg Ernst & Manbeck

(57) ABSTRACT

The invention relates to relatively short peptides (termed I-conotoxins herein), about 30–50 residues in length, which are naturally available in minute amounts in the venom of the cone snails or analogous to the naturally available peptides, and which preferably include four disulfide bonds.

7 Claims, 2 Drawing Sheets

SEQUENCE LISTING

<160> NUMBER OF SEQ ID NOS: 506

<210> SEQ ID NO 1
<211> LENGTH: 50
<212> TYPE: PRT
<213> ORGANISM: Artificial Sequence
<220> FEATURE:
<223> OTHER INFORMATION: generic peptide
<221> NAME/KEY: PEPTIDE
<222> LOCATION: (1)..(3)
<223> OTHER INFORMATION: Xaa at residue 1 is des-Xaa or Gly; Xaa at
    residue 2 is des-Xaa, Pro, hydroxy-Pro (Hyp), Ala, His or Gly; Xaa
    at residue 3 is des-Xaa, Ser, Val, Pro, Hyp, Thr, g-Ser (where g
    is glycosylation), g-Thr, g-Hyp or any synthetic hydroxylated
    amino acid;
<221> NAME/KEY: PEPTIDE
<222> LOCATION: (4)..(4)
<223> OTHER INFORMATION: Xaa at residue 4 is des-Xaa4, Gly, Glu,
    g-carboxy-Glu (Gla), Phe, Pro, Hyp, Arg, Lys, ornithine, homo-Lys,
    homoarginine, nor-Lys, N-methyl-Lys, N,N'-dimethyl-Lys,
    N,N',N''-trimethyl-Lys or any synthetic basic amino acid or Xaa at
    residue 4 is
<221> NAME/KEY: PEPTIDE
<222> LOCATION: (4)..(6)
<223> OTHER INFORMATION: pyro-Glu if Xaa at residues 1, 2 and 3 are all
    des-Xaa; Xaa at residue 6 is an aliphatic amino acid bearing
    linear or branched saturated hydrocarbon chains such as Leu (D or
    L), Ile and Val or non-natural derivatives of the aliphatic amino
    acid, Lys, Arg
<221> NAME/KEY: PEPTIDE
<222> LOCATION: (6)..(7)
<223> OTHER INFORMATION: ornithine, homo-Lys, homoarginine, nor-Lys,
    N-methyl-Lys, N,N'-dimethyl-Lys, N,N',N''-trimethyl-Lys, any
    synthetic basic amino acid, Gly, Trp (D or L), neo-Trp, halo-Trp
    (D or L) or any synthetic aromatic amino acid; Xaa at residue 7 is
    Lys, Arg,
<221> NAME/KEY: PEPTIDE
<222> LOCATION: (7)..(7)
<223> OTHER INFORMATION: ornithine, homo-Lys, homoarginine, nor-Lys,
    N-methyl-Lys, N,N'-dimethyl-Lys, N,N',N''-trimethyl-Lys, any
    synthetic basic amino acid, Ala, an aliphatic amino acids bearing
    linear or branched saturated hydrocarbon chains such as Leu (D or
    L),
<221> NAME/KEY: PEPTIDE
<222> LOCATION: (7)..(9)
<223> OTHER INFORMATION: Ile and Val or non-natural derivatives of the
    aliphatic amino acid, Thr, Ser, g-Thr or g-Ser; Xaa at residue 7
    is Gly, Asp, Glu, Gla, Asn, Gln or any synthetic acidic amino
    acid; Xaa at residue 8 is Gly, Lys, Arg, ornithine, homo-Lys,
    homoarginine,
<221> NAME/KEY: PEPTIDE
<222> LOCATION: (9)..(10)
<223> OTHER INFORMATION: nor-Lys, N-methyl-Lys, N,N'-dimethyl-Lys,
    N,N',N''-trimethyl-Lys, any synthetic basic amino acid, Asp, Glu,
    Gla, Asn, Gln or any synthetic acidic amino acid; Xaa at residue
    10 is Ala, Val, Met, Lys, Arg, ornithine, homo-Lys, homoarginine,
<221> NAME/KEY: PEPTIDE
<222> LOCATION: (10)..(11)
<223> OTHER INFORMATION: nor-Lys, N-methyl-Lys, N,N'-dimethyl-Lys,
    N,N',N''-trimethyl-Lys or any synthetic basic amino acid; Xaa at
    residue 11 is Ala, His, Ser, Thr, Pro, Hyp, g-Ser, g-Thr, g-Hyp,
    any synthetic hydroxylated amino acid, Asn, Gln, Lys, Arg,
    ornithine,
<221> NAME/KEY: PEPTIDE
<222> LOCATION: (11)..(13)
<223> OTHER INFORMATION: homo-Lys, homoarginine, nor-Lys, N-methyl-Lys,
    N,N'-dimethyl-Lys, N,N',N''- trimethyl-Lys or any synthetic basic
    amino acid; Xaa at residue 13 is Gly, Ser, Thr, g-Ser, g-Thr, Asp,
    Glu, Gla, any synthetic acidic amino acid, Lys, Arg, ornithine,
<221> NAME/KEY: PEPTIDE
<222> LOCATION: (13)..(14)
<223> OTHER INFORMATION: homo-Lys, homoarginine, nor-Lys, N-methyl-Lys,
    N,N'-dimethyl-Lys, N,N',N''- trimethyl-Lys or any synthetic basic
    amino acid; Xaa at residue 14 is Phe, Tyr, meta-Tyr, ortho-Tyr,
    nor-Tyr, mono-halo-Tyr, di-halo-Tyr, O-sulpho-Tyr
<221> NAME/KEY: PEPTIDE

```
<222> LOCATION: (14)..(16)
<223> OTHER INFORMATION: O-phospho-Tyr, nitro-Tyr, any synthetic
      aromatic amino acid, Gln, Asn or Leu (D or L); Xaa at residue 15
      is Ser, Thr, g-Ser, g-Thr or His; Xaa at residue 16 is Ala, Gla,
      Glu, Asp, Asn, Gln, any synthetic acidic amino acid, Ser, Thr,
      g-Ser, g-Thr, His,
<221> NAME/KEY: PEPTIDE
<222> LOCATION: (16)..(17)
<223> OTHER INFORMATION: Lys, Arg, ornithine, homo-Lys, homoarginine,
      nor-Lys, N-methyl-Lys, N,N'- dimethyl-Lys, N,N',N''-trimethyl-Lys
      or any synthetic basic amino acid; Xaa at residue 17 is Asp, Glu,
      Gla, Asn, Gln, any synthetic acidic amino acid or His;
<221> NAME/KEY: PEPTIDE
<222> LOCATION: (20)..(20)
<223> OTHER INFORMATION: Xaa at residue 20 is des-Xaa, Gly, His, Ser,
      Pro, Hyp, Thr, g-Ser, g-Thr, g-Hyp, any synthetic hydroxylated
      amino acid, Lys, Arg, ornithine, homo-Lys, homoarginine, nor-Lys,
      N-methyl-Lys, N,N'-dimethyl-Lys, N,N',N''-trimethyl-Lys or any
      synthetic
<221> NAME/KEY: PEPTIDE
<222> LOCATION: (20)..(21)
<223> OTHER INFORMATION: basic amino acid; Xaa at residue 21 is des-Xaa,
      His, Ser, Thr, g-Ser, g-Thr, Lys, Arg, ornithine, homo-Lys,
      homoarginine, nor-Lys, N-methyl-Lys, N,N'-dimethyl-Lys,
      N,N',N''-trimethyl-Lys, any synthetic basic amino acid, Phe, Tyr,
      meta-Tyr,
<221> NAME/KEY: PEPTIDE
<222> LOCATION: (21)..(22)
<223> OTHER INFORMATION: ortho-Tyr, nor-Tyr, mono-halo-Tyr, di-halo-Tyr,
      O-sulpho-Tyr, O-phospho-Tyr, nitro-Tyr or any synthetic aromatic
      amino acid; Xaa at residue 22 is Val, Asn, Lys, Arg, ornithine,
      homo-Lys, homoarginine, nor-Lys, N-methyl-Lys,
<221> NAME/KEY: PEPTIDE
<222> LOCATION: (22)..(25)
<223> OTHER INFORMATION: N,N'-dimethyl-Lys, N,N',N''-trimethyl-Lys or
      any synthetic basic amino acid; Xaa at residue 25 is des-Xaa, Leu
      (D or L), Pro, Hyp, Phe, Tyr, meta-Tyr, ortho-Tyr, nor-Tyr,
      mono-halo-Tyr, di-halo-Tyr, O-sulpho-Tyr, O-phopho-Tyr, nitro-Tyr
      or
<221> NAME/KEY: PEPTIDE
<222> LOCATION: (25)..(26)
<223> OTHER INFORMATION: any synthetic aromatic amino acid; Xaa at
      residue 26 is Gly, Ile, Ser, Thr, g-Ser, g-Thr, His, Lys, Arg,
      ornithine, homo-Lys, homoarginine, nor-Lys, N-methyl-Lys,
      N,N'-dimethyl-Lys, N,N',N''-trimethyl-Lys, any synthetic basic
      amino acid,
<221> NAME/KEY: PEPTIDE
<222> LOCATION: (26)..(28)
<223> OTHER INFORMATION: Phe, Tyr, meta-Tyr, ortho-Tyr, nor-Tyr,
      mono-halo-Tyr, di-halo-Tyr, O-sulpho-Tyr, O-phospho-Tyr, nitro-Tyr
      or any synthetic aromatic amino acid; Xaa at residue 28 is Ser,
      Thr, g-Ser, g-Thr, an aliphatic amino acid bearing linear or
      branched
<221> NAME/KEY: PEPTIDE
<222> LOCATION: (28)..(28)
<223> OTHER INFORMATION: saturated hydrocarbon chains such as Leu
      (D or L), Ile and Val or non-natural derivatives of the aliphatic
      amino acid, Lys, Arg, ornithine, homo-Lys, homoarginine, nor-Lys,
      N-methyl-Lys, N,N'-dimethyl-Lys, N,N',N''-trimethyl-Lys, any
      synthetic
<221> NAME/KEY: PEPTIDE
<222> LOCATION: (28)..(30)
<223> OTHER INFORMATION: basic amino acid, Phe, Tyr, meta-Tyr,
      ortho-Tyr, nor-Tyr, mono-halo-Tyr, di-halo-Tyr, O-sulpho-Tyr,
      O-phospho-Tyr, nitro-Tyr or any synthetic aromatic amino acid; Xaa
      at residue 30 is Ala, Gln, Gla, Lys, Arg, ornithine, homo-Lys,
      homoarginine,
<221> NAME/KEY: PEPTIDE
<222> LOCATION: (30)..(31)
<223> OTHER INFORMATION: nor-Lys, N-methyl-Lys, N,N'-dimethyl-Lys, N,N',
      N''-trimethyl-Lys or any synthetic basic amino acid; Xaa at
      residue 31 is Ser, Pro, Hyp, Thr, g-Ser, g-Thr, g-Hyp, any
      synthetic hydroxylated amino acid, Lys, Arg, ornithine, homo-Lys,
<221> NAME/KEY: PEPTIDE
<222> LOCATION: (31)..(33)
<223> OTHER INFORMATION: homoarginine, nor-Lys, N-methyl-Lys, N,N'-
      dimethyl-Lys, N,N',N''-trimethyl-Lys or any synthetic basic amino
      acid; Xaa at residue 32 is Gln, Ser, Pro, Hyp, Thr, g-Ser, g-Thr,
      g-Hyp or any synthetic hydroxylated amino acid; Xaa at residue 33
```

```
            is
<221> NAME/KEY: PEPTIDE
<222> LOCATION: (33)..(35)
<223> OTHER INFORMATION: des-Xaa, Ser, Thr, g-Ser, g-Thr or any
      synthetic hydroxylated amino acid; Xaa at residue 34 is des-Xaa,
      Asn, Gln, Ser, Thr, g-Asn, g-Ser, g-Thr or any synthetic
      hydroxylated amino acid; Xaa at residue 35 is des-Xaa, Val, Gla,
      Trp (D or L),
<221> NAME/KEY: PEPTIDE
<222> LOCATION: (35)..(36)
<223> OTHER INFORMATION: neo-Trp, halo-Trp (D or L), any aromatic
      synthetic amino acid, Lys, Arg, ornithine, homo-Lys, homoarginine,
      nor-Lys, N-methyl-Lys, N,N'-dimethyl-Lys, N,N',N''- trimethyl-Lys
      or any synthetic basic amino acid; Xaa at residue 36 is des-Xaa,
      an
<221> NAME/KEY: PEPTIDE
<222> LOCATION: (36)..(37)
<223> OTHER INFORMATION: aliphatic amino acid bearing linear or branched
      saturated hydrocarbon chains such as Leu (D or L), Ile and Val or
      non-natural derivatives of the aliphatic amino acid; Xaa at
      residue 37 is des-Xaa, an aliphatic amino acid bearing linear or
<221> NAME/KEY: PEPTIDE
<222> LOCATION: (37)..(38)
<223> OTHER INFORMATION: branched saturated hydrocarbon chains such as
      Leu (D or L), Ile and Val or non-natural derivatives of the
      aliphatic amino acid; Xaa at residue 38 is des-Xaa, Ile, Ser, Pro,
      Hyp, Thr, g-Ser, g-Thr, g-Hyp, any synthetic hydroxylated
<221> NAME/KEY: PEPTIDE
<222> LOCATION: (38)..(41)
<223> OTHER INFORMATION: amino acid, Phe, Tyr, meta-Tyr, ortho-yr,
      nor-Tyr, mono-halo-Tyr, di-halo-Tyr, O-sulpho-Tyr, O-phospho-Tyr,
      nitro-Tyr or any synthetic aromatic amino acid; Xaa at residue 39
      is des-Xaa or Gly; Xaa at residue 41 is Ser, Thr, g-Ser, g-Thr,
<221> NAME/KEY: PEPTIDE
<222> LOCATION: (41)..(42)
<223> OTHER INFORMATION: Trp (D or L), neo-Trp, halo-Trp (D or L), any
      aromatic synthetic amino acid, Lys, Arg, ornithine, homo-Lys,
      homoarginine, nor-Lys, N-methyl-Lys, N,N'-dimethyl-Lys, N,N',N''-
      trimethyl-Lys or any synthetic basic amino acid; Xaa at residue 42
      is
<221> NAME/KEY: PEPTIDE
<222> LOCATION: (42)..(44)
<223> OTHER INFORMATION: Val, Ser, Thr, g-Ser, g-Thr, Trp (D or L),
      neo-Trp, halo-Trp (Dor L) or any aromatic synthetic amino acid;
      Xaa at residue 43 is Gly, Ile, Asp, Glu, Gla, Asn, Ser, Thr,
      g-Asn, g-Ser or g-Thr; Xaaat residue 44 is des-Xaa, Val, Met, Gln,
      Pro, Hyp,
<221> NAME/KEY: PEPTIDE
<222> LOCATION: (44)..(45)
<223> OTHER INFORMATION: Ser, Thr, g-Ser, g-Thr, g-Hyp or any synthetic
      hydroxylated amino acid; Xaa at residue 45 is des-Xaa, Val, Thr,
      Ser, g-Thr, g-Ser, Phe, Tyr, meta-Tyr, ortho-Tyr, nor-Tyr, mono-
      halo-Tyr, di-halo-Tyr, O-sulpho-Tyr, O-phospho-Tyr, nitro-Tyr or
<221> NAME/KEY: PEPTIDE
<222> LOCATION: (45)..(46)
<223> OTHER INFORMATION: any synthetic aromatic amino acid; Xaa at
      residue 46 is des-Xaa, Gln, Asn, Thr, Ser, g-Ser, g-Ser, g-Asn,
      Met, Leu, Phe, Tyr, meta-Tyr, ortho-Tyr, nor-Tyr, mono-halo-Tyr,
      di-halo-Tyr, O-sulpho-Tyr, O-phospho-Tyr, nitro-Tyr, any
<221> NAME/KEY: PEPTIDE
<222> LOCATION: (46)..(47)
<223> OTHER INFORMATION: synthetic aromatic amino acid, Lys, Arg,
      ornithine, homo-Lys, homoarginine, nor-Lys, N-methyl-Lys, N,N'-
      dimethyl-Lys, N,N',N''-trimethyl-Lys or any synthetic basic amino
      acids des-Xaa, Leu, Ser, Thr, g-Ser,
<221> NAME/KEY: PEPTIDE
<222> LOCATION: (47)..(48)
<223> OTHER INFORMATION: g-Thr, Lys, Arg, ornithine, homo-Lys,
      homoarginine, nor-Lys, N-methyl-Lys, N,N'-dimethyl-Lys, N,N',N''-
      trimethyl-Lys or any synthetic basic amino acid; Xaa at residue 48
      is des-Xaa, Ile, Ala, Thr< Ser, g-Ser, g-Thr, Lys, Arg, ornithine,
<221> NAME/KEY: PEPTIDE
<222> LOCATION: (48)..(49)
<223> OTHER INFORMATION: homo-Lys, homoarginine, nor-Lys, N-methyl-Lys,
      N,N'-dimethyl-Lys, N,N',N''- trimethyl-Lys or any synthetic basic
      amino acid; Xaa at residue 49 is des-Xaa, Asp, Lys, Arg,
      ornithine, homo-Lys, homoarginine, nor-Lys, N-methyl-Lys,
<221> NAME/KEY: PEPTIDE
<222> LOCATION: (49)..(50)
```

-continued

```
<223> OTHER INFORMATION: N,N'-dimethyl-Lys, N,N',N''-trimethyl-Lys or
      any synthetic basic amino acid; and Xaa at residue 50 is des-Xaa,
      Phe, Tyr, meta-Tyr, ortho-Tyr, nor-Tyr, mono-halo-Tyr, di-halo-
      Tyr, O-sulpho-Tyr, O-phospho-Tyr, nitro-Tyr or any synthetic
      aromati
<221> NAME/KEY: PEPTIDE
<222> LOCATION: (50)..(50)
<223> OTHER INFORMATION: amino acid

<400> SEQUENCE: 1

Xaa Xaa Xaa Xaa Cys Xaa Xaa Xaa Xaa Xaa Cys Xaa Xaa Xaa Xaa
1               5                   10                  15

Xaa Cys Cys Xaa Xaa Xaa Cys Cys Xaa Xaa Gly Xaa Cys Xaa Xaa Xaa
            20                  25                  30

Xaa Xaa Xaa Xaa Xaa Xaa Xaa Cys Xaa Xaa Xaa Xaa Xaa Xaa Xaa
        35                  40                  45

Xaa Xaa
    50

<210> SEQ ID NO 2
<211> LENGTH: 46
<212> TYPE: PRT
<213> ORGANISM: Conus radiatus
<220> FEATURE:
<221> NAME/KEY: PEPTIDE
<222> LOCATION: (1)..(46)
<223> OTHER INFORMATION: Xaa is Pro or Hydroxy-Pro

<400> SEQUENCE: 2

Gly Xaa Ser Phe Cys Lys Ala Asp Glu Lys Xaa Cys Glu Tyr His Ala
1               5                   10                  15

Asp Cys Cys Asn Cys Cys Leu Ser Gly Ile Cys Ala Xaa Ser Thr Asn
            20                  25                  30

Trp Ile Leu Xaa Gly Cys Ser Thr Ser Ser Phe Phe Lys Ile
        35                  40                  45

<210> SEQ ID NO 3
<211> LENGTH: 36
<212> TYPE: PRT
<213> ORGANISM: Hadronyche versuta

<400> SEQUENCE: 3

Thr Ile Cys Thr Gly Ala Asp Arg Pro Cys Ala Ala Cys Cys Pro Cys
1               5                   10                  15

Cys Pro Gly Thr Ser Cys Gln Gly Pro Glu Ser Asn Gly Val Val Tyr
            20                  25                  30

Cys Arg Asn Phe
        35

<210> SEQ ID NO 4
<211> LENGTH: 36
<212> TYPE: PRT
<213> ORGANISM: Hadronyche versuta

<400> SEQUENCE: 4

Thr Ile Cys Thr Gly Ala Asp Arg Pro Cys Ala Ala Cys Cys Pro Cys
1               5                   10                  15

Cys Pro Gly Thr Ser Cys Gln Gly Pro Glu Pro Asn Gly Val Ser Tyr
            20                  25                  30

Cys Arg Asn Asp
        35
```

<210> SEQ ID NO 5
<211> LENGTH: 37
<212> TYPE: PRT
<213> ORGANISM: Hadronyche versuta

<400> SEQUENCE: 5

```
Ala Ile Cys Thr Gly Ala Asp Arg Pro Cys Ala Ala Cys Cys Pro Cys
1               5                   10                  15
Cys Pro Gly Thr Ser Cys Lys Ala Glu Ser Asn Gly Val Ser Tyr Cys
            20                  25                  30
Arg Lys Asp Glu Pro
        35
```

<210> SEQ ID NO 6
<211> LENGTH: 46
<212> TYPE: PRT
<213> ORGANISM: Conus radiatus

<400> SEQUENCE: 6

```
Gly Pro Ser Phe Cys Lys Ala Asp Glu Lys Pro Cys Glu Tyr His Ala
1               5                   10                  15
Asp Cys Cys Asn Cys Cys Leu Ser Gly Ile Cys Ala Pro Ser Thr Asn
            20                  25                  30
Trp Ile Leu Pro Gly Cys Ser Thr Ser Ser Phe Phe Lys Ile
        35                  40                  45
```

<210> SEQ ID NO 7
<211> LENGTH: 46
<212> TYPE: PRT
<213> ORGANISM: Conus radiatus

<400> SEQUENCE: 7

```
Gly Pro Ser Phe Cys Lys Ala Asp Glu Lys Pro Cys Glu Tyr His Ser
1               5                   10                  15
Asp Cys Cys Asn Cys Cys Leu Ser Gly Ile Cys Ala Pro Ser Thr Asn
            20                  25                  30
Trp Ile Leu Pro Cys Gly Ser Thr Ser Ser Phe Phe Lys Ile
        35                  40                  45
```

<210> SEQ ID NO 8
<211> LENGTH: 507
<212> TYPE: DNA
<213> ORGANISM: Conus radiatus

<400> SEQUENCE: 8

```
ttcgccagct atttaggtga cactatagaa tactcaagct tgcatgcctg caggtcgact      60
ctagaggatc caggcttcag acgaggacaa cccagctatc agcacttcgc agcagtcgag     120
gctttcaaat cctaatcata gaagaaggca aaaatatctg ctggtcaata tgaagctgtg     180
cctgacgttc cttcttgttc tgatgattct ggcatcagtg actggggaga agtcaagcaa     240
gcatacactg agtcgtgctg ctagggtaaa aaacagaggc tgtaagaaag acagaaagcc     300
atgctcgtat catgcagatt gctgtaattg ctgtctcagt ggaatctgtg caccaagcac     360
aaattggatt ttacctggat gctcgacgag tacgttcact tgacgcgctg actttcagcc     420
agctaggcca tgcctaggtc ctcatgcaca ttcacatttg ctgtgaattg aattcatgtg     480
cattaaagcc attaggcgta gaaagat                                         507
```

<210> SEQ ID NO 9
<211> LENGTH: 77

```
<212> TYPE: PRT
<213> ORGANISM: Conus radiatus

<400> SEQUENCE: 9
```

Met Lys Leu Cys Leu Thr Phe Leu Leu Val Leu Met Ile Leu Ala Ser
1               5                   10                  15

Val Thr Gly Glu Lys Ser Ser Lys His Thr Leu Ser Arg Ala Ala Arg
            20                  25                  30

Val Lys Asn Arg Gly Cys Lys Lys Asp Arg Lys Pro Cys Ser Tyr His
        35                  40                  45

Ala Asp Cys Cys Asn Cys Leu Ser Gly Ile Cys Ala Pro Ser Thr
    50                  55                  60

Asn Trp Ile Leu Pro Gly Cys Ser Thr Ser Thr Phe Thr
65                  70                  75

```
<210> SEQ ID NO 10
<211> LENGTH: 41
<212> TYPE: PRT
<213> ORGANISM: Conus radiatus
<220> FEATURE:
<221> NAME/KEY: PEPTIDE
<222> LOCATION: (1)..(41)
<223> OTHER INFORMATION: Xaa at residues 8, 26 and 33 is Pro or hydroxy-
      Pro; Xaa at residue 30 is Trp or bromo-Trp; Xaa at residue 11 is
      Tyr, 125I-Tyr, mono-iodo-Tyr, di-iodo-Tyr, O-sulpho-Tyr or O-
      phospho-Ty

<400> SEQUENCE: 10
```

Gly Cys Lys Lys Asp Arg Lys Xaa Cys Ser Xaa His Ala Asp Cys Cys
1               5                   10                  15

Asn Cys Cys Leu Ser Gly Ile Cys Ala Xaa Ser Thr Asn Xaa Ile Leu
            20                  25                  30

Xaa Gly Cys Ser Thr Ser Thr Phe Thr
        35                  40

```
<210> SEQ ID NO 11
<211> LENGTH: 430
<212> TYPE: DNA
<213> ORGANISM: Conus radiatus

<400> SEQUENCE: 11
ccagctatca gcacttcgca gcagtcgagg ctttgaaatc ctaatcatag aagaaggcaa      60
aaatatctgc tggtcaatat gaagctgtgc ctgacgttcc ttcttgttct gatgattctg     120
gcatcagtga ctgggagaa  gtcaagcaag catacactga gtcgtgctgc tagggtaaaa     180
aacagaggcc ctagtttttg taaggcagac gaaaagccat gcgagtatca tgcagattgc     240
tgtaattgct gtctcagtgg aatctgtgca ccaagcacaa attggatttt acctggatgc     300
tcgacgagtt cgttcttcaa gatctgactt tcagccagct aggccatgcc taggtcctca     360
tgcacattca catttgctgt gaattgaatt catgtgcatt aaagccatta ggcgtagaaa     420
gatgaaaaaa                                                            430

<210> SEQ ID NO 12
<211> LENGTH: 82
<212> TYPE: PRT
<213> ORGANISM: Conus radiatus

<400> SEQUENCE: 12
```

Met Lys Leu Cys Leu Thr Phe Leu Leu Val Leu Met Ile Leu Ala Ser
1               5                   10                  15

```
Val Thr Gly Glu Lys Ser Ser Lys His Thr Leu Ser Arg Ala Ala Arg
            20                  25                  30

Val Lys Asn Arg Gly Pro Ser Phe Cys Lys Ala Asp Glu Lys Pro Cys
            35                  40                  45

Glu Tyr His Ala Asp Cys Cys Asn Cys Cys Leu Ser Gly Ile Cys Ala
    50                  55                  60

Pro Ser Thr Asn Trp Ile Leu Pro Gly Cys Ser Thr Ser Phe Phe
65                  70                  75              80

Lys Ile
```

```
<210> SEQ ID NO 13
<211> LENGTH: 46
<212> TYPE: PRT
<213> ORGANISM: Conus radiatus
<220> FEATURE:
<221> NAME/KEY: PEPTIDE
<222> LOCATION: (1)..(46)
<223> OTHER INFORMATION: Xaa at residues 9 and 13 is Glu or gamma-
      carboxy-Glu; Xaa at residues 2, 11, 29 and 36 is Pro or hydroxy-
      Pro; Xaa at residue 33 is Trp or bromo-Trp; Xaa at residue 14 is
      Tyr, 125I-Tyr, mono-iodo-Tyr, di-iodo-Tyr, O-sulpho-Tyr or O-
      phospho-Ty

<400> SEQUENCE: 13
```

```
Gly Xaa Ser Phe Cys Lys Ala Asp Xaa Lys Xaa Cys Xaa Xaa His Ala
1               5                   10                  15

Asp Cys Cys Asn Cys Cys Leu Ser Gly Ile Cys Ala Xaa Ser Thr Asn
            20                  25                  30

Xaa Ile Leu Xaa Gly Cys Ser Thr Ser Ser Phe Phe Lys Ile
            35                  40                  45
```

```
<210> SEQ ID NO 14
<211> LENGTH: 425
<212> TYPE: DNA
<213> ORGANISM: Conus radiatus

<400> SEQUENCE: 14
cggaattccg atcagcactt cgcagcagtc gaggctttga tatcctaatc atagaagaag     60
gcaaaaatat ctgctggtca atatgaagct gtgcctgacg ttccttcttg ttctgatgat    120
tctggcatca gtgactgggg agaagttaag cgagcaaaca ctgcgtcgtg ctgctaggaa    180
aaacaaaggc catgttccat gcgggaaaga cggaaggaaa tgcgggtatc atgcagattg    240
ctgtaattgc tgtctcagtg aatctgtaaa accaagcaca agttggactg gatgctcgac    300
gagtaccgtt cgattgacgc gctgactttc agccagctag gccatgccta ggtcctcatg    360
cacattcaca tttgctgtga attgaattca tgtgcattaa agccattagg cgtagaaaga    420
ttaaa                                                                425
```

```
<210> SEQ ID NO 15
<211> LENGTH: 80
<212> TYPE: PRT
<213> ORGANISM: Conus radiatus

<400> SEQUENCE: 15
```

```
Met Lys Leu Cys Leu Thr Phe Leu Leu Val Leu Met Ile Leu Ala Ser
1               5                   10                  15

Val Thr Gly Glu Lys Leu Ser Glu Gln Thr Leu Arg Arg Ala Ala Arg
            20                  25                  30

Lys Asn Lys Gly His Val Pro Cys Gly Lys Asp Gly Arg Lys Cys Gly
            35                  40                  45
```

```
Tyr His Ala Asp Cys Cys Asn Cys Cys Leu Ser Gly Ile Cys Lys Pro
    50                  55                  60

Ser Thr Ser Trp Thr Gly Cys Ser Thr Ser Val Arg Leu Thr Arg
65                  70                  75                  80

<210> SEQ ID NO 16
<211> LENGTH: 45
<212> TYPE: PRT
<213> ORGANISM: Conus radiatus
<220> FEATURE:
<221> NAME/KEY: PEPTIDE
<222> LOCATION: (1)..(45)
<223> OTHER INFORMATION: Xaa at residues 4 and 29 is Pro or hydroxy-Pro;
      Xaa at residue 33 is Trp or bromo-Trp; Xaa at residue 14 is Tyr,
      125I-Tyr, mono-iodo-Tyr, di-iodo-Tyr, O-sulpho-Tyr or O-phospho-Ty

<400> SEQUENCE: 16

Gly His Val Xaa Cys Gly Lys Asp Gly Arg Lys Cys Gly Xaa His Ala
1               5                   10                  15

Asp Cys Cys Asn Cys Cys Leu Ser Gly Ile Cys Lys Xaa Ser Thr Ser
                20                  25                  30

Xaa Thr Gly Cys Ser Thr Ser Val Arg Leu Thr Arg
        35                  40                  45

<210> SEQ ID NO 17
<211> LENGTH: 385
<212> TYPE: DNA
<213> ORGANISM: Conus radiatus

<400> SEQUENCE: 17
aatcatagaa gaaggcaaaa atatctgctg gtcaatatga agctgtgcct gacgttcctt      60
cttgttctga tgattctggc atcagtgact ggggagaagt taagcaagca tacactgagt     120
catgctacta gagaacccaa caaaggcgct gttccatgcg ggaaagacgg aaggcaatgc     180
aggaatcatg cagattgctg taattgctgt cccattggaa cctgtgcacc aagcacaaat     240
tggattttac ctggatgctc gacgggtccg ttcatgacgc gctgactttc agccagctag     300
gccatgccta ggtcctcatg cacattcaca tttgctgtga attgaattaa tgtgcattaa     360
agccattagg cgtagaaaga tgaaa                                            385

<210> SEQ ID NO 18
<211> LENGTH: 82
<212> TYPE: PRT
<213> ORGANISM: Conus radiatus

<400> SEQUENCE: 18

Met Lys Leu Cys Leu Thr Phe Leu Leu Val Leu Met Ile Leu Ala Ser
1               5                   10                  15

Val Thr Gly Glu Lys Leu Ser Lys His Thr Leu Ser His Ala Thr Arg
                20                  25                  30

Arg Pro Asn Lys Gly Ala Val Pro Cys Gly Lys Asp Gly Arg Gln Cys
        35                  40                  45

Arg Asn His Ala Asp Cys Cys Asn Cys Cys Pro Ile Gly Thr Cys Ala
    50                  55                  60

Pro Ser Thr Asn Trp Ile Leu Pro Gly Cys Ser Thr Gly Pro Phe Met
65                  70                  75                  80

Thr Arg

<210> SEQ ID NO 19
```

```
<211> LENGTH: 46
<212> TYPE: PRT
<213> ORGANISM: Conus radiatus
<220> FEATURE:
<221> NAME/KEY: PEPTIDE
<222> LOCATION: (1)..(46)
<223> OTHER INFORMATION: Xaa at residues 4, 23, 29, 36 and 42 is Pro or
      hydroxy-Pro; Xaa at residue 33 is Trp or bromo-Tr

<400> SEQUENCE: 19

Gly Ala Val Xaa Cys Gly Lys Asp Gly Arg Gln Cys Arg Asn His Ala
1               5                  10                  15

Asp Cys Cys Asn Cys Cys Xaa Ile Gly Thr Cys Ala Xaa Ser Thr Asn
            20                  25                  30

Xaa Ile Leu Xaa Gly Cys Ser Thr Gly Xaa Phe Met Thr Arg
        35                  40                  45

<210> SEQ ID NO 20
<211> LENGTH: 431
<212> TYPE: DNA
<213> ORGANISM: Conus radiatus
<220> FEATURE:
<221> NAME/KEY: misc_feature
<222> LOCATION: (1)..(431)
<223> OTHER INFORMATION: n is any nucleotide

<400> SEQUENCE: 20
cagacgagga catcccagct atcagcactt cgcagcagtc gaggctttga atcctaatc      60 atagaagaag gcaaaaatat ctgctggtca atatgaagct gtgcctgacg ttccttcttg   120
ttctgatgat tctggcatca gtgactgggg agaagttaag cgagcaaaca ctgcgtcgtg   180
ctgctaggaa aaacaaaggc cctcgatgct gggtcggccg tgtccattgc acctatcata   240
aagactgctg tccgtcggta tgttgtttca agggaaggtg taaaccacaa tcatggggat   300
gctggtcggg tccgacctag gcgtgctggc cttgaggcag ctaggccatg cctaggtcct   360
catgcacatt cacatttgct gtgaattgaa ttcatgtgca ttaaagccat tangcgtaga   420
aagattaaaa a                                                         431

<210> SEQ ID NO 21
<211> LENGTH: 75
<212> TYPE: PRT
<213> ORGANISM: Conus radiatus

<400> SEQUENCE: 21

Met Lys Leu Cys Leu Thr Phe Leu Leu Val Leu Met Ile Leu Ala Ser
1               5                  10                  15

Val Thr Gly Glu Lys Leu Ser Glu Gln Thr Leu Arg Arg Ala Ala Arg
            20                  25                  30

Lys Asn Lys Gly Pro Arg Cys Trp Val Gly Arg Val His Cys Thr Tyr
        35                  40                  45

His Lys Asp Cys Cys Pro Ser Val Cys Cys Phe Lys Gly Arg Cys Lys
    50                  55                  60

Pro Gln Ser Trp Gly Cys Trp Ser Gly Pro Thr
65                  70                  75

<210> SEQ ID NO 22
<211> LENGTH: 40
<212> TYPE: PRT
<213> ORGANISM: Conus radiatus
<220> FEATURE:
<221> NAME/KEY: PEPTIDE
<222> LOCATION: (1)..(40)
```

-continued

<223> OTHER INFORMATION: Xaa at residues 2, 19, 30 and 39 is Pro or
hydroxy-Pro; Xaa at residues 5, 33 and 36 is Trp or bromo-Trp; Xaa
at residue 13 is Tyr, 125I-Tyr, mono-iodo-Tyr, di-iodo-Tyr, O-
sulpho-Tyr or O-phospho-Ty

<400> SEQUENCE: 22

Gly Xaa Arg Cys Xaa Val Gly Arg Val His Cys Thr Xaa His Lys Asp
1               5                   10                  15

Cys Cys Xaa Ser Val Cys Cys Phe Lys Gly Arg Cys Lys Xaa Gln Ser
            20                  25                  30

Xaa Gly Cys Xaa Ser Gly Xaa Thr
        35                  40

<210> SEQ ID NO 23
<211> LENGTH: 464
<212> TYPE: DNA
<213> ORGANISM: Conus radiatus

<400> SEQUENCE: 23
cccagctatc agcactccgc aggcttcaga cgaggacatc ccagctatca gcacttcgca      60
gcagtcgagg ctttgaaatc ctaatcatag aagaaggcaa aaatatctgc tggtcaatat     120
gaagctgtgc ctgacgttcc ttcttgttct gatgattctg gcatcagtga ctggggagaa     180
gtcaagcaag catacactga gtcgtgctgc tagggtaaaa acagaggcc ctagtttttg      240 taaggcagac gaaaagccat gcaagtatca tgcagattgc tgtaactgct gtctcggtgg     300
aatctgtaaa ccaagcacaa gttggattgg atgctcgacg aatgtgttct tgacgcgctg     360
actttcagcc agctaggcca tgcctaggtc ctcatgcaca ttcacatttg ctgtgaattg     420
aattcatgtg cattaaagcc attaggcgta gaaagatgaa aaaa                     464

<210> SEQ ID NO 24
<211> LENGTH: 80
<212> TYPE: PRT
<213> ORGANISM: Conus radiatus

<400> SEQUENCE: 24

Met Lys Leu Cys Leu Thr Phe Leu Leu Val Leu Met Ile Leu Ala Ser
1               5                   10                  15

Val Thr Gly Glu Lys Ser Ser Lys His Thr Leu Ser Arg Ala Ala Arg
            20                  25                  30

Val Lys Asn Arg Gly Pro Ser Phe Cys Lys Ala Asp Glu Lys Pro Cys
        35                  40                  45

Lys Tyr His Ala Asp Cys Cys Asn Cys Cys Leu Gly Gly Ile Cys Lys
    50                  55                  60

Pro Ser Thr Ser Trp Ile Gly Cys Ser Thr Asn Val Phe Leu Thr Arg
65              70                  75                  80

<210> SEQ ID NO 25
<211> LENGTH: 44
<212> TYPE: PRT
<213> ORGANISM: Conus radiatus
<220> FEATURE:
<221> NAME/KEY: PEPTIDE
<222> LOCATION: (1)..(44)
<223> OTHER INFORMATION: Xaa at residues 2, 11 and 29 is Pro or hydroxy-
Pro; Xaa at residue 9 is Glu or gamma-carboxy-Glu; Xaa at residue
33 is Trp or bromo-Trp; Xaa at residue 14 is Tyr, 125I-Tyr, mono-
iodo-Tyr, di-iodo-Tyr, O-sulpho-Tyr or O-phospho-Ty

<400> SEQUENCE: 25

Gly Xaa Ser Phe Cys Lys Ala Asp Xaa Lys Xaa Cys Lys Xaa His Ala

```
              1               5              10              15

Asp Cys Cys Asn Cys Cys Leu Gly Gly Ile Cys Lys Xaa Ser Thr Ser
                        20              25              30

Xaa Ile Gly Cys Ser Thr Asn Val Phe Leu Thr Arg
            35              40

<210> SEQ ID NO 26
<211> LENGTH: 446
<212> TYPE: DNA
<213> ORGANISM: Conus radiatus

<400> SEQUENCE: 26
cggaattccg cggaattccg ccagctatca gcacttcgca gcagtcgagg ctttgaaatc      60
ctaatcatag aagaaggcaa aaatatctgc tggtcaatat gaagctgtgc ctgacgttcc     120
ttcttgttct gatgattctg gcatcagtga ctggggagaa gttaagcaag catacactga     180
gtcatgctgc taggagaccc aacaaaggcg ctgttccatg cgggaaagac ggaaggcaat     240
gcaggaatca tgcagattgc tgtaattgct gtcccattgg aacctgtgca ccaagcacaa     300
attggatttt acctggatgc tcgacgggtc aattcatgac cgctgacttt tagccagcta     360
ggccatgcct aggtcttatg cacattacat ttgctgggaa tgaattattg tgcattaaag     420
ccataggcgt taaagatgga aaaaaa                                          446

<210> SEQ ID NO 27
<211> LENGTH: 84
<212> TYPE: PRT
<213> ORGANISM: Conus radiatus

<400> SEQUENCE: 27

Met Lys Leu Cys Leu Thr Phe Leu Leu Val Leu Met Ile Leu Ala Ser
1               5                  10                  15

Val Thr Gly Glu Lys Leu Ser Lys His Thr Leu Ser His Ala Ala Arg
                20                  25                  30

Arg Pro Asn Lys Gly Ala Val Pro Cys Gly Lys Asp Gly Arg Gln Cys
            35                  40                  45

Arg Asn His Ala Asp Cys Cys Asn Cys Cys Pro Ile Gly Thr Cys Ala
        50                  55                  60

Pro Ser Thr Asn Trp Ile Leu Pro Gly Cys Ser Thr Gly Gln Phe Met
65                  70                  75                  80

Thr Ala Asp Phe

<210> SEQ ID NO 28
<211> LENGTH: 48
<212> TYPE: PRT
<213> ORGANISM: Conus radiatus
<220> FEATURE:
<221> NAME/KEY: PEPTIDE
<222> LOCATION: (1)..(48)
<223> OTHER INFORMATION: Xaa at residues 4, 23, 29 and 36 is Pro or
      hydroxy-Pro; Xaa at residue 33 is Trp or bromo-Tr

<400> SEQUENCE: 28

Gly Ala Val Xaa Cys Gly Lys Asp Gly Arg Gln Cys Arg Asn His Ala
1               5                  10                  15

Asp Cys Cys Asn Cys Cys Xaa Ile Gly Thr Cys Ala Xaa Ser Thr Asn
                20                  25                  30

Xaa Ile Leu Xaa Gly Cys Ser Thr Gly Gln Phe Met Thr Ala Asp Phe
            35                  40                  45
```

<210> SEQ ID NO 29
<211> LENGTH: 440
<212> TYPE: DNA
<213> ORGANISM: Conus radiatus

<400> SEQUENCE: 29

```
cagacgagga caacccagct atcagcactt cgcagcagtc aggctttgaa atcctaatca      60
tagaagaagg caaaaatatc tgctggtcaa tatgaagctg tgcctgacgt tccttcttgt     120
tctgatgatt ctggcatcag tgactgggga gaagtcaagc aagcatacac tgagtcgtgc     180
tgctagggta aaaacagag gccctagttt ttgtaaggca gacgaaaagc catgcgagta      240
tcattcagat gctgtaatt gctgtctcag tggaatctgt gcaccaagca caaattggat      300
tttacctgga tgctcgacga gttcgttctt caagatctga ctttcagcca gctaggccat      360
gcctaggtcc tcatgcacat tcacatttgc tgtgaattga attcatgtgc attaaagcca     420
ttaggcgtag aaagatgaaa                                                 440
```

<210> SEQ ID NO 30
<211> LENGTH: 82
<212> TYPE: PRT
<213> ORGANISM: Conus radiatus

<400> SEQUENCE: 30

```
Met Lys Leu Cys Leu Thr Phe Leu Leu Val Leu Met Ile Leu Ala Ser
1               5                   10                  15

Val Thr Gly Glu Lys Ser Ser Lys His Thr Leu Ser Arg Ala Ala Arg
            20                  25                  30

Val Lys Asn Arg Gly Pro Ser Phe Cys Lys Ala Asp Glu Lys Pro Cys
        35                  40                  45

Glu Tyr His Ser Asp Cys Cys Asn Cys Cys Leu Ser Gly Ile Cys Ala
    50                  55                  60

Pro Ser Thr Asn Trp Ile Leu Pro Gly Cys Ser Thr Ser Ser Phe Phe
65                  70                  75                  80

Lys Ile
```

<210> SEQ ID NO 31
<211> LENGTH: 46
<212> TYPE: PRT
<213> ORGANISM: Conus radiatus
<220> FEATURE:
<221> NAME/KEY: PEPTIDE
<222> LOCATION: (1)..(46)
<223> OTHER INFORMATION: Xaa at residues 2, 11, 29 and 36 is Pro or
      hydroxy-Pro; Xaa at residues 9 and 13 is Glu or gamma-carboxy-Glu;
      Xaa at residue 33 is Trp or bromo-Trp; Xaa at residue 14 is Tyr,
      125I-Tyr, mono-iodo-Tyr, di-iodo-Tyr, O-sulpho-Tyr or O-phospho-Ty

<400> SEQUENCE: 31

```
Gly Xaa Ser Phe Cys Lys Ala Asp Xaa Lys Pro Cys Xaa Xaa His Ser
1               5                   10                  15

Asp Cys Cys Asn Cys Cys Leu Ser Gly Ile Cys Ala Xaa Ser Thr Asn
            20                  25                  30

Xaa Ile Leu Xaa Gly Cys Ser Thr Ser Ser Phe Phe Lys Ile
        35                  40                  45
```

<210> SEQ ID NO 32
<211> LENGTH: 433
<212> TYPE: DNA
<213> ORGANISM: Conus radiatus -continued

```
<400> SEQUENCE: 32
cgaggacatc ccagctatca gcacttcgca gcagtcgagg ctttgaaatc ctaatcatag      60
aagaaggcaa aaatatctgc tggtcaatat gaagctgtgc ctgacgttcc ttcttgttct    120
gatgattctg gcatcagtga ctggggagaa gttaagcgag caaacactgc gtcgtgctgc    180
taggaaaaac aaaggccatg ttccatgcgg gaaagacgga aggaaatgcg gtatcatgc    240 agattgctgt aattgctgtc tcagtggaat ctgtaaacca agcacaagtt ggactggatg    300
ctcgacgagt accgttcaat tgacgcgctg actttcagcc agctaggcca tgcctaggtc    360
ctcatgcaca ttcacatttg ctgtgaattg aattcatgtg cattaaagcc attaggcgta    420
gaaagatgaa aaa                                                        433

<210> SEQ ID NO 33
<211> LENGTH: 80
<212> TYPE: PRT
<213> ORGANISM: Conus radiatus

<400> SEQUENCE: 33

Met Lys Leu Cys Leu Thr Phe Leu Leu Val Leu Met Ile Leu Ala Ser
1               5                   10                  15

Val Thr Gly Glu Lys Leu Ser Glu Gln Thr Leu Arg Arg Ala Ala Arg
            20                  25                  30

Lys Asn Lys Gly His Val Pro Cys Gly Lys Asp Gly Arg Lys Cys Gly
        35                  40                  45

Tyr His Ala Asp Cys Cys Asn Cys Cys Leu Ser Gly Ile Cys Lys Pro
    50                  55                  60

Ser Thr Ser Trp Thr Gly Cys Ser Thr Ser Thr Val Gln Leu Thr Arg
65                  70                  75                  80

<210> SEQ ID NO 34
<211> LENGTH: 45
<212> TYPE: PRT
<213> ORGANISM: Conus radiatus
<220> FEATURE:
<221> NAME/KEY: PEPTIDE
<222> LOCATION: (1)..(45)
<223> OTHER INFORMATION: Xaa at residues 4 and 29 is Pro or hydroxy-Pro;
      Xaa at residue 33 is Trp or bromo-Trp; Xaa at residue 14 is Tyr,
      125I-Tyr, mono-iodo-Tyr, di-iodo-Tyr, O-sulpho-Tyr or O-phospho-Ty

<400> SEQUENCE: 34

Gly His Val Xaa Cys Gly Lys Asp Gly Arg Lys Cys Gly Xaa His Ala
1               5                   10                  15

Asp Cys Cys Asn Cys Cys Leu Ser Gly Ile Cys Lys Xaa Ser Thr Ser
            20                  25                  30

Xaa Thr Gly Cys Ser Thr Ser Thr Val Gln Leu Thr Arg
        35                  40                  45

<210> SEQ ID NO 35
<211> LENGTH: 438
<212> TYPE: DNA
<213> ORGANISM: Conus radiatus

<400> SEQUENCE: 35
cagacgagga catcccagct atcagcactt cgcagcagtc gaggctttga atcctaatc      60 atagaagaag gcaaaaatat ctgctggtca atatgaagct gtgcctgacg ttccttcttg    120
ttctgatgat tctggcatcc gtgactgggg agaagtcaag caagcataca ctgagtcgtg    180
ctgctagggt aaaaaacaaa ggccatgttt catgcgggaa agacggaagg gcatgcgatt    240
```

```
atcatgcaga ttgctgtaac tgctgtctcg gtggaatctg taaaccaagc acaagttgga      300
ttggatgctc gacgaatgtg ttcttgacgc gctgactttc agccagctag ccatgccta       360 ggtcctcatg cacattcaca tttgctgtga attgaattca tgtgcattaa agccattagg      420
cgtagaaaga tgaaaaaa                                                    438
```

```
<210> SEQ ID NO 36
<211> LENGTH: 80
<212> TYPE: PRT
<213> ORGANISM: Conus radiatus

<400> SEQUENCE: 36
```

Met Lys Leu Cys Leu Thr Phe Leu Leu Val Leu Met Ile Leu Ala Ser
1               5                   10                  15

Val Thr Gly Glu Lys Ser Ser Lys His Thr Leu Ser Arg Ala Ala Arg
            20                  25                  30

Val Lys Asn Lys Gly His Val Ser Cys Gly Lys Asp Gly Arg Ala Cys
        35                  40                  45

Asp Tyr His Ala Asp Cys Cys Asn Cys Cys Leu Gly Gly Ile Cys Lys
    50                  55                  60

Pro Ser Thr Ser Trp Ile Gly Cys Ser Thr Asn Val Phe Leu Thr Arg
65                  70                  75                  80

```
<210> SEQ ID NO 37
<211> LENGTH: 44
<212> TYPE: PRT
<213> ORGANISM: Conus radiatus
<220> FEATURE:
<221> NAME/KEY: PEPTIDE
<222> LOCATION: (1)..(44)
<223> OTHER INFORMATION: Xaa at residue 29 is Pro or hydroxy-Pro; Xaa at
      residue 33 is Trp or bromo-Trp; Xaa at residue 14 is Tyr, 125I-
      Tyr, mono-iodo-Tyr, di-iodo-Tyr, O-sulpho-Tyr or O-phospho-Ty

<400> SEQUENCE: 37
```

Gly His Val Ser Cys Gly Lys Asp Gly Arg Ala Cys Asp Xaa His Ala
1               5                   10                  15

Asp Cys Cys Asn Cys Cys Leu Gly Gly Ile Cys Lys Xaa Ser Thr Ser
            20                  25                  30

Xaa Ile Gly Cys Ser Thr Asn Val Phe Leu Thr Arg
        35                  40

```
<210> SEQ ID NO 38
<211> LENGTH: 423
<212> TYPE: DNA
<213> ORGANISM: Conus radiatus

<400> SEQUENCE: 38
cagctatcaa cacttcgcag cagtcgaggc tttgaaatcc taatcataga agaaggcaaa       60
aatatctgct ggtcaatatg aagctgtgcc tgacgttcct tcttgttctg atgattctgg      120
catcagtgac tggggagaag ttaagcgagc aaacactgcg tcgtgctgct aggaaaaaca      180
aaggccatgt tccatgcggg aaagaccgaa ggaaatgcgg gtatcatgca gattgctgta      240
attgctgtct cagtggaatc tgtaaaccaa gcacaagttg gactggatgc tcgacgagta      300 cgttttatt gacgcgctga ctttcagcca gctaggccat gcctaggtcc tcatgcacat      360
tcacatttgc tgtgaattga attcatgtgc attaaagcca tttggcgtag aaagatgaaa      420
aaa                                                                    423
```

```
<210> SEQ ID NO 39
<211> LENGTH: 80
<212> TYPE: PRT
<213> ORGANISM: Conus radiatus

<400> SEQUENCE: 39

Met Lys Leu Cys Leu Thr Phe Leu Leu Val Leu Met Ile Leu Ala Ser
1               5                   10                  15

Val Thr Gly Glu Lys Leu Ser Glu Gln Thr Leu Arg Arg Ala Ala Arg
            20                  25                  30

Lys Asn Lys Gly His Val Pro Cys Gly Lys Asp Arg Arg Lys Cys Gly
        35                  40                  45

Tyr His Ala Asp Cys Cys Asn Cys Cys Leu Ser Gly Ile Cys Lys Pro
    50                  55                  60

Ser Thr Ser Trp Thr Gly Cys Ser Thr Ser Thr Phe Leu Leu Thr Arg
65                  70                  75                  80

<210> SEQ ID NO 40
<211> LENGTH: 45
<212> TYPE: PRT
<213> ORGANISM: Conus radiatus
<220> FEATURE:
<221> NAME/KEY: PEPTIDE
<222> LOCATION: (1)..(45)
<223> OTHER INFORMATION: Xaa at residues 4 and 29 is Pro or hydroxy-Pro;
      Xaa at residue 33 is Trp or bromo-Trp; Xaa at residue 14 is Tyr,
      125I-Tyr, mono-iodo-Tyr, di-iodo-Tyr, O-sulpho-Tyr or O-phospho-Ty

<400> SEQUENCE: 40

Gly His Val Xaa Cys Gly Lys Asp Arg Arg Lys Cys Gly Xaa His Ala
1               5                   10                  15

Asp Cys Cys Asn Cys Cys Leu Ser Gly Ile Cys Lys Xaa Ser Thr Ser
            20                  25                  30

Xaa Thr Gly Cys Ser Thr Ser Thr Phe Leu Leu Thr Arg
        35                  40                  45

<210> SEQ ID NO 41
<211> LENGTH: 443
<212> TYPE: DNA
<213> ORGANISM: Conus radiatus

<400> SEQUENCE: 41
ggcttcagac gaggacatcc cagctatcag cacttcgcag cagtcgaggc tttgaaatcc     60
taatcataga agaaggcaaa aatatctgct ggtcaatatg aagctgtgcc tgacgttcct    120
tcttgttctg atgattctgg catcagtgac tggggagaag ttaagcgagc aaacactgcg    180
tcgtgctgct aggaaaaaca aaggccatgt tccatgcggg aaagacggaa ggaaatgcgg    240
gtatcatgca gattgctgta attgctgtct cagtggaatc tgtaaaccaa gcacaagttg    300
gactggatgc tcgacgagta cgttttttatt gacgcgctga ctttcagcca gctaggccat    360
gcctaggtcc tcatgcacat tcacatttgc tgtgaattga attcatgtgc attaaagcca    420
ttaggcgtag aaagatgaaa aaa                                            443

<210> SEQ ID NO 42
<211> LENGTH: 80
<212> TYPE: PRT
<213> ORGANISM: Conus radiatus

<400> SEQUENCE: 42

Met Lys Leu Cys Leu Thr Phe Leu Leu Val Leu Met Ile Leu Ala Ser
```

```
                 1               5                  10                  15

Val Thr Gly Glu Lys Leu Ser Glu Gln Thr Leu Arg Arg Ala Ala Arg
                20                  25                  30

Lys Asn Lys Gly His Val Pro Cys Gly Lys Asp Gly Arg Lys Cys Gly
            35                  40                  45

Tyr His Ala Asp Cys Cys Asn Cys Cys Leu Ser Gly Ile Cys Lys Pro
        50                  55                  60

Ser Thr Ser Trp Thr Gly Cys Ser Thr Ser Thr Phe Leu Leu Thr Arg
65                  70                  75                  80
```

<210> SEQ ID NO 43
<211> LENGTH: 45
<212> TYPE: PRT
<213> ORGANISM: Conus radiatus
<220> FEATURE:
<221> NAME/KEY: PEPTIDE
<222> LOCATION: (1)..(45)
<223> OTHER INFORMATION: Xaa at residues 4 and 29 is Pro or hydroxy-Pro;
      Xaa at residue 33 is Trp or bromo-Trp; Xaa at residue 14 is Tyr,
      125I-Tyr, mono-iodo-Tyr, di-iodo-Tyr, O-sulpho-Tyr or O-phospho-Ty

<400> SEQUENCE: 43

```
Gly His Val Xaa Cys Gly Lys Asp Gly Arg Lys Cys Gly Xaa His Ala
1               5                  10                  15

Asp Cys Cys Asn Cys Cys Leu Ser Gly Ile Cys Lys Xaa Ser Thr Ser
            20                  25                  30

Xaa Thr Gly Cys Ser Thr Ser Thr Phe Leu Leu Thr Arg
        35                  40                  45
```

<210> SEQ ID NO 44
<211> LENGTH: 451
<212> TYPE: DNA
<213> ORGANISM: Conus radiatus

<400> SEQUENCE: 44

```
gcttcagacg aggacaaccc agctatcagc acttcgcagc agtcgaggct ttgaaatcct      60
aatcatagaa gaaggcaaaa atatctgctg gtcaatatga agctgtgcct gacgttcctt     120
cttgttctga tgattctggc atcagtgact ggggagaagt caagcaagca tacactgagt     180
cgtgctgcta gggtaaaaaa cagaggccct agttttttgta aggcaaacgg aaagccatgc    240
tcgtatcatg cagattgctg taattgctgt ctcagtggaa tctgtaaacc aagcacaaat     300
gtgattttac ctggatgctc gacgagttcg ttcttcagga tctgactttc agccagctag     360
gccatgccta ggttctcatg cacattcaca tttgctgtga attgaattca tgtgcattaa     420
agccattagg cgtagaaaga tgaaaaaaaa a                                    451
```

<210> SEQ ID NO 45
<211> LENGTH: 82
<212> TYPE: PRT
<213> ORGANISM: Conus radiatus

<400> SEQUENCE: 45

```
Met Lys Leu Cys Leu Thr Phe Leu Leu Val Leu Met Ile Leu Ala Ser
1               5                  10                  15

Val Thr Gly Glu Lys Ser Ser Lys His Thr Leu Ser Arg Ala Ala Arg
                20                  25                  30

Val Lys Asn Arg Gly Pro Ser Phe Cys Lys Ala Asn Gly Lys Pro Cys
            35                  40                  45

Ser Tyr His Ala Asp Cys Cys Asn Cys Cys Leu Ser Gly Ile Cys Lys
```

-continued

```
                50                  55                  60
Pro Ser Thr Asn Val Ile Leu Pro Gly Cys Ser Thr Ser Ser Phe Phe
 65                  70                  75                  80

Arg Ile

<210> SEQ ID NO 46
<211> LENGTH: 46
<212> TYPE: PRT
<213> ORGANISM: Conus radiatus
<220> FEATURE:
<221> NAME/KEY: PEPTIDE
<222> LOCATION: (1)..(46)
<223> OTHER INFORMATION: Xaa at residues 2, 11, 29 and 36 is Pro or
      hydroxy-Pro; Xaa at residue 14 is Tyr, 125I-Tyr, mono-iodo-Tyr,
      di-iodo-Tyr, O-sulpho-Tyr or O-phospho-Ty

<400> SEQUENCE: 46

Gly Xaa Ser Phe Cys Lys Ala Asn Gly Lys Xaa Cys Ser Xaa His Ala
  1               5                  10                  15

Asp Cys Cys Asn Cys Cys Leu Ser Gly Ile Cys Lys Xaa Ser Thr Asn
                 20                  25                  30

Val Ile Leu Xaa Gly Cys Ser Thr Ser Ser Phe Phe Arg Ile
             35                  40                  45

<210> SEQ ID NO 47
<211> LENGTH: 425
<212> TYPE: DNA
<213> ORGANISM: Conus radiatus

<400> SEQUENCE: 47
cagctatcag cacttcgcag cagtcgaggc tttgaaatcc taatcataga agaaggcaaa      60
aatatctgct ggtcaatatg aagctgtgcc tgacgttcct tcttgttctg atgattctgg    120
catcagtgac tggggagaag ttaagcgagc aaacactgcg tcgtgctgct aggaaaaaca    180
aaggccatgt tccatgcggg aaagacggaa ggaaatgcgg gtatcatgca gattgctgta    240
attgctgtct cagtggaatc tgtaaaccaa gcacaagttg gactggatgc tcgacgagta    300
cgttcaattg acgcgctgac tttcagccag ctaggccatg cctaggtcct catgcacatt    360
cacatttgct gtgaattgaa ttcatgtgca ttaaagccat taggcgtaaa agatgaaaaa    420
aaaaa                                                                425

<210> SEQ ID NO 48
<211> LENGTH: 77
<212> TYPE: PRT
<213> ORGANISM: Conus radiatus

<400> SEQUENCE: 48

Met Lys Leu Cys Leu Thr Phe Leu Leu Val Leu Met Ile Leu Ala Ser
  1               5                  10                  15

Val Thr Gly Glu Lys Leu Ser Glu Gln Thr Leu Arg Arg Ala Ala Arg
                 20                  25                  30

Lys Asn Lys Gly His Val Pro Cys Gly Lys Asp Gly Arg Lys Cys Gly
             35                  40                  45

Tyr His Ala Asp Cys Cys Asn Cys Cys Leu Ser Gly Ile Cys Lys Pro
         50                  55                  60

Ser Thr Ser Trp Thr Gly Cys Ser Thr Ser Thr Phe Asn
 65                  70                  75

<210> SEQ ID NO 49
```

```
<211> LENGTH: 42
<212> TYPE: PRT
<213> ORGANISM: Conus radiatus
<220> FEATURE:
<221> NAME/KEY: PEPTIDE
<222> LOCATION: (1)..(42)
<223> OTHER INFORMATION: Xaa at residues 4 and 29 is Pro or hydroxy-Pro;
    Xaa at residue 33 is Trp or bromo-Trp; Xaa at residue 14 is Tyr,
    125I-Tyr, mono-iodo-Tyr, di-iodo-Tyr, O-sulpho-Tyr or O-phospho-Ty

<400> SEQUENCE: 49

Gly His Val Xaa Cys Gly Lys Asp Gly Arg Lys Cys Gly Xaa His Ala
1               5                  10                  15

Asp Cys Cys Asn Cys Cys Leu Ser Gly Ile Cys Lys Xaa Ser Thr Ser
            20                  25                  30

Xaa Thr Gly Cys Ser Thr Ser Thr Phe Asn
        35                  40

<210> SEQ ID NO 50
<211> LENGTH: 438
<212> TYPE: DNA
<213> ORGANISM: Conus radiatus

<400> SEQUENCE: 50
gcttcagacg aggacatccc agctatcagc acttcgcagc agtcgaggct ttgaaatcct      60
aatcatagaa gaaggcaaaa atatctgctg gtcaatatga agctgtgcct gacgttcctt     120
cttgttctga tgattctggc atcagtgact ggggagaagt caagcaagca tacactgagt     180
cgtgctgcta gggtaaaaaa caaaggccat gttccatgcg ggaaagacgg aaggaaatgc     240
gggtatcata cacattgctg taattgctgt ctcagtggaa tctgtaaacc aagcacaagt     300
ttgattggat gctcgacgag ttcgttcact tgacgcgctg actttcagcc agctaggcca     360
tgcctaggtc ctcatgcaca ttcacatttg ctgtgaattg aattcatgtg cattaaagcc     420
attaggcgta gaaagatt                                                    438

<210> SEQ ID NO 51
<211> LENGTH: 78
<212> TYPE: PRT
<213> ORGANISM: Conus radiatus

<400> SEQUENCE: 51

Met Lys Leu Cys Leu Thr Phe Leu Leu Val Leu Met Ile Leu Ala Ser
1               5                  10                  15

Val Thr Gly Glu Lys Ser Ser Lys His Thr Leu Ser Arg Ala Ala Arg
            20                  25                  30

Val Lys Asn Lys Gly His Val Pro Cys Gly Lys Asp Gly Arg Lys Cys
        35                  40                  45

Gly Tyr His Thr His Cys Cys Asn Cys Cys Leu Ser Gly Ile Cys Lys
    50                  55                  60

Pro Ser Thr Ser Leu Ile Gly Cys Ser Thr Ser Ser Phe Thr
65                  70                  75

<210> SEQ ID NO 52
<211> LENGTH: 42
<212> TYPE: PRT
<213> ORGANISM: Conus radiatus
<220> FEATURE:
<221> NAME/KEY: PEPTIDE
<222> LOCATION: (1)..(42)
<223> OTHER INFORMATION: Xaa at residues 4 and 29 is Pro or hydroxy-Pro;
    Xaa at residue 14 is Tyr, 125I-Tyr, mono-iodo-Tyr, di-iodo-Tyr,
    O-sulpho-Tyr or O-phospho-Ty
```

<400> SEQUENCE: 52

Gly His Val Xaa Cys Gly Lys Asp Gly Arg Lys Cys Gly Xaa His Thr
1               5                   10                  15

His Cys Cys Asn Cys Cys Leu Ser Gly Ile Cys Lys Xaa Ser Thr Ser
            20                  25                  30

Leu Ile Gly Cys Ser Thr Ser Ser Phe Thr
        35                  40

<210> SEQ ID NO 53
<211> LENGTH: 498
<212> TYPE: DNA
<213> ORGANISM: Conus radiatus

<400> SEQUENCE: 53

```
gatccccaag ctatttaggt gacactatag aatactcaag cttgcatgcc tgcaggtcga      60
ctctagagga tcccagctat cagcacttcg cagcagtcga ggctttgaaa tcctaatcat     120
agaagaaggc aaaaatatct gctggtcaat atgaagctgt gcctgacgtt ccttcttgtt     180
ctgatgattc tggcatcagt gactggggag aagtcaagca agcatacact gagtcgtgct     240
gctagggtaa aaacagagg ccctagtttt tgtaaggcaa acggaaagcc atgctcgtat      300
catgcagatt gctgtaattg ctgtctcagt ggaatctgtg caccaagcac aaattggatt     360
ttacctggat gctcgacgag ttcgttcttc aagatctgac tttcagccag ctaggccatg     420
cctaggtcct catgcacatt cacatttgct gtgaattgaa ttcatgtgca ttaaagccat     480
taggcgtaga aagatgaa                                                   498
```

<210> SEQ ID NO 54
<211> LENGTH: 82
<212> TYPE: PRT
<213> ORGANISM: Conus radiatus

<400> SEQUENCE: 54

Met Lys Leu Cys Leu Thr Phe Leu Leu Val Leu Met Ile Leu Ala Ser
1               5                   10                  15

Val Thr Gly Glu Lys Ser Ser Lys His Thr Leu Ser Arg Ala Ala Arg
            20                  25                  30

Val Lys Asn Arg Gly Pro Ser Phe Cys Lys Ala Asn Gly Lys Pro Cys
        35                  40                  45

Ser Tyr His Ala Asp Cys Cys Asn Cys Cys Leu Ser Gly Ile Cys Ala
    50                  55                  60

Pro Ser Thr Asn Trp Ile Leu Pro Gly Cys Ser Thr Ser Ser Phe Phe
65                  70                  75                  80

Lys Ile

<210> SEQ ID NO 55
<211> LENGTH: 46
<212> TYPE: PRT
<213> ORGANISM: Conus radiatus
<220> FEATURE:
<221> NAME/KEY: PEPTIDE
<222> LOCATION: (1)..(46)
<223> OTHER INFORMATION: Xaa at residues 2, 11, 29 and 36 is Pro or
      hydroxy-Pro; Xaa at residue 33 is Trp or bromo-Trp; Xaa at residue
      14 is Tyr, 125I-Tyr, mono-iodo-Tyr, di-iodo-Tyr, O-sulpho-Tyr or
      O-phospho-Ty

<400> SEQUENCE: 55

Gly Xaa Ser Phe Cys Lys Ala Asn Gly Lys Xaa Cys Ser Xaa His Ala

```
                1               5                  10                 15
Asp Cys Cys Asn Cys Cys Leu Ser Gly Ile Cys Ala Xaa Ser Thr Asn
                20                 25                 30

Xaa Ile Leu Xaa Gly Cys Ser Thr Ser Ser Phe Phe Lys Ile
         35                 40                 45

<210> SEQ ID NO 56
<211> LENGTH: 417
<212> TYPE: DNA
<213> ORGANISM: Conus radiatus

<400> SEQUENCE: 56
cccagctatc agcacttcgc agcagtcgag gctttgaaat cctaatcata gaagaaggca      60
aaaatatctg ctggtcaata tgaagctgtg cctgacgttc cttcttgttc tgatgattct     120
ggcatcagtg actggggaga agtcaagcaa gcatacactg agtcgtgctg ctagggtaaa     180
aaacaaaggc gctgttccat gcgggaaaga cggaaggcaa tgcaggaatc atgcagattg     240
ctgtaattgc tgtcccttt gaacctgtgc accaagcaca aatcggattt tacctggatg      300
ctcgacgggt atgttcttga cgcgctgact ttcagccagc taggccatgc ctaggtcctc     360
atgcacattc acatttgctg tgaattgaat tcatgtgcat taaagccatt aggcgta        417

<210> SEQ ID NO 57
<211> LENGTH: 82
<212> TYPE: PRT
<213> ORGANISM: Conus radiatus

<400> SEQUENCE: 57

Met Lys Leu Cys Leu Thr Phe Leu Leu Val Leu Met Ile Leu Ala Ser
1               5                  10                 15

Val Thr Gly Glu Lys Ser Ser Lys His Thr Leu Ser Arg Ala Ala Arg
                20                 25                 30

Val Lys Asn Lys Gly Ala Val Pro Cys Gly Lys Asp Gly Arg Gln Cys
         35                 40                 45

Arg Asn His Ala Asp Cys Cys Asn Cys Cys Pro Phe Gly Thr Cys Ala
     50                 55                 60

Pro Ser Thr Asn Arg Ile Leu Pro Gly Cys Ser Thr Gly Met Phe Leu
65                 70                 75                 80

Thr Arg

<210> SEQ ID NO 58
<211> LENGTH: 46
<212> TYPE: PRT
<213> ORGANISM: Conus radiatus
<220> FEATURE:
<221> NAME/KEY: PEPTIDE
<222> LOCATION: (1)..(46)
<223> OTHER INFORMATION: Xaa at residues 4, 23, 29 and 36 is Pro or
      hydroxy-Pro

<400> SEQUENCE: 58

Gly Ala Val Xaa Cys Gly Lys Asp Gly Arg Gln Cys Arg Asn His Ala
1               5                  10                 15

Asp Cys Cys Asn Cys Cys Xaa Phe Gly Thr Cys Ala Xaa Ser Thr Asn
                20                 25                 30

Arg Ile Leu Xaa Gly Cys Ser Thr Gly Met Phe Leu Thr Arg
         35                 40                 45

<210> SEQ ID NO 59
```

```
<211> LENGTH: 46
<212> TYPE: PRT
<213> ORGANISM: Conus radiatus
<220> FEATURE:
<221> NAME/KEY: PEPTIDE
<222> LOCATION: (1)..(46)
<223> OTHER INFORMATION: Xaa at residues 2, 11, 29 and 36 is Pro or
      hydroxy-Pro; Xaa at residues 9 and 13 is Glu or gamma-carboxy-Glu;
      Xaa at residue 33 is Trp or bromo-Trp; Xaa at residue 14 is Tyr,
      125I-Tyr, mono-iodo-Tyr, di-iodo-Tyr, O-sulpho-Tyr or O-phospho-Ty

<400> SEQUENCE: 59

Gly Xaa Ser Phe Cys Lys Ala Asp Xaa Lys Xaa Cys Xaa Xaa His Ala
1               5                   10                  15

Asp Cys Cys Asn Cys Cys Leu Ser Gly Ile Cys Ala Xaa Ser Thr Asn
            20                  25                  30

Xaa Ile Leu Xaa Gly Cys Ser Thr Ser Ser Phe Phe Lys Ile
        35                  40                  45

<210> SEQ ID NO 60
<211> LENGTH: 37
<212> TYPE: PRT
<213> ORGANISM: Conus radiatus
<220> FEATURE:
<221> NAME/KEY: PEPTIDE
<222> LOCATION: (1)..(37)
<223> OTHER INFORMATION: Xaa at residue 37 is Pro or hydroxy-Pro; Xaa at
      residues 1, 13 and 14 is Glu or gamma-carboxy-Glu; Xaa at residue
      34 is Trp or bromo-Tr

<400> SEQUENCE: 60

Xaa Cys Lys Thr Asn Lys Met Ser Cys Ser Leu His Xaa Xaa Cys Cys
1               5                   10                  15

Arg Phe Arg Cys Cys Phe His Gly Lys Cys Gln Thr Ser Val Phe Gly
            20                  25                  30

Cys Xaa Val Asp Xaa
        35

<210> SEQ ID NO 61
<211> LENGTH: 424
<212> TYPE: DNA
<213> ORGANISM: Conus caracteristicus

<400> SEQUENCE: 61
ccagctatca gcacttcgca gcagtcgagg ctttaaaatc ctaatcgtag aagaaggcaa      60
aaccatctgg tggtcagtat gaagctgtgt gtgacgtttc ttcttgttct ggtgattctg     120
ccatcggtga ccgggagaa gtctagcgag cgtacacgga ttggtgctgt tctgaaaggc      180
cattggtgcg gatacccagg agaacgcgga tgccgatatc atagccaatg ctgtggggac     240
atgtgttgtt acgaccgcaa gtgtgttgcg actgctatgc catgtgactt tccctactag     300
tgcgatggac ctaggcgtgc tggccttgtg gcagactcgc tcagtatgcc tgacctgtcc     360
aagtgaaacg accggacacg atcgtcgtat tcctttgcca agagctagct aggccatgcc     420
tagg                                                                  424

<210> SEQ ID NO 62
<211> LENGTH: 73
<212> TYPE: PRT
<213> ORGANISM: Conus caracteristicus

<400> SEQUENCE: 62

Met Lys Leu Cys Val Thr Phe Leu Leu Val Leu Val Ile Leu Pro Ser
1               5                   10                  15
```

```
Val Thr Gly Glu Lys Ser Ser Glu Arg Thr Arg Ile Gly Ala Val Leu
        20                  25                  30

Lys Gly His Trp Cys Gly Tyr Pro Gly Glu Arg Gly Cys Arg Tyr His
            35                  40                  45

Ser Gln Cys Cys Gly Asp Met Cys Cys Tyr Asp Arg Lys Cys Val Ala
    50                  55                  60

Thr Ala Met Pro Cys Asp Phe Pro Tyr
65                  70
```

<210> SEQ ID NO 63
<211> LENGTH: 40
<212> TYPE: PRT
<213> ORGANISM: Conus caracteristicus
<220> FEATURE:
<221> NAME/KEY: PEPTIDE
<222> LOCATION: (1)..(40)
<223> OTHER INFORMATION: Xaa at residues 7, 35 and 39 is Pro or hydroxy-
      Pro; Xaa at residue 9 is Glu or gamma-carboxy-Glu; Xaa at residue
      2 is Trp or bromo-Trp; Xaa at residues 6, 25 and 40 is Tyr, 125I-
      Tyr, mono-iodo-Tyr, di-iodo-Tyr, O-sulpho-Tyr or O-phospho-Ty

<400> SEQUENCE: 63

```
Gly His Xaa Cys Gly Xaa Xaa Gly Xaa Arg Gly Cys Arg Xaa His Ser
1               5                   10                  15

Gln Cys Cys Gly Asp Met Cys Xaa Asp Arg Lys Cys Val Ala Thr
        20                  25                  30

Ala Met Xaa Cys Asp Phe Xaa Xaa
            35                  40
```

<210> SEQ ID NO 64
<211> LENGTH: 346
<212> TYPE: DNA
<213> ORGANISM: Conus magus

<400> SEQUENCE: 64

```
ccgctatcag cacttcgcag cagtcgaggc tttgaaatcc taatcataga agagggcaaa      60
aatatctgct ggtcaatatg aagctgtgcc tgacgttcct tcttgttctg atgattctgg    120
catcagtgac tggggagaag tcaagcaagc atacactgag tcgtgctgct agggtaaaaa    180
acagaggctg taagaaagac agaaagccat gctcgtatca tgcagattgc tgtaattgct    240
gtctcagtgg gatctgtgca ccaagcacaa attggatttt acctggatgc tcgacgagta    300
cgttcacttg acgcgctgac tttcagccag ctaggccatg cctagg                   346
```

<210> SEQ ID NO 65
<211> LENGTH: 77
<212> TYPE: PRT
<213> ORGANISM: Conus magus

<400> SEQUENCE: 65

```
Met Lys Leu Cys Leu Thr Phe Leu Leu Val Leu Met Ile Leu Ala Ser
1               5                   10                  15

Val Thr Gly Glu Lys Ser Ser Lys His Thr Leu Ser Arg Ala Ala Arg
            20                  25                  30

Val Lys Asn Arg Gly Cys Lys Lys Asp Arg Lys Pro Cys Ser Tyr His
        35                  40                  45

Ala Asp Cys Cys Asn Cys Cys Leu Ser Gly Ile Cys Ala Pro Ser Thr
    50                  55                  60

Asn Trp Ile Leu Pro Gly Cys Ser Thr Ser Thr Phe Thr
65                  70                  75
```

<210> SEQ ID NO 66
<211> LENGTH: 41
<212> TYPE: PRT
<213> ORGANISM: Conus magus
<220> FEATURE:
<221> NAME/KEY: PEPTIDE
<222> LOCATION: (1)..(41)
<223> OTHER INFORMATION: Xaa at residues 8, 26 and 33 is Pro or hydroxy-Pro; Xaa at residue 30 is Trp or bromo-Trp; Xaa at residue 11 is Tyr, 125I-Tyr, mono-iodo-Tyr, di-iodo-Tyr, O-sulpho-Tyr or O-phospho-Ty

<400> SEQUENCE: 66

Gly Cys Lys Lys Asp Arg Lys Xaa Cys Ser Xaa His Ala Asp Cys Cys
1               5                   10                  15

Asn Cys Cys Leu Ser Gly Ile Cys Ala Xaa Ser Thr Asn Xaa Ile Leu
            20                  25                  30

Xaa Gly Cys Ser Thr Ser Thr Phe Thr
        35                  40

<210> SEQ ID NO 67
<211> LENGTH: 347
<212> TYPE: DNA
<213> ORGANISM: Conus magus

<400> SEQUENCE: 67
ccgctatcag cacttcgcag cagtcgaggc tttgaaatcc tagtcataga agaaggcaaa      60
aatatctgct ggtcaatatg aagctgtgcc tgacgttcct tcttgttctg atgattctgg     120
catccgtgac tggggagaag tcaagcaagc atacactgag tcgtgctgct agggtaaaaa     180
acaaaggcca tgtttcatgc gggaaagacg gaagggcatg cgattatcat gcagattgct     240
gtaactgctg tctcggtgga atctgtaaac caagcacaag ttggattgga tgctcgacga     300
atgtgttctt gacgcgctga ctttcagcca gctaggccat gcctagg                  347

<210> SEQ ID NO 68
<211> LENGTH: 80
<212> TYPE: PRT
<213> ORGANISM: Conus magus

<400> SEQUENCE: 68

Met Lys Leu Cys Leu Thr Phe Leu Leu Val Leu Met Ile Leu Ala Ser
1               5                   10                  15

Val Thr Gly Glu Lys Ser Ser Lys His Thr Leu Ser Arg Ala Ala Arg
            20                  25                  30

Val Lys Asn Lys Gly His Val Ser Cys Gly Lys Asp Gly Arg Ala Cys
        35                  40                  45

Asp Tyr His Ala Asp Cys Cys Asn Cys Cys Leu Gly Gly Ile Cys Lys
    50                  55                  60

Pro Ser Thr Ser Trp Ile Gly Cys Ser Thr Asn Val Phe Leu Thr Arg
65                  70                  75                  80

<210> SEQ ID NO 69
<211> LENGTH: 44
<212> TYPE: PRT
<213> ORGANISM: Conus magus
<220> FEATURE:
<221> NAME/KEY: PEPTIDE
<222> LOCATION: (1)..(44)
<223> OTHER INFORMATION: Xaa at residue 29 is Pro or hydroxy-Pro; Xaa at residue 33 is Trp or bromo-Trp; Xaa at residue 14 is Tyr, 125I-Tyr, mono-iodo-Tyr, di-iodo-Tyr, O-sulpho-Tyr or O-phospho-Ty

```
<400> SEQUENCE: 69

Gly His Val Ser Cys Gly Lys Asp Gly Arg Ala Cys Asp Xaa His Ala
1               5                   10                  15

Asp Cys Cys Asn Cys Cys Leu Gly Gly Ile Cys Lys Xaa Ser Thr Ser
            20                  25                  30

Xaa Ile Gly Cys Ser Thr Asn Val Phe Leu Thr Arg
        35                  40

<210> SEQ ID NO 70
<211> LENGTH: 353
<212> TYPE: DNA
<213> ORGANISM: Conus striatus

<400> SEQUENCE: 70
ccgctatcag cacttcgcag cagtcgaggc tttgaaatcc taatcataga agaaggcaaa      60
aatatctgct ggtcaatatg aagctgtgcc tgacgttcct tcttgttctg atgattctgg    120
catcagtgac tggggagaag tcaagcaagc atacactgag tcgtgctgct agggtaaaaa    180
acagaggccc tagttttttgt aaggcaaacg gaaagccatg ctcgtatcat gcagattgct    240
gtaattgctg tctcagtgga atctgtaaac caagcacaaa tgtgatttta cctggatgct    300
cgacgagttc gttcttcagg atctgacttt cagccagcta ggccatgcct agg           353

<210> SEQ ID NO 71
<211> LENGTH: 82
<212> TYPE: PRT
<213> ORGANISM: Conus striatus

<400> SEQUENCE: 71

Met Lys Leu Cys Leu Thr Phe Leu Leu Val Leu Met Ile Leu Ala Ser
1               5                   10                  15

Val Thr Gly Glu Lys Ser Ser Lys His Thr Leu Ser Arg Ala Ala Arg
            20                  25                  30

Val Lys Asn Arg Gly Pro Ser Phe Cys Lys Ala Asn Gly Lys Pro Cys
        35                  40                  45

Ser Tyr His Ala Asp Cys Cys Asn Cys Cys Leu Ser Gly Ile Cys Lys
    50                  55                  60

Pro Ser Thr Asn Val Ile Leu Pro Gly Cys Ser Thr Ser Ser Phe Phe
65                  70                  75                  80

Arg Ile

<210> SEQ ID NO 72
<211> LENGTH: 46
<212> TYPE: PRT
<213> ORGANISM: Conus striatus
<220> FEATURE:
<221> NAME/KEY: PEPTIDE
<222> LOCATION: (1)..(46)
<223> OTHER INFORMATION: Xaa at residues 2, 11, 29 and 36 is Pro or
      hydroxy-Pro; Xaa at residue 14 is Tyr, 125I-Tyr, mono-iodo-Tyr,
      di-iodo-Tyr, O-sulpho-Tyr or O-phospho-Ty

<400> SEQUENCE: 72

Gly Xaa Ser Phe Cys Lys Ala Asn Gly Lys Xaa Cys Ser Xaa His Ala
1               5                   10                  15

Asp Cys Cys Asn Cys Cys Leu Ser Gly Ile Cys Lys Xaa Ser Thr Asn
            20                  25                  30

Val Ile Leu Xaa Gly Cys Ser Thr Ser Ser Phe Phe Arg Ile
        35                  40                  45
```

<210> SEQ ID NO 73
<211> LENGTH: 431
<212> TYPE: DNA
<213> ORGANISM: Conus striatus

<400> SEQUENCE: 73

```
ccagctatca gcacttcgca gcagtcgagg ctttaaaatc ctaatcgtag aagaaggcaa      60
aaacatctgg tggtcagtat gaagctgtgt gtgacgtttc ttcttgttct ggtgattctg     120
ccatcagtaa ctggggagga gtctagcgag cgtacactga gtggtgctac tctgacaggc     180
gatcggggaa cgtgctcatt cttaggacaa ggatgcggag atcattccga ctgctgttgg     240
aacatgtgtt gtgccagcga aatgtgcgtt gtgactctcc ttcaatgtaa atgatttccc     300
ttctagggcg atggacctag gcgtgctggc ctagcggtag actcgctcag tatgcctgat     360
ctgtctgagt gaaacgacct gacacgatcc gtcgtattcc tttgccaaga gccagctagg     420
ccatgcctag g                                                         431
```

<210> SEQ ID NO 74
<211> LENGTH: 71
<212> TYPE: PRT
<213> ORGANISM: Conus striatus

<400> SEQUENCE: 74

```
Met Lys Leu Cys Val Thr Phe Leu Leu Val Leu Val Ile Leu Pro Ser
1               5                   10                  15

Val Thr Gly Glu Glu Ser Ser Glu Arg Thr Leu Ser Gly Ala Thr Leu
            20                  25                  30

Thr Gly Asp Arg Gly Thr Cys Ser Phe Leu Gly Gln Gly Cys Gly Asp
        35                  40                  45

His Ser Asp Cys Cys Trp Asn Met Cys Cys Ala Ser Glu Met Cys Val
    50                  55                  60

Val Thr Leu Leu Gln Cys Lys
65                  70
```

<210> SEQ ID NO 75
<211> LENGTH: 35
<212> TYPE: PRT
<213> ORGANISM: Conus striatus
<220> FEATURE:
<221> NAME/KEY: PEPTIDE
<222> LOCATION: (1)..(35)
<223> OTHER INFORMATION: Xaa at residue 25 is Glu or gamma-carboxy-Glu;
      Xaa at residue 18 is Trp or bromo-Tr

<400> SEQUENCE: 75

```
Gly Thr Cys Ser Phe Leu Gly Gln Gly Cys Gly Asp His Ser Asp Cys
1               5                   10                  15

Cys Xaa Asn Met Cys Cys Ala Ser Xaa Met Cys Val Val Thr Leu Leu
            20                  25                  30

Gln Cys Lys
        35
```

<210> SEQ ID NO 76
<211> LENGTH: 345
<212> TYPE: DNA
<213> ORGANISM: Conus striatus

<400> SEQUENCE: 76

```
ccagctatca gcacttcgca gcagtcgagg ctttgaaatc ctaatcatag aagaaggcaa      60
```

-continued

```
aaatatctgc tggtcaatat gaagctgtgc ctgacgttcc ttcttgttct gatgattctg      120
gcatcagtga ctggggagaa gtcaagcaag catacactga gtcgtgctgc tagggtaaaa      180
aacagaggct gtaagaaaga cagaaagcca tgctcgtatc aggcagattg ctgtaattgc      240
tgtcccattg gaacctgtgc accaagcaca aattggattt tacctggatg ctcgacgggt      300
ccgttcatgg cgcgctgact ttcagccagc taggccatgc ctagg                      345
```

<210> SEQ ID NO 77
<211> LENGTH: 79
<212> TYPE: PRT
<213> ORGANISM: Conus striatus

<400> SEQUENCE: 77

```
Met Lys Leu Cys Leu Thr Phe Leu Leu Val Leu Met Ile Leu Ala Ser
  1               5                  10                  15

Val Thr Gly Glu Lys Ser Ser Lys His Thr Leu Ser Arg Ala Ala Arg
             20                  25                  30

Val Lys Asn Arg Gly Cys Lys Lys Asp Arg Lys Pro Cys Ser Tyr Gln
         35                  40                  45

Ala Asp Cys Cys Asn Cys Cys Pro Ile Gly Thr Cys Ala Pro Ser Thr
     50                  55                  60

Asn Trp Ile Leu Pro Gly Cys Ser Thr Gly Pro Phe Met Ala Arg
 65                  70                  75
```

<210> SEQ ID NO 78
<211> LENGTH: 43
<212> TYPE: PRT
<213> ORGANISM: Conus striatus
<220> FEATURE:
<221> NAME/KEY: PEPTIDE
<222> LOCATION: (1)..(43)
<223> OTHER INFORMATION: Xaa at residues 8, 20, 26, 33 and 39 is Pro or
      hydroxy-Pro; Xaa at residue 30 is Trp or bromo-Trp; Xaa at residue
      11 is Tyr, 125I-Tyr, mono-iodo-Tyr, di-iodo-Tyr, O-sulpho-Tyr or
      O-phospho-Ty

<400> SEQUENCE: 78

```
Gly Cys Lys Lys Asp Arg Lys Xaa Cys Ser Xaa Gln Ala Asp Cys Cys
  1               5                  10                  15

Asn Cys Cys Xaa Ile Gly Thr Cys Ala Xaa Ser Thr Asn Xaa Ile Leu
             20                  25                  30

Xaa Gly Cys Ser Thr Gly Xaa Phe Met Ala Arg
         35                  40
```

<210> SEQ ID NO 79
<211> LENGTH: 348
<212> TYPE: DNA
<213> ORGANISM: Conus striatus

<400> SEQUENCE: 79

```
ccagctatca gcacttcgca gcagtcgagg ctttgaaatc ctaatcatag aagaaggcaa       60
aaatatctgc tggtcaatat gaagctgtgc ctgacgttcc ttcttgttct gatgattctg      120
gcatcagtga ctggggagaa gtcaagcaag catacactgg gtcgtgctgc tagggtaaaa      180
aacagaggcc ctagtttttg taaggcagac gaaaagccat gcaagtatca tgcagattgc      240
tgtaactgct gtctcggtgg aatctgtaaa ccaagcacaa gttggattgg atgctcgacg      300
aatgtgttct tgacgcgctg actttcagcc agctaggcca tgcctagg                   348
```

```
<210> SEQ ID NO 80
<211> LENGTH: 80
<212> TYPE: PRT
<213> ORGANISM: Conus striatus

<400> SEQUENCE: 80

Met Lys Leu Cys Leu Thr Phe Leu Leu Val Leu Met Ile Leu Ala Ser
1               5                   10                  15

Val Thr Gly Glu Lys Ser Ser Lys His Thr Leu Gly Arg Ala Ala Arg
            20                  25                  30

Val Lys Asn Arg Gly Pro Ser Phe Cys Lys Ala Asp Glu Lys Pro Cys
        35                  40                  45

Lys Tyr His Ala Asp Cys Cys Asn Cys Cys Leu Gly Gly Ile Cys Lys
    50                  55                  60

Pro Ser Thr Ser Trp Ile Gly Cys Ser Thr Asn Val Phe Leu Thr Arg
65                  70                  75                  80

<210> SEQ ID NO 81
<211> LENGTH: 44
<212> TYPE: PRT
<213> ORGANISM: Conus striatus
<220> FEATURE:
<221> NAME/KEY: PEPTIDE
<222> LOCATION: (1)..(44)
<223> OTHER INFORMATION: Xaa at residues 2, 11 and 29 is Pro or hydroxy-
      Pro; Xaa at residue 9 is Glu or gamma-carboxy-Glu; Xaa at residue
      33 is Trp or bromo-Trp; Xaa at residue 14 is Tyr, 125I-Tyr, mono-
      iodo-Tyr, di-iodo-Tyr, O-sulpho-Tyr or O-phospho-Ty

<400> SEQUENCE: 81

Gly Xaa Ser Phe Cys Lys Ala Asp Xaa Lys Xaa Cys Lys Xaa His Ala
1               5                   10                  15

Asp Cys Cys Asn Cys Cys Leu Gly Gly Ile Cys Lys Xaa Ser Thr Ser
            20                  25                  30

Xaa Ile Gly Cys Ser Thr Asn Val Phe Leu Thr Arg
        35                  40

<210> SEQ ID NO 82
<211> LENGTH: 347
<212> TYPE: DNA
<213> ORGANISM: Conus striatus

<400> SEQUENCE: 82
ccgctatcag cacttcgcag cagtcgaggc tttgaaatcc taatcataga agaaggcaaa        60
aatatctgct ggtcaatatg aagctgtgcc tgacgttcct tcttgttctg atgattctgg       120
catcagtgac tggggagaag tcaagcaagc atacactgag tcgtgctgct agggtaaaaa       180
acagaggccc tagttttttgt aaggcagacg aaaagccatg caagtatcat gcaggttgct       240
gtaactgctg tctcggtgga atctgtaaac caagcacaag ttggattgga tgctcgacga       300
atgtgttctt gacgcgctga ctttcagcca gctaggccat gcctagg                    347

<210> SEQ ID NO 83
<211> LENGTH: 80
<212> TYPE: PRT
<213> ORGANISM: Conus striatus

<400> SEQUENCE: 83

Met Lys Leu Cys Leu Thr Phe Leu Leu Val Leu Met Ile Leu Ala Ser
1               5                   10                  15

Val Thr Gly Glu Lys Ser Ser Lys His Thr Leu Ser Arg Ala Ala Arg
            20                  25                  30
```

-continued

```
Val Lys Asn Arg Gly Pro Ser Phe Cys Lys Ala Asp Glu Lys Pro Cys
             35                  40                  45

Lys Tyr His Ala Gly Cys Cys Asn Cys Leu Gly Gly Ile Cys Lys
         50                  55                  60

Pro Ser Thr Ser Trp Ile Gly Cys Ser Thr Asn Val Phe Leu Thr Arg
 65                  70                  75                  80

<210> SEQ ID NO 84
<211> LENGTH: 44
<212> TYPE: PRT
<213> ORGANISM: Conus striatus
<220> FEATURE:
<221> NAME/KEY: PEPTIDE
<222> LOCATION: (1)..(44)
<223> OTHER INFORMATION: Xaa at residues 2, 11 and 29 is Pro or hydroxy-
      Pro; Xaa at residue 9 is Glu or gamma-carboxy-Glu; Xaa at residue
      33 is Trp or bromo-Trp; Xaa at residue 14 is Tyr, 125I-Tyr, mono-
      iodo-Tyr, di-iodo-Tyr, O-sulpho-Tyr or O-phospho-Ty

<400> SEQUENCE: 84

Gly Xaa Ser Phe Cys Lys Ala Asp Xaa Lys Xaa Cys Lys Xaa His Ala
 1               5                  10                  15

Gly Cys Cys Asn Cys Leu Gly Gly Ile Cys Lys Xaa Ser Thr Ser
             20                  25                  30

Xaa Ile Gly Cys Ser Thr Asn Val Phe Leu Thr Arg
         35                  40

<210> SEQ ID NO 85
<211> LENGTH: 424
<212> TYPE: DNA
<213> ORGANISM: Conus caracteristicus

<400> SEQUENCE: 85
ccagctatca gcacttcgca gcagtcgagg ctttaaaatc ctaatcgtag aagaaggcaa      60
aaccatctgg tggtcagtat gaagctgtgt gtgacgtttc ttcttgttct ggtgattctg    120
ccatcggtga ccggggagaa gtctagcgag cgtacacgga ttggtgctgt tctgaaaggc    180
cattggtgcg gatacctagg agaacgcgga tgccgatatc atagccaatg ctgtggggac    240
atgtgttgtt acgaccgcaa gtgtgttgtg actgctatgc catgtgactt tccctactag    300
tgcgatggac ctaggcgtgc cggccttgtg gcagactcgc tcagtatgcc tgatctgtcc    360
aagtgaaacg accggacacg atcgtcgtat tcctttgcca agagccagct aggccatgcc    420
tagg                                                                424

<210> SEQ ID NO 86
<211> LENGTH: 73
<212> TYPE: PRT
<213> ORGANISM: Conus caracteristicus

<400> SEQUENCE: 86

Met Lys Leu Cys Val Thr Phe Leu Leu Val Leu Val Ile Leu Pro Ser
 1               5                  10                  15

Val Thr Gly Glu Lys Ser Ser Glu Arg Thr Arg Ile Gly Ala Val Leu
             20                  25                  30

Lys Gly His Trp Cys Gly Tyr Leu Gly Glu Arg Gly Cys Arg Tyr His
         35                  40                  45

Ser Gln Cys Cys Gly Asp Met Cys Cys Tyr Asp Arg Lys Cys Val Val
 50                  55                  60

Thr Ala Met Pro Cys Asp Phe Pro Tyr
```

-continued

<210> SEQ ID NO 87
<211> LENGTH: 40
<212> TYPE: PRT
<213> ORGANISM: Conus caracteristicus
<220> FEATURE:
<221> NAME/KEY: PEPTIDE
<222> LOCATION: (1)..(40)
<223> OTHER INFORMATION: Xaa at residues 35 and 39 is Pro or hydroxy-
    Pro; Xaa at residue 9 is Glu or gamma-carboxy-Glu; Xaa at residue
    3 is Trp or bromo-Trp; Xaa at residues 6, 14, 25 and 40 is Tyr,
    125I-Tyr, mono-iodo-Tyr, di-iodo-Tyr, O-sulpho-Tyr or O-phospho-Ty

<400> SEQUENCE: 87

Gly His Xaa Cys Gly Xaa Leu Gly Xaa Arg Gly Cys Arg Xaa His Ser
1               5                   10                  15

Gln Cys Cys Gly Asp Met Cys Cys Xaa Asp Arg Lys Cys Val Val Thr
            20                  25                  30

Ala Met Xaa Cys Asp Phe Xaa Xaa
        35                  40

<210> SEQ ID NO 88
<211> LENGTH: 424
<212> TYPE: DNA
<213> ORGANISM: Conus caracteristicus

<400> SEQUENCE: 88
ccagctatca gcacttcgca gcagtcgagg ctttaaaatc ctaatcgtag aagaaggcaa      60
aaccatctgg tggtcagtat gaagctgtgt gtgacgtttc ttcttgttct ggtgattctg     120
ccatcggtga ccggggagaa gtctagcgag cgtacacgga ttggtgctgt tctgaaaggc     180
cattggtgcg gatacccagg agaacgcgga tgccgatatc atagccaatg ctgtggggac     240
atgtgttgtt acgaccgcaa gtgtgttgtg actgctatgc catgtgactt tccctactag     300
tgcgatggac ctaggcgtgc tggccttgtg gcagactcgc tcagtatgcc tgatctgtcc     360
aagtgaaacg accggacacg atcgtcgtat tcctttgcca agagccagct aggccatgcc     420
tagg                                                                 424

<210> SEQ ID NO 89
<211> LENGTH: 73
<212> TYPE: PRT
<213> ORGANISM: Conus caracteristicus

<400> SEQUENCE: 89

Met Lys Leu Cys Val Thr Phe Leu Leu Val Leu Val Ile Leu Pro Ser
1               5                   10                  15

Val Thr Gly Glu Lys Ser Ser Glu Arg Thr Arg Ile Gly Ala Val Leu
            20                  25                  30

Lys Gly His Trp Cys Gly Tyr Pro Gly Glu Arg Gly Cys Arg Tyr His
        35                  40                  45

Ser Gln Cys Cys Gly Asp Met Cys Cys Tyr Asp Arg Lys Cys Val Val
    50                  55                  60

Thr Ala Met Pro Cys Asp Phe Pro Tyr
65                  70

<210> SEQ ID NO 90
<211> LENGTH: 40
<212> TYPE: PRT
<213> ORGANISM: Conus caracteristicus
<220> FEATURE:

```
<221> NAME/KEY: PEPTIDE
<222> LOCATION: (1)..(40)
<223> OTHER INFORMATION: Xaa at residues 7, 35 and 39 is Pro or hydroxy-
      Pro; Xaa at residue 9 is Glu or gamma-carboxy-Glu; Xaa at residue
      3 is Trp or bromo-Trp; Xaa at residues 6, 14, 25 and 40 is Tyr,
      125I-Tyr, mono-iodo-Tyr, di-iodo-Tyr, O-sulpho-Tyr or O-phospho-Ty

<400> SEQUENCE: 90

Gly His Xaa Cys Gly Xaa Pro Gly Xaa Arg Gly Cys Arg Xaa His Ser
1               5                   10                  15

Gln Cys Cys Gly Asp Met Cys Cys Xaa Asp Arg Lys Cys Val Val Thr
            20                  25                  30

Ala Met Xaa Cys Asp Phe Xaa Xaa
        35                  40

<210> SEQ ID NO 91
<211> LENGTH: 424
<212> TYPE: DNA
<213> ORGANISM: Conus caracteristicus

<400> SEQUENCE: 91
ccagctatca gcacttcgca gcagtcgagg ctttaaaatc ctaatcgtag aagaaggcaa      60
aaccatctgg tggtcagtat gaagctgtgt gtgacgtttc ttcttgttct ggtgattctg     120
ccatcggtga ccggggagaa gtctagcgag cgtacacgga ttggtgctgt tctgaaaggc     180
cattggtgcg gataccctagg agaacgcgga tgccgatatc atagccaatg ctgtggggac    240
atgtgttgtt acgaccgcaa gtgtgctgtg actgctatgc catgtgactt tccctactag    300
tgcgatggac ctaggcgtgc tggccttgtg gcagactcgc tcagtatgcc tgatctgtcc    360
aagtgaaacg accggacacg atcgtcgtat tcctttgcca agagccagct aggccatgcc    420
tagg                                                                 424

<210> SEQ ID NO 92
<211> LENGTH: 73
<212> TYPE: PRT
<213> ORGANISM: Conus caracteristicus

<400> SEQUENCE: 92

Met Lys Leu Cys Val Thr Phe Leu Leu Val Leu Val Ile Leu Pro Ser
1               5                   10                  15

Val Thr Gly Glu Lys Ser Ser Glu Arg Thr Arg Ile Gly Ala Val Leu
            20                  25                  30

Lys Gly His Trp Cys Gly Tyr Leu Gly Glu Arg Gly Cys Arg Tyr His
        35                  40                  45

Ser Gln Cys Cys Gly Asp Met Cys Cys Tyr Asp Arg Lys Cys Ala Val
    50                  55                  60

Thr Ala Met Pro Cys Asp Phe Pro Tyr
65                  70

<210> SEQ ID NO 93
<211> LENGTH: 40
<212> TYPE: PRT
<213> ORGANISM: Conus caracteristicus
<220> FEATURE:
<221> NAME/KEY: PEPTIDE
<222> LOCATION: (1)..(40)
<223> OTHER INFORMATION: Xaa at residues 35 and 39 is Pro or hydroxy-
      Pro; Xaa at residue 9 is Glu or gamma-carboxy-Glu; Xaa at residue
      3 is Trp or bromo-Trp; Xaa at residues 6, 14, 25 and 40 is Tyr,
      125I-Tyr, mono-iodo-Tyr, di-iodo-Tyr, O-sulpho-Tyr or O-phospho-Ty

<400> SEQUENCE: 93
```

```
Gly His Xaa Cys Gly Xaa Leu Gly Xaa Arg Gly Cys Arg Xaa His Ser
1               5                   10                  15

Gln Cys Cys Gly Asp Met Cys Cys Xaa Asp Arg Lys Cys Ala Val Thr
            20                  25                  30

Ala Met Xaa Cys Asp Phe Xaa Xaa
        35                  40

<210> SEQ ID NO 94
<211> LENGTH: 423
<212> TYPE: DNA
<213> ORGANISM: Conus caracteristicus

<400> SEQUENCE: 94
ccgctatcag cacttcgcag cagtcgaggc tttaaaatcc taatcataga agaaggcaaa      60
accatctggt ggtcagtatg aagctgtgtg tgacgtttct tcttgttctg gtgattctgc    120
catcggtgac cggggagaag tctagcgagc gtacacggat tggtgctgtt ctgaaaggcc    180
attggtgcgg atacccagga gaacgcggat gccgatatca tagccaatgc tgtgggggaca   240 tgtgttgtta cgaccgcatg tgtgttgtga ctgctatgcc atgtgacttt ccctactagt    300
gcgatggacc taggcgtgct ggccttgtgg cagactcgct cagtatgcct gatctgtcca    360
agtgaaacga ccggacacga tcgtcgtatt cctttgccaa gagccagcta ggccatgcct    420
agg                                                                  423

<210> SEQ ID NO 95
<211> LENGTH: 73
<212> TYPE: PRT
<213> ORGANISM: Conus caracteristicus

<400> SEQUENCE: 95

Met Lys Leu Cys Val Thr Phe Leu Leu Val Leu Val Ile Leu Pro Ser
1               5                   10                  15

Val Thr Gly Glu Lys Ser Ser Glu Arg Thr Arg Ile Gly Ala Val Leu
            20                  25                  30

Lys Gly His Trp Cys Gly Tyr Pro Gly Glu Arg Gly Cys Arg Tyr His
        35                  40                  45

Ser Gln Cys Cys Gly Asp Met Cys Cys Tyr Asp Arg Met Cys Val Val
    50                  55                  60

Thr Ala Met Pro Cys Asp Phe Pro Tyr
65                  70

<210> SEQ ID NO 96
<211> LENGTH: 40
<212> TYPE: PRT
<213> ORGANISM: Conus caracteristicus
<220> FEATURE:
<221> NAME/KEY: PEPTIDE
<222> LOCATION: (1)..(40)
<223> OTHER INFORMATION: Xaa at residues 7, 35 and 39 is Pro or hydroxy-
      Pro; Xaa at residue 9 is Glu or gamma-carboxy-Glu; Xaa at residue
      3 is Trp or bromo-Trp; Xaa at residues 6, 14, 25 and 40 is Tyr,
      125I-Tyr, mono-iodo-Tyr, di-iodo-Tyr, O-sulpho-Tyr or O-phospho-Ty

<400> SEQUENCE: 96

Gly His Xaa Cys Gly Xaa Xaa Gly Xaa Arg Gly Cys Arg Xaa His Ser
1               5                   10                  15

Gln Cys Cys Gly Asp Met Cys Cys Xaa Asp Arg Met Cys Val Val Thr
            20                  25                  30

Ala Met Xaa Cys Asp Phe Xaa Xaa
        35                  40
```

```
                35                  40

<210> SEQ ID NO 97
<211> LENGTH: 423
<212> TYPE: DNA
<213> ORGANISM: Conus caracteristicus
<220> FEATURE:
<221> NAME/KEY: misc_feature
<222> LOCATION: (1)..(423)
<223> OTHER INFORMATION: n is any nucleotide

<400> SEQUENCE: 97
ccagctatag cacttcgcag cagncgaggc tttaaaatcc taatcataga agaaggcaaa      60
accatctggt ggtcagtatg aagctgtgtg tgacgtttct tcttgttctg gtgattctgc     120
catcggtgac cggggagaag tctagcgagc gtacacggat tggtgctgtt ctgaaaggcc     180
attggtgcgg atacctagga gaacgcggat gccgatatca tggccaatgc tgtggggaca     240
tgtgttgtta cgaccgcaag tgtgttgtga ctgctatgcc atgtgacttt ccctactagt     300
gcgatggacc taggcgtgct ggccttgtgg cagactcgct cagtatgcct gatctgtcca     360
agcgaaacga ccggacacga tcgtcgtatt cctttgccaa gagccagcta ggccatgcct     420
agg                                                                  423

<210> SEQ ID NO 98
<211> LENGTH: 73
<212> TYPE: PRT
<213> ORGANISM: Conus caracteristicus

<400> SEQUENCE: 98

Met Lys Leu Cys Val Thr Phe Leu Leu Val Leu Ile Leu Pro Ser
1               5                   10                  15

Val Thr Gly Glu Lys Ser Ser Glu Arg Thr Arg Ile Gly Ala Val Leu
            20                  25                  30

Lys Gly His Trp Cys Gly Tyr Leu Gly Glu Arg Gly Cys Arg Tyr His
        35                  40                  45

Gly Gln Cys Cys Gly Asp Met Cys Cys Tyr Asp Arg Lys Cys Val Val
    50                  55                  60

Thr Ala Met Pro Cys Asp Phe Pro Tyr
65                  70

<210> SEQ ID NO 99
<211> LENGTH: 40
<212> TYPE: PRT
<213> ORGANISM: Conus caracteristicus
<220> FEATURE:
<221> NAME/KEY: PEPTIDE
<222> LOCATION: (1)..(40)
<223> OTHER INFORMATION: Xaa at residues 35 and 39 is Pro or hydroxy-
      Pro; Xaa at residue 9 is Glu or gamma-carboxy-Glu; Xaa at residue
      3 is Trp or bromo-Trp; Xaa at residues 6, 14, 25 and 40 is Tyr,
      125I-Tyr, mono-iodo-Tyr, di-iodo-Tyr, O-sulpho-Tyr or O-phospho-Ty

<400> SEQUENCE: 99

Gly His Xaa Cys Gly Xaa Leu Gly Xaa Arg Gly Cys Arg Xaa His Gly
1               5                   10                  15

Gln Cys Cys Gly Asp Met Cys Cys Xaa Asp Arg Lys Cys Val Val Thr
            20                  25                  30

Ala Met Xaa Cys Asp Phe Xaa Xaa
        35                  40

<210> SEQ ID NO 100
```

```
<211> LENGTH: 353
<212> TYPE: DNA
<213> ORGANISM: Conus caracteristicus

<400> SEQUENCE: 100
ccgctatcag cacttcgcag cagtcgaggc tttgaaatcc taatcataga agaaggcaaa      60
aatatctgct ggtcaatatg aagctgtgcc tgacgttcct tcttgttctg atgattctgg     120
catcagtgac tggggtgagg tcaagcaagc atacactgag tcgtgctgct agggtaaaaa     180
acagaggccc tagttttgt aaggcaaacg gaaagccatg ctcgtatcat gcagattgct     240
gtaattgctg tctcagtgga atctgtgaac caagcacaaa tgtgatttta cctggatgct     300
cgacgagttc gttcttcagg atctgacttt cagccagcta ggccatgcct agg           353

<210> SEQ ID NO 101
<211> LENGTH: 82
<212> TYPE: PRT
<213> ORGANISM: Conus caracteristicus

<400> SEQUENCE: 101

Met Lys Leu Cys Leu Thr Phe Leu Leu Val Leu Met Ile Leu Ala Ser
1               5                   10                  15

Val Thr Gly Val Arg Ser Ser Lys His Thr Leu Ser Arg Ala Ala Arg
            20                  25                  30

Val Lys Asn Arg Gly Pro Ser Phe Cys Lys Ala Asn Gly Lys Pro Cys
        35                  40                  45

Ser Tyr His Ala Asp Cys Cys Asn Cys Cys Leu Ser Gly Ile Cys Glu
    50                  55                  60

Pro Ser Thr Asn Val Ile Leu Pro Gly Cys Ser Thr Ser Ser Phe Phe
65                  70                  75                  80

Arg Ile

<210> SEQ ID NO 102
<211> LENGTH: 46
<212> TYPE: PRT
<213> ORGANISM: Conus caracteristicus
<220> FEATURE:
<221> NAME/KEY: PEPTIDE
<222> LOCATION: (1)..(46)
<223> OTHER INFORMATION: Xaa at residues 2, 11, 29 and 36 is Pro or
      hydroxy-Pro; Xaa at residue 28 is Glu or gamma-carboxy-Glu;  Xaa
      at residue 14 is Tyr, 125I-Tyr, mono-iodo-Tyr, di-iodo-Tyr, O-
      sulpho-Tyr or O-phospho-Ty

<400> SEQUENCE: 102

Gly Xaa Ser Phe Cys Lys Ala Asn Gly Lys Xaa Cys Ser Xaa His Ala
1               5                   10                  15

Asp Cys Cys Asn Cys Cys Leu Ser Gly Ile Cys Xaa Xaa Ser Thr Asn
            20                  25                  30

Val Ile Leu Xaa Gly Cys Ser Thr Ser Ser Phe Phe Arg Ile
        35                  40                  45

<210> SEQ ID NO 103
<211> LENGTH: 353
<212> TYPE: DNA
<213> ORGANISM: Conus magus

<400> SEQUENCE: 103
ccgctatcag cacttcgcag cagtcgaggc tttgaagtcc taatcataga agaaggcaaa      60
aatatctgct ggtcaatatg aagctgtgcc tgacgttcct tcttgttctg atgattctgg     120
```

-continued

| | |
|---|---|
| catcagtgac tggggagaag ttgagcaagc atacactgag tcatgctgct aggagaccca | 180 |
| acaaaggcgc tgttccatgc gggaaagacg gaaggcaatg caggaatcat gcagattgct | 240 |
| gtaattgctg tcccattgga acctgtgcac caagcacaaa ttggatttta cctggatgct | 300 |
| cgacgggtca attcatgacg cgctgacttt cagccagcta ggccatgcct agg | 353 |

<210> SEQ ID NO 104
<211> LENGTH: 82
<212> TYPE: PRT
<213> ORGANISM: Conus magus

<400> SEQUENCE: 104

```
Met Lys Leu Cys Leu Thr Phe Leu Leu Val Leu Met Ile Leu Ala Ser
1               5                   10                  15
Val Thr Gly Glu Lys Leu Ser Lys His Thr Leu Ser His Ala Ala Arg
                20                  25                  30
Arg Pro Asn Lys Gly Ala Val Pro Cys Gly Lys Asp Gly Arg Gln Cys
            35                  40                  45
Arg Asn His Ala Asp Cys Cys Asn Cys Cys Pro Ile Gly Thr Cys Ala
        50                  55                  60
Pro Ser Thr Asn Trp Ile Leu Pro Gly Cys Ser Thr Gly Gln Phe Met
65                  70                  75                  80
Thr Arg
```

<210> SEQ ID NO 105
<211> LENGTH: 46
<212> TYPE: PRT
<213> ORGANISM: Conus magus
<220> FEATURE:
<221> NAME/KEY: PEPTIDE
<222> LOCATION: (1)..(46)
<223> OTHER INFORMATION: Xaa at residues 4, 23, 29 and 36 is Pro or
    hydroxy-Pro; Xaa at residue 33 is Trp or bromo-Tr

<400> SEQUENCE: 105

```
Gly Ala Val Xaa Cys Gly Lys Asp Gly Arg Gln Cys Arg Asn His Ala
1               5                   10                  15
Asp Cys Cys Asn Cys Cys Xaa Ile Gly Thr Cys Ala Xaa Ser Thr Asn
                20                  25                  30
Xaa Ile Leu Xaa Gly Cys Ser Thr Gly Gln Phe Met Thr Arg
            35                  40                  45
```

<210> SEQ ID NO 106
<211> LENGTH: 416
<212> TYPE: DNA
<213> ORGANISM: Conus magus
<220> FEATURE:
<221> NAME/KEY: misc_feature
<222> LOCATION: (1)..(416)
<223> OTHER INFORMATION: n is any nucleotide

<400> SEQUENCE: 106

| | |
|---|---|
| ccagctatca gcacttcgca gcagnngagg ctttaaaatc ctaatcgtag aagaaggcaa | 60 |
| aaacatctgg tgtcagtatg aagctgtgtg tgacgtttct tcttgttctg gtgattctgc | 120 |
| catcagtaac tggggagaag tctagcgagc gtacactgag tggtgctgct ctgagaggcg | 180 |
| atcggagaac gtgctcaaac aaaggacaac aatgcggaga tgattccgac tgctgttggc | 240 |
| atttgtgttg tgtgaacaac aagtgcgctc acttgatcct attatgtaac ttatagtgcg | 300 |
| atggacctag gcgtgctggc ctagcagccg actcgctcag tatgcctgat ctgtccgagt | 360 |

```
gacctgacac gatccgtcgt attcctttgc caagagccag ctaggccatg cctagg         416
```

<210> SEQ ID NO 107
<211> LENGTH: 72
<212> TYPE: PRT
<213> ORGANISM: Conus magus

<400> SEQUENCE: 107

```
Met Lys Leu Cys Val Thr Phe Leu Leu Val Leu Val Ile Leu Pro Ser
1               5                   10                  15

Val Thr Gly Glu Lys Ser Ser Glu Arg Thr Leu Ser Gly Ala Ala Leu
            20                  25                  30

Arg Gly Asp Arg Arg Thr Cys Ser Asn Lys Gly Gln Gln Cys Gly Asp
        35                  40                  45

Asp Ser Asp Cys Cys Trp His Leu Cys Cys Val Asn Asn Lys Cys Ala
    50                  55                  60

His Leu Ile Leu Leu Cys Asn Leu
65                  70
```

<210> SEQ ID NO 108
<211> LENGTH: 35
<212> TYPE: PRT
<213> ORGANISM: Conus magus
<220> FEATURE:
<221> NAME/KEY: PEPTIDE
<222> LOCATION: (1)..(35)
<223> OTHER INFORMATION: Xaa at residue 17 is Trp or bromo-Trp

<400> SEQUENCE: 108

```
Thr Cys Ser Asn Lys Gly Gln Gln Cys Gly Asp Asp Ser Asp Cys Cys
1               5                   10                  15

Xaa His Leu Cys Cys Val Asn Asn Lys Cys Ala His Leu Ile Leu Leu
            20                  25                  30

Cys Asn Leu
        35
```

<210> SEQ ID NO 109
<211> LENGTH: 354
<212> TYPE: DNA
<213> ORGANISM: Conus magus
<220> FEATURE:
<221> NAME/KEY: misc_feature
<222> LOCATION: (1)..(354)
<223> OTHER INFORMATION: n is any nucleotide

<400> SEQUENCE: 109

```
ccagctatca gcacttcgca gcagtcgagg ntttgaaatc ctaatcatag aagaaggcaa    60
aaatatctgc tggtcaatat gaagctgtgc ctgacgttcc ttcttgttct gatgattctg   120
gcatcagtga ctgggagaa gtcaagcaag catacactga gtcgtgctgc agggtaaaa    180 aacagaggcc cgagttttg taaggcagac gaaaagccat gcgagtatca tgcagattgc   240
tgtaattgct gtctcagtgg aatctgtgca ccaagcacaa attggatttt acctggatgc   300
tcgacgagtt cgttcttcga gatctgactt tcagccagct aggccatgcc tagg         354
```

<210> SEQ ID NO 110
<211> LENGTH: 82
<212> TYPE: PRT
<213> ORGANISM: Conus magus

<400> SEQUENCE: 110

```
Met Lys Leu Cys Leu Thr Phe Leu Leu Val Leu Met Ile Leu Ala Ser
```

```
                  1               5                  10                 15

Val Thr Gly Glu Lys Ser Ser Lys His Thr Leu Ser Arg Ala Ala Arg
                20                  25                 30

Val Lys Asn Arg Gly Pro Ser Phe Cys Lys Ala Asp Glu Lys Pro Cys
                35                  40                 45

Glu Tyr His Ala Asp Cys Cys Asn Cys Cys Leu Ser Gly Ile Cys Ala
                50                  55                 60

Pro Ser Thr Asn Trp Ile Leu Pro Gly Cys Ser Thr Ser Ser Phe Phe
65                  70                  75                 80

Glu Ile

<210> SEQ ID NO 111
<211> LENGTH: 46
<212> TYPE: PRT
<213> ORGANISM: Conus magus
<220> FEATURE:
<221> NAME/KEY: PEPTIDE
<222> LOCATION: (1)..(46)
<223> OTHER INFORMATION: Xaa at residues 3, 11, 29 and 36 is Pro or
      hydroxy-Pro; Xaa at residues 9, 13 and 45 is Glu or gamma-carboxy-
      Glu; Xaa at residue 33 is Trp or bromo-Trp; Xaa at residue 14 is
      Tyr, 125I-Tyr, mono-iodo-Tyr, di-iodo-Tyr, O-sulpho-Tyr or O-
      phospho-Ty

<400> SEQUENCE: 111

Gly Xaa Ser Phe Cys Lys Ala Asp Xaa Lys Xaa Cys Xaa Xaa His Ala
1               5                   10                 15

Asp Cys Cys Asn Cys Cys Leu Ser Gly Ile Cys Ala Xaa Ser Thr Asn
                20                  25                 30

Xaa Ile Leu Xaa Gly Cys Ser Thr Ser Ser Phe Phe Xaa Ile
            35                  40                 45

<210> SEQ ID NO 112
<211> LENGTH: 353
<212> TYPE: DNA
<213> ORGANISM: Conus magus

<400> SEQUENCE: 112
ccgctatcag cacttcgcag cagtcgaggc tttgaaatcc taatcataga agaaggcaaa      60
aatatctgct ggtcaatatg aggctgtgcc tgacgttcct tcttgttctg atgattctgg    120
catcagtgac tggggagaag tcaagcaagc atacactgag tcgtgctgct agggtaaaaa    180
acagaggccc tagtttttgt aaggcagacg aaaagccatg cgagtatcat gcagattgct    240
gtaattgctg tctcagtgga atctgtgcac caagcacaaa ttggatttta cctggatgct    300
cgacgagttc gttcttcaag acctgacttt cagctagcta ggccatgcct agg          353

<210> SEQ ID NO 113
<211> LENGTH: 82
<212> TYPE: PRT
<213> ORGANISM: Conus magus

<400> SEQUENCE: 113

Met Arg Leu Cys Leu Thr Phe Leu Leu Val Leu Met Ile Leu Ala Ser
1               5                   10                 15

Val Thr Gly Glu Lys Ser Ser Lys His Thr Leu Ser Arg Ala Ala Arg
                20                  25                 30

Val Lys Asn Arg Gly Pro Ser Phe Cys Lys Ala Asp Glu Lys Pro Cys
                35                  40                 45

Glu Tyr His Ala Asp Cys Cys Asn Cys Cys Leu Ser Gly Ile Cys Ala
```

```
                50                  55                  60
Pro Ser Thr Asn Trp Ile Leu Pro Gly Cys Ser Thr Ser Ser Phe Phe
 65                  70                  75                  80

Lys Thr

<210> SEQ ID NO 114
<211> LENGTH: 46
<212> TYPE: PRT
<213> ORGANISM: Conus magus
<220> FEATURE:
<221> NAME/KEY: PEPTIDE
<222> LOCATION: (1)..(46)
<223> OTHER INFORMATION: Xaa at residues 2, 11, 29 and 36 is Pro or
      hydroxy-Pro; Xaa at residues 9 and 13 is Glu or gamma-carboxy-Glu;
      Xaa at residue 33 is Trp or bromo-Trp; Xaa at residue 14 is Tyr,
      125I-Tyr, mono-iodo-Tyr, di-iodo-Tyr, O-sulpho-Tyr or O-phospho-Ty

<400> SEQUENCE: 114

Gly Xaa Ser Phe Cys Lys Ala Asp Xaa Lys Xaa Cys Xaa Xaa His Ala
 1               5                  10                  15

Asp Cys Cys Asn Cys Cys Leu Ser Gly Ile Cys Ala Xaa Ser Thr Asn
                20                  25                  30

Xaa Ile Leu Xaa Gly Cys Ser Thr Ser Ser Phe Phe Lys Thr
        35                  40                  45

<210> SEQ ID NO 115
<211> LENGTH: 347
<212> TYPE: DNA
<213> ORGANISM: Conus magus

<400> SEQUENCE: 115
ccagctatca gcacttcgca gcagtcgagg ctttgatatc ctaatcatag aagaaggcaa      60
aaatatctgc tggtcaatat gaagctgtgc ctgacgttcc ttcttgttct gatgattctg    120
gcatcagtga ctggggagaa gttaagcgag caaacactgc gtcgtgctgc taggaaaaac    180
aaaggccatg ttccatgcgg gaaagacgga aggaaatgcg gtatcatgc agattgctgt     240 aattgctgtc tcagtggaat ctgtaaacca agcacaagtt ggactggatg ctcgacgagt    300
acgttcgatt gacgcgctga ctttcagcta gctaggccat gcctagg                 347

<210> SEQ ID NO 116
<211> LENGTH: 77
<212> TYPE: PRT
<213> ORGANISM: Conus magus

<400> SEQUENCE: 116

Met Lys Leu Cys Leu Thr Phe Leu Leu Val Leu Met Ile Leu Ala Ser
 1               5                  10                  15

Val Thr Gly Glu Lys Leu Ser Glu Gln Thr Leu Arg Arg Ala Ala Arg
                20                  25                  30

Lys Asn Lys Gly His Val Pro Cys Gly Lys Asp Gly Arg Lys Cys Gly
        35                  40                  45

Tyr His Ala Asp Cys Cys Asn Cys Cys Leu Ser Gly Ile Cys Lys Pro
 50                  55                  60

Ser Thr Ser Trp Thr Gly Cys Ser Thr Ser Thr Phe Asp
 65                  70                  75

<210> SEQ ID NO 117
<211> LENGTH: 42
<212> TYPE: PRT
<213> ORGANISM: Conus magus
```

```
<220> FEATURE:
<221> NAME/KEY: PEPTIDE
<222> LOCATION: (1)..(42)
<223> OTHER INFORMATION: Xaa at residues 4 and 29 is Pro or hydroxy-Pro;
      Xaa at residue 33 is Trp or bromo-Trp; Xaa at residue 14 is Tyr,
      125I-Tyr, mono-iodo-Tyr, di-iodo-Tyr, O-sulpho-Tyr or O-phospho-Ty

<400> SEQUENCE: 117

Gly His Val Xaa Cys Gly Lys Asp Gly Arg Lys Cys Gly Xaa His Ala
1               5                   10                  15

Asp Cys Cys Asn Cys Cys Leu Ser Gly Ile Cys Lys Xaa Ser Thr Ser
                20                  25                  30

Xaa Thr Gly Cys Ser Thr Ser Thr Phe Asp
            35                  40

<210> SEQ ID NO 118
<211> LENGTH: 431
<212> TYPE: DNA
<213> ORGANISM: Conus magus

<400> SEQUENCE: 118
ccagctatca gcacttcgca gcagtcgagg ctttaaaatc ctaatcgtag aagaaggcaa      60
aaacatctgg tggtcagtat gaagctgtgt gtgacgtttc ttcttgttct ggtgattctg     120
ccatcagtaa ctggggagga gtctagcgag cgtacactga gtggtgctac tctgacaggc     180
gatcggggaa tgtgctcact cttaggacaa cgatgcggag atcattccga ctgctgttgg     240
gacatgtgtt gtgccagcga aatgtgcgtt gtgactttcc ttccatgtaa atgatttccc     300
tactagggcg atggacctag gcgtgctggc ctagcggtag actcgctcag tatgcctgat     360
ctgtctgagt gaaacgacct gacacgatcc gtcgtattcc tttgccaaga gccagctagg     420
ccatgcctag g                                                         431

<210> SEQ ID NO 119
<211> LENGTH: 71
<212> TYPE: PRT
<213> ORGANISM: Conus magus

<400> SEQUENCE: 119

Met Lys Leu Cys Val Thr Phe Leu Leu Val Leu Val Ile Leu Pro Ser
1               5                   10                  15

Val Thr Gly Glu Glu Ser Ser Glu Arg Thr Leu Ser Gly Ala Thr Leu
                20                  25                  30

Thr Gly Asp Arg Gly Met Cys Ser Leu Leu Gly Gln Arg Cys Gly Asp
            35                  40                  45

His Ser Asp Cys Cys Trp Asp Met Cys Cys Ala Ser Glu Met Cys Val
        50                  55                  60

Val Thr Phe Leu Pro Cys Lys
65                  70

<210> SEQ ID NO 120
<211> LENGTH: 35
<212> TYPE: PRT
<213> ORGANISM: Conus magus
<220> FEATURE:
<221> NAME/KEY: PEPTIDE
<222> LOCATION: (1)..(35)
<223> OTHER INFORMATION: Xaa at residue 33 is Pro or hydroxy-Pro; Xaa at
      residue 25 is Glu or gamma-carboxy-Glu; Xaa at residue 18 is Trp
      or bromo-Tr

<400> SEQUENCE: 120
```

```
Gly Met Cys Ser Leu Leu Gly Gln Arg Cys Gly Asp His Ser Asp Cys
1               5                   10                  15

Cys Xaa Asp Met Cys Cys Ala Ser Xaa Met Cys Val Val Thr Phe Leu
            20                  25                  30

Xaa Cys Lys
        35

<210> SEQ ID NO 121
<211> LENGTH: 354
<212> TYPE: DNA
<213> ORGANISM: Conus magus
<220> FEATURE:
<221> NAME/KEY: misc_feature
<222> LOCATION: (1)..(354)
<223> OTHER INFORMATION: n is any nucleotide

<400> SEQUENCE: 121
ccagctatca gcacttcgca gcagtcgngg ntttgaaatc ctaatcatag aagaaggcaa      60
aaatatctgc tggtcaatat gaagctgtgc ctgacgttcc ttcttgttct gatgattctg    120
gcatcagtga ctggggagaa gtcaagcaag catacactga gtcgtgctgc tagggtaaaa    180
aacagaggcc ctagtttttg taaggcaaac ggaaagccat gctcgtatca tgcagattgc    240
tgtaattgct gtctcagtgg aatctgtaaa ccaagcacaa atgtgatttt acctggatgc    300
tcgacgagtt cgctcttcag gatctgactt tcagctagct aggccatgcc tagg          354

<210> SEQ ID NO 122
<211> LENGTH: 82
<212> TYPE: PRT
<213> ORGANISM: Conus magus

<400> SEQUENCE: 122

Met Lys Leu Cys Leu Thr Phe Leu Leu Val Leu Met Ile Leu Ala Ser
1               5                   10                  15

Val Thr Gly Glu Lys Ser Ser Lys His Thr Leu Ser Arg Ala Ala Arg
            20                  25                  30

Val Lys Asn Arg Gly Pro Ser Phe Cys Lys Ala Asn Gly Lys Pro Cys
        35                  40                  45

Ser Tyr His Ala Asp Cys Cys Asn Cys Cys Leu Ser Gly Ile Cys Lys
    50                  55                  60

Pro Ser Thr Asn Val Ile Leu Pro Gly Cys Ser Thr Ser Ser Leu Phe
65                  70                  75                  80

Arg Ile

<210> SEQ ID NO 123
<211> LENGTH: 46
<212> TYPE: PRT
<213> ORGANISM: Conus magus
<220> FEATURE:
<221> NAME/KEY: PEPTIDE
<222> LOCATION: (1)..(46)
<223> OTHER INFORMATION: Xaa at residues 2, 11, 29 and 36 is Pro or
      hydroxy-Pro; Xaa at residue 14 is Tyr, 125I-Tyr, mono-iodo-Tyr,
      di-iodo-Tyr, O-sulpho-Tyr or O-phospho-Ty

<400> SEQUENCE: 123

Gly Xaa Ser Phe Cys Lys Ala Asn Gly Lys Xaa Cys Ser Xaa His Ala
1               5                   10                  15

Asp Cys Cys Asn Cys Cys Leu Ser Gly Ile Cys Lys Xaa Ser Thr Asn
            20                  25                  30

Val Ile Leu Xaa Gly Cys Ser Thr Ser Ser Leu Phe Arg Ile
```

<210> SEQ ID NO 124
<211> LENGTH: 430
<212> TYPE: DNA
<213> ORGANISM: Conus magus

<400> SEQUENCE: 124

| | | | | | |
|---|---|---|---|---|---|
| ccgctatcag | cacttcgcag | cagtcgaggc | tttaaaatcc | taatcgtaga | agaaggcaaa | 60 |
| aacatctggt | ggtcagtatg | aagctgtgtg | tgacgtttct | tcttgttctg | gtgattctgc | 120 |
| catcagtaac | tggggtgaag | tctagcgagc | gtacactgag | tggtgctgct | ctgagaggcg | 180 |
| atcgggaac | gtgctcaggc | agaggacaag | aatgcaaaca | tgattccgac | tgctgtgggc | 240 |
| atttgtgttg | tgccggcata | acgtgccaat | tcacttacat | tccatgtaaa | tgatttccct | 300 |
| actagtgcga | tggacctagg | cgtgctggcc | tagcggtaga | ctcgctcagt | atgcctgatc | 360 |
| tgtccgagtg | aaacgacctg | acatgatccg | tcgtattcct | ttgccaagag | ccagctaggc | 420 |
| catgcctagg | | | | | 430 |

<210> SEQ ID NO 125
<211> LENGTH: 71
<212> TYPE: PRT
<213> ORGANISM: Conus magus

<400> SEQUENCE: 125

Met Lys Leu Cys Val Thr Phe Leu Leu Val Leu Val Ile Leu Pro Ser
1               5                   10                  15

Val Thr Gly Val Lys Ser Ser Glu Arg Thr Leu Ser Gly Ala Ala Leu
            20                  25                  30

Arg Gly Asp Arg Gly Thr Cys Ser Gly Arg Gly Gln Glu Cys Lys His
        35                  40                  45

Asp Ser Asp Cys Cys Gly His Leu Cys Cys Ala Gly Ile Thr Cys Gln
50                  55                  60

Phe Thr Tyr Ile Pro Cys Lys
65                  70

<210> SEQ ID NO 126
<211> LENGTH: 35
<212> TYPE: PRT
<213> ORGANISM: Conus magus
<220> FEATURE:
<221> NAME/KEY: PEPTIDE
<222> LOCATION: (1)..(35)
<223> OTHER INFORMATION: Xaa at residue 33 is Pro or hydroxy-Pro; Xaa at
      residue 9 is Glu or gamma-carboxy-Glu; Xaa at residue 31 is Tyr,
      125I-Tyr, mono-iodo-Tyr, di-iodo-Tyr, O-sulpho-Tyr or O-phospho-Ty

<400> SEQUENCE: 126

Gly Thr Cys Ser Gly Arg Gly Gln Xaa Cys Lys His Asp Ser Asp Cys
1               5                   10                  15

Cys Gly His Leu Cys Cys Ala Gly Ile Thr Cys Gln Phe Thr Xaa Ile
            20                  25                  30

Xaa Cys Lys
        35

<210> SEQ ID NO 127
<211> LENGTH: 353
<212> TYPE: DNA
<213> ORGANISM: Conus caracteristicus

<400> SEQUENCE: 127

```
ccgctatcag cacttcgcag cagtcgaggc tttgaaatcc taatcataga agaaggcaaa      60
aatatctgct ggtcaatatg aagctgtgcc tgacgttcct tcttgttctg atgattctgg    120
catcagtgac tggggagaag tcaagcaagc atacactgag tcgtgctgct agggtaaaaa    180
acagaggccc tagttttgt aaggcagacg aaaagccatg cgagtatcat gcagattgct     240
gtaattgctt tctcagtgga atctgtgcac caagcacaaa ttggatttta cctggatgct    300
cgacgagttc gttcttcaag atctgacttt cagccagcta ggccatgcct agg           353
```

<210> SEQ ID NO 128
<211> LENGTH: 82
<212> TYPE: PRT
<213> ORGANISM: Conus caracteristicus

<400> SEQUENCE: 128

```
Met Lys Leu Cys Leu Thr Phe Leu Leu Val Leu Met Ile Leu Ala Ser
1               5                   10                  15

Val Thr Gly Glu Lys Ser Ser Lys His Thr Leu Ser Arg Ala Ala Arg
            20                  25                  30

Val Lys Asn Arg Gly Pro Ser Phe Cys Lys Ala Asp Glu Lys Pro Cys
        35                  40                  45

Glu Tyr His Ala Asp Cys Cys Asn Cys Phe Leu Ser Gly Ile Cys Ala
    50                  55                  60

Pro Ser Thr Asn Trp Ile Leu Pro Gly Cys Ser Thr Ser Ser Phe Phe
65                  70                  75                  80

Lys Ile
```

<210> SEQ ID NO 129
<211> LENGTH: 46
<212> TYPE: PRT
<213> ORGANISM: Conus caracteristicus
<220> FEATURE:
<221> NAME/KEY: PEPTIDE
<222> LOCATION: (1)..(46)
<223> OTHER INFORMATION: Xaa at residues 2, 11, 29 and 36 is Pro or
      hydroxy-Pro; Xaa at residues 6 and 13 is Glu or gamma-carboxy-Glu;
      Xaa at residue 33 is Trp or bromo-Trp; Xaa at residue 14 is Tyr,
      125I-Tyr, mono-iodo-Tyr, di-iodo-Tyr, O-sulpho-Tyr or O-phospho-Ty

<400> SEQUENCE: 129

```
Gly Xaa Ser Phe Cys Lys Ala Asp Xaa Lys Xaa Cys Xaa Xaa His Ala
1               5                   10                  15

Asp Cys Cys Asn Cys Phe Leu Ser Gly Ile Cys Ala Xaa Ser Thr Asn
            20                  25                  30

Xaa Ile Leu Xaa Gly Cys Ser Thr Ser Ser Phe Phe Lys Ile
        35                  40                  45
```

<210> SEQ ID NO 130
<211> LENGTH: 348
<212> TYPE: DNA
<213> ORGANISM: Conus caracteristicus

<400> SEQUENCE: 130

```
ccagctatca gcacttcgca gcagtcgagg ctttgaaatc ctaatcatag aagaaggcaa      60
aaatatctgc tggtcaatat gaagctgtgc ctgacgttcc ttcttgttct gatgattctg    120
gcatcagtga ctggggagaa gtcaagcaag catacactga gtcgtgctgc tagggtaaaa    180
aacagaggcc ctagttttg taaggcagac gaaaagccat gcaagtatca tgcagattgc     240
tgtaactgct gtctcggtgg aatctgtaaa ccaagcacaa gttggattgg atgctcgacg    300
```

```
aatgtgttcc tgacgcgctg actttcagcc agctaggcca tgcctagg          348
```

<210> SEQ ID NO 131
<211> LENGTH: 80
<212> TYPE: PRT
<213> ORGANISM: Conus caracteristicus

<400> SEQUENCE: 131

```
Met Lys Leu Cys Leu Thr Phe Leu Leu Val Leu Met Ile Leu Ala Ser
1               5                   10                  15

Val Thr Gly Glu Lys Ser Ser Lys His Thr Leu Ser Arg Ala Ala Arg
            20                  25                  30

Val Lys Asn Arg Gly Pro Ser Phe Cys Lys Ala Asp Glu Lys Pro Cys
        35                  40                  45

Lys Tyr His Ala Asp Cys Cys Asn Cys Cys Leu Gly Gly Ile Cys Lys
    50                  55                  60

Pro Ser Thr Ser Trp Ile Gly Cys Ser Thr Asn Val Phe Leu Thr Arg
65                  70                  75                  80
```

<210> SEQ ID NO 132
<211> LENGTH: 44
<212> TYPE: PRT
<213> ORGANISM: Conus caracteristicus
<220> FEATURE:
<221> NAME/KEY: PEPTIDE
<222> LOCATION: (1)..(44)
<223> OTHER INFORMATION: Xaa at residues 2, 11 and 29 is Pro or hydroxy-
      Pro; Xaa at residue 9 is Glu or gamma-carboxy-Glu; Xaa at residue
      33 is Trp or bromo-Trp; Xaa at residue 14 is Tyr, 125I-Tyr, mono-
      iodo-Tyr, di-iodo-Tyr, O-sulpho-Tyr or O-phospho-Ty

<400> SEQUENCE: 132

```
Gly Xaa Ser Phe Cys Lys Ala Asp Xaa Lys Xaa Cys Lys Xaa His Ala
1               5                   10                  15

Asp Cys Cys Asn Cys Cys Leu Gly Gly Ile Cys Lys Xaa Ser Thr Ser
            20                  25                  30

Xaa Ile Gly Cys Ser Thr Asn Val Phe Leu Thr Arg
        35                  40
```

<210> SEQ ID NO 133
<211> LENGTH: 347
<212> TYPE: DNA
<213> ORGANISM: Conus caracteristicus

<400> SEQUENCE: 133

```
ccgctatcag cacttcgcag cagtcgaggc tttgaaatcc taatcataga agaaggcaaa    60
aatatctgct ggtcaatatg aagctgtgcc tgacgttcct tcttgttctg atgattctgg   120
catcagtgac tggggagaag tcaagcaagc atacactgag tcgtgctgct agggtaaaaa   180
acagaggccc tagttttgt aaggcagacg aaaagccatg caagtatcat gcagattgct   240
gtaactgctg tctcggtgga atctgtaaac caagcacaag ttggattgga tgctcgacga   300
atgtgttctt gacgcgctga ctttcagcca gctaggccat gcctagg                347
```

<210> SEQ ID NO 134
<211> LENGTH: 80
<212> TYPE: PRT
<213> ORGANISM: Conus caracteristicus

<400> SEQUENCE: 134

```
Met Lys Leu Cys Leu Thr Phe Leu Leu Val Leu Met Ile Leu Ala Ser
```

```
                1               5                   10                  15
Val Thr Gly Glu Lys Ser Ser Lys His Thr Leu Ser Arg Ala Ala Arg
                                20                  25                  30

Val Lys Asn Arg Gly Pro Ser Phe Cys Lys Ala Asp Glu Lys Pro Cys
                35                  40                  45

Lys Tyr His Ala Asp Cys Cys Asn Cys Cys Leu Gly Gly Ile Cys Lys
            50                  55                  60

Pro Ser Thr Ser Trp Ile Gly Cys Ser Thr Asn Val Phe Leu Thr Arg
65                      70                  75                  80
```

<210> SEQ ID NO 135
<211> LENGTH: 44
<212> TYPE: PRT
<213> ORGANISM: Conus caracteristicus
<220> FEATURE:
<221> NAME/KEY: PEPTIDE
<222> LOCATION: (1)..(44)
<223> OTHER INFORMATION: Xaa at residues 2 and 29 is Pro or hydroxy-Pro;
      Xaa at residue 9 is Glu or gamma-carboxy-Glu; Xaa at residue 33 is
      Trp or bromo-Trp; Xaa at residue 14 is Tyr, 125I-Tyr, mono-iodo-
      Tyr, di-iodo-Tyr, O-sulpho-Tyr or O-phospho-Ty

<400> SEQUENCE: 135

```
Gly Xaa Ser Phe Cys Lys Ala Asp Xaa Lys Xaa Cys Lys Xaa His Ala
1               5                   10                  15

Asp Cys Cys Asn Cys Cys Leu Gly Gly Ile Cys Lys Xaa Ser Thr Ser
            20                  25                  30

Xaa Ile Gly Cys Ser Thr Asn Val Phe Leu Thr Arg
            35                  40
```

<210> SEQ ID NO 136
<211> LENGTH: 342
<212> TYPE: DNA
<213> ORGANISM: Conus caracteristicus
<220> FEATURE:
<221> NAME/KEY: misc_feature
<222> LOCATION: (1)..(342)
<223> OTHER INFORMATION: n is any nucleotide

<400> SEQUENCE: 136

```
ccagctatca gcacttcgca gcagtcgagg ntttgaaatc ctaatcatag aagaaggcaa       60
aaatatctgc tggtcaatat gaagctgtgc ctgacgttcc ttcttgttct gatgattctg      120
gcatccgtga ctggggagaa gttaagcgag caaacactgc gccgtgctgc taggaaaaac      180
aaaggccctc gatgctgggt cggccgtgtc cattgcacct atcataaaga ctgctgtccg      240
tcggtatgtt gtttcaaggg aaggtgtaaa ccacaatcat ggggatgctg gtcgggtccg      300
acctaggcgt gctggccttg aggcagctag gccatgccta gg                         342
```

<210> SEQ ID NO 137
<211> LENGTH: 75
<212> TYPE: PRT
<213> ORGANISM: Conus caracteristicus

<400> SEQUENCE: 137

```
Met Lys Leu Cys Leu Thr Phe Leu Leu Val Leu Met Ile Leu Ala Ser
1               5                   10                  15

Val Thr Gly Glu Lys Leu Ser Glu Gln Thr Leu Arg Arg Ala Ala Arg
                20                  25                  30

Lys Asn Lys Gly Pro Arg Cys Trp Val Gly Arg Val His Cys Thr Tyr
            35                  40                  45
```

```
His Lys Asp Cys Cys Pro Ser Val Cys Phe Lys Gly Arg Cys Lys
        50                  55                  60

Pro Gln Ser Trp Gly Cys Trp Ser Gly Pro Thr
 65                  70                  75

<210> SEQ ID NO 138
<211> LENGTH: 40
<212> TYPE: PRT
<213> ORGANISM: Conus caracteristicus
<220> FEATURE:
<221> NAME/KEY: PEPTIDE
<222> LOCATION: (1)..(40)
<223> OTHER INFORMATION: Xaa at residues 2, 19, 30 and 39 is Pro or
      hydroxy-Pro; Xaa at residues 5, 33 and 36 is Trp or bromo-Trp; Xaa
      at residue 13 is Tyr, 125I-Tyr, mono-iodo-Tyr, di-iodo-Tyr, O-
      sulpho-Tyr or O-phospho-Ty

<400> SEQUENCE: 138

Gly Xaa Arg Cys Xaa Val Gly Arg Val His Cys Thr Xaa His Lys Asp
 1               5                  10                  15

Cys Cys Xaa Ser Val Cys Cys Phe Lys Gly Arg Cys Lys Xaa Gln Ser
            20                  25                  30

Xaa Gly Cys Xaa Ser Gly Xaa Thr
            35                  40

<210> SEQ ID NO 139
<211> LENGTH: 354
<212> TYPE: DNA
<213> ORGANISM: Conus caracteristicus
<220> FEATURE:
<221> NAME/KEY: misc_feature
<222> LOCATION: (1)..(354)
<223> OTHER INFORMATION: n is any nucleotide

<400> SEQUENCE: 139
ccagctatca gcacttcgca gcagnngagg ctttgaaatc ctaatcatag aagaaggcaa      60
aaatatctgc tggtcaatat gaagctgtgc ctgacgttcc ttcttgttct gatgattctg    120
gcatcagtga ctggggagaa gtcaagcaag catacactga gtcgtgctgc tagggtaaaa    180
aacagaggcc ctagtttttg taaggcagac gaaaagccat gcgagtatca tgcagattgc    240
tgtaattgct gtctcagtgg aatctgtgca ccaagcacaa attggatttt acctggatgc    300
tcgacgagtt cgttcttcaa gatctgactt tcagccagct aggccatgcc tagg          354

<210> SEQ ID NO 140
<211> LENGTH: 82
<212> TYPE: PRT
<213> ORGANISM: Conus caracteristicus

<400> SEQUENCE: 140

Met Lys Leu Cys Leu Thr Phe Leu Leu Val Leu Met Ile Leu Ala Ser
 1               5                  10                  15

Val Thr Gly Glu Lys Ser Ser Lys His Thr Leu Ser Arg Ala Ala Arg
                20                  25                  30

Val Lys Asn Arg Gly Pro Ser Phe Cys Lys Ala Asp Glu Lys Pro Cys
            35                  40                  45

Glu Tyr His Ala Asp Cys Cys Asn Cys Cys Leu Ser Gly Ile Cys Ala
        50                  55                  60

Pro Ser Thr Asn Trp Ile Leu Pro Gly Cys Ser Thr Ser Ser Phe Phe
 65                  70                  75                  80

Lys Ile
```

<210> SEQ ID NO 141
<211> LENGTH: 46
<212> TYPE: PRT
<213> ORGANISM: Conus caracteristicus
<220> FEATURE:
<221> NAME/KEY: PEPTIDE
<222> LOCATION: (1)..(46)
<223> OTHER INFORMATION: Xaa at residues 2, 11, 29 and 36 is Pro or
hydroxy-Pro; Xaa at residues 9 and 13 is Glu or gamma-carboxy-Glu;
Xaa at residue 33 is Trp or bromo-Trp; Xaa at residue 14 is Tyr,
125I-Tyr, mono-iodo-Tyr, di-iodo-Tyr, O-sulpho-Tyr or O-phospho-Ty

<400> SEQUENCE: 141

Gly Xaa Ser Phe Cys Lys Ala Asp Xaa Lys Xaa Cys Xaa Xaa His Ala
 1               5                  10                  15

Asp Cys Cys Asn Cys Cys Leu Ser Gly Ile Cys Ala Xaa Ser Thr Asn
            20                  25                  30

Xaa Ile Leu Xaa Gly Cys Ser Thr Ser Ser Phe Phe Lys Ile
        35                  40                  45

<210> SEQ ID NO 142
<211> LENGTH: 354
<212> TYPE: DNA
<213> ORGANISM: Conus caracteristicus

<400> SEQUENCE: 142
ccagctatca gcacttcgca gcagtcgagg ctttgaaatc ctaatcatag aagaaggcaa      60
aaatatctgc tggtcaatat gaagctgtgc ctgacgttcc ttcttgttct gatgattctg     120
gcatcagtga ctggggagaa gtcaagcaag catacactga gtcgtgctgc tagggtaaaa     180
aacagaggcc ctagtttttg taaggcaaac ggaaagccat gctcgtatca tgcagattgc     240
tgtaattgct gtctcagtgg aatctgtaaa ccaagcacaa atgtgatttt acctggatgc     300
tcgacgagtt cgttcttcag gatctgactt tcagccagct aggccatgcc tagg           354

<210> SEQ ID NO 143
<211> LENGTH: 82
<212> TYPE: PRT
<213> ORGANISM: Conus caracteristicus

<400> SEQUENCE: 143

Met Lys Leu Cys Leu Thr Phe Leu Leu Val Leu Met Ile Leu Ala Ser
 1               5                  10                  15

Val Thr Gly Glu Lys Ser Ser Lys His Thr Leu Ser Arg Ala Ala Arg
            20                  25                  30

Val Lys Asn Arg Gly Pro Ser Phe Cys Lys Ala Asn Gly Lys Pro Cys
        35                  40                  45

Ser Tyr His Ala Asp Cys Cys Asn Cys Cys Leu Ser Gly Ile Cys Lys
    50                  55                  60

Pro Ser Thr Asn Val Ile Leu Pro Gly Cys Ser Thr Ser Ser Phe Phe
65                  70                  75                  80

Arg Ile

<210> SEQ ID NO 144
<211> LENGTH: 46
<212> TYPE: PRT
<213> ORGANISM: Conus caracteristicus
<220> FEATURE:
<221> NAME/KEY: PEPTIDE
<222> LOCATION: (1)..(46)
<223> OTHER INFORMATION: Xaa at residues 2, 11, 29 and 36 is Pro or
hydroxy-Pro; Xaa at residue 14 is Tyr, 125I-Tyr, mono-iodo-Tyr, -continued di-iodo-Tyr, O-sulpho-Tyr or O-phospho-Ty

<400> SEQUENCE: 144

Gly Xaa Ser Phe Cys Lys Ala Asn Gly Lys Xaa Cys Ser Xaa His Ala
1               5                   10                  15

Asp Cys Cys Asn Cys Cys Leu Ser Gly Ile Cys Lys Xaa Ser Thr Asn
            20                  25                  30

Val Ile Leu Xaa Gly Cys Ser Thr Ser Ser Phe Phe Arg Ile
        35                  40                  45

<210> SEQ ID NO 145
<211> LENGTH: 353
<212> TYPE: DNA
<213> ORGANISM: Conus striatus

<400> SEQUENCE: 145
ccgctatcag cacttcgcag cagtcgaggc tttgaaatcc taatcataga agagggcaaa      60
aatatctgct ggtcaatatg aagctgtgcc tgacgttcct tcttgttctg atgattctgg    120
catcagtgac tggggagaag tcaagcaagc atacactgag tcgtgctgct agggtaaaaa    180
acagaggccc tagtttttgt aaggcagacg aaaagccatg cgagtatcat gcagattgct    240
gtaattgctg tctcagcgga atctgtgcac caagcacaaa ttggattta  cctggatgct    300 cgacgagttc gttcttcaag atctgacttt cagctagcta ggccatgcct agg           353

<210> SEQ ID NO 146
<211> LENGTH: 82
<212> TYPE: PRT
<213> ORGANISM: Conus striatus

<400> SEQUENCE: 146

Met Lys Leu Cys Leu Thr Phe Leu Leu Val Leu Met Ile Leu Ala Ser
1               5                   10                  15

Val Thr Gly Glu Lys Ser Ser Lys His Thr Leu Ser Arg Ala Ala Arg
            20                  25                  30

Val Lys Asn Arg Gly Pro Ser Phe Cys Lys Ala Asp Glu Lys Pro Cys
        35                  40                  45

Glu Tyr His Ala Asp Cys Cys Asn Cys Leu Ser Gly Ile Cys Ala
    50                  55                  60

Pro Ser Thr Asn Trp Ile Leu Pro Gly Cys Ser Thr Ser Ser Phe Phe
65                  70                  75                  80

Lys Ile

<210> SEQ ID NO 147
<211> LENGTH: 46
<212> TYPE: PRT
<213> ORGANISM: Conus striatus
<220> FEATURE:
<221> NAME/KEY: PEPTIDE
<222> LOCATION: (1)..(46)
<223> OTHER INFORMATION: Xaa at residues 2, 11, 29 and 36 is Pro or
      hydroxy-Pro; Xaa at residues 9 and 13 is Glu or gamma-carboxy-Glu;
      Xaa at residue 33 is Trp or bromo-Trp; Xaa at residue 14 is Tyr,
      125I-Tyr, mono-iodo-Tyr, di-iodo-Tyr, O-sulpho-Tyr or O-phospho-Ty

<400> SEQUENCE: 147

Gly Xaa Ser Phe Cys Lys Ala Asp Xaa Lys Xaa Cys Xaa Xaa His Ala
1               5                   10                  15

Asp Cys Cys Asn Cys Cys Leu Ser Gly Ile Cys Ala Xaa Ser Thr Asn
            20                  25                  30

```
Xaa Ile Leu Xaa Gly Cys Ser Thr Ser Ser Phe Phe Lys Ile
        35              40                  45
```

<210> SEQ ID NO 148
<211> LENGTH: 347
<212> TYPE: DNA
<213> ORGANISM: Conus striatus

<400> SEQUENCE: 148

```
ccagctatca gcacttcgca gcagtcgagg ctttgaaatc ctaatcatag aagaaggcaa      60
aaatatctgc tggtcaatat gaagctgtgc ctggcgttcc ttcttgttct gatgattctg     120
gcatcagtga ctggggagaa gtcaagcaag catacactga gtcgtgctgc tagggtaaaa     180
aacagaggct gtaagaaaga cagaaagcca tgctcgtatc atgcagattg ctgtaattgc     240
tgtctcagtg gaatctgtgc accaagcaca aattggattt tacctggatg ctcgacgagt     300
acgttcactt gacgcgctga ctttcagcca gctaggccat gcctagg                   347
```

<210> SEQ ID NO 149
<211> LENGTH: 77
<212> TYPE: PRT
<213> ORGANISM: Conus striatus

<400> SEQUENCE: 149

```
Met Lys Leu Cys Leu Ala Phe Leu Leu Val Leu Met Ile Leu Ala Ser
1               5                   10                  15

Val Thr Gly Glu Lys Ser Ser Lys His Thr Leu Ser Arg Ala Ala Arg
            20                  25                  30

Val Lys Asn Arg Gly Cys Lys Lys Asp Arg Lys Pro Cys Ser Tyr His
        35                  40                  45

Ala Asp Cys Cys Asn Cys Cys Leu Ser Gly Ile Cys Ala Pro Ser Thr
    50                  55                  60

Asn Trp Ile Leu Pro Gly Cys Ser Thr Ser Thr Phe Thr
65                  70                  75
```

<210> SEQ ID NO 150
<211> LENGTH: 41
<212> TYPE: PRT
<213> ORGANISM: Conus striatus
<220> FEATURE:
<221> NAME/KEY: PEPTIDE
<222> LOCATION: (1)..(41)
<223> OTHER INFORMATION: Xaa at residues 8, 26 and 33 is Pro or hydroxy-
      Pro; Xaa at residue 30 is Trp or bromo-Trp; Xaa at residue 11 is
      Tyr, 125I-Tyr, mono-iodo-Tyr, di-iodo-Tyr, O-sulpho-Tyr or O-
      phospho-Ty

<400> SEQUENCE: 150

```
Gly Cys Lys Lys Asp Arg Lys Xaa Cys Ser Xaa His Ala Asp Cys Cys
1               5                   10                  15

Asn Cys Cys Leu Ser Gly Ile Cys Ala Xaa Ser Thr Asn Xaa Ile Leu
            20                  25                  30

Xaa Gly Cys Ser Thr Ser Thr Phe Thr
        35                  40
```

<210> SEQ ID NO 151
<211> LENGTH: 347
<212> TYPE: DNA
<213> ORGANISM: Conus striatus

<400> SEQUENCE: 151

```
ccgctatcag cacttcgcag cagtcgaggc tttaaaatcc taatcgtaga agaaggcaaa      60
```

-continued

```
aatatctgct ggtcaatatg aagctgtgcc tgacgttcct tcttgttctg atgattctgg    120
catcagtgac tggggagaag tcaagcaagc atacactgag tcgtgctgct agggtaaaaa    180
acagaggccc tagtttttgt aaggcagacg aaaagccatg caagtatcat gcagattgct    240
gtaactgctg tctcggtgga atctgtaaac caagcacaag ttggattgga tgctcgacga    300
atgtgttctt gacgcgctga ctttcagcca gctaggccat gcctagg                 347
```

<210> SEQ ID NO 152
<211> LENGTH: 80
<212> TYPE: PRT
<213> ORGANISM: Conus striatus

<400> SEQUENCE: 152

```
Met Lys Leu Cys Leu Thr Phe Leu Leu Val Leu Met Ile Leu Ala Ser
1               5                   10                  15

Val Thr Gly Glu Lys Ser Ser Lys His Thr Leu Ser Arg Ala Ala Arg
            20                  25                  30

Val Lys Asn Arg Gly Pro Ser Phe Cys Lys Ala Asp Glu Lys Pro Cys
        35                  40                  45

Lys Tyr His Ala Asp Cys Cys Asn Cys Cys Leu Gly Gly Ile Cys Lys
    50                  55                  60

Pro Ser Thr Ser Trp Ile Gly Cys Ser Thr Asn Val Phe Leu Thr Arg
65                  70                  75                  80
```

<210> SEQ ID NO 153
<211> LENGTH: 44
<212> TYPE: PRT
<213> ORGANISM: Conus striatus
<220> FEATURE:
<221> NAME/KEY: PEPTIDE
<222> LOCATION: (1)..(44)
<223> OTHER INFORMATION: Xaa at residues 2, 11 and 29 is Pro or hydroxy-
    Pro; Xaa at residue 9 is Glu or gamma-carboxy-Glu; Xaa at residue
    33 is Trp or bromo-Trp; Xaa at residue 14 is Tyr, 125I-Tyr, mono-
    iodo-Tyr, di-iodo-Tyr, O-sulpho-Tyr or O-phospho-Ty

<400> SEQUENCE: 153

```
Gly Xaa Ser Phe Cys Lys Ala Asp Xaa Lys Xaa Cys Lys Xaa His Ala
1               5                   10                  15

Asp Cys Cys Asn Cys Cys Leu Gly Gly Ile Cys Lys Xaa Ser Thr Ser
            20                  25                  30

Xaa Ile Gly Cys Ser Thr Asn Val Phe Leu Thr Arg
        35                  40
```

<210> SEQ ID NO 154
<211> LENGTH: 424
<212> TYPE: DNA
<213> ORGANISM: Conus betulinus

<400> SEQUENCE: 154

```
ccagctatca gcacttcgca gcagtcgagg ctttaaaatc ctaatcgtag aagaagggaa     60
acatatctgg tggtcagtat gaagctgtgt gtggcgtttc ttcttgttct ggtgattctg    120
ccatcggtga ttgggggggaa gcctagcgag cgtacactga gtggtgctac tcggagaggc    180
gatcggagaa tgtgcttatc cctaggacaa agatgcgaac gtcattccaa ctgctgtggc    240
tatctgtgtt gtttctacga caagtgtgtt gtgactgcca tagggtgtgg ccactactag    300
tgcgatggac ctaggcgcgc tggccctgtg gcagactcgc tcagtatgcc tgatctgtcc    360
```

```
aagtgacacg acctgacacg atcgtcgtat tcctttgcca agagtcagct aggccatgcc    420
tagg                                                                 424

<210> SEQ ID NO 155
<211> LENGTH: 73
<212> TYPE: PRT
<213> ORGANISM: Conus betulinus

<400> SEQUENCE: 155

Met Lys Leu Cys Val Ala Phe Leu Leu Val Leu Ile Leu Pro Ser
1               5                   10                  15

Val Ile Gly Gly Lys Pro Ser Glu Arg Thr Leu Ser Gly Ala Thr Arg
            20                  25                  30

Arg Gly Asp Arg Arg Met Cys Leu Ser Leu Gly Gln Arg Cys Glu Arg
        35                  40                  45

His Ser Asn Cys Cys Gly Tyr Leu Cys Cys Phe Tyr Asp Lys Cys Val
    50                  55                  60

Val Thr Ala Ile Gly Cys Gly His Tyr
65                  70

<210> SEQ ID NO 156
<211> LENGTH: 36
<212> TYPE: PRT
<213> ORGANISM: Conus betulinus
<220> FEATURE:
<221> NAME/KEY: PEPTIDE
<222> LOCATION: (1)..(36)
<223> OTHER INFORMATION: Xaa at residue 10 is Glu or gamma-carboxy-Glu;
      Xaa at residues 18, 23 and 36 is Tyr, 125I-Tyr, mono-iodo-Tyr, di-
      iodo-Tyr, O-sulpho-Tyr or O-phospho-Ty

<400> SEQUENCE: 156

Met Cys Leu Ser Leu Gly Gln Arg Cys Xaa Arg His Ser Asn Cys Cys
1               5                   10                  15

Gly Xaa Leu Cys Cys Phe Xaa Asp Lys Cys Val Val Thr Ala Ile Gly
            20                  25                  30

Cys Gly His Xaa
        35

<210> SEQ ID NO 157
<211> LENGTH: 423
<212> TYPE: DNA
<213> ORGANISM: Conus betulinus

<400> SEQUENCE: 157
ccgctatcag cacttcgcag cagtcgaggc tttaaaatcc taatcgtaga agaagggaaa    60
catatctggt ggtcagtatg aagctgtgtg tggcgtttct tcttgttctg gtgattctgc    120
catcggtgat tggggggaag cctagcgagc gtacactgag tggtgctact cggagaggcg    180
atcggagaat gtgctcattc ctaggacaaa gatgcgaacg tcatttcaac tgctgtggcg    240
acctgtgttg tttcgacgac atgtgtcttg tggctgccat agggtgtggc tactaataat    300
gcgatggacc taggcgcgct ggctctgtgg caggctcgtt cagtatgcct gatctgtcca    360
agtgacacga cctgacacga tcgtcgtatt tctttgccaa gagccagcta ggccatgcct    420
agg                                                                  423

<210> SEQ ID NO 158
<211> LENGTH: 72
<212> TYPE: PRT
<213> ORGANISM: Conus betulinus
```

-continued

```
<400> SEQUENCE: 158

Met Lys Leu Cys Val Ala Phe Leu Leu Val Leu Val Ile Leu Pro Ser
1               5                   10                  15

Val Ile Gly Gly Lys Pro Ser Glu Arg Thr Leu Ser Gly Ala Thr Arg
            20                  25                  30

Arg Gly Asp Arg Arg Met Cys Ser Phe Leu Gly Gln Arg Cys Glu Arg
        35                  40                  45

His Phe Asn Cys Cys Gly Asp Leu Cys Cys Phe Asp Asp Met Cys Leu
    50                  55                  60

Val Ala Ala Ile Gly Cys Gly Tyr
65                  70

<210> SEQ ID NO 159
<211> LENGTH: 35
<212> TYPE: PRT
<213> ORGANISM: Conus betulinus
<220> FEATURE:
<221> NAME/KEY: PEPTIDE
<222> LOCATION: (1)..(35)
<223> OTHER INFORMATION: Xaa at residue 10 is Glu or gamma-carboxy-Glu

<400> SEQUENCE: 159

Met Cys Ser Phe Leu Gly Gln Arg Cys Xaa Arg His Phe Asn Cys Cys
1               5                   10                  15

Gly Asp Leu Cys Cys Phe Asp Asp Met Cys Leu Val Ala Ala Ile Gly
            20                  25                  30

Cys Gly Tyr
        35

```
Arg Gly Asp Arg Arg Ile Cys Ser Phe Leu Gly Cys Glu Arg His Phe
            35                  40                  45

Asn Cys Cys Gly Asp Leu Cys Cys Phe Asp Asp Met Cys Val Val Thr
    50                  55                  60

Ala Ile Gly Cys Gly His
65                  70

<210> SEQ ID NO 162
<211> LENGTH: 33
<212> TYPE: PRT
<213> ORGANISM: Conus betulinus
<220> FEATURE:
<221> NAME/KEY: PEPTIDE
<222> LOCAT
<212> TYPE: PRT
<213> ORGANISM: Conus betulinus
<220> FEATURE:
<221> NAME/KEY: PEPTIDE -continued

```
Met Cys Leu Ser Leu Gly Gln Arg Cys Xaa Arg His Ser Asp Cys Cys
1               5                   10                  15

Gly Xaa Leu Cys Cys Phe Xaa Asp Lys Cys Val Val Thr Ala Ile Gly
            20                  25                  30

Cys Gly His Xaa
            35
```

<210> SEQ ID NO 169
<211> LENGTH: 350
<212> TYPE: DNA
<213> ORGANISM: Conus betulinus

<400> SEQUENCE: 169

```
ccagctatca

<210> SEQ ID NO 172
<211> LENGTH: 423
<212> TYPE: DNA
<213> ORGANISM: Conus betulinus

<400> SEQ

```
gagcgtacac tgagtggtgc tactcggaga ggcgatcgga gaatgtgctt atccctagga      180
caaagatgcg aacgtcattc caactgctgt ggctatctgt gttgcttcta cgacaagtgt      240
gttatgactg ccatagggtg tggccactac tagtgcgatg gacctaggcg cgctggccct      300
gtggcagact cgctcagtat gcctgatctg tccaagtgac acgacctgac acgatcgtcg      360
tattcctttg acaagagtaa cgctaggcca tgcctagg                              398
```

<210> SEQ ID NO 176
<211> LENGTH: 73
<212> TYPE: PRT
<213> ORGANISM: Conus betulinus

<400> SEQUENCE: 176

Met Lys Leu Cys Val Ala Phe Leu Leu Val Leu Val Ile Leu Pro Ser
1               5                   10                  15

Val Ile Gly Gly Lys Pro Asn Glu Arg Thr Leu Ser Gly Ala Thr Arg
            20                  25                  30

Arg Gly Asp Ar

-continued

```
<212> TYPE: PRT
<213> ORGANISM: Conus figulinus

<400> SEQUENCE: 179

Met Lys Leu Cys Leu Thr Phe Leu Leu Val Leu Met Ile Leu Ala Ser
1               5                   10                  15

Val Thr Gly Glu Lys Ser Ser Lys His Thr Leu Ser Arg Ala Ala Arg
                20                  25                  30

Val Lys Ser Lys Gly His Val Ser Cys Gly Lys Asp Gly Arg Ala Cys
            35                  40                  45

Asp Tyr His Ala Asp Cys Cys Asn Cys Cys Leu Gly Gly Ile Cys Lys
    50                  55                  60

Pro Ser Thr Ser Trp Ile Gly Cys Ser Thr Asn Val Phe Leu Thr Arg
65                  70                  75                  80

<210> SEQ ID NO 180
<211> LENGTH: 44
<212> TYPE: PRT
<213> ORGANISM: Conus figulinus
<220> FEATURE:
<221> NAME/KEY: PEPTIDE
<222> LOCATION: (1)..(44)
<223> OTHER INFORMATION: Xaa at residue 29 is Pro or hydroxy-Pro; Xaa at
      residue 33 is Trp or bromo-Trp; Xaa at residue 14 is Tyr, 125I-
      Tyr, mono-iodo-Tyr, di-iodo-Tyr, O-sulpho-Tyr or O-phospho-Ty

<400> SEQUENCE: 180

Gly His Val Ser Cys Gly Lys Asp Gly Arg Ala Cys Asp Xaa His Ala
1               5                   10                  15

Asp Cys Cys Asn Cys Cys Leu Gly Gly Ile Cys Lys Xaa Ser Thr Ser
                20                  25                  30

Xaa Ile Gly Cys Ser Thr Asn Val Phe Leu Thr Arg
            35                  40

<210> SEQ ID NO 181
<211> LENGTH: 353
<212> TYPE: DNA
<213> ORGANISM: Conus figulinus

<400> SEQUENCE: 181
ccgctatcag cacttcgcag cagtcgaggc tttgaaatcc taatcataga agaaggcaaa      60
aatatctact ggtcaatatg aagctgtgcc tgacgttcct tcttgttctg atgattctgg    120
catcagcgac tggggagaag tcaagcaagc atacactgag tcgtgctgct agggtaaaaa    180
acagaggccc tagttttttgt aaggcagacg aaaagccatg cgagtatcat gcagattgct    240
gtaattgctg tctcagtgga atctgtgcac caagcacaaa ttggatttta cctggatgct    300
cgacgagttc gttcttcaag atctgacttt cagccagcta ggccatgcct agg           353

<210> SEQ ID NO 182
<211> LENGTH: 82
<212> TYPE: PRT
<213> ORGANISM: Conus figulinus

<400> SEQUENCE: 182

Met Lys Leu Cys Leu Thr Phe Leu Leu Val Leu Met Ile Leu Ala Ser
1               5                   10                  15

Ala Thr Gly Glu Lys Ser Ser Lys His Thr Leu Ser Arg Ala Ala Arg
                20                  25                  30

Val Lys Asn Arg Gly Pro Ser Phe Cys Lys Ala Asp Glu Lys Pro Cys
            35                  40                  45
```

```
Glu Tyr His Ala Asp Cys Cys Asn Cys Cys Leu Ser Gly Ile Cys Ala
    50                  55                  60

Pro Ser Thr Asn Trp Ile Leu Pro Gly Cys Ser Thr Ser Ser Phe Phe
65                  70                  75                  80

Lys Ile
```

<210> SEQ ID NO 183
<211> LENGTH: 46
<212> TYPE: PRT
<213> ORGANISM: Conus figulinus
<220> FEATURE:
<221> NAME/KEY: PEPTIDE
<222> LOCATION: (1)..(46)
<223> OTHER INFORMATION: Xaa at residues 2, 11, 29 and 36 is Pro or
      hydroxy-Pro; Xaa at residues 9 and 13 is Glu or gamma-carboxy-Glu;
      Xaa at residue 33 is Trp or bromo-Trp; Xaa at residue 14 is Tyr,
      125I-Tyr, mono-iodo-Tyr, di-iodo-Tyr, O-sulpho-Tyr or O-phospho-Ty

<400> SEQUENCE: 183

```
Gly Xaa Ser Phe Cys Lys Ala Asp Xaa Lys Xaa Cys Xaa Xaa His Ala
1               5                   10                  15

Asp Cys Cys Asn Cys Cys Leu Ser Gly Ile Cys Ala Xaa Ser Thr Asn
                20                  25                  30

Xaa Ile Leu Xaa Gly Cys Ser Thr Ser Ser Phe Phe Lys Ile
            35                  40                  45
```

<210> SEQ ID NO 184
<211> LENGTH: 354
<212> TYPE: DNA
<213> ORGANISM: Conus figulinus

<400> SEQUENCE: 184

```
ccagctatca gcacttcgca gcagtcgagg ctttgaaatc ctaatcatag aagaaggcaa      60
aaatatctgc tgggcaatat gaagctgtgc ctgacgttcc ttcttgttct gatgattctg    120
gcatcagtga ctggggagaa gtcaagcaag catacactga gtcgtgctgc tagggtaaaa    180
aacagaggcc ctagtttttg taaggcagac gaaaagccat gcgagtatca tgcagattgc    240
tgtaattgct gtctcagtgg aatctgtgca ccaagcacaa attggatttt acctggatgc    300
tcgacgagtt cgttcttcaa gatccgactt tcggccagct aggccatgcc tagg           354
```

<210> SEQ ID NO 185
<211> LENGTH: 87
<212> TYPE: PRT
<213> ORGANISM: Conus figulinus

<400> SEQUENCE: 185

```
Met Lys Leu Cys Leu Thr Phe Leu Leu Val Leu Met Ile Leu Ala Ser
1               5                   10                  15

Val Thr Gly Glu Lys Ser Ser Lys His Thr Leu Ser Arg Ala Ala Arg
                20                  25                  30

Val Lys Asn Arg Gly Pro Ser Phe Cys Lys Ala Asp Glu Lys Pro Cys
            35                  40                  45

Glu Tyr His Ala Asp Cys Cys Asn Cys Cys Leu Ser Gly Ile Cys Ala
    50                  55                  60

Pro Ser Thr Asn Trp Ile Leu Pro Gly Cys Ser Thr Ser Ser Phe Phe
65                  70                  75                  80

Lys Ile Arg Leu Ser Ala Ser
                85
```

```
<210> SEQ ID NO 186
<211> LENGTH: 51
<212> TYPE: PRT
<213> ORGANISM: Conus figulinus
<220> FEATURE:
<221> NAME/KEY: PEPTIDE
<222> LOCATION: (1)..(51)
<223> OTHER INFORMATION: Xaa at residues 2, 11, 29 and 36 is Pro or
      hydroxy-Pro; Xaa at residues 9 and 13 is Glu or gamma-carboxy-Glu;
      Xaa at residue 33 is Trp or bromo-Trp; Xaa at residue 14 is Tyr,
      125I-Tyr, mono-iodo-Tyr, di-iodo-Tyr, O-sulpho-Tyr or O-phospho-Ty

<400> SEQUENCE: 186

Gly Xaa Ser Phe Cys Lys Ala Asp Xaa Lys Xaa Cys Xaa Xaa His Ala
1               5                   10                  15

Asp Cys Cys Asn Cys Cys Leu Ser Gly Ile Cys Ala Xaa Ser Thr Asn
            20                  25                  30

Xaa Ile Leu Xaa Gly Cys Ser Thr Ser Ser Phe Phe Lys Ile Arg Leu
        35                  40                  45

Ser Ala Ser
    50

<210> SEQ ID NO 187
<211> LENGTH: 345
<212> TYPE: DNA
<213> ORGANISM: Conus figulinus

<400> SEQUENCE: 187
ccagctatca gcacttcgca gcagtcgagg ctttgaaatc ctaatcatag aagaaggcaa      60
aaatatctgc tggtcaatat gaagctgtgc ctgacgttcc ttcttgttct gatgattctg    120
gcatcagtga ctggggagaa gtcaagcaag catacactga gtcgtgctgc tagggtaaaa    180
aacaaaggcc ctcgatgctg ggtcggccgt gtccattgca cctatcataa agactgctgt    240
ccgtcggtat gttgcttcaa gggaaggtgt aaaccacaat catggggatg ctggtcgggt    300
ccgacctagg cgtgctggcc ttgaggcagc taggccatgc ctagg                    345

<210> SEQ ID NO 188
<211> LENGTH: 76
<212> TYPE: PRT
<213> ORGANISM: Conus figulinus

<400> SEQUENCE: 188

Met Lys Leu Cys Leu Thr Phe Leu Leu Val Leu Met Ile Leu Ala Ser
1               5                   10                  15

Val Thr Gly Glu Lys Ser Ser Lys His Thr Leu Ser Arg Ala Ala Arg
            20                  25                  30

Val Lys Asn Lys Gly Pro Arg Cys Trp Val Gly Arg Val His Cys Thr
        35                  40                  45

Tyr His Lys Asp Cys Cys Pro Ser Val Cys Phe Lys Gly Arg Cys
    50                  55                  60

Lys Pro Gln Ser Trp Gly Cys Trp Ser Gly Pro Thr
65                  70                  75

<210> SEQ ID NO 189
<211> LENGTH: 40
<212> TYPE: PRT
<213> ORGANISM: Conus figulinus
<220> FEATURE:
<221> NAME/KEY: PEPTIDE
<222> LOCATION: (1)..(40)
<223> OTHER INFORMATION: Xaa at residues 2, 19, 30 and 39 is Pro or
``` hydroxy-Pro; Xaa at residue 5, 33 and 36 is Trp or bromo-Trp; Xaa at residue 131 is Tyr, 125I-Tyr, mono-iodo-Tyr, di-iodo-Tyr, O-sulpho-Tyr or O-phospho-Ty

<400> SEQUENCE: 189

Gly Xaa Arg Cys Xaa Val Gly Arg Val His Cys Thr Xaa His Lys Asp
1               5                   10                  15

Cys Cys Xaa Ser Val Cys Cys Phe Lys Gly Arg Cys Lys Xaa Gln Ser
            20                  25                  30

Xaa Gly Cys Xaa Ser Gly Xaa Thr
            35              40

<210> SEQ ID NO 190
<211> LENGTH: 346
<212> TYPE: DNA
<213> ORGANISM: Conus figulinus

<400> SEQUENCE: 190
ccgctatcag cacttcgcag cagtcgaggc tttgaaatcc taatcataga agaaggcaaa    60
aatatctgct ggtcaatatg aagctgtgcc tgacgttcct tcttgttctg atgattctgg   120
catcagtgac tggggagaag tcaagcaagc atacactgag tcgtgctgct agggtaaaaa   180
acagaggctg taagaaagac agaaagccat gctcgtatca tgcagattgc tgtaattgct   240
gtctcagtgg aatctgtgca ccaagcacaa attggatttt acctggatgc tcgacgagta   300
cgttcacttg acgcgctgac tttcagccag ctaggccatg cctagg                  346

<210> SEQ ID NO 191
<211> LENGTH: 77
<212> TYPE: PRT
<213> ORGANISM: Conus figulinus

<400> SEQUENCE: 191

Met Lys Leu Cys Leu Thr Phe Leu Leu Val Leu Met Ile Leu Ala Ser
1               5                   10                  15

Val Thr Gly Glu Lys Ser Ser Lys His Thr Leu Ser Arg Ala Ala Arg
            20                  25                  30

Val Lys Asn Arg Gly Cys Lys Lys Asp Arg Lys Pro Cys Ser Tyr His
            35                  40                  45

Ala Asp Cys Cys Asn Cys Cys Leu Ser Gly Ile Cys Ala Pro Ser Thr
        50                  55                  60

Asn Trp Ile Leu Pro Gly Cys Ser Thr Ser Thr Phe Thr
65                  70                  75

<210> SEQ ID NO 192
<211> LENGTH: 41
<212> TYPE: PRT
<213> ORGANISM: Conus figulinus
<220> FEATURE:
<221> NAME/KEY: PEPTIDE
<222> LOCATION: (1)..(41)
<223> OTHER INFORMATION: Xaa at residues 8, 26 and 33 is Pro or hydroxy-Pro; Xaa at residue 30 is Trp or bromo-Trp; Xaa at residue 11 is Tyr, 125I-Tyr, mono-iodo-Tyr, di-iodo-Tyr, O-sulpho-Tyr or O-phospho-Ty

<400> SEQUENCE: 192

Gly Cys Lys Lys Asp Arg Lys Xaa Cys Ser Xaa His Ala Asp Cys Cys
1               5                   10                  15

Asn Cys Cys Leu Ser Gly Ile Cys Ala Xaa Ser Thr Asn Xaa Ile Leu
            20                  25                  30

-continued

```
Xaa Gly Cys Ser Thr Ser Thr Phe Thr
        35                  40
```

<210> SEQ ID NO 193
<211> LENGTH: 345
<212> TYPE: DNA
<213> ORGANISM: Conus figulinus
<220> FEATURE:
<221> NAME/KEY: misc_feature
<222> LOCATION: (1)..(345)
<223> OTHER INFORMATION: n is any nucleotide

<400> SEQUENCE: 193

```
ccagctatca ncacttcgca gcngncgagg ctttgaagtc ctaatcatag aagaaggcaa      60
aaatatctgc tggtcaatat gaagctgtgc ctgacgttcc ttcttgttct gatgattctg     120
gcatcagtga ctggggagaa gtcaagcaag catacactga gtcgtgctgc tagggtaaaa     180
aacagaggct gtaagaaaga cagaaagcca tgctcgtatc atgcagattg ctgtaattgc     240
tgtctcagtg gaatctgtgc accaagcaca aattggattt tacctggatg ctcgacgagt     300
tcgttcttca agatctgact ttcagccagc taggccatgc ctagg                     345
```

<210> SEQ ID NO 194
<211> LENGTH: 79
<212> TYPE: PRT
<213> ORGANISM: Conus figulinus

<400> SEQUENCE: 194

```
Met Lys Leu Cys Leu Thr Phe Leu Leu Val Leu Met Ile Leu Ala Ser
1               5                   10                  15

Val Thr Gly Glu Lys Ser Ser Lys His Thr Leu Ser Arg Ala Ala Arg
            20                  25                  30

Val Lys Asn Arg Gly Cys Lys Lys Asp Arg Lys Pro Cys Ser Tyr His
        35                  40                  45

Ala Asp Cys Cys Asn Cys Cys Leu Ser Gly Ile Cys Ala Pro Ser Thr
    50                  55                  60

Asn Trp Ile Leu Pro Gly Cys Ser Thr Ser Ser Phe Phe Lys Ile
65                  70                  75
```

<210> SEQ ID NO 195
<211> LENGTH: 43
<212> TYPE: PRT
<213> ORGANISM: Conus figulinus
<220> FEATURE:
<221> NAME/KEY: PEPTIDE
<222> LOCATION: (1)..(43)
<223> OTHER INFORMATION: Xaa at residues 8, 26 and 33 is Pro or hydroxy-
      Pro; Xaa at residue 30 is Trp or bromo-Trp; Xaa at residue 11 is
      Tyr, 125I-Tyr, mono-iodo-Tyr, di-iodo-Tyr, O-sulpho-Tyr or O-
      phospho-Ty

<400> SEQUENCE: 195

```
Gly Cys Lys Lys Asp Arg Lys Xaa Cys Ser Xaa His Ala Asp Cys Cys
1               5                   10                  15

Asn Cys Cys Leu Ser Gly Ile Cys Ala Xaa Ser Thr Asn Xaa Ile Leu
            20                  25                  30

Xaa Gly Cys Ser Thr Ser Ser Phe Phe Lys Ile
        35                  40
```

<210> SEQ ID NO 196
<211> LENGTH: 353
<212> TYPE: DNA
<213> ORGANISM: Conus figulinus
<220> FEATURE:
<221> NAME/KEY: misc_feature
<222> LOCATION: (1)..(353)
<223> OTHER INFORMATION: n is any nucleotide

<400> SEQUENCE: 196

```
ccgctatcag cacttcgcag cagncgaggc tttgaagtcc taatcataga agaaggcaaa      60
aatatctgct ggtcaatatg aagctgtgcc tgacgttcct tcttgttctg atgattctgg    120
catcagtgac tggggagaag tcaagcaagc atacactgag tcgtgctgct agggtaaaaa    180
acagaggccc tagttcttgt aaggcagacg aagagccatg cgagtatcat gcagattgct    240
gtaattgctg tctcagtgga atctgtgcac caagcacaaa ttggatttta cctggatgct    300
cgacgagttc gttcttcaag atctgacttt cagccagcta ggccatgcct agg           353
```

<210> SEQ ID NO 197
<211> LENGTH: 82
<212> TYPE: PRT
<213> ORGANISM: Conus figulinus

<400> SEQUENCE: 197

```
Met Lys Leu Cys Leu Thr Phe Leu Leu Val Leu Met Ile Leu Ala Ser
  1               5                  10                  15

Val Thr Gly Glu Lys Ser Ser Lys His Thr Leu Ser Arg Ala Ala Arg
             20                  25                  30

Val Lys Asn Arg Gly Pro Ser Ser Cys Lys Ala Asp Glu Glu Pro Cys
         35                  40                  45

Glu Tyr His Ala Asp Cys Cys Asn Cys Cys Leu Ser Gly Ile Cys Ala
     50                  55                  60

Pro Ser Thr Asn Trp Ile Leu Pro Gly Cys Ser Thr Ser Ser Phe Phe
 65                  70                  75                  80

Lys Ile
```

<210> SEQ ID NO 198
<211> LENGTH: 46
<212> TYPE: PRT
<213> ORGANISM: Conus figulinus
<220> FEATURE:
<221> NAME/KEY: PEPTIDE
<222> LOCATION: (1)..(46)
<223> OTHER INFORMATION: Xaa at residues 2, 11, 29 and 36 is Pro or
      hydroxy-Pro; Xaa at residues 9, 10 and 13 is Glu or gamma-carboxy-
      Glu; Xaa at residue 33 is Trp or bromo-Trp; Xaa at residue 14 is
      Tyr, 125I-Tyr, mono-iodo-Tyr, di-iodo-Tyr, O-sulpho-Tyr or O-
      phospho-Ty

<400> SEQUENCE: 198

```
Gly Xaa Ser Ser Cys Lys Ala Asp Xaa Xaa Xaa Cys Xaa Xaa His Ala
  1               5                  10                  15

Asp Cys Cys Asn Cys Cys Leu Ser Gly Ile Cys Ala Xaa Ser Thr Asn
             20                  25                  30

Xaa Ile Leu Xaa Gly Cys Ser Thr Ser Ser Phe Phe Lys Ile
         35                  40                  45
```

<210> SEQ ID NO 199
<211> LENGTH: 342
<212> TYPE: DNA
<213> ORGANISM: Conus lynceus

<400> SEQUENCE: 199

```
ccagctatca gcacttcgca gcagtcgagg ctttgaaatc ctaatcatag aagaaggcaa      60
```

```
aaatatctgc tggtcaatat gaagctgtgt gtgacgttcc ttcttgttct gatgattctg      120
ccatcggtga ctggggagaa gtctagcaag cgtacactga atggtgctct tctgaaacgc      180
aattggagct ggtgcttcaa cgctggagta aaatgcgaca atcattccga ctgctgtgag      240
gatacctgtt gttacgataa cacctgtgtt gtggctgtcg cggcgtgcta ggtgcgatgg      300
acctaggcga gctggccttg agctagctag gccatgccta gg                         342
```

<210> SEQ ID NO 200
<211> LENGTH: 70
<212> TYPE: PRT
<213> ORGANISM: Conus lynceus

<400> SEQUENCE: 200

```
Met Lys Leu Cys Val Thr Phe Leu Leu Val Leu Met Ile Leu Pro Ser
1               5                   10                  15

Val Thr Gly Glu Lys Ser Ser Lys Arg Thr Leu Asn Gly Ala Leu Leu
            20                  25                  30

Lys Arg Asn Trp Ser Trp Cys Phe Asn Ala Gly Val Lys Cys Asp Asn
        35                  40                  45

His Ser Asp Cys Cys Glu Asp Thr Cys Cys Tyr Asp Asn Thr Cys Val
    50                  55                  60

Val Ala Val Ala Ala Cys
65                  70
```

<210> SEQ ID NO 201
<211> LENGTH: 36
<212> TYPE: PRT
<213> ORGANISM: Conus lynceus
<220> FEATURE:
<221> NAME/KEY: PEPTIDE
<222> LOCATION: (1)..(36)
<223> OTHER INFORMATION: Xaa at residue 20 is Glu or gamma-carboxy-Glu;
      Xaa at residues 2 and 4 is Trp or bromo-Trp; Xaa at residue 25 is
      Tyr, 125I-Tyr, mono-iodo-Tyr, di-iodo-Tyr, O-sulpho-Tyr or O-
      phospho-Ty

<400> SEQUENCE: 201

```
Asn Xaa Ser Xaa Cys Phe Asn Ala Gly Val Lys Cys Asp Asn His Ser
1               5                   10                  15

Asp Cys Cys Xaa Asp Thr Cys Cys Xaa Asp Asn Thr Cys Val Val Ala
            20                  25                  30

Val Ala Ala Cys
        35
```

<210> SEQ ID NO 202
<211> LENGTH: 363
<212> TYPE: DNA
<213> ORGANISM: Conus lynceus

<400> SEQUENCE: 202

```
ccagctatca gcacttcgca gcagtcgagg ctttgaaatc ctaatcatag aagaaggtaa      60
aaatatctgc tggtcagtat gaagctgagt gtgacgttcc ttcttattct gatgattccg      120
ccatcggtga ctggggaaaa gtcaagcaag catacactga gtcgtgctct tctgacaggc      180
tatcgcgctg gaagaagcac tgaaaaaaga tgctacttca atggagcacc atgcgacaga      240
catgaagagt gctgtacgtg gcaaagatgt tgttttttcgc aaaggtgtgg cacagctacc      300
tttggatgct gggtggatcc gtactaggcg tgctggcctt gagccagcta ggccatgcct      360
agg                                                                    363
```

```
<210> SEQ ID NO 203
<211> LENGTH: 82
<212> TYPE: PRT
<213> ORGANISM: Conus lynceus

<400> SEQUENCE: 203

Met Lys Leu Ser Val Thr Phe Leu Leu Ile Leu Met Ile Pro Pro Ser
1               5                   10                  15

Val Thr Gly Glu Lys Ser Ser Lys His Thr Leu Ser Arg Ala Leu Leu
            20                  25                  30

Thr Gly Tyr Arg Ala Gly Arg Ser Thr Glu Lys Arg Cys Tyr Phe Asn
        35                  40                  45

Gly Ala Pro Cys Asp Arg His Glu Glu Cys Cys Thr Trp Gln Arg Cys
    50                  55                  60

Cys Phe Ser Gln Arg Cys Gly Thr Ala Thr Phe Gly Cys Trp Val Asp
65                  70                  75                  80

Pro Tyr

<210> SEQ ID NO 204
<211> LENGTH: 38
<212> TYPE: PRT
<213> ORGANISM: Conus lynceus
<220> FEATURE:
<221> NAME/KEY: PEPTIDE
<222> LOCATION: (1)..(38)
<223> OTHER INFORMATION: Xaa at residues 7 and 37 is Pro or hydroxy-Pro;
      Xaa at residues 12 and 13 is Glu or gamma-carboxy-Glu; Xaa at
      residues 17 and 34 is Trp or bromo-Trp; Xaa at residues 2 and 38
      is Tyr, 125I-Tyr, mono-iodo-Tyr, di-iodo-Tyr, O-sulpho-Tyr or O-
      phospho-Ty

<400> SEQUENCE: 204

Cys Xaa Phe Asn Gly Ala Xaa Cys Asp Arg His Xaa Xaa Cys Cys Thr
1               5                   10                  15

Xaa Gln Arg Cys Cys Phe Ser Gln Arg Cys Gly Thr Ala Thr Phe Gly
            20                  25                  30

Cys Xaa Val Asp Xaa Xaa
        35

<210> SEQ ID NO 205
<211> LENGTH: 342
<212> TYPE: DNA
<213> ORGANISM: Conus lynceus

<400> SEQUENCE: 205
ccagctatca gcacttcgca gcagtcgagg ctttgaaatc ctaatcatag aagaaggcaa      60
aaatatctgc tggtcaatat gaagctgtgt gtgacgttcc ttcttgttct gatgattctg     120
ccatcggtga ctgggagaa gtctagcaag cgtacactga atggtgctct tctgaaacgc     180
aattggagct ggtgcttcaa cgctggagta gaatgcgaca tcattccga ctgctgtgag     240 gataccctgtt gttacgataa cacctgtgtt gtggctgtcg cggcgtgcta ggtgcgatgg     300
acctaggcga gctggccttg agctagctag gccatgccta gg                       342

<210> SEQ ID NO 206
<211> LENGTH: 70
<212> TYPE: PRT
<213> ORGANISM: Conus lynceus

<400> SEQUENCE: 206

Met Lys Leu Cys Val Thr Phe Leu Leu Val Leu Met Ile Leu Pro Ser
```

```
                   1               5                  10                 15
Val Thr Gly Glu Lys Ser Ser Lys Arg Thr Leu Asn Gly Ala Leu Leu
                   20                 25                 30

Lys Arg Asn Trp Ser Trp Cys Phe Asn Ala Gly Val Glu Cys Asp Asn
                   35                 40                 45

His Ser Asp Cys Cys Glu Asp Thr Cys Cys Tyr Asp Asn Thr Cys Val
         50                   55                 60

Val Ala Val Ala Ala Cys
65              70
```

<210> SEQ ID NO 207
<211> LENGTH: 36
<212> TYPE: PRT
<213> ORGANISM: Conus lynceus
<220> FEATURE:
<221> NAME/KEY: PEPTIDE
<222> LOCATION: (1)..(36)
<223> OTHER INFORMATION: Xaa at residues 11 and 20 is Glu or gamma-
      carboxy-Glu; Xaa at residues 2 and 4 is Trp or bromo-Trp; Xaa at
      residue 25 is Tyr, 125I-Tyr, mono-iodo-Tyr, di-iodo-Tyr, O-sulpho-
      Tyr or O-phospho-Ty

<400> SEQUENCE: 207

```
Asn Xaa Ser Xaa Cys Phe Asn Ala Gly Val Xaa Cys Asp Asn His Ser
1               5                  10                 15

Asp Cys Cys Xaa Asp Thr Cys Cys Xaa Asp Asn Thr Cys Val Val Ala
              20                 25                 30

Val Ala Ala Cys
         35
```

<210> SEQ ID NO 208
<211> LENGTH: 346
<212> TYPE: DNA
<213> ORGANISM: Conus lynceus

<400> SEQUENCE: 208

```
ccagctatca gcacttcgca gcagtcgagg ctttgaaatc ctaatcatag aagaaggcaa      60
aaatatctgc tggcacgcca atatgaagct gtgtgtgacg ttccttcttg ttctgatgat     120
tctgccatcg gtgactgggg agaagtctag caagcgtaca ctgaatggtg ctcttctgaa     180
acgcaattgg agctggtgct caacgctgg agtaaaatgc gacaatcatt ccgactgctg      240
tgctgatacc tgttgttacg ataacacctg tgttgtggct gtcgcggcgt gctaggtgcg     300
atggacctag gcgagctggc cttgagctag ctaggccatg cctagg                    346
```

<210> SEQ ID NO 209
<211> LENGTH: 70
<212> TYPE: PRT
<213> ORGANISM: Conus lynceus

<400> SEQUENCE: 209

```
Met Lys Leu Cys Val Thr Phe Leu Leu Val Leu Met Ile Leu Pro Ser
1               5                  10                 15

Val Thr Gly Glu Lys Ser Ser Lys Arg Thr Leu Asn Gly Ala Leu Leu
                   20                 25                 30

Lys Arg Asn Trp Ser Trp Cys Phe Asn Ala Gly Val Lys Cys Asp Asn
                   35                 40                 45

His Ser Asp Cys Cys Ala Asp Thr Cys Cys Tyr Asp Asn Thr Cys Val
         50                   55                 60

Val Ala Val Ala Ala Cys
```

```
<210> SEQ ID NO 210
<211> LENGTH: 36
<212> TYPE: PRT
<213> ORGANISM: Conus lynceus
<220> FEATURE:
<221> NAME/KEY: PEPTIDE
<222> LOCATION: (1)..(36)
<223> OTHER INFORMATION: Xaa at residues 2 and 4 is Trp or bromo-Trp;
      Xaa at residue 25 is Tyr, 125I-Tyr, mono-iodo-Tyr, di-iodo-Tyr, O-
      sulpho-Tyr or O-phospho-Ty

<400> SEQUENCE: 210

Asn Xaa Ser Xaa Cys Phe Asn Ala Gly Val Lys Cys Asp Asn His Ser
1               5                   10                  15

Asp Cys Cys Ala Asp Thr Cys Cys Xaa Asp Asn Thr Cys Val Val Ala
            20                  25                  30

Val Ala Ala Cys
        35

<210> SEQ ID NO 211
<211> LENGTH: 315
<212> TYPE: DNA
<213> ORGANISM: Conus lynceus

<400> SEQUENCE: 211
ccagctatca gcacttcgca gcagtcgagg ctttgaaatc ctaatcatag aagaaggcaa    60
aaatatctgc tggtcaatat gaagctgtgt gtgacgttcc ttcttgttct gatgactctg   120
ccatcggtga ctggggagaa gtctagcatg cgtacactga atcgtcttct gaaacgcaat   180
tggagttggt gctcaggctc tggagaagga tgcgactatc attccgagtg ctgtggggag   240
agatgttgta tcgaaagcat gtgtattggg gatggcgtgg cgtgctggcc ttgagccagc   300
taggccatgc ctagg                                                     315

<210> SEQ ID NO 212
<211> LENGTH: 71
<212> TYPE: PRT
<213> ORGANISM: Conus lynceus

<400> SEQUENCE: 212

Met Lys Leu Cys Val Thr Phe Leu Leu Val Leu Met Thr Leu Pro Ser
1               5                   10                  15

Val Thr Gly Glu Lys Ser Ser Met Arg Thr Leu Asn Arg Leu Leu Lys
            20                  25                  30

Arg Asn Trp Ser Trp Cys Ser Gly Ser Gly Glu Gly Cys Asp Tyr His
            35                  40                  45

Ser Glu Cys Cys Gly Glu Arg Cys Cys Ile Glu Ser Met Cys Ile Gly
        50                  55                  60

Asp Gly Val Ala Cys Trp Pro
65                  70

<210> SEQ ID NO 213
<211> LENGTH: 38
<212> TYPE: PRT
<213> ORGANISM: Conus lynceus
<220> FEATURE:
<221> NAME/KEY: PEPTIDE
<222> LOCATION: (1)..(38)
<223> OTHER INFORMATION: Xaa at residue 38 is Pro or hydroxy-Pro; Xaa at
      residues 10, 17, 21 and 26 is Glu or gamma-carboxy-Glu; Xaa at
      residues 2, 4 and 37 is Trp or bromo-Trp; Xaa at residue 14 is
```

Tyr, 125I-Tyr, mono-iodo-Tyr, di-iodo-Tyr, O-sulpho-Tyr or O-phospho-Ty

<400> SEQUENCE: 213

Asn Xaa Ser Xaa Cys Ser Gly Ser Gly Xaa Gly Cys Asp Xaa His Ser
1               5                   10                  15

Xaa Cys Cys Gly Xaa Arg Cys Cys Ile Xaa Ser Met Cys Ile Gly Asp
            20                  25                  30

Gly Val Ala Cys Xaa Xaa
            35

<210> SEQ ID NO 214
<211> LENGTH: 342
<212> TYPE: DNA
<213> ORGANISM: Conus lynceus

<400> SEQUENCE: 214
ccagctatca gcacttcgca gcagtcgagg ctttgaaatc ctaatcatag aagaaggcaa       60
aaatatctgc tggtcaatat gaagctgtgt gtgacgttcc ttcttgttct gatgattctg     120
ccatcggtga ctggggagaa gtctagcaag cgtacactga atggtgctct tctgaaacgc     180
aattggagct ggtgcttcaa cgctggagta aaatgcgaca atcattccga ctgctgtgag     240
gatacctgtt gttacgatag cacctgtgtt gtggctgtcg cggcgtgcta ggtgcgatgg     300
acctaggcga gccggccttg agctagctag gccatgccta gg                       342

<210> SEQ ID NO 215
<211> LENGTH: 70
<212> TYPE: PRT
<213> ORGANISM: Conus lynceus

<400> SEQUENCE: 215

Met Lys Leu Cys Val Thr Phe Leu Leu Val Leu Met Ile Leu Pro Ser
1               5                   10                  15

Val Thr Gly Glu Lys Ser Ser Lys Arg Thr Leu Asn Gly Ala Leu Leu
            20                  25                  30

Lys Arg Asn Trp Ser Trp Cys Phe Asn Ala Gly Val Lys Cys Asp Asn
        35                  40                  45

His Ser Asp Cys Cys Glu Asp Thr Cys Cys Tyr Asp Ser Thr Cys Val
    50                  55                  60

Val Ala Val Ala Ala Cys
65                  70

<210> SEQ ID NO 216
<211> LENGTH: 36
<212> TYPE: PRT
<213> ORGANISM: Conus lynceus
<220> FEATURE:
<221> NAME/KEY: PEPTIDE
<222> LOCATION: (1)..(36)
<223> OTHER INFORMATION: Xaa at residue 20 is Glu or gamma-carboxy-Glu;
      Xaa at residues 2 and 4 is Trp or bromo-Trp; Xaa at residue 25 is
      Tyr, 125I-Tyr, mono-iodo-Tyr, di-iodo-Tyr, O-sulpho-Tyr or O-phospho-Ty

<400> SEQUENCE: 216

Asn Xaa Ser Xaa Cys Phe Asn Ala Gly Val Lys Cys Asp Asn His Ser
1               5                   10                  15

Asp Cys Cys Xaa Asp Thr Cys Cys Tyr Asp Ser Thr Cys Val Val Ala
            20                  25                  30

Val Ala Ala Cys

<210> SEQ ID NO 217
<211> LENGTH: 32
<212> TYPE: PRT
<213> ORGANISM: Conus brunneus
<220> FEATURE:
<221> NAME/KEY: PEPTIDE
<222> LOCATION: (1)..(32)
<223> OTHER INFORMATION: Xaa at residue 24 is Glu or gamma-carboxy-Glu;
    Xaa at residue 2 is Tyr, 125I-Tyr, mono-iodo-Tyr, di-iodo-Tyr, O-
    sulpho-Tyr or O-phospho-Ty

<400> SEQUENCE: 217

Cys Gly Xaa Val Gly Gln Ala Cys Asp Asp Asp Ser Asp Cys Cys Gly
1               5                   10                  15

Ser Ile Cys Cys Val Ala Gly Xaa Cys Val Ile Thr Gly Arg Arg Cys
            20                  25                  30

<210> SEQ ID NO 218
<211> LENGTH: 419
<212> TYPE: DNA
<213> ORGANISM: Conus emaciatus

<400> SEQUENCE: 218
gctatcagca cttcgcagca gtcgaggctt taaaatcctg atcgtagaag gctaaaacaa      60
ctggtggtca gcatgaaact gtgttcgacg tctcttctta ttctggtgat tctgccatcg     120
gtgactggag agaagtctgg caagcataca ctgagtggtg ctgctctgag aggcaatcgg     180
ggagcgtgct cagacacagg acaaggatgc atacatcatt tcaactgctg ttgggatttg     240
tgctgttacg gccgcacgtg tggtgtgaat gtcatggggt gtcctccctt ctagtgcgat     300
ggagccaggc gtgctggcct cgtggcagac tcgctcagtg tgcctgatct gtccaagtgg     360
aacgacctga catgatcatc gtattccttt gccaagagca agctaggcca tgcctaggt      419

<210> SEQ ID NO 219
<211> LENGTH: 73
<212> TYPE: PRT
<213> ORGANISM: Conus emaciatus

<400> SEQUENCE: 219

Met Lys Leu Cys Ser Thr Ser Leu Leu Ile Leu Val Ile Leu Pro Ser
1               5                   10                  15

Val Thr Gly Glu Lys Ser Gly Lys His Thr Leu Ser Gly Ala Ala Leu
            20                  25                  30

Arg Gly Asn Arg Gly Ala Cys Ser Asp Thr Gly Gln Gly Cys Ile His
        35                  40                  45

His Phe Asn Cys Cys Trp Asp Leu Cys Cys Tyr Gly Arg Thr Cys Gly
    50                  55                  60

Val Asn Val Met Gly Cys Pro Pro Phe
65                  70

<210> SEQ ID NO 220
<211> LENGTH: 37
<212> TYPE: PRT
<213> ORGANISM: Conus emaciatus
<220> FEATURE:
<221> NAME/KEY: PEPTIDE
<222> LOCATION: (1)..(37)
<223> OTHER INFORMATION: Xaa at residues 35 and 36 is Pro or hydroxy-
    Pro; Xaa at residue 18 is Trp or bromo-Trp; Xaa at residue 23 is
    Tyr, 125I-Tyr, mono-iodo-Tyr, di-iodo-Tyr, O-sulpho-Tyr or O-
    phospho-Ty

<400> SEQUENCE: 220

Gly Ala Cys Ser Asp Thr Gly Gln Gly Cys Ile His His Phe Asn Cys
1               5                   10                  15

Cys Xaa Asp Leu Cys Cys Xaa Gly Arg Thr Cys Gly Val Asn Val Met
            20                  25                  30

Gly Cys Xaa Xaa Phe
        35

<210> SEQ ID NO 221
<211> LENGTH: 419
<212> TYPE: DNA
<213> ORGANISM: Conus emaciatus

<400> SEQUENCE: 221
gctatcagca cttcgcagca gtcgaggctt taaaatcctg atcgtagaag ctaaaacaa      60
ctggtggtca gcatgaaact gtgtttgacg tttcttctta ttctggtgat tctgccatcg   120
gtgactggag agaagtctgg caagcataca ctgagtggtg ctgctctgag aggcgatcgg   180
ggagcgtgct cagacacagg acaaggatgc atacatcatt ccaactgctg ttgggatttg   240
tgctgttacg gccgcacgtg tggtgtgaat gtcatggggt gtcctccctt ctagtgcgat   300
ggagccaggc gtgctggcct cgtggcagac tcgctcagtg tgcctgatct gtccaagtgg   360
aacgacctga catgatcatc gtattccttt gccaagagcc agctaggcca tgcctaggt    419

<210> SEQ ID NO 222
<211> LENGTH: 73
<212> TYPE: PRT
<213> ORGANISM: Conus emaciatus

<400> SEQUENCE: 222

Met Lys Leu Cys Leu Thr Phe Leu Leu Ile Leu Val Ile Leu Pro Ser
1               5                   10                  15

Val Thr Gly Glu Lys Ser Gly Lys His Thr Leu Ser Gly Ala Ala Leu
            20                  25                  30

Arg Gly Asp Arg Gly Ala Cys Ser Asp Thr Gly Gln Gly Cys Ile His
        35                  40                  45

His Ser Asn Cys Cys Trp Asp Leu Cys Cys Tyr Gly Arg Thr Cys Gly
    50                  55                  60

Val Asn Val Met Gly Cys Pro Pro Phe
65                  70

<210> SEQ ID NO 223
<211> LENGTH: 37
<212> TYPE: PRT
<213> ORGANISM: Conus emaciatus
<220> FEATURE:
<221> NAME/KEY: PEPTIDE
<222> LOCATION: (1)..(37)
<223> OTHER INFORMATION: Xaa at residues 35 and 36 is Pro or hydroxy-
      Pro; Xaa at residue 18 is Trp or bromo-Trp; Xaa at residue 23 is
      Tyr, 125I-Tyr, mono-iodo-Tyr, di-iodo-Tyr, O-sulpho-Tyr or O-
      phospho-Ty

<400> SEQUENCE: 223

Gly Ala Cys Ser Asp Thr Gly Gln Gly Cys Ile His His Ser Asn Cys
1               5                   10                  15

Cys Xaa Asp Leu Cys Cys Xaa Gly Arg Thr Cys Gly Val Asn Val Met
            20                  25                  30

Gly Cys Xaa Xaa Phe

<210> SEQ ID NO 224
<211> LENGTH: 425
<212> TYPE: DNA
<213> ORGANISM: Conus emaciatus

<400> SEQUENCE: 224

```
gctatcagca cttcgcagca gtcgaggctt taaaatcctg ctcgtagaag aaggcaaaaa      60
catctggtgg tcagtatgga gctgtgtgtg gcgtttcttc ttattctggt gattctgcca     120
tcggtgactg gggagaagtc tagcaagcgt acactgagtg gtgctgctct gagaggcgat     180
cggggaacgt gctcaggcat aggacaagga tgcatacatc atttgaactg ctgttgggat     240
atgtgctgtt acggccacac gtgtgttgtg aatatcatag ggtgtcctcc acactagtgc     300
gatgggcta ggcgtgctgg cctcgtggcg gactcgctca ctatgcctga tctgtccaag     360
tgaaacgacc agatgacatg atcgtcgtat tcctttgcca ggagccagct aggccatgcc     420
taggt                                                                 425
```

<210> SEQ ID NO 225
<211> LENGTH: 73
<212> TYPE: PRT
<213> ORGANISM: Conus emaciatus

<400> SEQUENCE: 225

```
Met Glu Leu Cys Val Ala Phe Leu Leu Ile Leu Val Ile Leu Pro Ser
 1               5                  10                  15
Val Thr Gly Glu Lys Ser Ser Lys Arg Thr Leu Ser Gly Ala Ala Leu
            20                  25                  30
Arg Gly Asp Arg Gly Thr Cys Ser Gly Ile Gly Gln Gly Cys Ile His
        35                  40                  45
His Leu Asn Cys Cys Trp Asp Met Cys Cys Tyr Gly His Thr Cys Val
    50                  55                  60
Val Asn Ile Ile Gly Cys Pro Pro His
65                  70
```

<210> SEQ ID NO 226
<211> LENGTH: 37
<212> TYPE: PRT
<213> ORGANISM: Conus emaciatus
<220> FEATURE:
<221> NAME/KEY: PEPTIDE
<222> LOCATION: (1)..(37)
<223> OTHER INFORMATION: Xaa at residues 35 and 36 is Pro or hydroxy-
      Pro; Xaa at residue 18 is Trp or bromo-Trp; Xaa at residue 23 is
      Tyr, 125I-Tyr, mono-iodo-Tyr, di-iodo-Tyr, O-sulpho-Tyr or O-
      phospho-Ty

<400> SEQUENCE: 226

```
Gly Thr Cys Ser Gly Ile Gly Gln Gly Cys Ile His His Leu Asn Cys
 1               5                  10                  15
Cys Xaa Asp Met Cys Cys Xaa Gly His Thr Cys Val Val Asn Ile Ile
            20                  25                  30
Gly Cys Xaa Xaa His
        35
```

<210> SEQ ID NO 227
<211> LENGTH: 422
<212> TYPE: DNA
<213> ORGANISM: Conus emaciatus -continued

```
<400> SEQUENCE: 227
gctatcagca cttcgcagca gtcgaggctt taaaatcctg atcgtagaag aaggctaaaa      60
caactggtgg tcagcatgaa actgtgtttg acgtttcttc ttattctggt ggttctgcca     120
tcggtgactg gagagaagtc tggcaagcat acactgagtg gtgctgctct gagaggcgat     180
cggggagcgt gctcagacac aggacaagga tgcatacatc attccgactg ctgttgggat     240
ttgtgctgtt acggccgcac gtgtggtgtg aatgtcatgg ggtgtcctcc cttctagtgc     300
gatggagcca ggcgtgctgg cctcgtggca gactcgctca gtgtgcctga tctgtccaag     360
tggaacgacc tgcatgatc atcgtattcc tttgccaaga gccagctagg ccatgcctag     420
gt                                                                    422

<210> SEQ ID NO 228
<211> LENGTH: 73
<212> TYPE: PRT
<213> ORGANISM: Conus emaciatus

<400> SEQUENCE: 228

Met Lys Leu Cys Leu Thr Phe Leu Leu Ile Leu Val Val Leu Pro Ser
1               5                   10                  15

Val Thr Gly Glu Lys Ser Gly Lys His Thr Leu Ser Gly Ala Ala Leu
            20                  25                  30

Arg Gly Asp Arg Gly Ala Cys Ser Asp Thr Gly Gln Gly Cys Ile His
        35                  40                  45

His Ser Asp Cys Cys Trp Asp Leu Cys Cys Tyr Gly Arg Thr Cys Gly
    50                  55                  60

Val Asn Val Met Gly Cys Pro Pro Phe
65                  70

<210> SEQ ID NO 229
<211> LENGTH: 37
<212> TYPE: PRT
<213> ORGANISM: Conus emaciatus
<220> FEATURE:
<221> NAME/KEY: PEPTIDE
<222> LOCATION: (1)..(37)
<223> OTHER INFORMATION: Xaa at residues 35 and 36 is Pro or hydroxy-
      Pro; Xaa at residue 18 is Trp or bromo-Trp; Xaa at residue 23 is
      Tyr, 125I-Tyr, mono-iodo-Tyr, di-iodo-Tyr, O-sulpho-Tyr or O-
      phospho-Ty

<400> SEQUENCE: 229

Gly Ala Cys Ser Asp Thr Gly Gln Gly Cys Ile His His Ser Asp Cys
1               5                   10                  15

Cys Xaa Asp Leu Cys Cys Xaa Gly Arg Thr Cys Gly Val Asn Val Met
            20                  25                  30

Gly Cys Xaa Xaa Phe
        35

<210> SEQ ID NO 230
<211> LENGTH: 31
<212> TYPE: PRT
<213> ORGANISM: Conus episcopatus
<220> FEATURE:
<221> NAME/KEY: PEPTIDE
<222> LOCATION: (1)..(31)
<223> OTHER INFORMATION: Xaa at residues 7 and 27 is Pro or hydroxy-Pro;
      Xaa at residues 4 and 25 is Glu or gamma-carboxy-Glu; Xaa at
      residue 30 is Trp or bromo-Trp; Xaa at residue 23 is Tyr, 125I-
      Tyr, mono-iodo-Tyr, di-iodo-Tyr, O-sulpho-Tyr or O-phospho-Ty

<400> SEQUENCE: 230
```

```
Cys Ile Arg Xaa Asp Ala Xaa Cys Ser Phe Ser Ala His Cys Cys Gly
1               5                   10                  15

Arg Asn Cys Cys Arg Gly Xaa Cys Xaa Arg Xaa Cys Arg Xaa Ile
                20                  25                  30
```

<210> SEQ ID NO 231
<211> LENGTH: 240
<212> TYPE: DNA
<213> ORGANISM: Conus emaciatus

<400> SEQUENCE: 231

```
atgatgtttc gtgtgacgtc agtcagctgt tcctgctgg tcatcgtttg tctgaacttg      60
attgtgctta ccaatgcctg cctccatgaa acgtcgccct gcagacgtag tttccaatgc    120
tgtcacggaa tttgctgttt cggagatgc agtaattcgt gtcgatttgg aaagagggcg    180
acattccaag aattcattct acatcgctga tatgttgccc agaggtctgc tgcttctcgt    240
```

<210> SEQ ID NO 232
<211> LENGTH: 69
<212> TYPE: PRT
<213> ORGANISM: Conus emaciatus

<400> SEQUENCE: 232

```
Met Met Phe Arg Val Thr Ser Val Ser Cys Phe Leu Leu Val Ile Val
1               5                   10                  15

Cys Leu Asn Leu Ile Val Leu Thr Asn Ala Cys Leu His Glu Thr Ser
                20                  25                  30

Pro Cys Arg Arg Ser Phe Gln Cys Cys His Gly Ile Cys Cys Phe Arg
            35                  40                  45

Arg Cys Ser Asn Ser Cys Arg Phe Gly Lys Arg Ala Thr Phe Gln Glu
        50                  55                  60

Phe Ile Leu His Arg
65
```

<210> SEQ ID NO 233
<211> LENGTH: 43
<212> TYPE: PRT
<213> ORGANISM: Conus emaciatus
<220> FEATURE:
<221> NAME/KEY: PEPTIDE
<222> LOCATION: (1)..(43)
<223> OTHER INFORMATION: Xaa at residue 7 is Pro or hydroxy-Pro; Xaa at
      residues 4 and 38 is Glu or gamma-carboxy-Gl

<400> SEQUENCE: 233

```
Cys Leu His Xaa Thr Ser Xaa Cys Arg Arg Ser Phe Gln Cys Cys His
1               5                   10                  15

Gly Ile Cys Cys Phe Arg Arg Cys Ser Asn Ser Cys Arg Phe Gly Lys
                20                  25                  30

Arg Ala Thr Phe Gln Xaa Phe Ile Leu His Arg
            35                  40
```

<210> SEQ ID NO 234
<211> LENGTH: 243
<212> TYPE: DNA
<213> ORGANISM: Conus emaciatus

<400> SEQUENCE: 234

```
atgatgtttc gtgtgacgtc agtcagctgt tcctgctgg tcatcgcttg tctgaacttg      60
gttgtgctta ccaatgcctg cctccgtgac ggacagtcct gcagatatca ttccgattgc    120
```

-continued tgtagatact cttgctgttg ggggtattgc gatcagaagt gtctaattat tggaaagagg    180
gcgacattcc aagaactcat cctacatcgt tgaaatgttg cccagaggtc tgctgcttct    240
cgt                                                                 243

<210> SEQ ID NO 235
<211> LENGTH: 70
<212> TYPE: PRT
<213> ORGANISM: Conus emaciatus

<400> SEQUENCE: 235

Met Met Phe Arg Val Thr Ser Val Ser Cys Phe Leu Leu Val Ile Ala
1               5                   10                  15

Cys Leu Asn Leu Val Val Leu Thr Asn Ala Cys Leu Arg Asp Gly Gln
            20                  25                  30

Ser Cys Arg Tyr His Ser Asp Cys Cys Arg Tyr Ser Cys Cys Trp Gly
        35                  40                  45

Tyr Cys Asp Gln Lys Cys Leu Ile Ile Gly Lys Arg Ala Thr Phe Gln
    50                  55                  60

Glu Leu Ile Leu His Arg
65                  70

<210> SEQ ID NO 236
<211> LENGTH: 44
<212> TYPE: PRT
<213> ORGANISM: Conus emaciatus
<220> FEATURE:
<221> NAME/KEY: PEPTIDE
<222> LOCATION: (1)..(44)
<223> OTHER INFORMATION: Xaa at residue 39 is Glu or gamma-carboxy-Glu;
      Xaa at residue 21 is Trp or bromo-Trp; Xaa at residues 10, 17 and
      23 is Tyr, 125I-Tyr, mono-iodo-Tyr, di-iodo-Tyr, O-sulpho-Tyr or
      O-phospho-Ty

<400> SEQUENCE: 236

Cys Leu Arg Asp Gly Gln Ser Cys Arg Xaa His Ser Asp Cys Cys Arg
1               5                   10                  15

Xaa Ser Cys Cys Xaa Gly Xaa Cys Asp Gln Lys Cys Leu Ile Ile Gly
            20                  25                  30

Lys Arg Ala Thr Phe Gln Xaa Leu Ile Leu His Arg
        35                  40

<210> SEQ ID NO 237
<211> LENGTH: 243
<212> TYPE: DNA
<213> ORGANISM: Conus emaciatus

<400> SEQUENCE: 237
atgatgtttc gtgtgacgtc agtcggctgt ttcctgctgg tcatcgtttg tctgaacttg     60
gttgtgctta ccaatgcctg ccgccgtgaa ggatcgtcct gcagacgttc ttaccagtgc    120
tgtcgtaaga gttgctgtat tggggagtgc gaatttccgt gtcgatgggt tggaaagagg    180
gcaacattcc gagaactcat cctacatcat tgaaatgttg cccagaggtc tgctgcttct    240
cgt                                                                 243

<210> SEQ ID NO 238
<211> LENGTH: 70
<212> TYPE: PRT
<213> ORGANISM: Conus emaciatus

<400> SEQUENCE: 238

```
Met Met Phe Arg Val Thr Ser Val Gly Cys Phe Leu Leu Val Ile Val
1               5                   10                  15

Cys Leu Asn Leu Val Val Leu Thr Asn Ala Cys Arg Arg Glu Gly Ser
            20                  25                  30

Ser Cys Arg Arg Ser Tyr Gln Cys Arg Lys Ser Cys Cys Ile Gly
        35                  40                  45

Glu Cys Glu Phe Pro Cys Arg Trp Val Gly Lys Arg Ala Thr Phe Arg
    50                  55                  60

Glu Leu Ile Leu His His
65                  70

<210> SEQ ID NO 239
<211> LENGTH: 44
<212> TYPE: PRT
<213> ORGANISM: Conus emaciatus
<220> FEATURE:
<221> NAME/KEY: PEPTIDE
<222> LOCATION: (1)..(44)
<223> OTHER INFORMATION: Xaa at residue 27 is Pro or hydroxy-Pro; Xaa at
      residues 4, 23, 25 and 39 is Glu or gamma-carboxy-Glu; Xaa at
      residue 30 is Trp or bromo-Trp; Xaa at residue 12 is Tyr, 125I-
      Tyr, mono-iodo-Tyr, di-iodo-Tyr, O-sulpho-Tyr or O-phospho-Ty

<400> SEQUENCE: 239

Cys Arg Arg Xaa Gly Ser Ser Cys Arg Arg Ser Xaa Gln Cys Cys Arg
1               5                   10                  15

Lys Ser Cys Cys Ile Gly Xaa Cys Xaa Phe Pro Cys Arg Xaa Val Gly
            20                  25                  30

Lys Arg Ala Thr Phe Arg Xaa Leu Ile Leu His His
        35                  40

<210> SEQ ID NO 240
<211> LENGTH: 243
<212> TYPE: DNA
<213> ORGANISM: Conus emaciatus

<400> SEQUENCE: 240
atgatgtttc gtgtgacgtc agtcagctgt ttcctactgg tcatcgtttg tctgaacttg     60
attgtgctta tcaatgcctg ctaccaagat gaaacgccct gcagaggtag tatcttctgc    120
tgtcgcaaaa aatgctgtat agggacatgc agatttccgt gttacgttaa attagagagg    180
gcgactttcc aagaactcat cctacaacct tgaaacgttg cccagaggtc tgctgcttct    240
cgt                                                                  243

<210> SEQ ID NO 241
<211> LENGTH: 70
<212> TYPE: PRT
<213> ORGANISM: Conus emaciatus

<400> SEQUENCE: 241

Met Met Phe Arg Val Thr Ser Val Ser Cys Phe Leu Leu Val Ile Val
1               5                   10                  15

Cys Leu Asn Leu Ile Val Leu Ile Asn Ala Cys Tyr Gln Asp Glu Thr
            20                  25                  30

Pro Cys Arg Gly Ser Ile Phe Cys Cys Arg Lys Lys Cys Cys Ile Gly
        35                  40                  45

Thr Cys Arg Phe Pro Cys Tyr Val Lys Leu Glu Arg Ala Thr Phe Gln
    50                  55                  60

Glu Leu Ile Leu Gln Pro
65              70
```

<210> SEQ ID NO 242
<211> LENGTH: 44
<212> TYPE: PRT
<213> ORGANISM: Conus emaciatus
<220> FEATURE:
<221> NAME/KEY: PEPTIDE
<222> LOCATION: (1)..(44)
<223> OTHER INFORMATION: Xaa at residues 7, 27 and 44 is Pro or hydroxy-
      Pro; Xaa at residues 5, 33 and 39 is Glu or gamma-carboxy-Glu; Xaa
      at residues 2 and 29 is Tyr, 125I-Tyr, mono-iodo-Tyr, di-iodo-Tyr,
      O-sulpho-Tyr or O-phospho-Ty

<400> SEQUENCE: 242

Cys Xaa Gln Asp Xaa Thr Xaa Cys Arg Gly Ser Ile Phe Cys Cys Arg
1               5                   10                  15

Lys Lys Cys Cys Ile Gly Thr Cys Arg Phe Xaa Cys Xaa Val Lys Leu
            20                  25                  30

Xaa Arg Ala Thr Phe Gln Xaa Leu Ile Leu Gln Pro
        35                  40

<210> SEQ ID NO 243
<211> LENGTH: 243
<212> TYPE: DNA
<213> ORGANISM: Conus emaciatus

<400> SEQUENCE: 243
atgatgtttc gtgtgacgtc agtcagctgt ttcctgctgg tcatcgcttg tctgaacctg      60
gttgtgctta ccaatgcctg cctccgtgac ggacagtcct gcggatatga ttccgattgc     120
tgtagatact cttgctgttg ggggtattgc gatcttacgt gtctaattat tggaaagagg     180
gcgacattcc aagaactcat cctacatcgt tgaaatgttg cccagaggtc tgctgcttct     240
cgt                                                                   243

<210> SEQ ID NO 244
<211> LENGTH: 70
<212> TYPE: PRT
<213> ORGANISM: Conus emaciatus

<400> SEQUENCE: 244

Met Met Phe Arg Val Thr Ser Val Ser Cys Phe Leu Leu Val Ile Ala
1               5                   10                  15

Cys Leu Asn Leu Val Val Leu Thr Asn Ala Cys Leu Arg Asp Gly Gln
            20                  25                  30

Ser Cys Gly Tyr Asp Ser Asp Cys Cys Arg Tyr Ser Cys Cys Trp Gly
        35                  40                  45

Tyr Cys Asp Leu Thr Cys Leu Ile Ile Gly Lys Arg Ala Thr Phe Gln
    50                  55                  60

Glu Leu Ile Leu His Arg
65              70

<210> SEQ ID NO 245
<211> LENGTH: 44
<212> TYPE: PRT
<213> ORGANISM: Conus emaciatus
<220> FEATURE:
<221> NAME/KEY: PEPTIDE
<222> LOCATION: (1)..(44)
<223> OTHER INFORMATION: Xaa at residue 39 is Glu or gamma-carboxy-Glu;
      Xaa at residue 21 is Trp or bromo-Trp; Xaa at residues 10, 17 and
      25 is Tyr, 125I-Tyr, mono-iodo-Tyr, di-iodo-Tyr, O-sulpho-Tyr or
      O-phospho-Ty -continued

```
<400> SEQUENCE: 245

Cys Leu Arg Asp Gly Gln Ser Cys Gly Xaa Asp Ser Asp Cys Cys Arg
1               5                   10                  15

Xaa Ser Cys Cys Xaa Gly Xaa Cys Asp Leu Thr Cys Leu Ile Ile Gly
            20                  25                  30

Lys Arg Ala Thr Phe Gln Xaa Leu Ile Leu His Arg
        35                  40

<210> SEQ ID NO 246
<211> LENGTH: 253
<212> TYPE: DNA
<213> ORGANISM: Conus emaciatus

<400> SEQUENCE: 246
atgatgtttc gtgtgacgtc agtcagctgt ttcctgctgg tcatcgcttg tctgaactcg      60
tttcaggttg tgcttaccag ccgctgcttc cctccaggaa tatactgcac accctatctc    120
ccctgctgtt ggggaatttg ctgtgggacg tgcagaaatg tgtgtcattt gaggattgga    180
aagagggcga cattccaaga atgaattcat tctacatcgt ttatatgttg cccagaggtc    240
tgctgcttct cgt                                                       253

<210> SEQ ID NO 247
<211> LENGTH: 67
<212> TYPE: PRT
<213> ORGANISM: Conus emaciatus

<400> SEQUENCE: 247

Met Met Phe Arg Val Thr Ser Val Ser Cys Phe Leu Leu Val Ile Ala
1               5                   10                  15

Cys Leu Asn Ser Phe Gln Val Val Leu Thr Ser Arg Cys Phe Pro Pro
            20                  25                  30

Gly Ile Tyr Cys Thr Pro Tyr Leu Pro Cys Cys Trp Gly Ile Cys Cys
        35                  40                  45

Gly Thr Cys Arg Asn Val Cys His Leu Arg Ile Gly Lys Arg Ala Thr
    50                  55                  60

Phe Gln Glu
65

<210> SEQ ID NO 248
<211> LENGTH: 39
<212> TYPE: PRT
<213> ORGANISM: Conus emaciatus
<220> FEATURE:
<221> NAME/KEY: PEPTIDE
<222> LOCATION: (1)..(39)
<223> OTHER INFORMATION: Xaa at residues 3, 4, 10 and 13 is Pro or
      hydroxy-Pro; Xaa at residue 39 is Glu or gamma-carboxy-Glu; Xaa at
      residue 16 is Trp or bromo-Trp; Xaa at residues 7 and 11 is Tyr,
      125I-Tyr, mono-iodo-Tyr, di-iodo-Tyr, O-sulpho-Tyr or O-phospho-Ty

<400> SEQUENCE: 248

Cys Phe Xaa Xaa Gly Ile Xaa Cys Thr Xaa Xaa Leu Xaa Cys Cys Xaa
1               5                   10                  15

Gly Ile Cys Cys Gly Thr Cys Arg Asn Val Cys His Leu Arg Ile Gly
            20                  25                  30

Lys Arg Ala Thr Phe Gln Xaa
        35

<210> SEQ ID NO 249
```

```
<211> LENGTH: 243
<212> TYPE: DNA
<213> ORGANISM: Conus emaciatus

<400> SEQUENCE: 249
atgatgtttc gtgtgacgtc agtcagctgt ttcctactgg tcatcgtttg tctgaacttg      60
attgtgctta tcaatgcctg ctaccaagat gaaacgccct gcagaggtag taccttctgc     120
tgtcgcaaaa aatgctgtat agggacatgc agatttccgt gttacgttaa attagagagg     180
gcgactttcc aagaactcat cctacaacct gaaacgttg cccagaggtc tgctgcttct     240
cgt                                                                   243

<210> SEQ ID NO 250
<211> LENGTH: 70
<212> TYPE: PRT
<213> ORGANISM: Conus emaciatus

<400> SEQUENCE: 250

Met Met Phe Arg Val Thr Ser Val Ser Cys Phe Leu Leu Val Ile Val
1               5                   10                  15

Cys Leu Asn Leu Ile Val Leu Ile Asn Ala Cys Tyr Gln Asp Glu Thr
            20                  25                  30

Pro Cys Arg Gly Ser Thr Phe Cys Cys Arg Lys Lys Cys Cys Ile Gly
        35                  40                  45

Thr Cys Arg Phe Pro Cys Tyr Val Lys Leu Glu Arg Ala Thr Phe Gln
    50                  55                  60

Glu Leu Ile Leu Gln Pro
65                  70

<210> SEQ ID NO 251
<211> LENGTH: 44
<212> TYPE: PRT
<213> ORGANISM: Conus emaciatus
<220> FEATURE:
<221> NAME/KEY: PEPTIDE
<222> LOCATION: (1)..(44)
<223> OTHER INFORMATION: Xaa at residues 7, 27 and 44 is Pro or hydroxy-
      Pro; Xaa at residues 5, 33 and 39 is Glu or gamma-carboxy-Glu; Xaa
      at residues 2 and 29 is Tyr, 125I-Tyr, mono-iodo-Tyr, di-iodo-Tyr,
      O-sulpho-Tyr or O-phospho-Ty

<400> SEQUENCE: 251

Cys Xaa Gln Asp Xaa Thr Xaa Cys Arg Gly Ser Thr Phe Cys Cys Arg
1               5                   10                  15

Lys Lys Cys Cys Ile Gly Thr Cys Arg Phe Xaa Cys Xaa Val Lys Leu
            20                  25                  30

Xaa Arg Ala Thr Phe Gln Xaa Leu Ile Leu Gln Xaa
            35                  40

<210> SEQ ID NO 252
<211> LENGTH: 243
<212> TYPE: DNA
<213> ORGANISM: Conus emaciatus

<400> SEQUENCE: 252
atgatgtttc gtgtgacgtc agtcagctgt ttcctgctgg tcatcgcttg tctgaacttg      60
gttgtgctta ccaatgcctg cctccgtgac ggacagtcct gcggatatca ttccgattgc     120
tgtagatact cttgctgttg ggggtattgc gatcagaagt gtctaattat tggaaagagg     180
gcgacattcc aagaactcat cctacatcct gaaatgttg cccagaggtc tgctgcttct     240
```

-continued

```
cgt                                                                      243
```

<210> SEQ ID NO 253
<211> LENGTH: 70
<212> TYPE: PRT
<213> ORGANISM: Conus emaciatus

<400> SEQUENCE: 253

Met Met Phe Arg Val Thr Ser Val Ser Cys Phe Leu Leu Val Ile Ala
1               5                   10                  15

Cys Leu Asn Leu Val Val Leu Thr Asn Ala Cys Leu Arg Asp Gly Gln
            20                  25                  30

Ser Cys Gly Tyr His Ser Asp Cys Cys Arg Tyr Ser Cys Cys Trp Gly
        35                  40                  45

Tyr Cys Asp Gln Lys Cys Leu Ile Ile Gly Lys Arg Ala Thr Phe Gln
    50                  55                  60

Glu Leu Ile Leu His Pro
65                  70

<210> SEQ ID NO 254
<211> LENGTH: 44
<212> TYPE: PRT
<213> ORGANISM: Conus emaciatus
<220> FEATURE:
<221> NAME/KEY: PEPTIDE
<222> LOCATION: (1)..(44)
<223> OTHER INFORMATION: Xaa at residue 44 is Pro or hydroxy-Pro; Xaa at
      residue 39 is Glu or gamma-carboxy-Glu; Xaa at residue 21 is Trp
      or bromo-Trp; Xaa at residues 10, 17 and 23 is Tyr, 125I-Tyr,
      mono-iodo-Tyr, di-iodo-Tyr, O-sulpho-Tyr or O-phospho-Ty

<400> SEQUENCE: 254

Cys Leu Arg Asp Gly Gln Ser Cys Gly Xaa His Ser Asp Cys Cys Arg
1               5                   10                  15

Xaa Ser Cys Cys Xaa Gly Xaa Cys Asp Gln Lys Cys Leu Ile Ile Gly
            20                  25                  30

Lys Arg Ala Thr Phe Gln Xaa Leu Ile Leu His Xaa
        35                  40

<210> SEQ ID NO 255
<211> LENGTH: 243
<212> TYPE: DNA
<213> ORGANISM: Conus virgo

<400> SEQUENCE: 255

```
atgatgtttc gtgtgacgtc agtcagctgt ttcctgctgg tcatcgcttg tctgaacttg     60
gttgtgctta ccaatgcctg ccttcgtgac ggacagtcct gcggatatga ttccgattgc    120
tgtagatact cttgctgttg ggggtattgc gatcttacgt gtctaattat tggaaagagg    180
gcgacattcc aagaactcat cctacatcgt tgaaatgttg cccagaggtc tgctgcttct    240
cgt                                                                  243
```

<210> SEQ ID NO 256
<211> LENGTH: 70
<212> TYPE: PRT
<213> ORGANISM: Conus virgo

<400> SEQUENCE: 256

Met Met Phe Arg Val Thr Ser Val Ser Cys Phe Leu Leu Val Ile Ala
1               5                   10                  15

Cys Leu Asn Leu Val Val Leu Thr Asn Ala Cys Leu Arg Asp Gly Gln

```
                     20                  25                  30
Ser Cys Gly Tyr Asp Ser Asp Cys Cys Arg Tyr Ser Cys Trp Gly
         35                  40                  45
Tyr Cys Asp Leu Thr Cys Leu Ile Ile Gly Lys Arg Ala Thr Phe Gln
     50                  55                  60
Glu Leu Ile Leu His Arg
65                  70

<210> SEQ ID NO 257
<211> LENGTH: 44
<212> TYPE: PRT
<213> ORGANISM: Conus virgo
<220> FEATURE:
<221> NAME/KEY: PEPTIDE
<222> LOCATION: (1)..(44)
<223> OTHER INFORMATION: Xaa at residue 39 is Glu or gamma-carboxy-Glu;
      Xaa at residue 21 is Trp or bromo-Trp; Xaa at residues 10, 17 and
      23 is Tyr, 125I-Tyr, mono-iodo-Tyr, di-iodo-Tyr, O-sulpho-Tyr or
      O-phospho-Ty

<400> SEQUENCE: 257

Cys Leu Arg Asp Gly Gln Ser Cys Gly Xaa Asp Ser Asp Cys Cys Arg
1               5                   10                  15

Xaa Ser Cys Cys Xaa Gly Xaa Cys Asp Leu Thr Cys Leu Ile Ile Gly
            20                  25                  30

Lys Arg Ala Thr Phe Gln Xaa Leu Ile Leu His Arg
            35                  40

<210> SEQ ID NO 258
<211> LENGTH: 240
<212> TYPE: DNA
<213> ORGANISM: Conus virgo

<400> SEQUENCE: 258
atgatgtttc gtgtgacgtc agtcggctgt ttcctgctgg ccatcgtttg tctgaacttg      60
attgtgctta ccaatgcctg cctccatgaa acgtcgccct gcagacgtag tttccaatgc     120
tgtcacggaa tttgctgttt tcggagatgc agtaattcgt gtcgatttgg aaagagggcg     180
acattccaag aattcattct acatcgctga tatgttgccc agaggtctgc tgcttctcgt     240

<210> SEQ ID NO 259
<211> LENGTH: 69
<212> TYPE: PRT
<213> ORGANISM: Conus virgo

<400> SEQUENCE: 259

Met Met Phe Arg Val Thr Ser Val Gly Cys Phe Leu Leu Ala Ile Val
1               5                   10                  15

Cys Leu Asn Leu Ile Val Leu Thr Asn Ala Cys Leu His Glu Thr Ser
            20                  25                  30

Pro Cys Arg Arg Ser Phe Gln Cys Cys His Gly Ile Cys Cys Phe Arg
            35                  40                  45

Arg Cys Ser Asn Ser Cys Arg Phe Gly Lys Arg Ala Thr Phe Gln Glu
        50                  55                  60

Phe Ile Leu His Arg
65

<210> SEQ ID NO 260
<211> LENGTH: 43
<212> TYPE: PRT
<213> ORGANISM: Conus virgo
```

```
<220> FEATURE:
<221> NAME/KEY: PEPTIDE
<222> LOCATION: (1)..(43)
<223> OTHER INFORMATION: Xaa at residue 7 is Pro or hydroxy-Pro; Xaa at
      residues 4 and 38 is Glu or gamma-carboxy-Gl

<400> SEQUENCE: 260

Cys Leu His Xaa Thr Ser Xaa Cys Arg Arg Ser Phe Gln Cys Cys His
1               5                  10                  15

Gly Ile Cys Cys Phe Arg Arg Cys Ser Asn Ser Cys Arg Phe Gly Lys
            20                  25                  30

Arg Ala Thr Phe Gln Xaa Phe Ile Leu His Arg
        35                  40

<210> SEQ ID NO 261
<211> LENGTH: 243
<212> TYPE: DNA
<213> ORGANISM: Conus virgo

<400> SEQUENCE: 261
atgatgtttc gtgtgacgtc agtcagctgt ttcctgctgg tcatcgcttg tctgaacttg      60
gttgtgctta ccaatgcctg cctccgtgac ggacagtcct gcggatatca ttccgattgc     120
tgtaggtact cttgctgttg ggggtattgc gatcagaagt gtctaattat tggaaagagg     180
gcgacattcc aagaactcat cctacatcgt tgaaatgttg cccagaggtc tgctgcttct     240
cgt                                                                   243

<210> SEQ ID NO 262
<211> LENGTH: 70
<212> TYPE: PRT
<213> ORGANISM: Conus virgo

<400> SEQUENCE: 262

Met Met Phe Arg Val Thr Ser Val Ser Cys Phe Leu Leu Val Ile Ala
1               5                  10                  15

Cys Leu Asn Leu Val Val Leu Thr Asn Ala Cys Leu Arg Asp Gly Gln
            20                  25                  30

Ser Cys Gly Tyr His Ser Asp Cys Cys Arg Tyr Ser Cys Cys Trp Gly
        35                  40                  45

Tyr Cys Asp Gln Lys Cys Leu Ile Ile Gly Lys Arg Ala Thr Phe Gln
    50                  55                  60

Glu Leu Ile Leu His Arg
65                  70

<210> SEQ ID NO 263
<211> LENGTH: 44
<212> TYPE: PRT
<213> ORGANISM: Conus virgo
<220> FEATURE:
<221> NAME/KEY: PEPTIDE
<222> LOCATION: (1)..(44)
<223> OTHER INFORMATION: Xaa at residue 39 is Glu or gamma-carboxy-Glu;
      Xaa at residue 21 is Trp or bromo-Trp; Xaa at residues 10, 17 and
      23 is Tyr, 125I-Tyr, mono-iodo-Tyr, di-iodo-Tyr, O-sulpho-Tyr or
      O-phospho-Ty

<400> SEQUENCE: 263

Cys Leu Arg Asp Gly Gln Ser Cys Gly Xaa His Ser Asp Cys Cys Arg
1               5                  10                  15

Xaa Ser Cys Cys Xaa Gly Xaa Cys Asp Gln Lys Cys Leu Ile Ile Gly
            20                  25                  30
```

Lys Arg Ala Thr Phe Gln Xaa Leu Ile Leu His Arg
            35                  40

<210> SEQ ID NO 264
<211> LENGTH: 240
<212> TYPE: DNA
<213> ORGANISM: Conus virgo

<400> SEQUENCE: 264
atgatgtttc gtgtgacgtc agtcagctgt ttcctgctgg tcatcgtttg tctgaacttg    60
gttgtgctta ccaatgcctg cctccatgaa acgccgccct gcagacgtag tttccaatgc   120
tgtcacggaa attgctgttt tcggagatgc agtaattcgt gtcgatttgg aaagagggcg   180
acattccaag aattcattct acatcgctga tatgttgccc agaggtctgc tgcttctcgt   240

<210> SEQ ID NO 265
<211> LENGTH: 69
<212> TYPE: PRT
<213> ORGANISM: Conus virgo

<400> SEQUENCE: 265

Met Met Phe Arg Val Thr Ser Val Ser Cys Phe Leu Leu Val Ile Val
1               5                   10                  15

Cys Leu Asn Leu Val Val Leu Thr Asn Ala Cys Leu His Glu Thr Pro
            20                  25                  30

Pro Cys Arg Arg Ser Phe Gln Cys Cys His Gly Asn Cys Cys Phe Arg
        35                  40                  45

Arg Cys Ser Asn Ser Cys Arg Phe Gly Lys Arg Ala Thr Phe Gln Glu
    50                  55                  60

Phe Ile Leu His Arg
65

<210> SEQ ID NO 266
<211> LENGTH: 43
<212> TYPE: PRT
<213> ORGANISM: Conus virgo
<220> FEATURE:
<221> NAME/KEY: PEPTIDE
<222> LOCATION: (1)..(43)
<223> OTHER INFORMATION: Xaa at residues 6 and 7 is Pro or hydroxy-Pro;
      Xaa at residues 4 and 38 is Glu or gamma-carboxy-Gl

<400> SEQUENCE: 266

Cys Leu His Xaa Thr Xaa Xaa Cys Arg Arg Ser Phe Gln Cys Cys His
1               5                   10                  15

Gly Asn Cys Cys Phe Arg Arg Cys Ser Asn Ser Cys Arg Phe Gly Lys
            20                  25                  30

Arg Ala Thr Phe Gln Xaa Phe Ile Leu His Arg
        35                  40

<210> SEQ ID NO 267
<211> LENGTH: 240
<212> TYPE: DNA
<213> ORGANISM: Conus virgo

<400> SEQUENCE: 267
atgatgtttc gtgtgacgtc agtcggctgt ttcctgctgg tcatcgtttg tctgaacttg    60
gttgtgctta ccaatgcctg cctccatgaa acgtcgccct gcggacgtag tttccaatgc   120
tgtcacggaa tttgttgttt tcggagatgc agtaattcgt gtcgatttgg aaagagggcg   180
acattccaag aattcattct acatcgctga tatgttgccc agaggtctgc tgcttctcgt   240

<210> SEQ ID NO 268
<211> LENGTH: 69
<212> TYPE: PRT
<213> ORGANISM: Conus virgo

<400> SEQUENCE: 268

Met Met Phe Arg Val Thr Ser Val Gly Cys Phe Leu Leu Val Ile Val
1               5                   10                  15

Cys Leu Asn Leu Val Val Leu Thr Asn Ala Cys Leu His Glu Thr Ser
            20                  25                  30

Pro Cys Gly Arg Ser Phe Gln Cys Cys His Gly Ile Cys Cys Phe Arg
        35                  40                  45

Arg Cys Ser Asn Ser Cys Arg Phe Gly Lys Arg Ala Thr Phe Gln Glu
    50                  55                  60

Phe Ile Leu His Arg
65

<210> SEQ ID NO 269
<211> LENGTH: 43
<212> TYPE: PRT
<213> ORGANISM: Conus virgo
<220> FEATURE:
<221> NAME/KEY: PEPTIDE
<222> LOCATION: (1)..(43)
<223> OTHER INFORMATION: Xaa at residue 7 is Pro or hydroxy-Pro; Xaa at
      residues 4 and 38 is Glu or gamma-carboxy-Gl

<400> SEQUENCE: 269

Cys Leu His Xaa Thr Ser Xaa Cys Gly Arg Ser Phe Gln Cys His
1               5                   10                  15

Gly Ile Cys Cys Phe Arg Arg Cys Ser Asn Ser Cys Arg Phe Gly Lys
            20                  25                  30

Arg Ala Thr Phe Gln Xaa Phe Ile Leu His Arg
        35                  40

<210> SEQ ID NO 270
<211> LENGTH: 240
<212> TYPE: DNA
<213> ORGANISM: Conus virgo

<400> SEQUENCE: 270
atgatgtttc gtgtgacgtc agtcagctgt ttcctgctgg tcatcgtttg tctgaacttg      60
gttgtgctta ccaatgcctg cctctatgaa acgtcgccct gcagacgtag tttccaatgc     120
tgtcacggaa tttgctgttt tcggagatgc agtaattcgt gtcgatttgg aaagagggcg     180
acattccaag aattcattct acatcgctga tatgttgccc agaggtctgc tgcttctcgt     240

<210> SEQ ID NO 271
<211> LENGTH: 69
<212> TYPE: PRT
<213> ORGANISM: Conus virgo

<400> SEQUENCE: 271

Met Met Phe Arg Val Thr Ser Val Ser Cys Phe Leu Leu Val Ile Val
1               5                   10                  15

Cys Leu Asn Leu Val Val Leu Thr Asn Ala Cys Leu Tyr Glu Thr Ser
            20                  25                  30

Pro Cys Arg Arg Ser Phe Gln Cys Cys His Gly Ile Cys Cys Phe Arg
        35                  40                  45

-continued

Arg Cys Ser Asn Ser Cys Arg Phe Gly Lys Arg Ala Thr Phe Gln Glu
    50                  55                  60

Phe Ile Leu His Arg
65

<210> SEQ ID NO 272
<211> LENGTH: 43
<212> TYPE: PRT
<213> ORGANISM: Conus virgo
<220> FEATURE:
<221> NAME/KEY: PEPTIDE
<222> LOCATION: (1)..(43)
<223> OTHER INFORMATION: Xaa at residue 7 is Pro or hydroxy-Pro; Xaa at
      residues 4 and 38 is Glu or gamma-carboxy-Glu; Xaa at residue 3 is
      Tyr, 125I-Tyr, mono-iodo-Tyr, di-iodo-Tyr, O-sulpho-Tyr or O-
      phospho-Ty

<400> SEQUENCE: 272

Cys Leu Xaa Xaa Thr Ser Xaa Cys Arg Arg Ser Phe Gln Cys Cys His
1               5                   10                  15

Gly Ile Cys Cys Phe Arg Arg Cys Ser Asn Ser Cys Arg Phe Gly Lys
            20                  25                  30

Arg Ala Thr Phe Gln Xaa Phe Ile Leu His Arg
        35                  40

<210> SEQ ID NO 273
<211> LENGTH: 256
<212> TYPE: DNA
<213> ORGANISM: Conus virgo

<400> SEQUENCE: 273
atgatgtttc gtgtgacgtc agtcggctgt ttcctgctgg tcatcgcttg tctgaacttg      60
tttcaggttg tgcttaccag acgctgcttc cctctaggaa cgttctgctc aagatatctc    120
ccctgctgta gtggaatgtg ctgttctggg tggtgcacac gaaggtgtgc cccaaggttt    180
ggaaagaggg cgacattcca agaatgaatt cattctacat cgttgatatg ttgcccagag    240
gtctgctgct tctcgt                                                    256

<210> SEQ ID NO 274
<211> LENGTH: 68
<212> TYPE: PRT
<213> ORGANISM: Conus virgo

<400> SEQUENCE: 274

Met Met Phe Arg Val Thr Ser Val Gly Cys Phe Leu Leu Val Ile Ala
1               5                   10                  15

Cys Leu Asn Leu Phe Gln Val Val Leu Thr Arg Arg Cys Phe Pro Leu
            20                  25                  30

Gly Thr Phe Cys Ser Arg Tyr Leu Pro Cys Cys Ser Gly Met Cys Cys
        35                  40                  45

Ser Gly Trp Cys Thr Arg Arg Cys Ala Pro Arg Phe Gly Lys Arg Ala
    50                  55                  60

Thr Phe Gln Glu
65

<210> SEQ ID NO 275
<211> LENGTH: 40
<212> TYPE: PRT
<213> ORGANISM: Conus virgo
<220> FEATURE:
<221> NAME/KEY: PEPTIDE
<222> LOCATION: (1)..(40)

<223> OTHER INFORMATION: Xaa at residues 3, 13 and 30 is Pro or hydroxy-
Pro; Xaa at residue 40 is Glu or gamma-carboxy-Glu; Xaa at residue
23 is Trp or bromo-Trp; Xaa at residue 11 is Tyr, 125I-Tyr, mono-
iodo-Tyr, di-iodo-Tyr, O-sulpho-Tyr or O-phospho-Ty

<400> SEQUENCE: 275

Cys Phe Xaa Leu Gly Thr Phe Cys Ser Arg Xaa Leu Xaa Cys Cys Ser
1               5                   10                  15

Gly Met Cys Cys Ser Gly Xaa Cys Thr Arg Arg Cys Ala Pro Arg Phe
            20                  25                  30

Gly Lys Arg Ala Thr Phe Gln Xaa
        35                  40

<210> SEQ ID NO 276
<211> LENGTH: 244
<212> TYPE: DNA
<213> ORGANISM: Conus figulinus

<400> SEQUENCE: 276
atgatgtttc gtgtgacgtc agtcggctgt ttcctgctgg tcatcgtttt tctgaacttg      60
gttgtgctta ccgatgcctg tcaccatgaa ggattgccct gcacaagtga tgacggttgc     120
tgtggcatgg aatgctgcgg cggggtttgc tcatcacatt gtggaaacgg gaggcgacgc     180
caagttccgt tgaaatcatt tggccaacgt tgatatgttt gaccagaggt ctgctgcttc     240
tcgt                                                                  244

<210> SEQ ID NO 277
<211> LENGTH: 70
<212> TYPE: PRT
<213> ORGANISM: Conus figulinus

<400> SEQUENCE: 277

Met Met Phe Arg Val Thr Ser Val Gly Cys Phe Leu Leu Val Ile Val
1               5                   10                  15

Phe Leu Asn Leu Val Val Leu Thr Asp Ala Cys His His Glu Gly Leu
            20                  25                  30

Pro Cys Thr Ser Asp Asp Gly Cys Cys Gly Met Glu Cys Cys Gly Gly
        35                  40                  45

Val Cys Ser Ser His Cys Gly Asn Gly Arg Arg Arg Gln Val Pro Leu
    50                  55                  60

Lys Ser Phe Gly Gln Arg
65                  70

<210> SEQ ID NO 278
<211> LENGTH: 44
<212> TYPE: PRT
<213> ORGANISM: Conus figulinus
<220> FEATURE:
<221> NAME/KEY: PEPTIDE
<222> LOCATION: (1)..(44)
<223> OTHER INFORMATION: Xaa at residues 7 and 37 is Pro or hydroxy-Pro;
Xaa at residues 4 and 18 is Glu or gamma-carboxy-Gl

<400> SEQUENCE: 278

Cys His His Xaa Gly Leu Xaa Cys Thr Ser Asp Asp Gly Cys Cys Gly
1               5                   10                  15

Met Xaa Cys Cys Gly Gly Val Cys Ser Ser His Cys Gly Asn Gly Arg
            20                  25                  30

Arg Arg Gln Val Pro Leu Lys Ser Phe Gly Gln Arg
        35                  40

<210> SEQ ID NO 279
<211> LENGTH: 244
<212> TYPE: DNA
<213> ORGANISM: Conus figulinus

<400> SEQUENCE: 279

```
atgatgtttc gtgtgacgtc agtcggctgt ttcctgctgg tcatcgtttt tctgaacttg      60
gttgtgctta ccgatgcctg tcaccatgaa ggattgccct gcacaagtga tgacggttgc     120
tgtggcatgg aatgctgcgg cggggtttgc tcatcacatt gtggaaacgg gaggcgacgc     180
cgagttccgt tgaaatcatt tggccaacgt tgatatgttt gaccagaggt ctgctgcttc     240
tcgt                                                                  244
```

<210> SEQ ID NO 280
<211> LENGTH: 70
<212> TYPE: PRT
<213> ORGANISM: Conus figulinus

<400> SEQUENCE: 280

Met Met Phe Arg Val Thr Ser Val Gly Cys Phe Leu Leu Val Ile Val
1               5                   10                  15

Phe Leu Asn Leu Val Val Leu Thr Asp Ala Cys His His Glu Gly Leu
            20                  25                  30

Pro Cys Thr Ser Asp Asp Gly Cys Cys Gly Met Glu Cys Cys Gly Gly
        35                  40                  45

Val Cys Ser Ser His Cys Gly Asn Gly Arg Arg Arg Val Pro Leu
    50                  55                  60

Lys Ser Phe Gly Gln Arg
65                  70

<210> SEQ ID NO 281
<211> LENGTH: 44
<212> TYPE: PRT
<213> ORGANISM: Conus figulinus
<220> FEATURE:
<221> NAME/KEY: PEPTIDE
<222> LOCATION: (1)..(44)
<223> OTHER INFORMATION: Xaa at residues 7 and 37 is Pro or hydroxy-Pro;
      Xaa at residues 4 and 18 is Glu or gamma-carboxy-Gl

<400> SEQUENCE: 281

Cys His His Xaa Gly Leu Xaa Cys Thr Ser Asp Asp Gly Cys Cys Gly
1               5                   10                  15

Met Xaa Cys Cys Gly Gly Val Cys Ser Ser His Cys Gly Asn Gly Arg
            20                  25                  30

Arg Arg Arg Val Xaa Leu Lys Ser Phe Gly Gln Arg
            35                  40

<210> SEQ ID NO 282
<211> LENGTH: 244
<212> TYPE: DNA
<213> ORGANISM: Conus figulinus

<400> SEQUENCE: 282

```
atgatgtttc gtgtgacgtc agtcggctgt ttcctgctgg tcatcgtttt tctgaacttg      60
gttgtgctta ccgatgcctg tcaccatgaa ggattgccct gcacaagtga tgacggttgc     120
tgtggcatgg aatgctgcgg cggggtttgc tcatcacatt gtggaaacgg ggggcgacgc     180
cgagttccgt tgaaatcatt tggccaacgt tgatatgttt gaccagaggt ctgctgcttc     240
```

-continued tcgt     244

<210> SEQ ID NO 283
<211> LENGTH: 70
<212> TYPE: PRT
<213> ORGANISM: Conus figulinus

<400> SEQUENCE: 283

Met Met Phe Arg Val Thr Ser Val Gly Cys Phe Leu Leu Val Ile Val
1               5                   10                  15

Phe Leu Asn Leu Val Val Leu Thr Asp Ala Cys His His Glu Gly Leu
            20                  25                  30

Pro Cys Thr Ser Asp Asp Gly Cys Cys Gly Met Glu Cys Cys Gly Gly
        35                  40                  45

Val Cys Ser Ser His Cys Gly Asn Gly Gly Arg Arg Arg Val Pro Leu
    50                  55                  60

Lys Ser Phe Gly Gln Arg
65                  70

<210> SEQ ID NO 284
<211> LENGTH: 44
<212> TYPE: PRT
<213> ORGANISM: Conus figulinus
<220> FEATURE:
<221> NAME/KEY: PEPTIDE
<222> LOCATION: (1)..(44)
<223> OTHER INFORMATION: Xaa at residues 7 and 37 is Pro or hydroxy-Pro;
      Xaa at residues 4 and 18 is Glu or gamma-carboxy-Gl

<400> SEQUENCE: 284

Cys His His Xaa Gly Leu Xaa Cys Thr Ser Asp Asp Gly Cys Cys Gly
1               5                   10                  15

Met Xaa Cys Cys Gly Gly Val Cys Ser Ser His Cys Gly Asn Gly Gly
            20                  25                  30

Arg Arg Arg Val Xaa Leu Lys Ser Phe Gly Gln Arg
        35                  40

<210> SEQ ID NO 285
<211> LENGTH: 234
<212> TYPE: DNA
<213> ORGANISM: Conus figulinus

<400> SEQUENCE: 285
atgatgtttc gtgtgacgtc agtcggctgt ttcctgctgg tcatcgtttt tctgaacttg     60
attgtgcctt ccagttcctg ccgcgctgaa ggagtgcgct gcgaatttga ttcccaatgc    120
tgtgaatctg aatgctgtat ggggagttgc gcaaatccgt gtcgaattcc tgggaagagg    180
gcgagactct ttcgacaacg ttgatatgtt gcccagaggt ctgctgcttc tcgt          234

<210> SEQ ID NO 286
<211> LENGTH: 67
<212> TYPE: PRT
<213> ORGANISM: Conus figulinus

<400> SEQUENCE: 286

Met Met Phe Arg Val Thr Ser Val Gly Cys Phe Leu Leu Val Ile Val
1               5                   10                  15

Phe Leu Asn Leu Ile Val Pro Ser Ser Ser Cys Arg Ala Glu Gly Val
            20                  25                  30

Arg Cys Glu Phe Asp Ser Gln Cys Cys Glu Ser Glu Cys Cys Met Gly
        35                  40                  45

-continued

Ser Cys Ala Asn Pro Cys Arg Ile Pro Gly Lys Arg Ala Arg Leu Phe
    50                       55                       60

Arg Gln Arg
65

<210> SEQ ID NO 287
<211> LENGTH: 41
<212> TYPE: PRT
<213> ORGANISM: Conus figulinus
<220> FEATURE:
<221> NAME/KEY: PEPTIDE
<222> LOCATION: (1)..(41)
<223> OTHER INFORMATION: Xaa at residues 27 and 31 is Pro or hydroxy-
     Pro; Xaa at residues 4, 9, 16 and 18 is Glu or gamma-carboxy-Gl

<400> SEQUENCE: 287

Cys Arg Ala Xaa Gly Val Arg Cys Xaa Phe Asp Ser Gln Cys Cys Xaa
1               5                    10                  15

Ser Xaa Cys Cys Met Gly Ser Cys Ala Asn Xaa Cys Arg Ile Xaa Gly
        20                       25                       30

Lys Arg Ala Arg Leu Phe Arg Gln Arg
        35                       40

<210> SEQ ID NO 288
<211> LENGTH: 243
<212> TYPE: DNA
<213> ORGANISM: Conus figulinus

<400> SEQUENCE: 288
atgatgtttc gtgtgacgtc agtcggctgt ttcctgctgg tcatcgtttt tctgaacttg    60
gttgtgccta ccagtgcctg ccgcgctgaa ggagtgtact gcgaatatgg ttcccaatgc   120
tgtctatctc aatgctgtat ggcgagttgc gcaaatccgt gtcgccatcc tggaaagagg   180
gcgagactcc aagaattctt tcgacaacgt tgatacgttg cccagaggtc tgctgcttct   240
cgt   243

<210> SEQ ID NO 289
<211> LENGTH: 70
<212> TYPE: PRT
<213> ORGANISM: Conus figulinus

<400> SEQUENCE: 289

Met Met Phe Arg Val Thr Ser Val Gly Cys Phe Leu Leu Val Ile Val
1               5                    10                  15

Phe Leu Asn Leu Val Val Pro Thr Ser Ala Cys Arg Ala Glu Gly Val
        20                       25                       30

Tyr Cys Glu Tyr Gly Ser Gln Cys Cys Leu Ser Gln Cys Cys Met Ala
            35                     40                    45

Ser Cys Ala Asn Pro Cys Arg His Pro Gly Lys Arg Ala Arg Leu Gln
    50                       55                       60

Glu Phe Phe Arg Gln Arg
65                 70

<210> SEQ ID NO 290
<211> LENGTH: 44
<212> TYPE: PRT
<213> ORGANISM: Conus figulinus
<220> FEATURE:
<221> NAME/KEY: PEPTIDE
<222> LOCATION: (1)..(44)
<223> OTHER INFORMATION: Xaa at residues 27 and 31 is Pro or hydroxy-
     Pro; Xaa at residues 4, 9 and 39 is Glu or gamma-carboxy-Glu; Xaa -continued at residues 7 and 10 is Tyr, 125I-Tyr, mono-iodo-Tyr, di-iodo-Tyr,
O-sulpho-Tyr or O-phospho-Ty

<400> SEQUENCE: 290

Cys Arg Ala Xaa Gly Val Xaa Cys Xaa Xaa Gly Ser Gln Cys Cys Leu
1               5                   10                  15

Ser Gln Cys Cys Met Ala Ser Cys Ala Asn Xaa Cys Arg His Xaa Gly
            20                  25                  30

Lys Arg Ala Arg Leu Gln Xaa Phe Phe Arg Gln Arg
        35                  40

<210> SEQ ID NO 291
<211> LENGTH: 243
<212> TYPE: DNA
<213> ORGANISM: Conus figulinus

<400> SEQUENCE: 291
atgatgtttc gtgtgacgtc agtcggctgt ttcctgctgg tcatcgtttt tctgaacttg      60
gttgtgccta ccagtgcctg ccgcgctgaa ggagtgtact gcgaatatgg ttcccaatgc     120
tgtctatctc aatgctgtat ggcgagttgc gcaaatccgt gtcgccatcc tggaaagagg     180
gcgagactcc aagaattctt tcgacgacgt tgatacgttg cccagaggtc tgctgcttct     240
cgt                                                                   243

<210> SEQ ID NO 292
<211> LENGTH: 70
<212> TYPE: PRT
<213> ORGANISM: Conus figulinus

<400> SEQUENCE: 292

Met Met Phe Arg Val Thr Ser Val Gly Cys Phe Leu Leu Val Ile Val
1               5                   10                  15

Phe Leu Asn Leu Val Val Pro Thr Ser Ala Cys Arg Ala Glu Gly Val
            20                  25                  30

Tyr Cys Glu Tyr Gly Ser Gln Cys Cys Leu Ser Gln Cys Cys Met Ala
        35                  40                  45

Ser Cys Ala Asn Pro Cys Arg His Pro Gly Lys Arg Ala Arg Leu Gln
    50                  55                  60

Glu Phe Phe Arg Arg Arg
65              70

<210> SEQ ID NO 293
<211> LENGTH: 44
<212> TYPE: PRT
<213> ORGANISM: Conus figulinus
<220> FEATURE:
<221> NAME/KEY: PEPTIDE
<222> LOCATION: (1)..(44)
<223> OTHER INFORMATION: Xaa at residues 27 and 31 is Pro or hydroxy-
    Pro; Xaa at residues 4, 9 and 39 is Glu or gamma-carboxy-Glu; Xaa
    at residues 7 and 10 is Tyr, 125I-Tyr, mono-iodo-Tyr, di-iodo-Tyr,
    O-sulpho-Tyr or O-phospho-Ty

<400> SEQUENCE: 293

Cys Arg Ala Xaa Gly Val Xaa Cys Xaa Xaa Gly Ser Gln Cys Cys Leu
1               5                   10                  15

Ser Gln Cys Cys Met Ala Ser Cys Ala Asn Xaa Cys Arg His Xaa Gly
            20                  25                  30

Lys Arg Ala Arg Leu Gln Xaa Phe Phe Arg Arg Arg
        35                  40

<210> SEQ ID NO 294
<211> LENGTH: 244
<212> TYPE: DNA
<213> ORGANISM: Conus figulinus

<400> SEQUENCE: 294

```
atgatgtttc gtgtgacgtc agtcggctgt ttcctgctgg tcatcgtttt tctgaacttg      60
gttgtgctta ccgatgcctg tcaccatgaa ggattgccct gcacaagtgg tgacggttgc     120
tgtggcatgg aatgctgcgg cggggtttgc tcatcacatt gtggaaacgg gaggcgacgc     180
caagttccgt tgaaatcatt tggccaacgt tgatatgttt gaccagaggt ctgctgcttc     240
tcgt                                                                  244
```

<210> SEQ ID NO 295
<211> LENGTH: 70
<212> TYPE: PRT
<213> ORGANISM: Conus figulinus

<400> SEQUENCE: 295

```
Met Met Phe Arg Val Thr Ser Val Gly Cys Phe Leu Leu Val Ile Val
1               5                   10                  15

Phe Leu Asn Leu Val Val Leu Thr Asp Ala Cys His His Glu Gly Leu
                20                  25                  30

Pro Cys Thr Ser Gly Asp Gly Cys Cys Gly Met Glu Cys Cys Gly Gly
            35                  40                  45

Val Cys Ser Ser His Cys Gly Asn Gly Arg Arg Arg Gln Val Pro Leu
        50                  55                  60

Lys Ser Phe Gly Gln Arg
65                  70
```

<210> SEQ ID NO 296
<211> LENGTH: 44
<212> TYPE: PRT
<213> ORGANISM: Conus figulinus
<220> FEATURE:
<221> NAME/KEY: PEPTIDE
<222> LOCATION: (1)..(44)
<223> OTHER INFORMATION: Xaa at residues 7 and 37 is Pro or hydroxy-Pro;
      Xaa at residues 4 and 18 is Glu or gamma-carboxy-Gl

<400> SEQUENCE: 296

```
Cys His His Xaa Gly Leu Xaa Cys Thr Ser Gly Asp Gly Cys Cys Gly
1               5                   10                  15

Met Xaa Cys Cys Gly Gly Val Cys Ser Ser His Cys Gly Asn Gly Arg
                20                  25                  30

Arg Arg Gln Val Xaa Leu Lys Ser Phe Gly Gln Arg
            35                  40
```

<210> SEQ ID NO 297
<211> LENGTH: 244
<212> TYPE: DNA
<213> ORGANISM: Conus figulinus

<400> SEQUENCE: 297

```
atgatgtttc gtgtgacgtc agtcggctgt ttcctgctgg tcatcgtttt tctgaacttg      60
gttgtgctca ccgatgcctg tcaccatgaa ggattgccct gcgcaagtga tgacggttgc     120
tgtggcatgg aatgctgcgg cggggtttgc tcatcacatt gtggaaacgg gaggcgacgc     180
cgagttccgt tgaaatcatt tggccaacgt tgatatgttt gaccagaggt ctgctgcttc     240
```

```
<210> SEQ ID NO 298
<211> LENGTH: 69
<212> TYPE: PRT
<213> ORGANISM: Conus figulinus

<400> SEQUENCE: 298

Met Phe Arg Val Thr Ser Val Gly Cys Phe Leu Leu Val Ile Val Phe
1               5                   10                  15

Leu Asn Leu Val Val Leu Thr Asp Ala Cys His His Glu Gly Leu Pro
            20                  25                  30

Cys Ala Ser Asp Asp Gly Cys Cys Gly Met Glu Cys Cys Gly Gly Val
        35                  40                  45

Cys Ser Ser His Cys Gly Asn Gly Arg Arg Arg Val Pro Leu Lys
    50                  55                  60

Ser Phe Gly Gln Arg
65

<210> SEQ ID NO 299
<211> LENGTH: 44
<212> TYPE: PRT
<213> ORGANISM: Conus figulinus
<220> FEATURE:
<221> NAME/KEY: PEPTIDE
<222> LOCATION: (1)..(44)
<223> OTHER INFORMATION: Xaa at residues 7 and 37 is Pro or hydroxy-Pro;
      Xaa at residues 4 and 18 is Glu or gamma-carboxy-Gl

<400> SEQUENCE: 299

Cys His His Xaa Gly Leu Xaa Cys Ala Ser Asp Asp Gly Cys Cys Gly
1               5                   10                  15

Met Xaa Cys Cys Gly Gly Val Cys Ser Ser His Cys Gly Asn Gly Arg
            20                  25                  30

Arg Arg Arg Val Xaa Leu Lys Ser Phe Gly Gln Arg
        35                  40

<210> SEQ ID NO 300
<211> LENGTH: 46
<212> TYPE: PRT
<213> ORGANISM: Conus radiatus
<220> FEATURE:
<221> NAME/KEY: PEPTIDE
<222> LOCATION: (1)..(46)
<223> OTHER INFORMATION: Xaa at residues 2, 11, 29 and 36 is Pro or
      hydroxy-Pro; Xaa at residues 9 and 13 is Glu or gamma-carboxy-Glu;
      Xaa at residue 33 is Trp or bromo-Trp; Xaa at residue 14 is Tyr,
      125I-Tyr, mono-iodo-Tyr, di-iodo-Tyr, O-sulpho-Tyr or O-phospho-Ty

<400> SEQUENCE: 300

Gly Xaa Ser Phe Cys Lys Ala Asp Xaa Lys Xaa Cys Xaa Xaa His Ala
1               5                   10                  15

Asp Cys Cys Asn Cys Cys Leu Ser Gly Ile Cys Ala Xaa Ser Thr Asn
            20                  25                  30

Xaa Ile Leu Xaa Gly Cys Ser Thr Ser Ser Phe Phe Lys Ile
        35                  40                  45

<210> SEQ ID NO 301
<211> LENGTH: 429
<212> TYPE: DNA
<213> ORGANISM: Conus aulicus

<400> SEQUENCE: 301
```

-continued

```
gctatcagca cttcgcagca gtcgaggctt taaaatccta atcgtagaag aaggcaaaaa      60
catctggtgg tcagtatgaa gctgtgtgtg acgtttcttc ttgttctggt gattctgcca     120
tcagtaactg gggagaagtc tagcgagcgt acactgagtg gtgctactct gagaggcgat     180
tggggaacgt gctcatggcc aggacaagaa tgcaaacatg attccgactg ctgtgggagt     240
ttctgttgtg tcggcaaaag gtgcttacac acttactttc catgtaactt atctcgctcc     300
tagtgcgatg gacctaggcg tgctggccta gcggtagact cgctcagtat gcctgatctg     360
tccgagtgaa acgacctgac gcgatccgtc gtattccttt gccaagagcc agctaggcca     420
tgcctaggt                                                            429
```

<210> SEQ ID NO 302
<211> LENGTH: 75
<212> TYPE: PRT
<213> ORGANISM: Conus aulicus

<400> SEQUENCE: 302

```
Met Lys Leu Cys Val Thr Phe Leu Leu Val Leu Val Ile Leu Pro Ser
1               5                   10                  15

Val Thr Gly Glu Lys Ser Ser Glu Arg Thr Leu Ser Gly Ala Thr Leu
            20                  25                  30

Arg Gly Asp Trp Gly Thr Cys Ser Trp Pro Gly Gln Glu Cys Lys His
        35                  40                  45

Asp Ser Asp Cys Cys Gly Ser Phe Cys Cys Val Gly Lys Arg Cys Leu
    50                  55                  60

His Thr Tyr Phe Pro Cys Asn Leu Ser Arg Ser
65                  70                  75
```

<210> SEQ ID NO 303
<211> LENGTH: 42
<212> TYPE: PRT
<213> ORGANISM: Conus aulicus
<220> FEATURE:
<221> NAME/KEY: PEPTIDE
<222> LOCATION: (1)..(42)
<223> OTHER INFORMATION: Xaa at residues 9 and 36 is Pro or hydroxy-Pro;
    Xaa at residue 12 is Glu or gamma-carboxy-Glu; Xaa at residues 3
    and 8 is Trp or bromo-Trp; Xaa at residue 34 is Tyr, 125I-Tyr,
    mono-iodo-Tyr, di-iodo-Tyr, O-sulpho-Tyr or O-phospho-Ty

<400> SEQUENCE: 303

```
Gly Asp Xaa Gly Thr Cys Ser Xaa Xaa Gly Gln Xaa Cys Lys His Asp
1               5                   10                  15

Ser Asp Cys Cys Gly Ser Phe Cys Cys Val Gly Lys Arg Cys Leu His
            20                  25                  30

Thr Xaa Phe Xaa Cys Asn Leu Ser Arg Ser
        35                  40
```

<210> SEQ ID NO 304
<211> LENGTH: 429
<212> TYPE: DNA
<213> ORGANISM: Conus aulicus

<400> SEQUENCE: 304

```
gctatcagca cttcgcagca gtcgaggctt taaaatccta atcgtagaag aaggcaaaaa      60
catctggtgg tcagtatgaa gctgtgtgtg acgtttcttc ttgttctggt gattctgcca     120
tcagtaactg gggagaagtc tagcgagcgc acactgagtg gtgctactct gagaggcgat     180
tggggaacgt gctcatggtc aggacaagaa tgcaaacatg tttccgactg ctgtgggagt     240
```

```
ttctgttgtg tcggcaaaag gtgcttacac atttactttc catgtaactt atctcgctcc      300
tagtgcgatg gacctaggcg tgctggccta gtggtagact cgctcagtat gcctgatctg      360
tccgagtgaa acgacctgac gcgatccgtc gtattccttt gccaagagcc agctaggcca      420
tgcctaggt                                                              429
```

<210> SEQ ID NO 305
<211> LENGTH: 75
<212> TYPE: PRT
<213> ORGANISM: Conus aulicus

<400> SEQUENCE: 305

```
Met Lys Leu Cys Val Thr Phe Leu Leu Val Leu Val Ile Leu Pro Ser
1               5                   10                  15

Val Thr Gly Glu Lys Ser Ser Glu Arg Thr Leu Ser Gly Ala Thr Leu
            20                  25                  30

Arg Gly Asp Trp Gly Thr Cys Ser Trp Ser Gly Gln Glu Cys Lys His
        35                  40                  45

Val Ser Asp Cys Cys Gly Ser Phe Cys Cys Val Gly Lys Arg Cys Leu
    50                  55                  60

His Ile Tyr Phe Pro Cys Asn Leu Ser Arg Ser
65                  70                  75
```

<210> SEQ ID NO 306
<211> LENGTH: 42
<212> TYPE: PRT
<213> ORGANISM: Conus aulicus
<220> FEATURE:
<221> NAME/KEY: PEPTIDE
<222> LOCATION: (1)..(42)
<223> OTHER INFORMATION: Xaa at residue 36 is Pro or hydroxy-Pro; Xaa at
     residue 12 is Glu or gamma-carboxy-Glu; Xaa at residues 3 and 8 is
     Trp or bromo-Trp; Xaa at residue 34 is Tyr, 125I-Tyr, mono-iodo-
     Tyr, di-iodo-Tyr, O-sulpho-Tyr or O-phospho-Ty

<400> SEQUENCE: 306

```
Gly Asp Xaa Gly Thr Cys Ser Xaa Ser Gly Gln Xaa Cys Lys His Val
1               5                   10                  15

Ser Asp Cys Cys Gly Ser Phe Cys Cys Val Gly Lys Arg Cys Leu His
            20                  25                  30

Ile Xaa Phe Xaa Cys Asn Leu Ser Arg Ser
        35                  40
```

<210> SEQ ID NO 307
<211> LENGTH: 429
<212> TYPE: DNA
<213> ORGANISM: Conus aulicus

<400> SEQUENCE: 307

```
gctatcagca cttcgcagca gtcgaggctt taaaatccta atcgtagaag aaggcaaaaa      60
catctggtgg tcagtatgaa gctgtgtgtg acgtttcttc ttgttctggt gattctgcca     120
tcagtaactg gggagaagtc tagcgagcgt acactgagtg gtgctactct gagaggcgat     180
tggggaacgt gctcatggtc aggacaagaa tgcaaacatg attccgactg ctgtgggagt     240
ttctgttgtg tcggcaaaag gtgcttacac atttactttc catgtaactt atctcgcccc     300
tagtgcgatg gacctaggcg tgctggccta gtggtagact cgctcagtat gcctgatctg     360
tccgagtgaa acgacctgac gcgatccgtc gtattccttt gccaagagcc agctaggcca     420
tgcctaggt                                                             429
```

```
<210> SEQ ID NO 308
<211> LENGTH: 75
<212> TYPE: PRT
<213> ORGANISM: Conus aulicus

<400> SEQUENCE: 308

Met Lys Leu Cys Val Thr Phe Leu Leu Val Leu Val Ile Leu Pro Ser
1               5                   10                  15

Val Thr Gly Glu Lys Ser Ser Glu Arg Thr Leu Ser Gly Ala Thr Leu
            20                  25                  30

Arg Gly Asp Trp Gly Thr Cys Ser Trp Ser Gly Gln Glu Cys Lys His
        35                  40                  45

Asp Ser Asp Cys Cys Gly Ser Phe Cys Cys Val Gly Lys Arg Cys Leu
    50                  55                  60

His Ile Tyr Phe Pro Cys Asn Leu Ser Arg Pro
65                  70                  75

<210> SEQ ID NO 309
<211> LENGTH: 42
<212> TYPE: PRT
<213> ORGANISM: Conus aulicus
<220> FEATURE:
<221> NAME/KEY: PEPTIDE
<222> LOCATION: (1)..(42)
<223> OTHER INFORMATION: Xaa at residues 36 and 42 is Pro or hydroxy-
      Pro; Xaa at residue 12 is Glu or gamma-carboxy-Glu; Xaa at
      residues 3 and 8 is Trp or bromo-Trp; Xaa at residue 34 is Tyr,
      125I-Tyr, mono-iodo-Tyr, di-iodo-Tyr, O-sulpho-Tyr or O-phospho-Ty

<400> SEQUENCE: 309

Gly Asp Xaa Gly Thr Cys Ser Xaa Ser Gly Gln Xaa Cys Lys His Asp
1               5                   10                  15

Ser Asp Cys Cys Gly Ser Phe Cys Cys Val Gly Lys Arg Cys Leu His
            20                  25                  30

Ile Xaa Phe Xaa Cys Asn Leu Ser Arg Xaa
        35                  40

<210> SEQ ID NO 310
<211> LENGTH: 429
<212> TYPE: DNA
<213> ORGANISM: Conus aulicus

<400> SEQUENCE: 310
gctatcagca cttcgcagca gtcgaggctt taaaatccta atcgtagaag aaggcaaaaa      60
catctggtgg tcagtatgaa gctgtgtgtg acgtttcttc ttgttctggt gattctgcca     120
tcagtaactg gggagaagtc tagcgagcgt acactgagtg gtgctactct gagaggcgat     180
tggggaacgt gctcatggtc aggacaagaa tgcaaacatg attccgactg ctgtgggagt     240
ttctgttgtg tcggcaaaag gtgcttacac atttactttc catgtaactt atctcgctcc     300
tagtgcgatg gacctaggcg tgctggccta gtggtagact cgctcagtat gcctgatctg     360
tccgagtgaa acgacctgac gcgatccgtc gtattccttt gccaagagcc agctaggcca     420
tgcctaggt                                                             429

<210> SEQ ID NO 311
<211> LENGTH: 75
<212> TYPE: PRT
<213> ORGANISM: Conus aulicus

<400> SEQUENCE: 311
```

-continued

Met Lys Leu Cys Val Thr Phe Leu Leu Val Leu Val Ile Leu Pro Ser
1               5                   10                  15

Val Thr Gly Glu Lys Ser Ser Glu Arg Thr Leu Ser Gly Ala Thr Leu
                20              25                  30

Arg Gly Asp Trp Gly Thr Cys Ser Trp Ser Gly Gln Glu Cys Lys His
            35                  40                  45

Asp Ser Asp Cys Cys Gly Ser Phe Cys Val Gly Lys Arg Cys Leu
        50                  55                  60

His Ile Tyr Phe Pro Cys Asn Leu Ser Arg Ser
65                  70                  75

<210> SEQ ID NO 312
<211> LENGTH: 42
<212> TYPE: PRT
<213> ORGANISM: Conus aulicus
<220> FEATURE:
<221> NAME/KEY: PEPTIDE
<222> LOCATION: (1)..(42)
<223> OTHER INFORMATION: Xaa at residue 36 is Pro or hydroxy-Pro; Xaa at
      residue 12 is Glu or gamma-carboxy-Glu; Xaa at residues 3 and 8 is
      Trp or bromo-Trp; Xaa at residue 34 is Tyr, 125I-Tyr, mono-iodo-
      Tyr, di-iodo-Tyr, O-sulpho-Tyr or O-phospho-Ty

<400> SEQUENCE: 312

Gly Asp Xaa Gly Thr Cys Ser Xaa Ser Gly Gln Xaa Cys Lys His Asp
1               5                   10                  15

Ser Asp Cys Cys Gly Ser Phe Cys Val Gly Lys Arg Cys Leu His
                20                  25                  30

Ile Xaa Phe Xaa Cys Asn Leu Ser Arg Ser
            35                  40

<210> SEQ ID NO 313
<211> LENGTH: 429
<212> TYPE: DNA
<213> ORGANISM: Conus aulicus
<220> FEATURE:
<221> NAME/KEY: misc_feature
<222> LOCATION: (1)..(429)
<223> OTHER INFORMATION: n is any nucleotide

<400> SEQUENCE: 313
gctatcagca cttcgcagca gtcgaggntt taaaatccta atcgtagaag aaggcaaaaa        60
catctggtgg tcagtatgaa gctgtgtgtg acgtttcttc ttgttctggt gattctgcca       120
tcagtaactg gggagaagtc tagcgagcgt acactgagtg gtgctactct gagaggcgat       180 ggggggaacgt gctcatggcc aggacaagaa tgcaaacatg attccgactg ctgtgggagt      240
ttctgttgtg tcggcaaaag gtgcttacac acttactttc catgtaactt atctcgctcc       300
tagtgcgatg gacctaggcg tgctggccta gcggtagact cgctcagtat gcctgatctg       360
tccgagtgaa acgacctgac gcgatccgtc gtattccttt gccaagagcc agctaggca        420 tgcctaggt                                                              429

<210> SEQ ID NO 314
<211> LENGTH: 75
<212> TYPE: PRT
<213> ORGANISM: Conus aulicus

<400> SEQUENCE: 314

Met Lys Leu Cys Val Thr Phe Leu Leu Val Leu Val Ile Leu Pro Ser
1               5                   10                  15

Val Thr Gly Glu Lys Ser Ser Glu Arg Thr Leu Ser Gly Ala Thr Leu

```
                   20                  25                  30

Arg Gly Asp Gly Thr Cys Ser Trp Pro Gly Gln Glu Cys Lys His
            35                  40                  45

Asp Ser Asp Cys Cys Gly Ser Phe Cys Val Gly Lys Arg Cys Leu
        50                  55                  60

His Thr Tyr Phe Pro Cys Asn Leu Ser Arg Ser
65                  70                  75

<210> SEQ ID NO 315
<211> LENGTH: 42
<212> TYPE: PRT
<213> ORGANISM: Conus aulicus
<220> FEATURE:
<221> NAME/KEY: PEPTIDE
<222> LOCATION: (1)..(42)
<223> OTHER INFORMATION: Xaa at residues 9 and 36 is Pro or hydroxy-Pro;
      Xaa at residue 12 is Glu or gamma-carboxy-Glu; Xaa at residue 8 is
      Trp or bromo-Trp; Xaa at residue 34 is Tyr, 125I-Tyr, mono-iodo-
      Tyr, di-iodo-Tyr, O-sulpho-Tyr or O-phospho-Ty

<400> SEQUENCE: 315

Gly Asp Gly Gly Thr Cys Ser Xaa Pro Gly Gln Xaa Cys Lys His Asp
1               5                   10                  15

Ser Asp Cys Cys Gly Ser Phe Cys Val Gly Lys Arg Cys Leu His
            20                  25                  30

Thr Xaa Phe Xaa Cys Asn Leu Ser Arg Ser
        35                  40

<210> SEQ ID NO 316
<211> LENGTH: 429
<212> TYPE: DNA
<213> ORGANISM: Conus aulicus

<400> SEQUENCE: 316
gctatcagca cttcgcagca gtcgaggctt taaaatccta atcgtagaag aaggcaaaaa      60
catctggtgg tcagtatgaa gctgtgtgtg acgtttcttc ttgttctggt gattctgcca    120
tcagtaactg gggagaagtc tagcgagcgt acactgagtg gtgctactct gagaggcgat    180
tggggaacgt gctcatggcc aggacaagaa tgcgaacatg attccgactg ctgcgggagt    240
ttctgttgtg tcggcagaag gtgcttacac atttactttc catgtaactt atctcgctcc    300
tagtgcgatg gacctaggcg tgctggccta gtggtagact cgctcagtat gcctgatctg    360
tccgagtgaa acgacctgac gcgatccgtc gtatttcttt gccaagagcc agctaggcca    420
tgcctaggt                                                            429

<210> SEQ ID NO 317
<211> LENGTH: 75
<212> TYPE: PRT
<213> ORGANISM: Conus aulicus

<400> SEQUENCE: 317

Met Lys Leu Cys Val Thr Phe Leu Leu Val Leu Ile Leu Pro Ser
1               5                   10                  15

Val Thr Gly Glu Lys Ser Ser Glu Arg Thr Leu Ser Gly Ala Thr Leu
            20                  25                  30

Arg Gly Asp Trp Gly Thr Cys Ser Trp Pro Gly Gln Glu Cys Glu His
            35                  40                  45

Asp Ser Asp Cys Cys Gly Ser Phe Cys Val Gly Arg Arg Cys Leu
        50                  55                  60
```

His Ile Tyr Phe Pro Cys Asn Leu Ser Arg Ser
65                  70                  75

<210> SEQ ID NO 318
<211> LENGTH: 42
<212> TYPE: PRT
<213> ORGANISM: Conus aulicus
<220> FEATURE:
<221> NAME/KEY: PEPTIDE
<222> LOCATION: (1)..(42)
<223> OTHER INFORMATION: Xaa at residues 9 and 36 is Pro or hydroxy-Pro;
    Xaa at residues 12 and 14 is Glu or gamma-carboxy-Glu; Xaa at
    residues 3 and 8 is Trp or bromo-Trp; Xaa at residue 34 is Tyr,
    125I-Tyr, mono-iodo-Tyr, di-iodo-Tyr, O-sulpho-Tyr or O-phospho-Ty

<400> SEQUENCE: 318

Gly Asp Xaa Gly Thr Cys Ser Xaa Xaa Gly Gln Xaa Cys Xaa His Asp
1               5                   10                  15

Ser Asp Cys Cys Gly Ser Phe Cys Val Gly Arg Arg Cys Leu His
            20                  25                  30

Ile Xaa Phe Xaa Cys Asn Leu Ser Arg Ser
        35                  40

<210> SEQ ID NO 319
<211> LENGTH: 435
<212> TYPE: DNA
<213> ORGANISM: Conus episcopatus

<400> SEQUENCE: 319
gctatcagca cttcgcagca gtcgaggctt taaaatccaa atcgtagaag aaggcaaaaa      60
cgtctggtga cagtatgaag ctgtgtgtga cgtttcttct tattctggtg attctgccat    120
cggtaactgg ggagaagtct agcaagcgta cactgagtgg tgctgctctg agaggcgatt    180
ggggaatgtg ctcaggcata ggacaaggat gcggacaaga ttccaactgc tgtggggata    240
tgtgctgtta tggccaaata tgcgctatga ctttcgcggc atgtggtccc taacttcttt    300
cccttctagt gcgatggacc taggcgtgct ggcctagcgg ccgactcgct cagtatgcct    360
gatctgtccg agtgaaacga cctgacacga tccgtcgtat tcctttgcca agagccagtt    420
aggccatgcc taggt                                                     435

<210> SEQ ID NO 320
<211> LENGTH: 72
<212> TYPE: PRT
<213> ORGANISM: Conus episcopatus

<400> SEQUENCE: 320

Met Lys Leu Cys Val Thr Phe Leu Leu Ile Leu Val Ile Leu Pro Ser
1               5                   10                  15

Val Thr Gly Glu Lys Ser Ser Lys Arg Thr Leu Ser Gly Ala Ala Leu
            20                  25                  30

Arg Gly Asp Trp Gly Met Cys Ser Gly Ile Gly Gln Gly Cys Gly Gln
        35                  40                  45

Asp Ser Asn Cys Cys Gly Asp Met Cys Cys Tyr Gly Gln Ile Cys Ala
    50                  55                  60

Met Thr Phe Ala Ala Cys Gly Pro
65                  70

<210> SEQ ID NO 321
<211> LENGTH: 39
<212> TYPE: PRT
<213> ORGANISM: Conus episcopatus -continued

```
<220> FEATURE:
<221> NAME/KEY: PEPTIDE
<222> LOCATION: (1)..(39)
<223> OTHER INFORMATION: Xaa at residue 39 is Pro or hydroxy-Pro; Xaa at
      residue 3 is Trp or bromo-Trp; Xaa at residue 26 is Tyr, 125I-Tyr,
      mono-iodo-Tyr, di-iodo-Tyr, O-sulpho-Tyr or O-phospho-Ty

<400> SEQUENCE: 321

Gly Asp Xaa Gly Met Cys Ser Gly Ile Gly Gln Gly Cys Gly Gln Asp
1               5                   10                  15

Ser Asn Cys Cys Gly Asp Met Cys Xaa Gly Gln Ile Cys Ala Met
            20                  25                  30

Thr Phe Ala Ala Cys Gly Xaa
            35

<210> SEQ ID NO 322
<211> LENGTH: 435
<212> TYPE: DNA
<213> ORGANISM: Conus episcopatus

<400> SEQUENCE: 322
gctatcagca cttcgcagca gtcgaggctt taaaatccta atcgtagaag aaggcaaaaa      60
cgtctggtgt cagtatgaag ctgtgtgtga cgtttcttct tattctggtg attctgccat     120
cagtaactgg ggagaagtct agcaagcgta cactgagtgg tgctgctctg agaggcgatc     180
ggggaatgtg ctctcgcata ggacaaggat gcggacaaga ttccgactgc tgtggggata     240
tgtgctgtta cggccaaata tgcgctatga ctttcgcggc atgtggtccc taacttcttt     300
cccttctagt gcgatggacc taggcgtgct ggcctagcgg ccgacacgct cagtatgcct     360
gatctgtccg agtgaaacga cctgacacga tccgtcgtat tcctttgcca agagccagct     420
aggccatgcc taggt                                                     435

<210> SEQ ID NO 323
<211> LENGTH: 72
<212> TYPE: PRT
<213> ORGANISM: Conus episcopatus

<400> SEQUENCE: 323

Met Lys Leu Cys Val Thr Phe Leu Leu Ile Leu Val Ile Leu Pro Ser
1               5                   10                  15

Val Thr Gly Glu Lys Ser Ser Lys Arg Thr Leu Ser Gly Ala Ala Leu
            20                  25                  30

Arg Gly Asp Arg Gly Met Cys Ser Arg Ile Gly Gln Gly Cys Gly Gln
        35                  40                  45

Asp Ser Asp Cys Cys Gly Asp Met Cys Cys Tyr Gly Gln Ile Cys Ala
    50                  55                  60

Met Thr Phe Ala Ala Cys Gly Pro
65                  70

<210> SEQ ID NO 324
<211> LENGTH: 36
<212> TYPE: PRT
<213> ORGANISM: Conus episcopatus
<220> FEATURE:
<221> NAME/KEY: PEPTIDE
<222> LOCATION: (1)..(36)
<223> OTHER INFORMATION: Xaa at residue 36 is Pro or hydroxy-Pro; Xaa at
      residue 23 is Tyr, 125I-Tyr, mono-iodo-Tyr, di-iodo-Tyr, O-sulpho-
      Tyr or O-phospho-Ty

<400> SEQUENCE: 324
```

```
Gly Met Cys Ser Arg Ile Gly Gln Gly Cys Gly Gln Asp Ser Asp Cys
 1               5                  10                  15

Cys Gly Asp Met Cys Cys Xaa Gly Gln Ile Cys Ala Met Thr Phe Ala
                20                  25                  30

Ala Cys Gly Xaa
            35
```

<210> SEQ ID NO 325
<211> LENGTH: 434
<212> TYPE: DNA
<213> ORGANISM: Conus episcopatus

<400> SEQUENCE: 325

```
gctatcagcc ttcgcagcag tcgaggcttt aaaatcctaa tcgtagaaga aggcaaaaac    60
gtctggtgtc agtatgaagc tgtgtgtgac gtttcttctt attctggtga ttctgccatc   120
ggtaactggg gagaagtcta gcaagcgtac actgagtggt gctgctctga gaggcgattg   180
gggaatgtgc tcaggcatag acaaggatg cggacaagat tccggctgct gtggggatat    240
gtgctgttat ggccaaatat gcgctatgac tttcgcggca tgtggtccct aacttctttc    300
ccttctagtg cgatggacct aggcgtgctg gcctagcggc cgactcgctc agtatgcctg    360
atctgtccga gtgaaacgac ctgacacgat ccgtcgtatt cctttgccaa gagccagcta    420
ggccatgcct aggt                                                     434
```

<210> SEQ ID NO 326
<211> LENGTH: 72
<212> TYPE: PRT
<213> ORGANISM: Conus episcopatus

<400> SEQUENCE: 326

```
Met Lys Leu Cys Val Thr Phe Leu Leu Ile Leu Val Ile Leu Pro Ser
 1               5                  10                  15

Val Thr Gly Glu Lys Ser Ser Lys Arg Thr Leu Ser Gly Ala Ala Leu
                20                  25                  30

Arg Gly Asp Trp Gly Met Cys Ser Gly Ile Gly Gln Gly Cys Gly Gln
            35                  40                  45

Asp Ser Gly Cys Cys Gly Asp Met Cys Tyr Gly Gln Ile Cys Ala
        50                  55                  60

Met Thr Phe Ala Ala Cys Gly Pro
 65                  70
```

<210> SEQ ID NO 327
<211> LENGTH: 39
<212> TYPE: PRT
<213> ORGANISM: Conus episcopatus
<220> FEATURE:
<221> NAME/KEY: PEPTIDE
<222> LOCATION: (1)..(39)
<223> OTHER INFORMATION: Xaa at residue 39 is Pro or hydroxy-Pro; Xaa at
      residue 3 is Trp or bromo-Trp; Xaa at residue 26 is Tyr, 125I-Tyr,
      mono-iodo-Tyr, di-iodo-Tyr, O-sulpho-Tyr or O-phospho-Ty

<400> SEQUENCE: 327

```
Gly Asp Xaa Gly Met Cys Ser Gly Ile Gly Gln Gly Cys Gly Gln Asp
 1               5                  10                  15

Ser Gly Cys Cys Gly Asp Met Cys Cys Xaa Gly Gln Ile Cys Ala Met
                20                  25                  30

Thr Phe Ala Ala Cys Gly Xaa
            35
```

```
<210> SEQ ID NO 328
<211> LENGTH: 435
<212> TYPE: DNA
<213> ORGANISM: Conus episcopatus

<400> SEQUENCE: 328
gctatcagca cttcgcagca gtcgaggctt taaaatccaa atcgtagaag aaggcaaaaa      60
cgtctggtga cagtatgaag ctgtgtgtga cgtttcttct tattctggtg attctgccat     120
cggtaactgg ggagaagtct agcaagcgta cactgagtgg tgctgctcta agaggcgatt     180
ggggaatgtg ctcaggcata ggacaaggat gcggacaaga ttccaactgc tgtgggata      240 agtgctgtta tggccaaata tgcgctatga cttcgcggc atgtggtccc taacttcttt     300
cccttctagt gcgatggacc taggcgtgct ggcctagcgg ccgactcgcc cagtatgcct     360
gatctgtccg agtgaaacga cctgacacga tccgtcgtat tcctttgcca agagccagct     420
aggccatgcc taggt                                                      435

<210> SEQ ID NO 329
<211> LENGTH: 72
<212> TYPE: PRT
<213> ORGANISM: Conus episcopatus

<400> SEQUENCE: 329

Met Lys Leu Cys Val Thr Phe Leu Leu Ile Leu Val Ile Leu Pro Ser
1               5                   10                  15

Val Thr Gly Glu Lys Ser Ser Lys Arg Thr Leu Ser Gly Ala Ala Leu
            20                  25                  30

Arg Gly Asp Trp Gly Met Cys Ser Gly Ile Gly Gln Gly Cys Gly Gln
        35                  40                  45

Asp Ser Asn Cys Cys Gly Asp Lys Cys Cys Tyr Gly Gln Ile Cys Ala
    50                  55                  60

Met Thr Phe Ala Ala Cys Gly Pro
65                  70

<210> SEQ ID NO 330
<211> LENGTH: 39
<212> TYPE: PRT
<213> ORGANISM: Conus episcopatus
<220> FEATURE:
<221> NAME/KEY: PEPTIDE
<222> LOCATION: (1)..(39)
<223> OTHER INFORMATION: Xaa at residue 39 is Pro or hydroxy-Pro; Xaa at
      residue 3 is Trp or bromo-Trp; Xaa at residue 26 is Tyr, 125I-Tyr,
      mono-iodo-Tyr, di-iodo-Tyr, O-sulpho-Tyr or O-phospho-Ty

<400> SEQUENCE: 330

Gly Asp Xaa Gly Met Cys Ser Gly Ile Gly Gln Gly Cys Gly Gln Asp
1               5                   10                  15

Ser Asn Cys Cys Gly Asp Lys Cys Cys Xaa Gly Gln Ile Cys Ala Met
            20                  25                  30

Thr Phe Ala Ala Cys Gly Xaa
        35

<210> SEQ ID NO 331
<211> LENGTH: 434
<212> TYPE: DNA
<213> ORGANISM: Conus episcopatus

<400> SEQUENCE: 331
gctatagcac ttcgcagcag tcgaggcttt aaaatccaaa tcgtagaaga gggcaaaaac      60
```

```
gtctggtgtc agtatgaagc tgtgtgtgac gtttcttctt attctggtga ttctgccatc    120
agtaactggg gagaagtcta gcaagcgtac actgagtggt gctgctctga gaggcgatcg    180
gggaatgtgc tctcgcatag gacaaggatg cggacaagat tccaactgct gtggggatat    240
gtgctgttat ggccaaatat gcgctatgac tttcgcggca tgtggtccct aacttctttc    300
ccttctagtg cgatggacct aggcgtgctg gcctagcggc cgactcgctc agtatgcctg    360
atctgtccga gtgaaacgac ctgacacgat ccgtcgtatt cctttgccaa gagcaagcta    420
ggccatgcct aggt    434
```

<210> SEQ ID NO 332
<211> LENGTH: 72
<212> TYPE: PRT
<213> ORGANISM: Conus episcopatus

<400> SEQUENCE: 332

```
Met Lys Leu Cys Val Thr Phe Leu Leu Ile Leu Val Ile Leu Pro Ser
1               5                   10                  15

Val Thr Gly Glu Lys Ser Ser Lys Arg Thr Leu Ser Gly Ala Ala Leu
            20                  25                  30

Arg Gly Asp Arg Gly Met Cys Ser Arg Ile Gly Gln Gly Cys Gly Gln
        35                  40                  45

Asp Ser Asn Cys Cys Gly Asp Met Cys Cys Tyr Gly Gln Ile Cys Ala
    50                  55                  60

Met Thr Phe Ala Ala Cys Gly Pro
65                  70
```

<210> SEQ ID NO 333
<211> LENGTH: 36
<212> TYPE: PRT
<213> ORGANISM: Conus episcopatus
<220> FEATURE:
<221> NAME/KEY: PEPTIDE
<222> LOCATION: (1)..(36)
<223> OTHER INFORMATION: Xaa at residue 36 is Pro or hydroxy-Pro; Xaa at
      residue 23 is Tyr, 125I-Tyr, mono-iodo-Tyr, di-iodo-Tyr, O-sulpho-
      Tyr or O-phospho-Ty

<400> SEQUENCE: 333

```
Gly Met Cys Ser Arg Ile Gly Gln Gly Cys Gly Gln Asp Ser Asn Cys
1               5                   10                  15

Cys Gly Asp Met Cys Cys Xaa Gly Gln Ile Cys Ala Met Thr Phe Ala
            20                  25                  30

Ala Cys Gly Xaa
        35
```

<210> SEQ ID NO 334
<211> LENGTH: 435
<212> TYPE: DNA
<213> ORGANISM: Conus episcopatus

<400> SEQUENCE: 334

```
gctatcagca cttcgcagca gtcgaggctt taaaatccaa atcgcagaag aaggcaaaaa     60
cgtctggtgt cagtatgaag ctgtgtgtgt cgtttcttct tattctggtg attctgccat    120
cggtaactgg ggagaagtct agcaagcgta cactgagtgg tgctgctctg agaggcgatc    180
ggggaatgtg ctcaggcata ggacaaggat gcggacaaga ttccggctgc tgtgggata    240 tgtgctgtta tggccaaata tgcgctatga ctttcgcggc atgtggtccc taacttcttt    300
```

-continued

```
cccttctagt gcgatggacc taggcgtgct ggcctagcgg ccgactcgct cagtatgcct    360
gatctgtccg agtgaaacga cctgacacga tccgtcgtat tcctttgcca agagccagct    420
aggccatgcc taggt                                                    435
```

<210> SEQ ID NO 335
<211> LENGTH: 72
<212> TYPE: PRT
<213> ORGANISM: Conus episcopatus

<400> SEQUENCE: 335

```
Met Lys Leu Cys Val Ser Phe Leu Leu Ile Leu Val Ile Leu Pro Ser
1               5                   10                  15

Val Thr Gly Glu Lys Ser Ser Lys Arg Thr Leu Ser Gly Ala Ala Leu
            20                  25                  30

Arg Gly Asp Arg Gly Met Cys Ser Gly Ile Gly Gln Gly Cys Gly Gln
        35                  40                  45

Asp Ser Gly Cys Cys Gly Asp Met Cys Cys Tyr Gly Gln Ile Cys Ala
    50                  55                  60

Met Thr Phe Ala Ala Cys Gly Pro
65                  70
```

<210> SEQ ID NO 336
<211> LENGTH: 36
<212> TYPE: PRT
<213> ORGANISM: Conus episcopatus
<220> FEATURE:
<221> NAME/KEY: PEPTIDE
<222> LOCATION: (1)..(36)
<223> OTHER INFORMATION: Xaa at residue 36 is Pro or hydroxy-Pro; Xaa at
      residue 23 is Tyr, 125I-Tyr, mono-iodo-Tyr, di-iodo-Tyr, O-sulpho-
      Tyr or O-phospho-Ty

<400> SEQUENCE: 336

```
Gly Met Cys Ser Gly Ile Gly Gln Gly Cys Gln Asp Ser Gly Cys
1               5                   10                  15

Cys Gly Asp Met Cys Cys Xaa Gly Gln Ile Cys Ala Met Thr Phe Ala
            20                  25                  30

Ala Cys Gly Xaa
        35
```

<210> SEQ ID NO 337
<211> LENGTH: 435
<212> TYPE: DNA
<213> ORGANISM: Conus episcopatus

<400> SEQUENCE: 337

```
gctatcagca cttcgcagca gtcgaggctt taaaatccta atcgtagaag aaggcaaaaa    60
cgtctggtgt cagtatgaag ctgtgtgtga cgtttcttct tattctggtg attctgccat    120
cagtaactgg ggagaagtct agcaagcgta cactgagtgg tgctgctctg agaggcgatc    180
ggggaatgtg ctctcgcata ggacaaggat gcggacaaga ttccgactgc tgtggggata    240
tgtgctgtca cggccaaata tgcgctatga ctttcgcggc atgtggtccc taacttcctt    300
cccttctagt gcgatggacc taggcgtgct ggcctagcgg ccgacacgct cagtatgcct    360
gatctgcccg agtgaaacga cctgacacga tccgtcgtat tcctttgcca agagccagct    420
aggccatgcc taggt                                                    435
```

<210> SEQ ID NO 338
<211> LENGTH: 72

-continued

<210> SEQ ID NO 338
<211> LENGTH: (not shown)
<212> TYPE: PRT
<213> ORGANISM: Conus episcopatus

<400> SEQUENCE: 338

Met Lys Leu Cys Val Thr Phe Leu Leu Ile Leu Val Ile Leu Pro Ser
1               5                   10                  15
Val Thr Gly Glu Lys Ser Ser Lys Arg Thr Leu Ser Gly Ala Ala Leu
            20                  25                  30
Arg Gly Asp Arg Gly Met Cys Ser Arg Ile Gly Gln Gly Cys Gly Gln
        35                  40                  45
Asp Ser Asp Cys Cys Gly Asp Met Cys His Gly Gln Ile Cys Ala
    50                  55                  60
Met Thr Phe Ala Ala Cys Gly Pro
65                  70

<210> SEQ ID NO 339
<211> LENGTH: 36
<212> TYPE: PRT
<213> ORGANISM: Conus episcopatus
<220> FEATURE:
<221> NAME/KEY: PEPTIDE
<222> LOCATION: (1)..(36)
<223> OTHER INFORMATION: Xaa at residue 36 is Pro or hydroxy-Pro

<400> SEQUENCE: 339

Gly Met Cys Ser Arg Ile Gly Gln Gly Cys Gly Gln Asp Ser Asp Cys
1               5                   10                  15
Cys Gly Asp Met Cys Cys His Gly Gln Ile Cys Ala Met Thr Phe Ala
            20                  25                  30
Ala Cys Gly Xaa
        35

<210> SEQ ID NO 340
<211> LENGTH: 435
<212> TYPE: DNA
<213> ORGANISM: Conus episcopatus

<400> SEQUENCE: 340
gctatcagca cttcgcagca gtcgaggctt taaaatccaa atcgtagaag aaggcaaaaa      60
cgtctggtga cagtatgaag ctgtgtgtga cgtttcttct tattctggtg attctgccat    120
cggtaactgg ggagaagtct agcaagcgta cactgagtgg tgctgctctg agaggcgatt    180
gggaatgtg ctcaggcata ggacaaggat gcggacaaga ttccaactgc tgtgggata     240
tgtgctgtca tggccaaata tgcgctatga cttccgcggc atgtggtccc taacttcttt    300
cccttctagt gcgatggacc taggcgtgct ggcctagcgg ccgactcgct cagtatgcct    360
gatctgtccg agtgaaacga cctgacacga tccgtcgtat tcctttgcca agagcaagct    420
aggccatgcc taggt                                                     435

<210> SEQ ID NO 341
<211> LENGTH: 72
<212> TYPE: PRT
<213> ORGANISM: Conus episcopatus

<400> SEQUENCE: 341

Met Lys Leu Cys Val Thr Phe Leu Leu Ile Leu Val Ile Leu Pro Ser
1               5                   10                  15
Val Thr Gly Glu Lys Ser Ser Lys Arg Thr Leu Ser Gly Ala Ala Leu
            20                  25                  30

Arg Gly Asp Trp Gly Met Cys Ser Gly Ile Gly Gln Gly Cys Gly Gln
        35                  40                  45

Asp Ser Asn Cys Cys Gly Asp Met Cys Cys His Gly Gln Ile Cys Ala
    50                  55                  60

Met Thr Phe Ala Ala Cys Gly Pro
65                  70

<210> SEQ ID NO 342
<211> LENGTH: 39
<212> TYPE: PRT
<213> ORGANISM: Conus episcopatus
<220> FEATURE:
<221> NAME/KEY: PEPTIDE
<222> LOCATION: (1)..(39)
<223> OTHER INFORMATION: Xaa at residue 39 is Pro or hydroxy-Pro; Xaa at
      residue 3 is Trp or bromo-Tr

<400> SEQUENCE: 342

Gly Asp Xaa Gly Met Cys Ser Gly Ile Gly Gln Gly Cys Gly Gln Asp
1               5                   10                  15

Ser Asn Cys Cys Gly Asp Met Cys Cys His Gly Gln Ile Cys Ala Met
            20                  25                  30

Thr Phe Ala Ala Cys Gly Xaa
        35

<210> SEQ ID NO 343
<211> LENGTH: 244
<212> TYPE: DNA
<213> ORGANISM: Conus striolatus

<400> SEQUENCE: 343
atgatgtttc gtgtgacgtc agtcagctgt tcttgctgg tcattgttct tctgaacttg      60
gttgtgctta ccgatgcctg tcaccatgaa gggttgccct gctcaagtga tgacggttgc     120
tgtggcatgg aatgctgcaa tggggtttgc tcatcaagtt gtggaaacgg gaggcgacgc    180
caagttccgt tgaaatcatt tggccaacgt cgatatgttt gaccagaggt ctgctgcttc    240
tcgt                                                                  244

<210> SEQ ID NO 344
<211> LENGTH: 73
<212> TYPE: PRT
<213> ORGANISM: Conus striolatus

<400> SEQUENCE: 344

Met Met Phe Arg Val Thr Ser Val Ser Cys Phe Leu Leu Val Ile Val
1               5                   10                  15

Leu Leu Asn Leu Val Val Leu Thr Asp Ala Cys His His Glu Gly Leu
            20                  25                  30

Pro Cys Ser Ser Asp Asp Gly Cys Cys Gly Met Glu Cys Cys Asn Gly
        35                  40                  45

Val Cys Ser Ser Ser Cys Gly Asn Gly Arg Arg Arg Gln Val Pro Leu
    50                  55                  60

Lys Ser Phe Gly Gln Arg Arg Tyr Val
65                  70

<210> SEQ ID NO 345
<211> LENGTH: 30
<212> TYPE: PRT
<213> ORGANISM: Conus striolatus
<220> FEATURE:
<221> NAME/KEY: PEPTIDE

```
<222> LOCATION: (1)..(30)
<223> OTHER INFORMATION: Xaa at residue 7 is Pro or hydroxy-Pro; Xaa at
      residue3 4 and 18 is Glu or gamma-carboxy-Gl

<400> SEQUENCE: 345

Cys His His Xaa Gly Leu Xaa Cys Ser Ser Asp Asp Gly Cys Cys Gly
1               5                   10                  15

Met Xaa Cys Cys Asn Gly Val Cys Ser Ser Ser Cys Gly Asn
            20                  25                  30

<210> SEQ ID NO 346
<211> LENGTH: 222
<212> TYPE: DNA
<213> ORGANISM: Conus striolatus

<400> SEQUENCE: 346
atgatgtttc gtgtgacgtc agtcctgctg gtcatcgttc ttctgaattt ggttgtgctt      60
accaatgcct gccacatgga ttgctcaaag atgacttgct gtagcggtat atgctgtttt     120
tactgcggac gtcctatgtg tcctggcact aggagggcgc tactccaaag attagtggga     180
catcaacgtt gatatgttgc ccagaggtct gctgcttctc gt                        222

<210> SEQ ID NO 347
<211> LENGTH: 63
<212> TYPE: PRT
<213> ORGANISM: Conus striolatus

<400> SEQUENCE: 347

Met Met Phe Arg Val Thr Ser Val Leu Leu Val Ile Val Leu Leu Asn
1               5                   10                  15

Leu Val Val Leu Thr Asn Ala Cys His Met Asp Cys Ser Lys Met Thr
            20                  25                  30

Cys Cys Ser Gly Ile Cys Cys Phe Tyr Cys Gly Arg Pro Met Cys Pro
        35                  40                  45

Gly Thr Arg Arg Ala Leu Leu Gln Arg Leu Val Gly His Gln Arg
    50                  55                  60

<210> SEQ ID NO 348
<211> LENGTH: 40
<212> TYPE: PRT
<213> ORGANISM: Conus striolatus
<220> FEATURE:
<221> NAME/KEY: PEPTIDE
<222> LOCATION: (1)..(40)
<223> OTHER INFORMATION: Xaa at residues 22 and 25 is Pro or hydroxy-
      Pro; Xaa at residue 18 is Tyr, 125I-Tyr, mono-iodo-Tyr, di-iodo-
      Tyr, O-sulpho-Tyr or O-phospho-Ty

<400> SEQUENCE: 348

Cys His Met Asp Cys Ser Lys Met Thr Cys Cys Ser Gly Ile Cys Cys
1               5                   10                  15

Phe Xaa Cys Gly Arg Xaa Met Cys Xaa Gly Thr Arg Arg Ala Leu Leu
            20                  25                  30

Gln Arg Leu Val Gly His Gln Arg
        35                  40

<210> SEQ ID NO 349
<211> LENGTH: 243
<212> TYPE: DNA
<213> ORGANISM: Conus episcopatus

<400> SEQUENCE: 349
```

```
atgatgtttc gtgtgacgtc agtcggctgt ttactgctgg tcatcgtttt cctgaacttg     60
gttgtgccta ccaatgcctg cgctggtcaa gaagagccct gcagttcacg tagcgattgc    120
tgtggttcag ttggttgctg ttttgggcag tgcgaaagtc cgtgccgaat gcctgggaag    180
aggaaactcc gacaattctt tcgacaacgt tgatatgttg cccagaggtc tgctgcttct    240
cgt                                                                  243
```

<210> SEQ ID NO 350
<211> LENGTH: 70
<212> TYPE: PRT
<213> ORGANISM: Conus episcopatus

<400> SEQUENCE: 350

Met Met Phe Arg Val Thr Ser Val Gly Cys Leu Leu Leu Val Ile Val
1               5                   10                  15

Phe Leu Asn Leu Val Val Pro Thr Asn Ala Cys Ala Gly Gln Glu Glu
                20                  25                  30

Pro Cys Ser Ser Arg Ser Asp Cys Cys Gly Ser Val Gly Cys Cys Phe
            35                  40                  45

Gly Gln Cys Glu Ser Pro Cys Arg Met Pro Gly Lys Arg Lys Leu Arg
        50                  55                  60

Gln Phe Phe Arg Gln Arg
65                  70

<210> SEQ ID NO 351
<211> LENGTH: 32
<212> TYPE: PRT
<213> ORGANISM: Conus episcopatus
<220> FEATURE:
<221> NAME/KEY: PEPTIDE
<222> LOCATION: (1)..(32)
<223> OTHER INFORMATION: Xaa at residues 7, 28 and 32 is Pro or hydroxy-
      Pro; Xaa at residues 5, 6 and 26 is Glu or gamma-carboxy-Gl

<400> SEQUENCE: 351

Cys Ala Gly Gln Xaa Xaa Xaa Cys Ser Ser Arg Ser Asp Cys Cys Gly
1               5                   10                  15

Ser Val Gly Cys Cys Phe Gly Gln Cys Xaa Ser Xaa Cys Arg Met Xaa
                20                  25                  30

<210> SEQ ID NO 352
<211> LENGTH: 243
<212> TYPE: DNA
<213> ORGANISM: Conus episcopatus

<400> SEQUENCE: 352

```
atgatgtttc gtgtgacgtc agtcggctgt ttactgctgg ccatcgtttt cctgaacttg     60
gttgtgccta ccaatgcctg cgctggtcaa gaagagccct gcagttcacg tgacgattgc    120
tgtggttcag ttggttgctg ttttgggcag tgcgaaactc cgtgccgaat gcctgggaaa    180
aggaaactcc gacaattctt tcgacaacgt tgatatgttg cccagaggtc tgctgcttct    240
cgt                                                                  243
```

<210> SEQ ID NO 353
<211> LENGTH: 70
<212> TYPE: PRT
<213> ORGANISM: Conus episcopatus

<400> SEQUENCE: 353

Met Met Phe Arg Val Thr Ser Val Gly Cys Leu Leu Leu Ala Ile Val

```
                1               5              10              15

Phe Leu Asn Leu Val Val Pro Thr Asn Ala Cys Ala Gly Gln Glu Glu
                       20                  25                  30

Pro Cys Ser Ser Arg Asp Asp Cys Cys Gly Ser Val Gly Cys Cys Phe
                35                  40                  45

Gly Gln Cys Glu Thr Pro Cys Arg Met Pro Gly Lys Arg Lys Leu Arg
            50                  55                  60

Gln Phe Phe Arg Gln Arg
65                  70

<210> SEQ ID NO 354
<211> LENGTH: 32
<212> TYPE: PRT
<213> ORGANISM: Conus episcopatus
<220> FEATURE:
<221> NAME/KEY: PEPTIDE
<222> LOCATION: (1)..(32)
<223> OTHER INFORMATION: Xaa at residues 7, 28 and 32 is Pro or hydroxy-
      Pro; Xaa at residues 5, 6 and 26 is Glu or gamma-carboxy-Gl

<400> SEQUENCE: 354

Cys Ala Gly Gln Xaa Xaa Xaa Cys Ser Ser Arg Asp Asp Cys Cys Gly
1               5                   10                  15

Ser Val Gly Cys Cys Phe Gly Gln Cys Xaa Thr Xaa Cys Arg Met Xaa
                20                  25                  30

<210> SEQ ID NO 355
<211> LENGTH: 243
<212> TYPE: DNA
<213> ORGANISM: Conus episcopatus

<400> SEQUENCE: 355
atgatgtttc gtgtgacgtc agtcggctgt ttcctgctgg ccatcgtttt cctgaacttg      60
attgtgccta ccaatgcctg cgcaggtcaa gaagagccct gcagttcacg tagtgattgc     120
tgtggttcag ttggttgctg ttttgggcag tgcgaaagtc cgtgccgaat gattgggaag     180
aggaaactcc gacaattctt tcgacaacgt tgatatgttg cccagaggtc tgctgcttct     240
cgt                                                                   243

<210> SEQ ID NO 356
<211> LENGTH: 70
<212> TYPE: PRT
<213> ORGANISM: Conus episcopatus

<400> SEQUENCE: 356

Met Met Phe Arg Val Thr Ser Val Gly Cys Phe Leu Leu Ala Ile Val
1               5                   10                  15

Phe Leu Asn Leu Ile Val Pro Thr Asn Ala Cys Ala Gly Gln Glu Glu
                       20                  25                  30

Pro Cys Ser Ser Arg Ser Asp Cys Cys Gly Ser Val Gly Cys Cys Phe
                35                  40                  45

Gly Gln Cys Glu Ser Pro Cys Arg Met Ile Gly Lys Arg Lys Leu Arg
            50                  55                  60

Gln Phe Phe Arg Gln Arg
65                  70

<210> SEQ ID NO 357
<211> LENGTH: 32
<212> TYPE: PRT
<213> ORGANISM: Conus episcopatus
```

```
<220> FEATURE:
<221> NAME/KEY: PEPTIDE
<222> LOCATION: (1)..(32)
<223> OTHER INFORMATION: Xaa at residues 7 and 28 is Pro or hydroxy-Pro;
      Xaa at residues 5, 6 and 26 is Glu or gamma-carboxy-Gl

<400> SEQUENCE: 357

Cys Ala Gly Gln Xaa Xaa Xaa Cys Ser Ser Arg Ser Asp Cys Cys Gly
1               5                  10                  15

Ser Val Gly Cys Cys Phe Gly Gln Cys Xaa Ser Xaa Cys Arg Met Ile
            20                  25                  30

<210> SEQ ID NO 358
<211> LENGTH: 243
<212> TYPE: DNA
<213> ORGANISM: Conus episcopatus

<400> SEQUENCE: 358
atgatgtttc gtgtgacgtc agtcggctgt ttcctgctgg tcatcctttc tctgaacttg      60
gttgtgctta ccaatgcctg cctttctgaa ggatctccct gcagtatgag tggcagttgc     120
tgtcacaaga gttgctgtcg ttcgacttgc acttttccgt gtctaattcc tgggaagagg     180
gcgaaactcc gagaattctt tcgacaacgt tgatatgttg cccagaggtc tgctgcttct     240
cgt                                                                   243

<210> SEQ ID NO 359
<211> LENGTH: 70
<212> TYPE: PRT
<213> ORGANISM: Conus episcopatus

<400> SEQUENCE: 359

Met Met Phe Arg Val Thr Ser Val Gly Cys Phe Leu Leu Val Ile Leu
1               5                  10                  15

Ser Leu Asn Leu Val Val Leu Thr Asn Ala Cys Leu Ser Glu Gly Ser
            20                  25                  30

Pro Cys Ser Met Ser Gly Ser Cys Cys His Lys Ser Cys Cys Arg Ser
        35                  40                  45

Th

-continued

```
<400> SEQUENCE: 361
atgatgtttc gtgtgacgtc agtcggctgt ttcctgctgg tcatcctttc tctgaacttg      60
gttatgctta ccaatgcctg cccttctgaa ggatctccct gcagtatgag tggcagttgc     120
tgtcacaaga gttgctgtcg ttcgacttgc acttttccgt gtctaattcc tgggaagagg     180
gcgaaactcc gagaattctt tcgacaacgt tgatatgttg cccagaggtc tgctgcttct     240
cgt                                                                    243

<210> SEQ ID NO 362
<211> LENGTH: 70
<212> TYPE: PRT
<213> ORGANISM: Conus episcopatus

<400> SEQUENCE: 362

Met Met Phe Arg Val Thr Ser Val Gly Cys Phe Leu Leu Val Ile Leu
1               5                   10                  15

Ser Leu Asn Leu Val Met Leu Thr Asn Ala Cys Pro Ser Glu Gly Ser
            20                  25                  30

Pro Cys Ser Met Ser Gly Ser Cys Cys His Lys Ser Cys Cys Arg Ser
        35                  40                  45

Thr Cys Thr Phe Pro Cys Leu Ile Pro Gly Lys Arg Ala Lys Leu Arg
    50                  55                  60

Glu Phe Phe Arg Gln Arg
65                  70

<210> SEQ ID NO 363
<211> LENGTH: 31
<212> TYPE: PRT
<213> ORGANISM: Conus episcopatus
<220> FEATURE:
<221> NAME/KEY: PEPTIDE
<222> LOCATION: (1)..(31)
<223> OTHER INFORMATION: Xaa at residues 2, 27 and 31 is Pro or hydroxy-
      Pro; Xaa at residue 4 is Glu or gamma-carboxy-Gl

<400> SEQUENCE: 363

Cys Xaa Ser Xaa Gly Ser Pro Cys Ser Met Ser Gly Ser Cys Cys His
1               5                   10                  15

Lys Ser Cys Cys Arg Ser Thr Cys Thr Phe Xaa Cys Leu Ile Xaa
            20                  25                  30

<210> SEQ ID NO 364
<211> LENGTH: 32
<212> TYPE: PRT
<213> ORGANISM: Conus brunneus

<400> SEQUENCE: 364

Cys Gly Tyr Val Gly Gln Ala Cys Asp Asp Ser Asp Cys Cys Gly
1               5                   10                  15

Ser Ile Cys Cys Val Ala Gly Glu Cys Val Ile Thr Gly Arg Arg Cys
            20                  25                  30

<210> SEQ ID NO 365
<211> LENGTH: 36
<212> TYPE: PRT
<213> ORGANISM: Conus betulinus

<400> SEQUENCE: 365

Met Cys Leu Ser Leu Gly Gln Arg Cys Glu Arg His Ser Asn Cys Cys
1               5                   10                  15
```

Gly Tyr Leu Cys Cys Phe Tyr Asp Lys Cys Val Val Thr Ala Ile Gly
            20                  25                  30

Cys Gly His Tyr
        35

<210> SEQ ID NO 366
<211> LENGTH: 35
<212> TYPE: PRT
<213> ORGANISM: Conus betulinus

<400> SEQUENCE: 366

Met Cys Ser Phe Leu Gly Gln Arg Cys Glu Arg His Phe Asn Cys Cys
1               5                   10                  15

Gly Asp Leu Cys Cys Phe Asp Asp Met Cys Leu Val Ala Ala Ile Gly
            20                  25                  30

Cys Gly Tyr
        35

<210> SEQ ID NO 367
<211> LENGTH: 33
<212> TYPE: PRT
<213> ORGANISM: Conus betulinus

<400> SEQUENCE: 367

Ile Cys Ser Phe Leu Gly Cys Glu Arg His Phe Asn Cys

-continued

<400> SEQUENCE: 370

Gly His Val Pro Cys Gly Lys Asp Gly Arg Lys Cys Gly Tyr His Thr
1               5                   10                  15
His Cys Cys Asn Cys Cys Leu Ser Gly Ile Cys Lys Pro Ser Thr Ser
                20                  25                  30
Leu Ile Gly Cys Ser Thr Ser Ser Phe Thr
        35                  40

<210> SEQ ID NO 371
<211> LENGTH: 36
<212> TYPE: PRT
<213> ORGANISM: Conus betulinus

<400> SEQUENCE: 371

Met Cys Leu Ser Leu Gly Gln Arg Cys Glu Arg His Ser Asn Cys Cys
1               5                   10                  15
Gly Tyr Leu Cys Cys Phe Tyr Asp Lys Cys Val Val Thr Ala Val Gly
                20 25 30

Cys Gly His Tyr
35

<210> SEQ ID NO 372
<211> LENGTH: 36
<212> TYPE: PRT
<213> ORGANISM: Conus betulinus

<400> SEQUENCE: 372

Met Cys Leu Ser Leu Gly Gln Arg Cys Glu Arg His Ser Asn Cys Cys
1 5 10 15

Gly Tyr Leu Cys Cys Phe Tyr Asp Lys Cys Val Met Thr Ala Ile Gly
20 25 30

Cys Gly His Tyr
35

<210> SEQ ID NO 373
<211> LENGTH: 40
<212> TYPE: PRT
<213> ORGANISM: Conus caracteristicus

<400> SEQUENCE: 373

Gly His Trp Cys Gly Tyr Pro Gly Glu Arg Gly Cys Arg Tyr His Ser
1 5 10 15

Gln Cys Cys Gly Asp Met Cys Cys Tyr Asp Arg Lys Cys Val Ala Thr
20 25 30

Ala Met Pro Cys Asp Phe Pro Tyr
35 40

<210> SEQ ID NO 374
<211> LENGTH: 44
<212> TYPE: PRT
<213> ORGANISM: Conus caracteristicus

<400> SEQUENCE: 374

Gly Pro Ser Phe Cys Lys Ala Asp Glu Lys Pro Cys Lys Tyr His Ala
1 5 10 15

Asp Cys Cys Asn Cys Cys Leu Gly Gly Ile Cys Lys Pro Ser Thr Ser
20 25 30

Trp Ile Gly Cys Ser Thr Asn Val Phe Leu Thr Arg
35 40

-continued

<210> SEQ ID NO 375
<211> LENGTH: 40
<212> TYPE: PRT
<213> ORGANISM: Conus caracteristicus

<400> SEQUENCE: 375

Gly Pro Arg Cys Trp Val Gly Arg Val His Cys Thr Tyr His Lys Asp
1               5                   10                  15

Cys Cys Pro Ser Val Cys Cys Phe Lys Gly Arg Cys Lys Pro Gln Ser
            20                  25                  30

Trp Gly Cys Trp Ser Gly Pro Thr
        35                  40

<210> SEQ ID NO 376
<211> LENGTH: 46
<212> TYPE: PRT
<213> ORGANISM: Conus caracteristicus

<400> SEQUENCE: 376

Gly Pro Ser Phe Cys Lys Ala Asp Glu Lys Pro Cys Glu Tyr His Ala
1               5                   10                  15

Asp Cys Cys Asn Cys Cys Leu Ser Gly Ile Cys Ala Pro Ser Thr Asn
            20                  25                  30

Trp Ile Leu Pro Gly Cys Ser Thr Ser Ser Phe Phe Lys Ile
        35                  40                  45

<210> SEQ ID NO 377
<211> LENGTH: 46
<212> TYPE: PRT
<213> ORGANISM: Conus caracteristicus

<400> SEQUENCE: 377

Gly Pro Ser Phe Cys Lys Ala Asn Gly Lys Pro Cys Ser Tyr His Ala
1               5                   10                  15

Asp Cys Cys Asn Cys Cys Leu Ser Gly Ile Cys Lys Pro Ser Thr Asn
            20                  25                  30

Val Ile Leu Pro Gly Cys Ser Thr Ser Ser Phe Phe Arg Ile
        35                  40                  45

<210> SEQ ID NO 378
<211> LENGTH: 40
<212> TYPE: PRT
<213> ORGANISM: Conus caracteristicus

<400> SEQUENCE: 378

Gly His Trp Cys Gly Tyr Leu Gly Glu Arg Gly Cys Arg Tyr His Ser
1               5                   10                  15

Gln Cys Cys Gly Asp Met Cys Cys Tyr Asp Arg Lys Cys Val Val Thr
            20                  25                  30

Ala Met Pro Cys Asp Phe Pro Tyr
        35                  40

<210> SEQ ID NO 379
<211> LENGTH: 40
<212> TYPE: PRT
<213> ORGANISM: Conus caracteristicus

<400> SEQUENCE: 379

Gly His Trp Cys Gly Tyr Pro Gly Glu Arg Gly Cys Arg Tyr His Ser
1               5                   10                  15

```
Gln Cys Cys Gly Asp Met Cys Cys Tyr Asp Arg Lys Cys Val Val Thr
        20                  25                  30

Ala Met Pro Cys Asp Phe Pro Tyr
        35                  40

<210> SEQ ID NO 380
<211> LENGTH: 40
<212> TYPE: PRT
<213> ORGANISM: Conus caracteristicus

<400> SEQUENCE: 380

Gly His Trp Cys Gly Tyr Leu Gly Glu Arg Gly Cys Arg Tyr His Ser
1               5                   10                  15

Gln Cys Cys Gly Asp Met Cys Cys Tyr Asp Arg Lys Cys Ala Val Thr
        20                  25                  30

Ala Met Pro Cys Asp Phe Pro Tyr
        35                  40

<210> SEQ ID NO 381
<211> LENGTH: 40
<212> TYPE: PRT
<213> ORGANISM: Conus caracteristicus

<400> SEQUENCE: 381

Gly His Trp Cys Gly Tyr Pro Gly Glu Arg Gly Cys Arg Tyr His Ser
1               5                   10                  15

Gln Cys Cys Gly Asp Met Cys Cys Tyr Asp Arg Met Cys Val Val Thr
        20                  25                  30

Ala Met Pro Cys Asp Phe Pro Tyr
        35                  40

<210> SEQ ID NO 382
<211> LENGTH: 40
<212> TYPE: PRT
<213> ORGANISM: Conus caracteristicus

<400> SEQUENCE: 382

Gly His Trp Cys Gly Tyr Leu Gly Glu Arg Gly Cys Arg Tyr His Gly
1               5                   10                  15

Gln Cys Cys Gly Asp Met Cys Cys Tyr Asp Arg Lys Cys Val Val Thr
        20                  25                  30

Ala Met Pro Cys Asp Phe Pro Tyr
        35                  40

<210> SEQ ID NO 383
<211> LENGTH: 46
<212> TYPE: PRT
<213> ORGANISM: Conus caracteristicus

<400> SEQUENCE: 383

Gly Pro Ser Phe Cys Lys Ala Asn Gly Lys Pro Cys Ser Tyr His Ala
1               5                   10                  15

Asp Cys Cys Asn Cys Cys Leu Ser Gly Ile Cys Glu Pro Ser Thr Asn
        20                  25                  30

Val Ile Leu Pro Gly Cys Ser Thr Ser Ser Phe Phe Arg Ile
        35                  40                  45

<210> SEQ ID NO 384
<211> LENGTH: 46
<212> TYPE: PRT
<213> ORGANISM: Conus caracteristicus
```

```
<400> SEQUENCE: 384

Gly Pro Ser Phe Cys Lys Ala Asp Glu Lys Pro Cys Glu Tyr His Ala
1               5                   10                  15

Asp Cys Cys Asn Cys Phe Leu Ser Gly Ile Cys Ala Pro Ser Thr Asn
            20                  25                  30

Trp Ile Leu Pro Gly Cys Ser Thr Ser Ser Phe Phe Lys Ile
        35                  40                  45

<210> SEQ ID NO 385
<211> LENGTH: 44
<212> TYPE: PRT
<213> ORGANISM: Conus caracteristicus

<400> SEQUENCE: 385

Gly Pro Ser Phe Cys Lys Ala Asp Glu Lys Pro Cys Lys Tyr His Ala
1               5                   10                  15

Asp Cys Cys Asn Cys Cys Leu Gly Gly Ile Cys Lys Pro Ser Thr Ser
            20                  25                  30

Trp Ile Gly Cys Ser Thr Asn Val Phe Leu Thr Arg
        35                  40

<210> SEQ ID NO 386
<211> LENGTH: 37
<212> TYPE: PRT
<213> ORGANISM: Conus emaciatus

<400> SEQUENCE: 386

Gly Ala Cys Ser Asp Thr Gly Gln Gly Cys Ile His His Phe Asn Cys
1               5                   10                  15

Cys Trp Asp Leu Cys Cys Tyr Gly Arg Thr Cys Gly Val Asn Val Met
            20                  25                  30

Gly Cys Pro Pro Phe
        35

<210> SEQ ID NO 387
<211> LENGTH: 37
<212> TYPE: PRT
<213> ORGANISM: Conus emaciatus

<400> SEQUENCE: 387

Gly Ala Cys Ser Asp Thr Gly Gln Gly Cys Ile His His Ser Asn Cys
1               5                   10                  15

Cys Trp Asp Leu Cys Cys Tyr Gly Arg Thr Cys Gly Val Asn Val Met
            20                  25                  30

Gly Cys Pro Pro Phe
        35

<210> SEQ ID NO 388
<211> LENGTH: 37
<212> TYPE: PRT
<213> ORGANISM: Conus emaciatus

<400> SEQUENCE: 388

Gly Thr Cys Ser Gly Ile Gly Gln Gly Cys Ile His His Leu Asn Cys
1               5                   10                  15

Cys Trp Asp Met Cys Cys Tyr Gly His Thr Cys Val Val Asn Ile Ile
            20                  25                  30

Gly Cys Pro Pro His
        35
```

<210> SEQ ID NO 389
<211> LENGTH: 37
<212> TYPE: PRT
<213> ORGANISM: Conus emaciatus

<400> SEQUENCE: 389

Gly Ala Cys Ser Asp Thr Gly Gln Gly Cys Ile His His Ser Asp Cys
1               5                   10                  15

Cys Trp Asp Leu Cys Cys Tyr Gly Arg Thr Cys Gly Val Asn Val Met
            20                  25                  30

Gly Cys Pro Pro Phe
        35

<210> SEQ ID NO 390
<211> LENGTH: 44
<212> TYPE: PRT
<213> ORGANISM: Conus figulinus

<400> SEQUENCE: 390

Gly His Val Ser Cys Gly Lys Asp Gly Arg Ala Cys Asp Tyr His Ala
1               5                   10                  15

Asp Cys Cys Asn Cys Cys Leu Gly Gly Ile Cys Lys Pro Ser Thr Ser
            20                  25                  30

Trp Ile Gly Cys Ser Thr Asn Val Phe Leu Thr Arg
        35                  40

<210> SEQ ID NO 391
<211> LENGTH: 46
<212> TYPE: PRT
<213> ORGANISM: Conus figulinus

<400> SEQUENCE: 391

Gly Pro Ser Phe Cys Lys Ala Asp Glu Lys Pro Cys Glu Tyr His Ala
1               5                   10                  15

Asp Cys Cys Asn Cys Cys Leu Ser Gly Ile Cys Ala Pro Ser Thr Asn
            20                  25                  30

Trp Ile Leu Pro Gly Cys Ser Thr Ser Ser Phe Phe Lys Ile
        35                  40                  45

<210> SEQ ID NO 392
<211> LENGTH: 51
<212> TYPE: PRT
<213> ORGANISM: Conus figulinus

<400> SEQUENCE: 392

Gly Pro Ser Phe Cys Lys Ala Asp Glu Lys Pro Cys Glu Tyr His Ala
1               5                   10                  15

Asp Cys Cys Asn Cys Cys Leu Ser Gly Ile Cys Ala Pro Ser Thr Asn
            20                  25                  30

Trp Ile Leu Pro Gly Cys Ser Thr Ser Ser Phe Phe Lys Ile Arg Leu
        35                  40                  45

Ser Ala Ser
    50

<210> SEQ ID NO 393
<211> LENGTH: 40
<212> TYPE: PRT
<213> ORGANISM: Conus figulinus

<400> SEQUENCE: 393

-continued

Gly Pro Arg Cys Trp Val Gly Arg Val His Cys Thr Tyr His Lys Asp
1               5                   10                  15

Cys Cys Pro Ser Val Cys Cys Phe Lys Gly Arg Cys Lys Pro Gln Ser
                20              25                  30

Trp Gly Cys Trp Ser Gly Pro Thr
        35                  40

<210> SEQ ID NO 394
<211> LENGTH: 41
<212> TYPE: PRT
<213> ORGANISM: Conus figulinus

<400> SEQUENCE: 394

Gly Cys Lys Lys Asp Arg Lys Pro Cys Ser Tyr His Ala Asp Cys Cys
1               5                   10                  15

Asn Cys Cys Leu Ser Gly Ile Cys Ala Pro Ser Thr Asn Trp Ile Leu
                20              25                  30

Pro Gly Cys Ser Thr Ser Thr Phe Thr
        35                  40

<210> SEQ ID NO 395
<211> LENGTH: 43
<212> TYPE: PRT
<213> ORGANISM: Conus figulinus

<400> SEQUENCE: 395

Gly Cys Lys Lys Asp Arg Lys Pro Cys Ser Tyr His Ala Asp Cys Cys
1               5                   10                  15

Asn Cys Cys Leu Ser Gly Ile Cys Ala Pro Ser Thr Asn Trp Ile Leu
                20              25                  30

Pro Gly Cys Ser Thr Ser Ser Phe Phe Lys Ile
        35                  40

<210> SEQ ID NO 396
<211> LENGTH: 46
<212> TYPE: PRT
<213> ORGANISM: Conus figulinus

<400> SEQUENCE: 396

Gly Pro Ser Ser Cys Lys Ala Asp Glu Glu Pro Cys Glu Tyr His Ala
1               5                   10                  15

Asp Cys Cys Asn Cys Cys Leu Ser Gly Ile Cys Ala Pro Ser Thr Asn
                20              25                  30

Trp Ile Leu Pro Gly Cys Ser Thr Ser Ser Phe Phe Lys Ile
        35                  40                  45

<210> SEQ ID NO 397
<211> LENGTH: 41
<212> TYPE: PRT
<213> ORGANISM: Conus radiatus
<220> FEATURE:
<221> NAME/KEY: PEPTIDE
<222> LOCATION: (1)..(41)
<223> OTHER INFORMATION: Xaa at residues 8 and 26 is hydroxy-Pro; Xaa at
      residue 30 is bromo-Tr

<400> SEQUENCE: 397

Gly Cys Lys Lys Asp Arg Lys Xaa Cys Ser Tyr His Ala Asp Cys Cys
1               5                   10                  15

Asn Cys Cys Leu Ser Gly Ile Cys Ala Xaa Ser Thr Asn Xaa Ile Leu
                20              25                  30

```
Pro Gly Cys Ser Thr Ser Thr Phe Thr
        35                  40
```

<210> SEQ ID NO 398
<211> LENGTH: 46
<212> TYPE: PRT
<213> ORGANISM: Conus radiatus
<220> FEATURE:
<221> NAME/KEY: PEPTIDE
<222> LOCATION: (1)..(46)
<223> OTHER INFORMATION: Xaa at residues 2, 11 and 29 is hydroxy-Pro

<400> SEQUENCE: 398

```
Gly Xaa Ser Phe Cys Lys Ala Asp Glu Lys Xaa Cys Glu Tyr His Ala
1               5                   10                  15

Asp Cys Cys Asn Cys Cys Leu Ser Gly Ile Cys Ala Xaa Ser Thr Asn
            20                  25                  30

Trp Ile Leu Pro Gly Cys Ser Thr Ser Ser Phe Phe Lys Ile
            35                  40                  45
```

<210> SEQ ID NO 399
<211> LENGTH: 46
<212> TYPE: PRT
<213> ORGANISM: Conus radiatus
<220> FEATURE:
<221> NAME/KEY: PEPTIDE
<222> LOCATION: (1)..(46)
<223> OTHER INFORMATION: Xaa at residues 2 and 29 is hydroxy-Pro

<400> SEQUENCE: 399

```
Gly Xaa Ser Phe Cys Lys Ala Asp Glu Lys Pro Cys Glu Tyr His Ala
1               5                   10                  15

Asp Cys Cys Asn Cys Cys Leu Ser Gly Ile Cys Ala Xaa Ser Thr Asn
            20                  25                  30

Trp Ile Leu Pro Gly Cys Ser Thr Ser Ser Phe Phe Lys Ile
            35                  40                  45
```

<210> SEQ ID NO 400
<211> LENGTH: 46
<212> TYPE: PRT
<213> ORGANISM: Conus radiatus
<220> FEATURE:
<221> NAME/KEY: PEPTIDE
<222> LOCATION: (1)..(46)
<223> OTHER INFORMATION: Xaa at residue 29 is hydroxy-Pro

<400> SEQUENCE: 400

```
Gly Pro Ser Phe Cys Lys Ala Asp Glu Lys Pro Cys Glu Tyr His Ala
1               5                   10                  15

Asp Cys Cys Asn Cys Cys Leu Ser Gly Ile Cys Ala Xaa Ser Thr Asn
            20                  25                  30

Trp Ile Leu Pro Gly Cys Ser Thr Ser Ser Phe Phe Lys Ile
            35                  40                  45
```

<210> SEQ ID NO 401
<211> LENGTH: 36
<212> TYPE: PRT
<213> ORGANISM: Conus lynceus

<400> SEQUENCE: 401

```
Asn Trp Ser Trp Cys Phe Asn Ala Gly Val Lys Cys Asp Asn His Ser
1               5                   10                  15

Asp Cys Cys Glu Asp Thr Cys Cys Tyr Asp Asn Thr Cys Val Val Ala
```

```
                    20                  25                  30

Val Ala Ala Cys
        35

<210> SEQ ID NO 402
<211> LENGTH: 38
<212> TYPE: PRT
<213> ORGANISM: Conus lynceus

<400> SEQUENCE: 402

Cys Tyr Phe Asn Gly Ala Pro Cys Asp Arg His Glu Glu Cys Cys Thr
1               5                   10                  15

Trp Gln Arg Cys Cys Phe Ser Gln Arg Cys Gly Thr Ala Thr Phe Gly
            20                  25                  30

Cys Trp Val Asp Pro Tyr
        35

<210> SEQ ID NO 403
<211> LENGTH: 36
<212> TYPE: PRT
<213> ORGANISM: Conus lynceus

<400> SEQUENCE: 403

Asn Trp Ser Trp Cys Phe Asn Ala Gly Val Glu Cys Asp Asn His Ser
1               5                   10                  15

Asp Cys Cys Glu Asp Thr Cys Cys Tyr Asp Asn Thr Cys Val Val Ala
            20                  25                  30

Val Ala Ala Cys
        35

<210> SEQ ID NO 404
<211> LENGTH: 36
<212> TYPE: PRT
<213> ORGANISM: Conus lynceus

<400> SEQUENCE: 404

Asn Trp Ser Trp Cys Phe Asn Ala Gly Val Lys Cys Asp Asn His Ser
1               5                   10                  15

Asp Cys Cys Ala Asp Thr Cys Cys Tyr Asp Asn Thr Cys Val Val Ala
            20                  25                  30

Val Ala Ala Cys
        35

<210> SEQ ID NO 405
<211> LENGTH: 38
<212> TYPE: PRT
<213> ORGANISM: Conus lynceus

<400> SEQUENCE: 405

Asn Trp Ser Trp Cys Ser Gly Ser Gly Glu Cys Asp Tyr His Ser
1               5                   10                  15

Glu Cys Cys Gly Glu Arg Cys Cys Ile Glu Ser Met Cys Ile Gly Asp
            20                  25                  30

Gly Val Ala Cys Trp Pro
        35

<210> SEQ ID NO 406
<211> LENGTH: 36
<212> TYPE: PRT
<213> ORGANISM: Conus lynceus
```

```
<400> SEQUENCE: 406

Asn Trp Ser Trp Cys Phe Asn Ala Gly Val Lys Cys Asp Asn His Ser
1               5                   10                  15

Asp Cys Cys Glu Asp Thr Cys Cys Tyr Asp Ser Thr Cys Val Val Ala
                20                  25                  30

Val Ala Ala Cys
        35

<210> SEQ ID NO 407
<211> LENGTH: 46
<212> TYPE: PRT
<213> ORGANISM: Conus magus

<400> SEQUENCE: 407

Gly Ala Val Pro Cys Gly Lys Asp Gly Arg Gln Cys Arg Asn His Ala
1               5                   10                  15

Asp Cys Cys Asn Cys Cys Pro Ile Gly Thr Cys Ala Pro Ser Thr Asn
                20                  25                  30

Trp Ile Leu Pro Gly Cys Ser Thr Gly Gln Phe Met Thr Arg
        35                  40                  45

<210> SEQ ID NO 408
<211> LENGTH: 44
<212> TYPE: PRT
<213> ORGANISM: Conus magus

<400> SEQUENCE: 408

Gly His Val Ser Cys Gly Lys Asp Gly Arg Ala Cys Asp Tyr His Ala
1               5                   10                  15

Asp Cys Cys Asn Cys Cys Leu Gly Gly Ile Cys Lys Pro Ser Thr Ser
                20                  25                  30

Trp Ile Gly Cys Ser Thr Asn Val Phe Leu Thr Arg
        35                  40

<210> SEQ ID NO 409
<211> LENGTH: 35
<212> TYPE: PRT
<213> ORGANISM: Conus magus

<400> SEQUENCE: 409

Thr Cys Ser Asn Lys Gly Gln Gln Cys Gly Asp Asp Ser Asp Cys Cys
1               5                   10                  15

Trp His Leu Cys Cys Val Asn Asn Lys Cys Ala His Leu Ile Leu Leu
                20                  25                  30

Cys Asn Leu
        35

<210> SEQ ID NO 410
<211> LENGTH: 46
<212> TYPE: PRT
<213> ORGANISM: Conus magus

<400> SEQUENCE: 410

Gly Pro Ser Phe Cys Lys Ala Asp Glu Lys Pro Cys Glu Tyr His Ala
1               5                   10                  15

Asp Cys Cys Asn Cys Cys Leu Ser Gly Ile Cys Ala Pro Ser Thr Asn
                20                  25                  30

Trp Ile Leu Pro Gly Cys Ser Thr Ser Ser Phe Phe Glu Ile
        35                  40                  45
```

<210> SEQ ID NO 411
<211> LENGTH: 46
<212> TYPE: PRT
<213> ORGANISM: Conus magus

<400> SEQUENCE: 411

Gly Pro Ser Phe Cys Lys Ala Asp Glu Lys Pro Cys Glu Tyr His Ala
1               5                   10                  15

Asp Cys Cys Asn Cys Cys Leu Ser Gly Ile Cys Ala Pro Ser Thr Asn
            20                  25                  30

Trp Ile Leu Pro Gly Cys Ser Thr Ser Ser Phe Phe Lys Thr
        35                  40                  45

<210> SEQ ID NO 412
<211> LENGTH: 42
<212> TYPE: PRT
<213> ORGANISM: Conus magus

<400> SEQUENCE: 412

Gly His Val Pro Cys Gly Lys Asp Gly Arg Lys Cys Gly Tyr His Ala
1               5                   10                  15

Asp Cys Cys Asn Cys Cys Leu Ser Gly Ile Cys Lys Pro Ser Thr Ser
            20                  25                  30

Trp Thr Gly Cys Ser Thr Ser Thr Phe Asp
        35                  40

<210> SEQ ID NO 413
<211> LENGTH: 35
<212> TYPE: PRT
<213> ORGANISM: Conus magus

<400> SEQUENCE: 413

Gly Met Cys Ser Leu Leu Gly Gln Arg Cys Gly Asp His Ser Asp Cys
1               5                   10                  15

Cys Trp Asp Met Cys Cys Ala Ser Glu Met Cys Val Val Thr Phe Leu
            20                  25                  30

Pro Cys Lys
        35

<210> SEQ ID NO 414
<211> LENGTH: 46
<212> TYPE: PRT
<213> ORGANISM: Conus magus

<400> SEQUENCE: 414

Gly Pro Ser Phe Cys Lys Ala Asn Gly Lys Pro Cys Ser Tyr His Ala
1               5                   10                  15

Asp Cys Cys Asn Cys Cys Leu Ser Gly Ile Cys Lys Pro Ser Thr Asn
            20                  25                  30

Val Ile Leu Pro Gly Cys Ser Thr Ser Ser Leu Phe Arg Ile
        35                  40                  45

<210> SEQ ID NO 415
<211> LENGTH: 35
<212> TYPE: PRT
<213> ORGANISM: Conus magus

<400> SEQUENCE: 415

Gly Thr Cys Ser Gly Arg Gly Gln Glu Cys Lys His Asp Ser Asp Cys
1               5                   10                  15

```
Cys Gly His Leu Cys Cys Ala Gly Ile Thr Cys Gln Phe Thr Tyr Ile
            20                  25                  30
Pro Cys Lys
        35

<210> SEQ ID NO 416
<211> LENGTH: 41
<212> TYPE: PRT
<213> ORGANISM: Conus magus

<400> SEQUENCE: 416

Gly Cys Lys Lys Asp Arg Lys Pro Cys Ser Tyr His Ala Asp Cys Cys
1               5                   10                  15
Asn Cys Cys Leu Ser Gly Ile Cys Ala Pro Ser Thr Asn Trp Ile Leu
            20                  25                  30
Pro Gly Cys Ser Thr Ser Thr Phe Thr
        35                  40

<210> SEQ ID NO 417
<211> LENGTH: 45
<212> TYPE: PRT
<213> ORGANISM: Conus radiatus

<400> SEQUENCE: 417

Gly His Val Pro Cys Gly Lys Asp Gly Arg Lys Cys Gly Tyr His Ala
1               5                   10                  15
Asp Cys Cys Asn Cys Cys Leu Ser Gly Ile Cys Lys Pro Ser Thr Ser
            20                  25                  30
Trp Thr Gly Cys Ser Thr Ser Thr Val Arg Leu Thr Arg
        35                  40                  45

<210> SEQ ID NO 418
<211> LENGTH: 45
<212> TYPE: PRT
<213> ORGANISM: Conus radiatus

<400> SEQUENCE: 418

Gly His Val Pro Cys Gly Lys Asp Gly Arg Lys Cys Gly Tyr His Ala
1               5                   10                  15
Asp Cys Cys Asn Cys Cys Leu Ser Gly Ile Cys Lys Pro Ser Thr Ser
            20                  25                  30
Trp Thr Gly Cys Ser Thr Ser Thr Val Gln Leu Thr Arg
        35                  40                  45

<210> SEQ ID NO 419
<211> LENGTH: 44
<212> TYPE: PRT
<213> ORGANISM: Conus radiatus

<400> SEQUENCE: 419

Gly His Val Ser Cys Gly Lys Asp Gly Arg Ala Cys Asp Tyr His Ala
1               5                   10                  15
Asp Cys Cys Asn Cys Cys Leu Gly Gly Ile Cys Lys Pro Ser Thr Ser
            20                  25                  30
Trp Ile Gly Cys Ser Thr Asn Val Phe Leu Thr Arg
        35                  40

<210> SEQ ID NO 420
<211> LENGTH: 45
<212> TYPE: PRT
<213> ORGANISM: Conus radiatus
```

```
<400> SEQUENCE: 420

Gly His Val Pro Cys Gly Lys Asp Arg Arg Lys Cys Gly Tyr His Ala
1               5                   10                  15

Asp Cys Cys Asn Cys Cys Leu Ser Gly Ile Cys Lys Pro Ser Thr Ser
                20                  25                  30

Trp Thr Gly Cys Ser Thr Ser Thr Phe Leu Leu Thr Arg
            35                  40                  45

<210> SEQ ID NO 421
<211> LENGTH: 45
<212> TYPE: PRT
<213> ORGANISM: Conus radiatus

<400> SEQUENCE: 421

Gly His Val Pro Cys Gly Lys Asp Gly Arg Lys Cys Gly Tyr His Ala
1               5                   10                  15

Asp Cys Cys Asn Cys Cys Leu Ser Gly Ile Cys Lys Pro Ser Thr Ser
                20                  25                  30

Trp Thr Gly Cys Ser Thr Ser Thr Phe Leu Leu Thr Arg
            35                  40                  45

<210> SEQ ID NO 422
<211> LENGTH: 46
<212> TYPE: PRT
<213> ORGANISM: Conus radiatus
<220> FEATURE:
<221> NAME/KEY: PEPTIDE
<222> LOCATION: (1)..(46)
<223> OTHER INFORMATION: Xaa at residues 2, 11 and 29 is hydroxy-Pro

<400> SEQUENCE: 422

Gly Xaa Ser Phe Cys Lys Ala Asn Gly Lys Xaa Cys Ser Tyr His Ala
1               5                   10                  15

Asp Cys Cys Asn Cys Cys Leu Ser Gly Ile Cys Lys Xaa Ser Thr Asn
                20                  25                  30

Val Ile Leu Pro Gly Cys Ser Thr Ser Ser Phe Phe Arg Ile
            35                  40                  45

<210> SEQ ID NO 423
<211> LENGTH: 42
<212> TYPE: PRT
<213> ORGANISM: Conus radiatus

<400> SEQUENCE: 423

Gly His Val Pro Cys Gly Lys Asp Gly Arg Lys Cys Gly Tyr His Ala
1               5                   10                  15

Asp Cys Cys Asn Cys Cys Leu Ser Gly Ile Cys Lys Pro Ser Thr Ser
                20                  25                  30

Trp Thr Gly Cys Ser Thr Ser Thr Phe Asn
            35                  40

<210> SEQ ID NO 424
<211> LENGTH: 42
<212> TYPE: PRT
<213> ORGANISM: Conus radiatus

<400> SEQUENCE: 424

Gly His Val Pro Cys Gly Lys Asp Gly Arg Lys Cys Gly Tyr His Thr
1               5                   10                  15

His Cys Cys Asn Cys Cys Leu Ser Gly Ile Cys Lys Pro Ser Thr Ser
```

```
                    20                  25                  30

Leu Ile Gly Cys Ser Thr Ser Ser Phe Thr
        35                  40
```

<210> SEQ ID NO 425
<211> LENGTH: 46
<212> TYPE: PRT
<213> ORGANISM: Conus radiatus

<400> SEQUENCE: 425

```
Gly Pro Ser Phe Cys Lys Ala Asn Gly Lys Pro Cys Ser Tyr His Ala
1               5                   10                  15

Asp Cys Cys Asn Cys Cys Leu Ser Gly Ile Cys Ala Pro Ser Thr Asn
                20                  25                  30

Trp Ile Leu Pro Gly Cys Ser Thr Ser Ser Phe Phe Lys Ile
        35                  40                  45
```

<210> SEQ ID NO 426
<211> LENGTH: 46
<212> TYPE: PRT
<213> ORGANISM: Conus radiatus

<400> SEQUENCE: 426

```
Gly Ala Val Pro Cys Gly Lys Asp Gly Arg Gln Cys Arg Asn His Ala
1               5                   10                  15

Asp Cys Cys Asn Cys Cys Pro Phe Gly Thr Cys Ala Pro Ser Thr Asn
                20                  25                  30

Arg Ile Leu Pro Gly Cys Ser Thr Gly Met Phe Leu Thr Arg
        35                  40                  45
```

<210> SEQ ID NO 427
<211> LENGTH: 37
<212> TYPE: PRT
<213> ORGANISM: Conus radiatus
<220> FEATURE:
<221> NAME/KEY: PEPTIDE
<222> LOCATION: (1)..(37)
<223> OTHER INFORMATION: Xaa at residues 13 and 14 is gamma-carboxy-
      Glu; Xaa at residue 34 is bromo-Tr

<400> SEQUENCE: 427

```
Glu Cys Lys Thr Asn Lys Met Ser Cys Ser Leu His Xaa Xaa Cys Cys
1               5                   10                  15

Arg Phe Arg Cys Cys Phe His Gly Lys Cys Gln Thr Ser Val Phe Gly
                20                  25                  30

Cys Xaa Val Asp Pro
        35
```

<210> SEQ ID NO 428
<211> LENGTH: 46
<212> TYPE: PRT
<213> ORGANISM: Conus radiatus

<400> SEQUENCE: 428

```
Gly Ala Val Pro Cys Gly Lys Asp Gly Arg Gln Cys Arg Asn His Ala
1               5                   10                  15

Asp Cys Cys Asn Cys Cys Pro Ile Gly Thr Cys Ala Pro Ser Thr Asn
                20                  25                  30

Trp Ile Leu Pro Gly Cys Ser Thr Gly Pro Phe Met Thr Arg
        35                  40                  45
```

```
<210> SEQ ID NO 429
<211> LENGTH: 40
<212> TYPE: PRT
<213> ORGANISM: Conus radiatus

<400> SEQUENCE: 429

Gly Pro Arg Cys Trp Val Gly Arg Val His Cys Thr Tyr His Lys Asp
1               5                   10                  15

Cys Cys Pro Ser Val Cys Cys Phe Lys Gly Arg Cys Lys Pro Gln Ser
            20                  25                  30

Trp Gly Cys Trp Ser Gly Pro Thr
        35                  40

<210> SEQ ID NO 430
<211> LENGTH: 44
<212> TYPE: PRT
<213> ORGANISM: Conus radiatus

<400> SEQUENCE: 430

Gly Pro Ser Phe Cys Lys Ala Asp Glu Lys Pro Cys Lys Tyr His Ala
1               5                   10                  15

Asp Cys Cys Asn Cys Cys Leu Gly Gly Ile Cys Lys Pro Ser Thr Ser
            20                  25                  30

Trp Ile Gly Cys Ser Thr Asn Val Phe Leu Thr Arg
        35                  40

<210> SEQ ID NO 431
<211> LENGTH: 48
<212> TYPE: PRT
<213> ORGANISM: Conus radiatus

<400> SEQUENCE: 431

Gly Ala Val Pro Cys Gly Lys Asp Gly Arg Gln Cys Arg Asn His Ala
1               5                   10                  15

Asp Cys Cys Asn Cys Cys Pro Ile Gly Thr Cys Ala Pro Ser Thr Asn
            20                  25                  30

Trp Ile Leu Pro Gly Cys Ser Thr Gly Gln Phe Met Thr Ala Asp Phe
        35                  40                  45

<210> SEQ ID NO 432
<211> LENGTH: 46
<212> TYPE: PRT
<213> ORGANISM: Conus radiatus

<400> SEQUENCE: 432

Gly Pro Ser Phe Cys Lys Ala Asp Glu Lys Pro Cys Glu Tyr His Ser
1               5                   10                  15

Asp Cys Cys Asn Cys Cys Leu Ser Gly Ile Cys Ala Pro Ser Thr Asn
            20                  25                  30

Trp Ile Leu Pro Gly Cys Ser Thr Ser Ser Phe Phe Lys Ile
        35                  40                  45

<210> SEQ ID NO 433
<211> LENGTH: 35
<212> TYPE: PRT
<213> ORGANISM: Conus striatus

<400> SEQUENCE: 433

Gly Thr Cys Ser Phe Leu Gly Gln Gly Cys Gly Asp His Ser Asp Cys
1               5                   10                  15

Cys Trp Asn Met Cys Cys Ala Ser Glu Met Cys Val Val Thr Leu Leu
```

```
            20                  25                  30

Gln Cys Lys
        35

<210> SEQ ID NO 434
<211> LENGTH: 43
<212> TYPE: PRT
<213> ORGANISM: Conus striatus

<400> SEQUENCE: 434

Gly Cys Lys Lys Asp Arg Lys Pro Cys Ser Tyr Gln Ala Asp Cys Cys
1               5                   10                  15

Asn Cys Cys Pro Ile Gly Thr Cys Ala Pro Ser Thr Asn Trp Ile Leu
            20                  25                  30

Pro Gly Cys Ser Thr Gly Pro Phe Met Ala Arg
        35                  40

<210> SEQ ID NO 435
<211> LENGTH: 44
<212> TYPE: PRT
<213> ORGANISM: Conus striatus

<400> SEQUENCE: 435

Gly Pro Ser Phe Cys Lys Ala Asp Glu Lys Pro Cys Lys Tyr His Ala
1               5                   10                  15

Asp Cys Cys Asn Cys Cys Leu Gly Gly Ile Cys Lys Pro Ser Thr Ser
            20                  25                  30

Trp Ile Gly Cys Ser Thr Asn Val Phe Leu Thr Arg
        35                  40

<210> SEQ ID NO 436
<211> LENGTH: 44
<212> TYPE: PRT
<213> ORGANISM: Conus striatus

<400> SEQUENCE: 436

Gly Pro Ser Phe Cys Lys Ala Asp Glu Lys Pro Cys Lys Tyr His Ala
1               5                   10                  15

Gly Cys Cys Asn Cys Cys Leu Gly Gly Ile Cys Lys Pro Ser Thr Ser
            20                  25                  30

Trp Ile Gly Cys Ser Thr Asn Val Phe Leu Thr Arg
        35                  40

<210> SEQ ID NO 437
<211> LENGTH: 46
<212> TYPE: PRT
<213> ORGANISM: Conus striatus

<400> SEQUENCE: 437

Gly Pro Ser Phe Cys Lys Ala Asn Gly Lys Pro Cys Ser Tyr His Ala
1               5                   10                  15

Asp Cys Cys Asn Cys Cys Leu Ser Gly Ile Cys Lys Pro Ser Thr Asn
            20                  25                  30

Val Ile Leu Pro Gly Cys Ser Thr Ser Ser Phe Phe Arg Ile
        35                  40                  45

<210> SEQ ID NO 438
<211> LENGTH: 46
<212> TYPE: PRT
<213> ORGANISM: Conus striatus
```

```
-continued

<400> SEQUENCE: 438

Gly Pro Ser Phe Cys Lys Ala Asp Glu Lys Pro Cys Glu Tyr His Ala
1               5                   10                  15

Asp Cys Cys Asn Cys Cys Leu Ser Gly Ile Cys Ala Pro Ser Thr Asn
            20                  25                  30

Trp Ile Leu Pro Gly Cys Ser Thr Ser Ser Phe Phe Lys Ile
        35                  40                  45

<210> SEQ ID NO 439
<211> LENGTH: 41
<212> TYPE: PRT
<213> ORGANISM: Conus striatus

<400> SEQUENCE: 439

Gly Cys Lys Lys Asp Arg Lys Pro Cys Ser Tyr His Ala Asp Cys Cys
1               5                   10                  15

Asn Cys Cys Leu Ser Gly Ile Cys Ala Pro Ser Thr Asn Trp Ile Leu
            20                  25                  30

Pro Gly Cys Ser Thr Ser Thr Phe Thr
        35                  40

<210> SEQ ID NO 440
<211> LENGTH: 44
<212> TYPE: PRT
<213> ORGANISM: Conus striatus

<400> SEQUENCE: 440

Gly Pro Ser Phe Cys Lys Ala Asp Glu Lys Pro Cys Lys Tyr His Ala
1               5                   10                  15

Asp Cys Cys Asn Cys Cys Leu Gly Gly Ile Cys Lys Pro Ser Thr Ser
            20                  25                  30

Trp Ile Gly Cys Ser Thr Asn Val Phe Leu Thr Arg
        35                  40

<210> SEQ ID NO 441
<211> LENGTH: 36
<212> TYPE: PRT
<213> ORGANISM: Conus episcopatus

<400> SEQUENCE: 441

Gly Met Cys Ser Arg Ile Gly Gln Gly Cys Gly Gln Asp Ser Asp Cys
1               5                   10                  15

Cys Gly Asp Met Cys Cys Tyr Gly Gln Ile Cys Ala Met Thr Phe Ala
            20                  25                  30

Ala Cys Gly Pro
        35

<210> SEQ ID NO 442
<211> LENGTH: 36
<212> TYPE: PRT
<213> ORGANISM: Conus episcopatus

<400> SEQUENCE: 442

Gly Met Cys Ser Arg Ile Gly Gln Gly Cys Gly Gln Asp Ser Asn Cys
1               5                   10                  15

Cys Gly Asp Met Cys Cys Tyr Gly Gln Ile Cys Ala Met Thr Phe Ala
            20                  25                  30

Ala Cys Gly Pro
        35
```

<210> SEQ ID NO 443
<211> LENGTH: 36
<212> TYPE: PRT
<213> ORGANISM: Conus episcopatus

<400> SEQUENCE: 443

Gly Met Cys Ser Arg Ile Gly Gln Gly Cys Gly Gln Asp Ser Asp Cys
1               5                   10                  15

Cys Gly Asp Met Cys Cys His Gly Gln Ile Cys Ala Met Thr Phe Ala
                20                  25                  30

Ala Cys Gly Pro
        35

<210> SEQ ID NO 444
<211> LENGTH: 39
<212> TYPE: PRT
<213> ORGANISM: Conus episcopatus

<400> SEQUENCE: 444

Gly Asp Trp Gly Met Cys Ser Gly Ile Gly Gln Gly Cys Gly Gln Asp
1               5                   10                  15

Ser Gly Cys Cys Gly Asp Met Cys Cys Tyr Gly Gln Ile Cys Ala Met
                20                  25                  30

Thr Phe Ala Ala Cys Gly Pro
        35

<210> SEQ ID NO 445
<211> LENGTH: 36
<212> TYPE: PRT
<213> ORGANISM: Conus episcopatus

<400> SEQUENCE: 445

Gly Met Cys Ser Gly Ile Gly Gln Gly Cys Gly Gln Asp Ser Gly Cys
1               5                   10                  15

Cys Gly Asp Met Cys Cys Tyr Gly Gln Ile Cys Ala Met Thr Phe Ala
                20                  25                  30

Ala Cys Gly Pro
        35

<210> SEQ ID NO 446
<211> LENGTH: 39
<212> TYPE: PRT
<213> ORGANISM: Conus episcopatus

<400> SEQUENCE: 446

Gly Asp Trp Gly Met Cys Ser Gly Ile Gly Gln Gly Cys Gly Gln Asp
1               5                   10                  15

Ser Asn Cys Cys Gly Asp Met Cys Cys Tyr Gly Gln Ile Cys Ala Met
                20                  25                  30

Thr Phe Ala Ala Cys Gly Pro
        35

<210> SEQ ID NO 447
<211> LENGTH: 39
<212> TYPE: PRT
<213> ORGANISM: Conus episcopatus

<400> SEQUENCE: 447

Gly Asp Trp Gly Met Cys Ser Gly Ile Gly Gln Gly Cys Gly Gln Asp
1               5                   10                  15

-continued

Ser Asn Cys Cys Gly Asp Lys Cys Cys Tyr Gly Gln Ile Cys Ala Met
            20                  25                  30

Thr Phe Ala Ala Cys Gly Pro
            35

<210> SEQ ID NO 448
<211> LENGTH: 39
<212> TYPE: PRT
<213> ORGANISM: Conus episcopatus

<400> SEQUENCE: 448

Gly Asp Trp Gly Met Cys Ser Gly Ile Gly Gln Gly Cys Gly Gln Asp
1               5                   10                  15

Ser Asn Cys Cys Gly Asp Met Cys Cys His Gly Gln Ile Cys Ala Met
            20                  25                  30

Thr Phe Ala Ala Cys Gly Pro
            35

<210> SEQ ID NO 449
<211> LENGTH: 42
<212> TYPE: PRT
<213> ORGANISM: Conus aulicus

<400> SEQUENCE: 449

Gly Asp Trp Gly Thr Cys Ser Trp Ser Gly Gln Glu Cys Lys His Asp
1               5                   10                  15

Ser Asp Cys Cys Gly Ser Phe Cys Cys Val Gly Lys Arg Cys Leu His
            20                  25                  30

Ile Tyr Phe Pro Cys Asn Leu Ser Arg Pro
            35                  40

<210> SEQ ID NO 450
<211> LENGTH: 42
<212> TYPE: PRT
<213> ORGANISM: Conus aulicus

<400> SEQUENCE: 450

Gly Asp Trp Gly Thr Cys Ser Trp Ser Gly Gln Glu Cys Lys His Asp
1               5                   10                  15

Ser Asp Cys Cys Gly Ser Phe Cys Cys Val Gly Lys Arg Cys Leu His
            20                  25                  30

Ile Tyr Phe Pro Cys Asn Leu Ser Arg Ser
            35                  40

<210> SEQ ID NO 451
<211> LENGTH: 42
<212> TYPE: PRT
<213> ORGANISM: Conus aulicus

<400> SEQUENCE: 451

Gly Asp Trp Gly Thr Cys Ser Trp Pro Gly Gln Glu Cys Lys His Asp
1               5                   10                  15

Ser Asp Cys Cys Gly Ser Phe Cys Cys Val Gly Lys Arg Cys Leu His
            20                  25                  30

Thr Tyr Phe Pro Cys Asn Leu Ser Arg Ser
            35                  40

<210> SEQ ID NO 452
<211> LENGTH: 42
<212> TYPE: PRT
<213> ORGANISM: Conus aulicus

```
<400> SEQUENCE: 452

Gly Asp Trp Gly Thr Cys Ser Trp Ser Gly Gln Glu Cys Lys His Val
1               5                   10                  15

Ser Asp Cys Cys Gly Ser Phe Cys Cys Val Gly Lys Arg Cys Leu His
            20                  25                  30

Ile Tyr Phe Pro Cys Asn Leu Ser Arg Ser
        35                  40

<210> SEQ ID NO 453
<211> LENGTH: 42
<212> TYPE: PRT
<213> ORGANISM: Conus aulicus

<400> SEQUENCE: 453

Gly Asp Trp Gly Thr Cys Ser Trp Pro Gly Gln Glu Cys Glu His Asp
1               5                   10                  15

Ser Asp Cys Cys Gly Ser Phe Cys Val Gly Arg Arg Cys Leu His
            20                  25                  30

Ile Tyr Phe Pro Cys Asn Leu Ser Arg Ser
        35                  40

<210> SEQ ID NO 454
<211> LENGTH: 42
<212> TYPE: PRT
<213> ORGANISM: Conus aulicus

<400> SEQUENCE: 454

Gly Asp Gly Gly Thr Cys Ser Trp Pro Gly Gln Glu Cys Lys His Asp
1               5                   10                  15

Ser Asp Cys Cys Gly Ser Phe Cys Cys Val Gly Lys Arg Cys Leu His
            20                  25                  30

Thr Tyr Phe Pro Cys Asn Leu Ser Arg Ser
        35                  40

<210> SEQ ID NO 455
<211> LENGTH: 31
<212> TYPE: PRT
<213> ORGANISM: Conus episcopatus
<220> FEATURE:
<221> NAME/KEY: PEPTIDE
<222> LOCATION: (1)..(31)
<223> OTHER INFORMATION: Xaa at residues 4 and 25 is gamma-carboxy-Glu

<400> SEQUENCE: 455

Cys Ile Arg Xaa Asp Ala Pro Cys Ser Phe Ser Ala His Cys Cys Gly
1               5                   10                  15

Arg Asn Cys Cys Arg Gly Tyr Cys Xaa Arg Pro Cys Arg Trp Ile
            20                  25                  30

<210> SEQ ID NO 456
<211> LENGTH: 30
<212> TYPE: PRT
<213> ORGANISM: Conus emaciatus

<400> SEQUENCE: 456

Cys Leu His Glu Thr Ser Pro Cys Arg Arg Ser Phe Gln Cys Cys His
1               5                   10                  15

Gly Ile Cys Cys Phe Arg Arg Cys Ser Asn Ser Cys Arg Phe
            20                  25                  30
```

```
<210> SEQ ID NO 457
<211> LENGTH: 31
<212> TYPE: PRT
<213> ORGANISM: Conus emaciatus

<400> SEQUENCE: 457

Cys Leu Arg Asp Gly Gln Ser Cys Arg Tyr His Ser Asp Cys Cys Arg
1               5                   10                  15

Tyr Ser Cys Cys Trp Gly Tyr Cys Asp Gln Lys Cys Leu Ile Ile
            20                  25                  30

<210> SEQ ID NO 458
<211> LENGTH: 31
<212> TYPE: PRT
<213> ORGANISM: Conus emaciatus

<400> SEQUENCE: 458

Cys Arg Arg Glu Gly Ser Ser Cys Arg Arg Ser Tyr Gln Cys Cys Arg
1               5                   10                  15

Lys Ser Cys Cys Ile Gly Glu Cys Glu Phe Pro Cys Arg Trp Val
            20                  25                  30

<210> SEQ ID NO 459
<211> LENGTH: 44
<212> TYPE: PRT
<213> ORGANISM: Conus emaciatus

<400> SEQUENCE: 459

Cys Tyr Gln Asp Glu Thr Pro Cys Arg Gly Ser Ile Phe Cys Cys Arg
1               5                   10                  15

Lys Lys Cys Cys Ile Gly Thr Cys Arg Phe Pro Cys Tyr Val Lys Leu
            20                  25                  30

Glu Arg Ala Thr Phe Gln Glu Leu Ile Leu Gln Pro
        35                  40

<210> SEQ ID NO 460
<211> LENGTH: 31
<212> TYPE: PRT
<213> ORGANISM: Conus emaciatus

<400> SEQUENCE: 460

Cys Leu Arg Asp Gly Gln Ser Cys Gly Tyr Asp Ser Asp Cys Cys Arg
1               5                   10                  15

Tyr Ser Cys Cys Trp Gly Tyr Cys Asp Leu Thr Cys Leu Ile Ile
            20                  25                  30

<210> SEQ ID NO 461
<211> LENGTH: 31
<212> TYPE: PRT
<213> ORGANISM: Conus emaciatus

<400> SEQUENCE: 461

Cys Phe Pro Pro Gly Ile Tyr Cys Thr Pro Tyr Leu Pro Cys Cys Trp
1               5                   10                  15

Gly Ile Cys Cys Gly Thr Cys Arg Asn Val Cys His Leu Arg Ile
            20                  25                  30

<210> SEQ ID NO 462
<211> LENGTH: 44
<212> TYPE: PRT
<213> ORGANISM: Conus emaciatus

<400> SEQUENCE: 462
```

-continued

Cys Tyr Gln Asp Glu Thr Pro Cys Arg Gly Ser Thr Phe Cys Cys Arg
1               5                   10                  15

Lys Lys Cys Cys Ile Gly Thr Cys Arg Phe Pro Cys Tyr Val Lys Leu
                20                  25                  30

Glu Arg Ala Thr Phe Gln Glu Leu Ile Leu Gln Pro
            35                  40

<210> SEQ ID NO 463
<211> LENGTH: 31
<212> TYPE: PRT
<213> ORGANISM: Conus emaciatus

<400> SEQUENCE: 463

Cys Leu Arg Asp Gly Gln Ser Cys Gly Tyr His Ser Asp Cys Cys Arg
1               5                   10                  15

Tyr Ser Cys Cys Trp Gly Tyr Cys Asp Gln Lys Cys Leu Ile Ile
                20                  25                  30

<210> SEQ ID NO 464
<211> LENGTH: 31
<212> TYPE: PRT
<213> ORGANISM: Conus virgo

<400> SEQUENCE: 464

Cys Leu Arg Asp Gly Gln Ser Cys Gly Tyr Asp Ser Asp Cys Cys Arg
1               5                   10                  15

Tyr Ser Cys Cys Trp Gly Tyr Cys Asp Leu Thr Cys Leu Ile Ile
                20                  25                  30

<210> SEQ ID NO 465
<211> LENGTH: 30
<212> TYPE: PRT
<213> ORGANISM: Conus virgo

<400> SEQUENCE: 465

Cys Leu His Glu Thr Ser Pro Cys Arg Arg Ser Phe Gln Cys Cys His
1               5                   10                  15

Gly Ile Cys Cys Phe Arg Arg Cys Ser Asn Ser Cys Arg Phe
                20                  25                  30

<210> SEQ ID NO 466
<211> LENGTH: 31
<212> TYPE: PRT
<213> ORGANISM: Conus virgo

<400> SEQUENCE: 466

Cys Leu Arg Asp Gly Gln Ser Cys Gly Tyr His Ser Asp Cys Cys Arg
1               5                   10                  15

Tyr Ser Cys Cys Trp Gly Tyr Cys Asp Gln Lys Cys Leu Ile Ile
                20                  25                  30

<210> SEQ ID NO 467
<211> LENGTH: 30
<212> TYPE: PRT
<213> ORGANISM: Conus virgo

<400> SEQUENCE: 467

Cys Leu His Glu Thr Pro Pro Cys Arg Arg Ser Phe Gln Cys Cys His
1               5                   10                  15

Gly Asn Cys Cys Phe Arg Arg Cys Ser Asn Ser Cys Arg Phe
                20                  25                  30

<210> SEQ ID NO 468
<211> LENGTH: 30
<212> TYPE: PRT
<213> ORGANISM: Conus virgo

<400> SEQUENCE: 468

Cys Leu His Glu Thr Ser Pro Cys Gly Arg Ser Phe Gln Cys Cys His
1               5                   10                  15

Gly Ile Cys Cys Phe Arg Arg Cys Ser Asn Ser Cys Arg Phe
            20                  25                  30

<210> SEQ ID NO 469
<211> LENGTH: 30
<212> TYPE: PRT
<213> ORGANISM: Conus virgo

<400> SEQUENCE: 469

Cys Leu Tyr Glu Thr Ser Pro Cys Arg Arg Ser Phe Gln Cys Cys His
1               5                   10                  15

Gly Ile Cys Cys Phe Arg Arg Cys Ser Asn Ser Cys Arg Phe
            20                  25                  30

<210> SEQ ID NO 470
<211> LENGTH: 32
<212> TYPE: PRT
<213> ORGANISM: Conus virgo

<400> SEQUENCE: 470

Cys Phe Pro Leu Gly Thr Phe Cys Ser Arg Tyr Leu Pro Cys Cys Ser
1               5                   10                  15

Gly Met Cys Cys Ser Gly Trp Cys Thr Arg Arg Cys Ala Pro Arg Phe
            20                  25                  30

<210> SEQ ID NO 471
<211> LENGTH: 30
<212> TYPE: PRT
<213> ORGANISM: Conus figulinus

<400> SEQUENCE: 471

Cys His His Glu Gly Leu Pro Cys Thr Ser Asp Asp Gly Cys Cys Gly
1               5                   10                  15

Met Glu Cys Cys Gly Gly Val Cys Ser Ser His Cys Gly Asn
            20                  25                  30

<210> SEQ ID NO 472
<211> LENGTH: 31
<212> TYPE: PRT
<213> ORGANISM: Conus figulinus

<400> SEQUENCE: 472

Cys Arg Ala Glu Gly Val Arg Cys Glu Phe Asp Ser Gln Cys Cys Glu
1               5                   10                  15

Ser Glu Cys Cys Met Gly Ser Cys Ala Asn Pro Cys Arg Ile Pro
            20                  25                  30

<210> SEQ ID NO 473
<211> LENGTH: 31
<212> TYPE: PRT
<213> ORGANISM: Conus figulinus

<400> SEQUENCE: 473

```
Cys Arg Ala Glu Gly Val Tyr Cys Glu Tyr Gly Ser Gln Cys Cys Leu
1               5                  10                  15

Ser Gln Cys Cys Met Ala Ser Cys Ala Asn Pro Cys Arg His Pro
            20                  25                  30
```

<210> SEQ ID NO 474
<211> LENGTH: 30
<212> TYPE: PRT
<213> ORGANISM: Conus figulinus

<400> SEQUENCE: 474

```
Cys His His Glu Gly Leu Pro Cys Thr Ser Asp Gly Cys Cys Gly
1               5                  10                  15

Met Glu Cys Cys Gly Gly Val Cys Ser Ser His Cys Gly Asn
            20                  25                  30
```

<210> SEQ ID NO 475
<211> LENGTH: 30
<212> TYPE: PRT
<213> ORGANISM: Conus figulinus

<400> SEQUENCE: 475

```
Cys His His Glu Gly Leu Pro Cys Ala Ser Asp Gly Cys Cys Gly
1               5                  10                  15

Met Glu Cys Cys Gly Gly Val Cys Ser Ser His Cys Gly Asn
            20                  25                  30
```

<210> SEQ ID NO 476
<211> LENGTH: 32
<212> TYPE: PRT
<213> ORGANISM: Conus episcopatus

<400> SEQUENCE: 476

```
Cys Ala Gly Gln Glu Glu Pro Cys Ser Ser Arg Ser Asp Cys Cys Gly
1               5                  10                  15

Ser Val Gly Cys Cys Phe Gly Gln Cys Glu Ser Pro Cys Arg Met Pro
            20                  25                  30
```

<210> SEQ ID NO 477
<211> LENGTH: 32
<212> TYPE: PRT
<213> ORGANISM: Conus episcopatus

<400> SEQUENCE: 477

```
Cys Ala Gly Gln Glu Glu Pro Cys Ser Ser Arg Asp Asp Cys Cys Gly
1               5                  10                  15

Ser Val Gly Cys Cys Phe Gly Gln Cys Glu Thr Pro Cys Arg Met Pro
            20                  25                  30
```

<210> SEQ ID NO 478
<211> LENGTH: 32
<212> TYPE: PRT
<213> ORGANISM: Conus episcopatus

<400> SEQUENCE: 478

```
Cys Ala Gly Gln Glu Glu Pro Cys Ser Ser Arg Ser Asp Cys Cys Gly
1               5                  10                  15

Ser Val Gly Cys Cys Phe Gly Gln Cys Glu Ser Pro Cys Arg Met Ile
            20                  25                  30
```

<210> SEQ ID NO 479
<211> LENGTH: 31

<212> TYPE: PRT
<213> ORGANISM: Conus episcopatus

<400> SEQUENCE: 479

Cys Leu Ser Glu Gly Ser Pro Cys Ser Met Ser Gly Ser Cys Cys His
1               5                   10                  15

Lys Ser Cys Cys Arg Ser Thr Cys Thr Phe Pro Cys Leu Ile Pro
            20                  25                  30

<210> SEQ ID NO 480
<211> LENGTH: 31
<212> TYPE: PRT
<213> ORGANISM: Conus episcopatus

<400> SEQUENCE: 480

Cys Pro Ser Glu Gly Ser Pro Cys Ser Met Ser Gly Ser Cys Cys His
1               5                   10                  15

Lys Ser Cys Cys Arg Ser Thr Cys Thr Phe Pro Cys Leu Ile Pro
            20                  25                  30

<210> SEQ ID NO 481
<211> LENGTH: 30
<212> TYPE: PRT
<213> ORGANISM: Conus striolatus

<400> SEQUENCE: 481

Cys His His Glu Gly Leu Pro Cys Ser Ser Asp Asp Gly Cys Cys Gly
1               5                   10                  15

Met Glu Cys Cys Asn Gly Val Cys Ser Ser Cys Gly Asn
            20                  25                  30

<210> SEQ ID NO 482
<211> LENGTH: 40
<212> TYPE: PRT
<213> ORGANISM: Conus striolatus

<400> SEQUENCE: 482

Cys His Met Asp Cys Ser Lys Met Thr Cys Cys Ser Gly Ile Cys Cys
1               5                   10                  15

Phe Tyr Cys Gly Arg Pro Met Cys Pro Gly Thr Arg Arg Ala Leu Leu
            20                  25                  30

Gln Arg Leu Val Gly His Gln Arg
        35                  40

<210> SEQ ID NO 483
<211> LENGTH: 43
<212> TYPE: PRT
<213> ORGANISM: Conus emaciatus

<400> SEQUENCE: 483

Cys Leu His Glu Thr Ser Pro Cys Arg Arg Ser Phe Gln Cys Cys His
1               5                   10                  15

Gly Ile Cys Cys Phe Arg Arg Cys Ser Asn Ser Cys Arg Phe Gly Lys
            20                  25                  30

Arg Ala Thr Phe Gln Glu Phe Ile Leu His Arg
        35                  40

<210> SEQ ID NO 484
<211> LENGTH: 43
<212> TYPE: PRT
<213> ORGANISM: Conus virgo -continued

```
<400> SEQUENCE: 484

Cys Leu His Glu Thr Ser Pro Cys Arg Arg Ser Phe Gln Cys Cys His
1               5                   10                  15
Gly Ile Cys Cys Phe Arg Arg Cys Ser Asn Ser Cys Arg Phe Gly Lys
            20                  25                  30
Arg Ala Thr Phe Gln Glu Phe Ile Leu His Arg
        35                  40

<210> SEQ ID NO 485
<211> LENGTH: 43
<212> TYPE: PRT
<213> ORGANISM: Conus virgo

<400> SEQUENCE: 485

Cys Leu His Glu Thr Pro Pro Cys Arg Arg Ser Phe Gln Cys Cys His
1               5                   10                  15
Gly Asn Cys Cys Phe Arg Arg Cys Ser Asn Ser Cys Arg Phe Gly Lys
            20                  25                  30
Arg Ala Thr Phe Gln Glu Phe Ile Leu His Arg
        35                  40

<210> SEQ ID NO 486
<211> LENGTH: 43
<212> TYPE: PRT
<213> ORGANISM: Conus virgo

<400> SEQUENCE: 486

Cys Leu His Glu Thr Ser Pro Cys Gly Arg Ser Phe Gln Cys Cys His
1               5                   10                  15
Gly Ile Cys Cys Phe Arg Arg Cys Ser Asn Ser Cys Arg Phe Gly Lys
            20                  25                  30
Arg Ala Thr Phe Gln Glu Phe Ile Leu His Arg
        35                  40

<210> SEQ ID NO 487
<211> LENGTH: 43
<212> TYPE: PRT
<213> ORGANISM: Conus virgo

<400> SEQUENCE: 487

Cys Leu Tyr Glu Thr Ser Pro Cys Arg Arg Ser Phe Gln Cys Cys His
1               5                   10                  15
Gly Ile Cys Cys Phe Arg Arg Cys Ser Asn Ser Cys Arg Phe Gly Lys
            20                  25                  30
Arg Ala Thr Phe Gln Glu Phe Ile Leu His Arg
        35                  40

<210> SEQ ID NO 488
<211> LENGTH: 44
<212> TYPE: PRT
<213> ORGANISM: Conus emaciatus

<400> SEQUENCE: 488

Cys Tyr Gln Asp Glu Thr Pro Cys Arg Gly Ser Ile Phe Cys Cys Arg
1               5                   10                  15
Lys Lys Cys Cys Ile Gly Thr Cys Arg Phe Pro Cys Tyr Val Lys Leu
            20                  25                  30
Glu Arg Ala Thr Phe Gln Glu Leu Ile Leu Gln Pro
        35                  40
```

-continued

```
<210> SEQ ID NO 489
<211> LENGTH: 44
<212> TYPE: PRT
<213> ORGANISM: Conus emaciatus

<400> SEQUENCE: 489

Cys Tyr Gln Asp Glu Thr Pro Cys Arg Gly Ser Thr Phe Cys Cys Arg
1               5                   10                  15

Lys Lys Cys Cys Ile Gly Thr Cys Arg Phe Pro Cys Tyr Val Lys Leu
            20                  25                  30

Glu Arg Ala Thr Phe Gln Glu Leu Ile Leu Gln Pro
        35                  40

<210> SEQ ID NO 490
<211> LENGTH: 44
<212> TYPE: PRT
<213> ORGANISM: Conus emaciatus

<400> SEQUENCE: 490

Cys Leu Arg Asp Gly Gln Ser Cys Arg Tyr His Ser Asp Cys Cys Arg
1               5                   10                  15

Tyr Ser Cys Cys Trp Gly Tyr Cys Asp Gln Lys Cys Leu Ile Ile Gly
            20                  25                  30

Lys Arg Ala Thr Phe Gln Glu Leu Ile Leu His Arg
        35                  40

<210> SEQ ID NO 491
<211> LENGTH: 44
<212> TYPE: PRT
<213> ORGANISM: Conus emaciatus

<400> SEQUENCE: 491

Cys Leu Arg Asp Gly Gln Ser Cys Gly Tyr Asp Ser Asp Cys Cys Arg
1               5                   10                  15

Tyr Ser Cys Cys Trp Gly Tyr Cys Asp Leu Thr Cys Leu Ile Ile Gly
            20                  25                  30

Lys Arg Ala Thr Phe Gln Glu Leu Ile Leu His Arg
        35                  40

<210> SEQ ID NO 492
<211> LENGTH: 44
<212> TYPE: PRT
<213> ORGANISM: Conus virgo

<400> SEQUENCE: 492

Cys Leu Arg Asp Gly Gln Ser Cys Gly Tyr Asp Ser Asp Cys Cys Arg
1               5                   10                  15

Tyr Ser Cys Cys Trp Gly Tyr Cys Asp Leu Thr Cys Leu Ile Ile Gly
            20                  25                  30

Lys Arg Ala Thr Phe Gln Glu Leu Ile Leu His Arg
        35                  40

<210> SEQ ID NO 493
<211> LENGTH: 44
<212> TYPE: PRT
<213> ORGANISM: Conus emaciatus

<400> SEQUENCE: 493

Cys Leu Arg Asp Gly Gln Ser Cys Gly Tyr Asp Ser Asp Cys Cys Arg
1               5                   10                  15
```

-continued

Tyr Ser Cys Cys Trp Gly Tyr Cys Asp Leu Thr Cys Leu Ile Ile Gly
            20                  25                  30

Lys Arg Ala Thr Phe Gln Glu Leu Ile Leu His Pro
            35                  40

<210> SEQ ID NO 494
<211> LENGTH: 44
<212> TYPE: PRT
<213> ORGANISM: Conus emaciatus

<400> SEQUENCE: 494

Cys Leu Arg Asp Gly Gln Ser Cys Gly Tyr His Ser Asp Cys Cys Arg
1               5                   10                  15

Tyr Ser Cys Cys Trp Gly Tyr Cys Asp Gln Lys Cys Leu Ile Ile Gly
            20                  25                  30

Lys Arg Ala Thr Phe Gln Glu Leu Ile Leu His Pro
            35                  40

<210> SEQ ID NO 495
<211> LENGTH: 44
<212> TYPE: PRT
<213> ORGANISM: Conus virgo

<400> SEQUENCE: 495

Cys Leu Arg Asp Gly Gln Ser Cys Gly Tyr His Ser Asp Cys Cys Arg
1               5                   10                  15

Tyr Ser Cys Cys Trp Gly Tyr Cys Asp Gln Lys Cys Leu Ile Ile Gly
            20                  25                  30

Lys Arg Ala Thr Phe Gln Glu Leu Ile Leu His Arg
            35                  40

<210> SEQ ID NO 496
<211> LENGTH: 44
<212> TYPE: PRT
<213> ORGANISM: Conus emaciatus

<400> SEQUENCE: 496

Cys Arg Arg Glu Gly Ser Ser Cys Arg Arg Ser Tyr Gln Cys Cys Arg
1               5                   10                  15

Lys Ser Cys Cys Ile Gly Glu Cys Glu Phe Pro Cys Arg Trp Val Gly
            20                  25                  30

Lys Arg Ala Thr Phe Arg Glu Leu Ile Leu His His
            35                  40

<210> SEQ ID NO 497
<211> LENGTH: 39
<212> TYPE: PRT
<213> ORGANISM: Conus emaciatus

<400> SEQUENCE: 497

Cys Phe Pro Pro Gly Ile Tyr Cys Thr Pro Tyr Leu Pro Cys Cys Trp
1               5                   10                  15

Gly Ile Cys Cys Gly Thr Cys Arg Asn Val Cys His Leu Arg Ile Gly
            20                  25                  30

Lys Arg Ala Thr Phe Gln Glu
            35

<210> SEQ ID NO 498
<211> LENGTH: 40
<212> TYPE: PRT
<213> ORGANISM: Conus virgo

```
<400> SEQUENCE: 498

Cys Phe Pro Leu Gly Thr Phe Cys Ser Arg Tyr Leu Pro Cys Cys Ser
1               5                   10                  15

Gly Met Cys Cys Ser Gly Trp Cys Thr Arg Arg Cys Ala Pro Arg Phe
            20                  25                  30

Gly Lys Arg Ala Thr Phe Gln Glu
        35                  40

<210> SEQ ID NO 499
<211> LENGTH: 44
<212> TYPE: PRT
<213> ORGANISM: Conus figulinus

<400> SEQUENCE: 499

Cys His His Glu Gly Leu Pro Cys Thr Ser Asp Asp Gly Cys Cys Gly
1               5                   10                  15

Met Glu Cys Cys Gly Gly Val Cys Ser Ser His Cys Gly Asn Gly Arg
            20                  25                  30

Arg Arg Gln Val Pro Leu Lys Ser Phe Gly Gln Arg
        35                  40

<210> SEQ ID NO 500
<211> LENGTH: 44
<212> TYPE: PRT
<213> ORGANISM: Conus figulinus

<400> SEQUENCE: 500

Cys His His Glu Gly Leu Pro Cys Thr Ser Asp Asp Gly Cys Cys Gly
1               5                   10                  15

Met Glu Cys Cys Gly Gly Val Cys Ser Ser His Cys Gly Asn Gly Arg
            20                  25                  30

Arg Arg Arg Val Pro Leu Lys Ser Phe Gly Gln Arg
        35                  40

<210> SEQ ID NO 501
<211> LENGTH: 44
<212> TYPE: PRT
<213> ORGANISM: Conus figulinus

<400> SEQUENCE: 501

Cys His His Glu Gly Leu Pro Cys Thr Ser Asp Asp Gly Cys Cys Gly
1               5                   10                  15

Met Glu Cys Cys Gly Gly Val Cys Ser Ser His Cys Gly Asn Gly Gly
            20                  25                  30

Arg Arg Arg Val Pro Leu Lys Ser Phe Gly Gln Arg
        35                  40

<210> SEQ ID NO 502
<211> LENGTH: 44
<212> TYPE: PRT
<213> ORGANISM: Conus figulinus

<400> SEQUENCE: 502

Cys His His Glu Gly Leu Pro Cys Thr Ser Gly Asp Gly Cys Cys Gly
1               5                   10                  15

Met Glu Cys Cys Gly Gly Val Cys Ser Ser His Cys Gly Asn Gly Arg
            20                  25                  30

Arg Arg Gln Val Pro Leu Lys Ser Phe Gly Gln Arg
        35                  40
```

<210> SEQ ID NO 503
<211> LENGTH: 44
<212> TYPE: PRT
<213> ORGANISM: Conus figulinus

<400> SEQUENCE: 503

Cys His His Glu Gly Leu Pro Cys Ala Ser Asp Asp Gly Cys Cys Gly
1               5                   10                  15

Met Glu Cys Cys Gly Gly Val Cys Ser Ser His Cys Gly Asn Gly Arg
            20                  25                  30

Arg Arg Arg Val Pro Leu Lys Ser Phe Gly Gln Arg
        35                  40

<210> SEQ ID NO 504
<211> LENGTH: 41
<212> TYPE: PRT
<213> ORGANISM: Conus figulinus

<400> SEQUENCE: 504

Cys Arg Ala Glu Gly Val Arg Cys Glu Phe Asp Ser Gln Cys Cys Glu
1               5                   10                  15

Ser Glu Cys Cys Met Gly Ser Cys Ala Asn Pro Cys Arg Ile Pro Gly
            20                  25                  30

Lys Arg Ala Arg Leu Phe Arg Gln Arg
        35                  40

<210> SEQ ID NO 505
<211> LENGTH: 44
<212> TYPE: PRT
<213> ORGANISM: Conus figulinus

<400> SEQUENCE: 505

Cys Arg Ala Glu Gly Val Tyr Cys Glu Tyr Gly Ser Gln Cys Cys Leu
1               5                   10                  15

Ser Gln Cys Cys Met Ala Ser Cys Ala Asn Pro Cys Arg His Pro Gly
            20                  25                  30

Lys Arg Ala Arg Leu Gln Glu Phe Phe Arg Gln Arg
        35                  40

<210> SEQ ID NO 506
<211> LENGTH: 44
<212> TYPE: PRT
<213> ORGANISM: Conus figulinus

<400> SEQUENCE: 506

Cys Arg Ala Glu Gly Val Tyr Cys Glu Tyr Gly Ser Gln Cys Cys Leu
1               5                   10                  15

Ser Gln Cys Cys Met Ala Ser Cys Ala Asn Pro Cys Arg His Pro Gly
            20                  25                  30

Lys Arg Ala Arg Leu Gln Glu Phe Phe Arg Arg Arg
        35                  40

I-SUPERFAMILY CONOTOXINS

CROSS-REFERENCE TO RELATED APPLICATIONS

Figure 1:
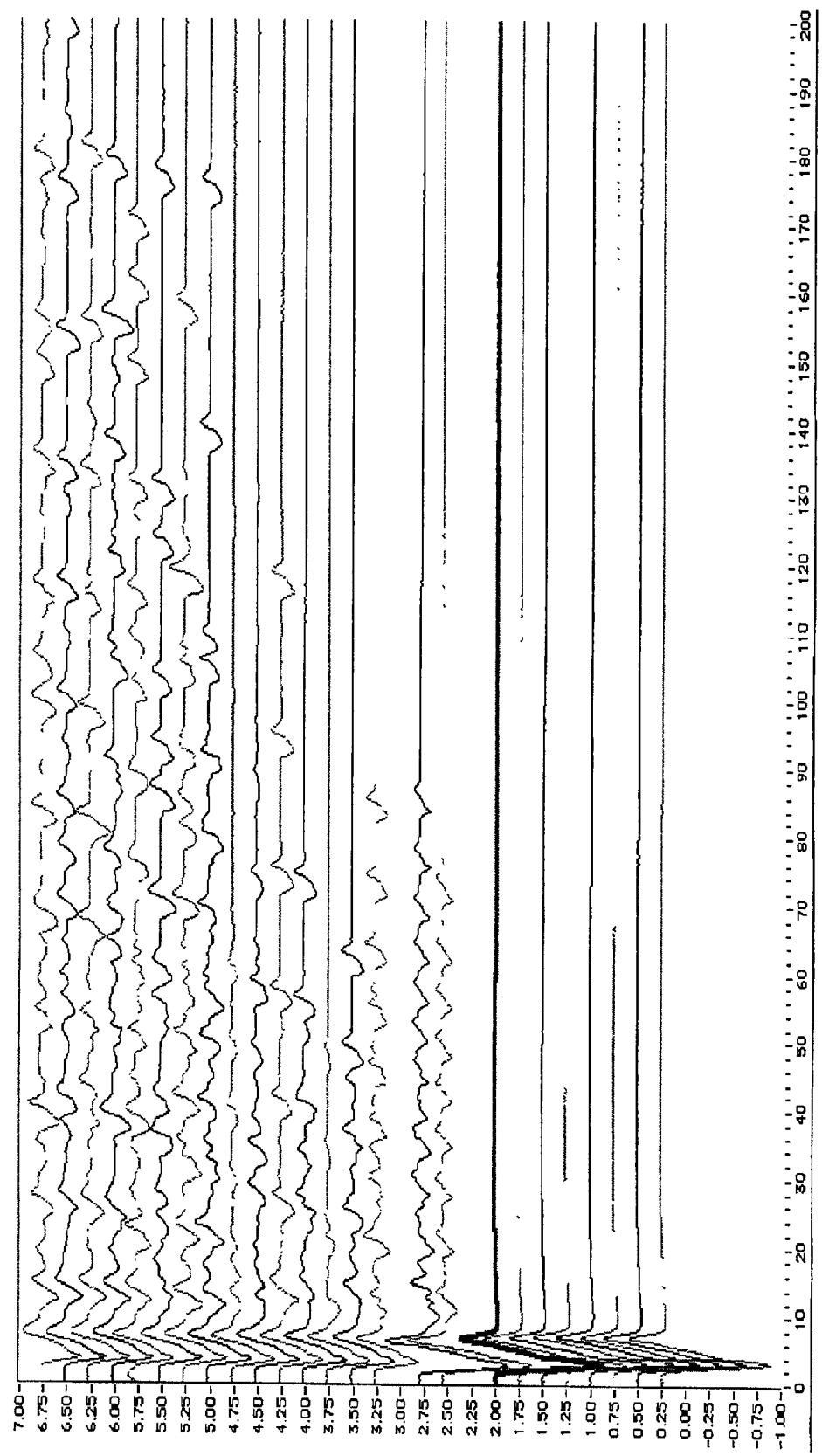

The present application claims benefit under 35 USC §119(e) to U.S. provisional patent applications Serial No. 60/304,166 filed Jun. 30, 2000 now abandoned, Serial No. 60/243,410 filed Oct. 27, 2000, Serial No. 60/246,581 filed Nov. 8, 2000, 60/247,714 filed Nov. 14, 2000 and 60/264,256 filed Jan. 29, 2001, each incorporated herein by reference.

This invention was made with Government support under Grant No. PO1 GM48677 awarded by the National Institute of General Medical Sciences, National Institutes of Health, Bethesda, Md. The United States Government has certain rights in the invention.

BACKGROUND OF THE INVENTION

The invention relates to relatively short peptides (termed I-conotoxins herein), about 30–50 residues in length, which are naturally available in minute amounts in the venom of the cone snails or analogous to the naturally available peptides, and which preferably include four disulfide bonds. The I-conotoxins are members of the I-Superfamily of conotoxins.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Conus is a genus of predatory marine gastropods (snails) which envenomate their prey. Venomous cone snails use a highly developed projectile apparatus to deliver their cocktail of toxic conotoxins into their prey. In fish-eating species such as Conus magus the cone detects the presence of the fish using chemosensors in its siphon and when close enough extends its proboscis and fires a hollow harpoon-like tooth containing venom into the fish. This immobilizes the fish and enables the cone snail to wind it into its mouth via an attached filament. For general information on Conus and their venom see the website "grimwade.biochem" at "unimelb.edu.au" Prey capture is accomplished through a sophisticated arsenal of peptides which target specific ion channel and receptor subtypes. Each Conus species venom appears to contain a unique set of 50–200 peptides. The composition of the venom differs greatly between species and between individual snails within each species, each optimally evolved to paralyse it's prey. The active components of the venom are small peptides toxins, typically 10–40 amino acid residues in length and are typically highly constrained peptides due to their high density of disulphide bonds.

The venoms consist of a large number of different peptide components that when separated exhibit a range of biological activities: when injected into mice they elicit a range of physiological responses from shaking to depression. The paralytic components of the venom that have been the focus of recent investigation are the α-, ω- and μ-conotoxins. All of these conotoxins act by preventing neuronal communication, but each targets a different aspect of the process to achieve this. The α-conotoxins target nicotinic ligand gated channels, the μ-conotoxins target the voltage-gated sodium channels and the co-conotoxins target the voltage-gated calcium channels (Olivera et al., 1985). For example a linkage has been established between α-, αA- & ψ-conotoxins and the nicotinic ligand-gated ion channel; ω-conotoxins and the voltage-gated calcium channel; μ-conotoxins and the voltage-gated sodium channel; δ-conotoxins and the voltage-gated sodium channel; κ-conotoxins and the voltage-gated potassium channel; conantokins and the ligand-gated glutamate (NMDA) channel. For a partial list of Conus peptides and their amino acid sequences see the website "pir" at "georgetown.edu".

However, the structure and function of only a small minority of these peptides have been determined to date. For peptides where function has been determined, three classes of targets have been elucidated: voltage-gated ion channels; ligand-gated ion channels, and G-protein-linked receptors.

Conus peptides which target voltage-gated ion channels include those that delay the inactivation of sodium channels, as well as blockers specific for sodium channels, calcium channels and potassium channels. Peptides that target ligand-gated ion channels include antagonists of NMDA and serotonin receptors, as well as competitive and noncompetitive nicotinic receptor antagonists. Peptides which act on G-protein receptors include neurotensin and vasopressin receptor agonists. The unprecedented pharmaceutical selectivity of conotoxins is at least in part defined by specific disulfide bond frameworks combined with hypervariable amino acids within disulfide loops (for a review see McIntosh et al., 1998).

There are drugs used in the treatment of pain, which are known in the literature and to the skilled artisan. See, for example, Merck Manual, 16th Ed. (1992). However, there is a demand for more active analgesic agents with diminished side effects and toxicity and which are non-addictive. The ideal analgesic would reduce the awareness of pain, produce analgesia over a wide range of pain types, act satisfactorily whether given orally or parenterally, produce minimal or no side effects, be free from tendency to produce tolerance and drug dependence.

Due to the high potency and exquisite selectivity of the conopeptides, several are in various stages of clinical development for treatment of human disorders. For example, two Conus peptides are being developed for the treatment of pain. The most advanced is ω-conotoxin MVIIA (ziconotide), an N-type calcium channel blocker (see Heading, C., 1999; U.S. Pat. No. 5,859,186). ω-Conotoxin MVIIA, isolated from *Conus magus*, is approximately 1000 times more potent than morphine, yet does not produce the tolerance or addictive properties of opiates. ω-Conotoxin MVIIA has completed Phase III (final stages) of human clinical trials and is now awaiting U.S. Food and Drug Administration approval as a therapeutic agent. ω-Conotoxin MVIIA is introduced into human patients by means of an implantable, programmable pump with a catheter threaded into the intrathecal space. Preclinical testing for use in post-surgical pain is being carried out on another Conus peptide, contulakin-G, isolated from *Conus geographus* (Craig et al. 1999). Contulakin-G is a 16 amino acid O-linked glycopeptide whose C-terminus resembles neurotensin. It is an agonist of neurotensin receptors, but appears significantly more potent than neurotensin in inhibiting pain in in vivo assays.

In view of a large number of biologically active substances in Conus species it is desirable to further characterize them and to identify peptides capable of treating disorders involving voltage gated ion channels, such as stroke and pain. Surprisingly, and in accordance with this invention, Applicants have discovered novel conotoxins that can be useful for the treatment of disorders involving voltage gated ion channels and could address a long felt need for a safe and effective treatment.

SUMMARY OF THE INVENTION

The invention relates to relatively short peptides (termed 1-conotoxins herein), about 30–50 residues in length, which are naturally available in minute amounts in the venom of the cone snails or analogous to the naturally available peptides, and which preferably include four disulfide bonds. The 1-conotoxins are useful for treating disorders involving voltage gated ion channels as described herein.

More specifically, the present invention is directed to 1-conotoxin peptides having the general formula I:

$Xaa_1$-$Xaa_2$-$Xaa_3$-$Xaa_4$-Cys-$Xaa_5$-$Xaa_6$-$Xaa_7$-$Xaa_8$-$Xaa_9$-$Xaa_{10}$-Cys-$Xaa_{11}$, $Xaa_{12}$-$Xaa_{13}$-$Xaa_{14}$-$Xaa_{15}$-Cys-Cys-$Xaa_{16}$-$Xaa_{17}$-$Xaa_{18}$-Cys-Cys-$Xaa_{19}$-$Xaa_{20}$-Gly-$Xaa_{21}$-Cys-$Xaa_{22}$-$Xaa_{23}$-$Xaa_{24}$-$Xaa_{25}$-$Xaa_{26}$-$Xaa_{27}$-$Xaa_{28}$-$Xaa_{29}$-$Xaa_{30}$-$Xaa_{30}$-Cys-$Xaa_{32}$-$Xaa_{33}$-$Xaa_{34}$-$Xaa_{35}$-$Xaa_{36}$-$Xaa_{37}$-$Xaa_{38}$-$Xaa_{39}$-$Xaa_{40}$-$Xaa_{41}$ (SEQ ID NO: 1), wherein $Xaa_1$ is des-$Xaa_1$ or Gly; $Xaa_2$ is des-$Xaa_2$, Pro, hydroxy-Pro (Hyp), Ala, His or Gly; $Xaa_3$ is des-$Xaa_3$, Ser, Val, Pro, Hyp, Thr, g-Ser (where g is glycosylation), g-Thr, g-Hyp or any synthetic hydroxylated amino acid; $Xaa_4$ is des-$Xaa_4$, Gly, Glu, γ-carboxy-Glu (Gla), Phe, Pro, Hyp, Arg, Lys, ornithine, homo-Lys, homoarginine, nor-Lys, N-methyl-Lys, N,N'-dimethyl-Lys, N,N',N"-trimethyl-Lys or any synthetic basic amino acid or $Xaa_4$ is pyro-Glu if $Xaa_1$, $Xaa_2$ and $Xaa_3$ are all des-Xaa; $Xaa_5$ is an aliphatic amino acid bearing linear or branched saturated hydrocarbon chains such as Leu (D or L), Ile and Val or non-natural derivatives of the aliphatic amino acid, Lys, Arg, ornithine, homo-Lys, homoarginine, nor-Lys, N-methyl-Lys, N,N'-dimethyl-Lys, N,N',N"-trimethyl-Lys, any synthetic basic amino acid, Gly, Trp (D or L), neo-Trp, halo-Trp (D or L) or any synthetic aromatic amino acid; $Xaa_6$ is Lys, Arg, ornithine, homo-Lys, homoarginine, nor-Lys, N-methyl-Lys, N,N'-dimethyl-Lys, N,N',N"-trimethyl-Lys, any synthetic basic amino acid, Ala, an aliphatic amino acids bearing linear or branched saturated hydrocarbon chains such as Leu (D or L), Ile and Val or non-natural derivatives of the aliphatic amino acid, Thr, Ser, g-Thr or g-Ser; $Xaa_7$ is Gly, Asp, Glu, Gla, Asn, Gln or any synthetic acidic amino acid; $Xaa_8$ is Gly, Lys, Arg, ornithine, homo-Lys, homoarginine, nor-Lys, N-methyl-Lys, N,N'-dimethyl-Lys, N,N',N"-trimethyl-Lys, any synthetic basic amino acid, Asp, Glu, Gla, Asn, Gln or any synthetic acidic amino acid; $Xaa_9$ is Ala, Val, Met, Lys, Arg, ornithine, homo-Lys, homoarginine, nor-Lys, N-methyl-Lys, N,N'-dimethyl-Lys, N,N',N"-trimethyl-Lys or any synthetic basic amino acid; $Xaa_{10}$ is Ala, His, Ser, Thr, Pro, Hyp, g-Ser, g-Thr, g-Hyp, any synthetic hydroxylated amino acid, Asn, Gln, Lys, Arg, ornithine, homo-Lys, homoarginine, nor-Lys, N-methyl-Lys, N,N'-dimethyl-Lys, N,N',N"-trimethyl-Lys or any synthetic basic amino acid; $Xaa_{11}$ is Gly, Ser, Thr, g-Ser, g-Thr, Asp, Glu, Gla, any synthetic acidic amino acid, Lys, Arg, ornithine, homo-Lys, homoarginine, nor-Lys, N-methyl-Lys, N,N'-dimethyl-Lys, N,N',N"-trimethyl-Lys or any synthetic basic amino acid; $Xaa_{12}$ is Phe, Tyr, meta-Tyr, ortho-Tyr, nor-Tyr, mono-halo-Tyr, di-halo-Tyr, halo-Tyr, O-sulpho-Tyr, O-phospho-Tyr, nitro-Tyr, any synthetic aromatic amino acid, Gln, Asn or Leu (D or L); $Xaa_{13}$ is Ser, Thr, g-Ser, g-Thr or His; $Xaa_{14}$ is Ala, Gla, Glu, Asp, Asn, Gln, any synthetic acidic amino acid, Ser, Thr, g-Ser, g-Thr, His, Lys, Arg, ornithine, homo-Lys, homoarginine, nor-Lys, N-methyl-Lys, N,N'-dimethyl-Lys, N,N',N"-trimethyl-Lys or any synthetic basic amino acid; $Xaa_{15}$ is Asp, Glu, Gla, Asn, Gln, any synthetic acidic amino acid or His; $Xaa_{16}$ is des-$Xaa_{16}$, Gly, His, Ser, Pro, Hyp, Thr, g-Ser, g-Thr, g-Hyp, any synthetic hydroxylated amino acid, Lys, Arg, ornithine, homo-Lys, homoarginine, nor-Lys, N-methyl-Lys, N,N'-dimethyl-Lys, N,N',N"-trimethyl-Lys or any synthetic basic amino acid; $Xaa_{17}$ is des-$Xaa_{17}$, His, Ser, Thr, g-Ser, g-Thr, Lys, Arg, ornithine, homo-Lys, homoarginine, nor-Lys, N-methyl-Lys, N,N'-dimethyl-Lys, N,N',N"-trimethyl-Lys, any synthetic basic amino acid, Phe, Tyr, meta-Tyr, ortho-Tyr, nor-Tyr, mono-halo-Tyr, di-halo-Tyr, O-sulpho-Tyr, O-phospho-Tyr, nitro-Tyr or any synthetic aromatic amino acid; $Xaa_{18}$ is Val, Asn, Lys, Arg, ornithine, homo-Lys, homoarginine, nor-Lys, N-methyl-Lys, N,N'-dimethyl-Lys, N,N',N"-trimethyl-Lys or any synthetic basic amino acid; $Xaa_{19}$ is des-$Xaa_{19}$, Leu (D or L), Pro, Hyp, Phe, Tyr, meta-Tyr, ortho-Tyr, nor-Tyr, mono-halo-Tyr, di-halo-Tyr, O-sulpho-Tyr, O-phospho-Tyr, nitro-Tyr or any synthetic aromatic amino acid; $Xaa_{20}$ is Gly, Ile, Ser, Thr, g-Ser, g-Thr, His, Lys, Arg, ornithine, homo-Lys, homoarginine, nor-Lys, N-methyl-Lys, N,N'-dimethyl-Lys, N,N',N"-trimethyl-Lys, any synthetic basic amino acid, Phe, Tyr, meta-Tyr, ortho-Tyr, nor-Tyr, mono-halo-Tyr, di-halo-Tyr, O-sulpho-Tyr, O-phospho-Tyr, nitro-Tyr or any synthetic aromatic amino acid; $Xaa_{21}$ is Ser, Thr, g-Ser, g-Thr, an aliphatic amino acid bearing linear or branched saturated hydrocarbon chains such as Leu (D or L), Ile and Val or non-natural derivatives of the aliphatic amino acid, Lys, Arg, ornithine, homo-Lys, homoarginine, nor-Lys, N-methyl-Lys, N,N'-dimethyl-Lys, N,N',N"-trimethyl-Lys, any synthetic basic amino acid, Phe, Tyr, meta-Tyr, ortho-Tyr, nor-Tyr, mono-halo-Tyr, di-halo-Tyr, O-sulpho-Tyr, O-phospho-Tyr, nitro-Tyr or any synthetic aromatic amino acid; $Xaa_{22}$ is Ala, Gln, Gla, Lys, Arg, ornithine, homo-Lys, homoarginine, nor-Lys, N-methyl-Lys, N,N'-dimethyl-Lys, N,N',N"-trimethyl-Lys or any synthetic basic amino acid; $Xaa_{23}$ is Ser, Pro, Hyp, Thr, g-Ser, g-Thr, g-Hyp, any synthetic hydroxylated amino acid, Lys, Arg, ornithine, homo-Lys, homoarginine, nor-Lys, N-methyl-Lys, N,N'-dimethyl-Lys, N,N',N"-trimethyl-Lys or any synthetic basic amino acid; $Xaa_{24}$ is Gln, Ser, Pro, Hyp, Thr, g-Ser, g-Thr, g-Hyp or any synthetic hydroxylated amino acid; $Xaa_{25}$ is des-$Xaa_{25}$, Ser, Thr, g-Ser, g-Thr or any synthetic hydroxylated amino acid; $Xaa_{26}$ is des-$Xaa_{26}$, Asn, Gln, Ser, Thr, g-Asn, g-Ser, g-Thr or any synthetic hydroxylated amino acid; $Xaa_{27}$ is des-$Xaa_{27}$, Val, Gla, Trp (D or L), neo-Trp, halo-Trp (D or L), any aromatic synthetic amino acid, Lys, Arg, ornithine, homo-Lys, homoarginine, nor-Lys, N-methyl-Lys, N,N'-dimethyl-Lys, N,N',N"-trimethyl-Lys or any synthetic basic amino acid; $Xaa_{28}$ is des-$Xaa_{28}$, an aliphatic amino acid bearing linear or branched saturated hydrocarbon chains such as Leu (D or L), Ile and Val or non-natural derivatives of the aliphatic amino acid; $Xaa_{29}$ is des-$Xaa_{29}$, an aliphatic amino acid bearing linear or branched saturated hydrocarbon chains such as Leu (D or L), Ile and Val or non-natural derivatives of the aliphatic amino acid; $Xaa_{30}$ is des-$Xaa_{30}$, Ile, Ser, Pro, Hyp, Thr, g-Ser, g-Thr, g-Hyp, any synthetic hydroxylated amino acid, Phe, Tyr, meta-Tyr, ortho-Tyr, nor-Tyr, mono-halo-Tyr, di-halo-Tyr, O-sulpho-Tyr, O-phospho-Tyr, nitro-Tyr or any synthetic aromatic amino acid; $Xaa_{31}$ is des-$Xaa_{31}$ or Gly; $Xaa_{32}$ is Ser, Thr, g-Ser, g-Thr, Trp (D or L), neo-Trp, halo-Tip (D or L), any aromatic synthetic amino acid, Lys, Arg, ornithine, homo-Lys, homoarginine, nor-Lys, N-methyl-Lys, N,N'-dimethyl-Lys, N,N',N"-trimethyl-Lys or any synthetic basic amino acid; $Xaa_{33}$ is Val, Ser, Thr, g-Ser, g-Thr, Trp (D or L), neo-Trp, halo-Trp (D or L) or any aromatic synthetic amino acid; $Xaa_{34}$ is Gly, Ile, Asp, Glu, Gla, Asn, Ser, Thr, g-Asn, g-Ser or g-Thr; $Xaa_{35}$ is des-$Xaa_{35}$, Val, Met, Gln, Pro, Hyp, Ser, Thr, g-Ser, g-Thr, g-Hyp or any synthetic hydroxylated amino acid; $Xaa_{36}$ is des-$Xaa_{36}$, Val, Thr, Ser, g-Thr, g-Ser, Phe, Tyr, meta-Tyr, ortho-Tyr, nor-Tyr, mono-halo-Tyr, di-halo-Tyr, O-sulpho-Tyr, O-phospho-Tyr, nitro-Tyr or any synthetic aromatic amino acid; $Xaa_{37}$ is des-$Xaa_{37}$, Gln, Asn, Thr, Ser, g-Ser, g-Ser, g-Asn, Met, Leu, Phe, Tyr, meta-Tyr, ortho-Tyr, nor-Tyr, mono-halo-Tyr, di-halo-Tyr, O-sulpho-Tyr, O-phospho-Tyr, nitro-Tyr, any synthetic aromatic amino acid, Lys, Arg, ornithine, homo-Lys, homoarginine, nor-Lys, N-methyl-Lys, N,N'-dimethyl-Lys, N,N',N"-trimethyl-Lys or any synthetic basic amino acid; $Xaa_{38}$ is des-$Xaa_{38}$, Leu, Ser, Thr, g-Ser, g-Thr, Lys, Arg, ornithine, homo-Lys, homoarginine, nor-Lys, N-methyl-Lys, N,N'-dimethyl-Lys, N,N',N"-trimethyl-Lys or any synthetic basic amino acid; $Xaa_{39}$ is des-$Xaa_{39}$, Ile, Ala, Thr, Ser, g-Ser, g-Thr, Lys, Arg, ornithine, homo-Lys, homoarginine, nor-Lys, N-methyl-Lys, N,N'-dimethyl-Lys, N,N',N"-trimethyl-Lys or any synthetic basic amino acid; $Xaa_{40}$ is des-$Xaa_{40}$, Asp, Lys, Arg, ornithine, homo-Lys, homoarginine, nor-Lys, N-methyl-Lys, N,N'-dimethyl-Lys, N,N',N"-trimethyl-Lys or any synthetic basic amino acid; and $Xaa_{41}$ is des-$Xaa_{41}$, Phe, Tyr, meta-Tyr, ortho-Tyr, nor-Tyr, mono-halo-Tyr, di-halo-Tyr, O-sulpho-Tyr, O-phospho-Tyr, nitro-Tyr or any synthetic aromatic amino acid, with the proviso that the peptide is not J029 as defined below. The Cys residues may be in D or L configuration and may optionally be substituted with homocysteine (D or L). The Tyr residues may be substituted with the 3-hydroxyl or 2-hydroxyl isomers and corresponding O-sulpho- and O-phospho-derivatives. The acidic amino acid residues may be substituted with any synthetic acidic amino acid, e.g., tetrazolyl derivatives of Gly and Ala. The nonnatural derivatives of the aliphatic amino acids include those synthetic derivatives bearing non-natural aliphatic branched or linear side chains $C_nH_{2n+2}$ up to and including n=8. The Met residues may be substituted with norleucine (Nle). The halogen is iodo, chloro, fluoro or bromo; preferably iodo for halogen substituted-Tyr and bromo for halogen-substituted Trp.

J029 has the sequence Gly-Xaa-Ser-Phe-Cys-Lys-Ala-Asp-Glu-Lys-Xaa-Cys-Glu-Tyr-His-Ala-Asp-Cys-Cys-Asn-Cys-Cys-Leu-Ser-Gly-Ile-Cys-Ala-Xaa-Ser-Thr-Asn-Trp-Ile-Leu-Xaa-Gly-Cys-Ser-Thr-Ser-Ser-Phe-Phe-Lys-Ile (SEQ ID NO:2), wherein Xaa is Pro or hydroxy-Pro.

The present invention is also directed to novel specific I-conotoxin peptides within general formula I having the mature toxin sequences set forth in Table 1. The present invention is further directed to 1-conotoxins having the amino acid sequences set forth in Tables 2–4.

In addition, the present invention is directed to the above I-contoxins in which the Arg residues may be substituted by Lys, ornithine, homoargine, nor-Lys, N-methyl-Lys, N,N-dimethyl-Lys, N,N,N-trimethyl-Lys or any synthetic basic amino acid; the Lys residues may be substituted by Arg, ornithine, homoargine, nor-Lys, or any synthetic basic amino acid; the Tyr residues may be substituted with any synthetic hydroxy containing amino acid; the Ser residues may be substituted with Thr or any synthetic hydroxylated amino acid; the Thr residues may be substituted with Ser or any synthetic hydroxylated amino acid; the Phe and Trp residues may be substituted with any synthetic aromatic amino acid; and the Asn, Ser, Thr or Hyp residues may be glycosylated. The Cys residues may be in D or L configuration and may optionally be substituted with homocysteine (D or L). The Tyr residues may also be substituted with the 3-hydroxyl or 2-hydroxyl isomers (meta-Tyr or ortho-Tyr, respectively) and corresponding O-sulpho- and O-phospho-derivatives. The acidic amino acid residues may be substituted with any synthetic acidic amino acid, e.g., tetrazolyl derivatives of Gly and Ala. The aliphatic amino acids may be substituted by synthetic derivatives bearing non-natural aliphatic branched or linear side chains $C_nH_{2n+2}$ up to and including n=8. The Leu residues may be substituted with Leu (D). The Glu residues may be substituted with Gla. The Gla residues may be substituted with Glu. The N-terminal Gln residues may be substituted with pyroGlu. The Met residues may be substituted with norleucine (Nle).

The present invention is further directed to derivatives of the above peptides and peptide derivatives which are acylic permutations in which the cyclic permutants retain the native bridging pattern of native toxin. See Craik et al. (2001).

Examples of synthetic aromatic amino acid include, but are not limited to, such as nitro-Phe, 4-substituted-Phe wherein the substituent is $C_1$–$C_3$ alkyl, carboxyl, hyrdroxymethyl, sulphomethyl, halo, phenyl, -CHO, -CN, -$SO_3H$ and -NHAc. Examples of non-natural hydroxy containing amino acid, include, but are not limited to, such as 4-hydroxymethyl-Phe, 4--hydroxyphenyl-Gly, 2,6-dimethyl-Tyr and 5-amino-Tyr. Examples of non-natural basic amino acids include, but are not limited to, N-1-(2-pyrazolinyl)-Arg, 2-(4-piperinyl)-Gly, 2-(4-piperinyl)-Ala, 2-[3-(2S)pyrrolininyl)-Gly and 2-[3-(2S)pyrrolininyl)-Ala. These and other non-natural basic amino acids, non-natural hydroxy containing amino acids or non-natural aromatic amino acids are described in Building Block Index, Version 3.0 (1999 Catalog, pages 4–47 for hydroxy containing amino acids and aromatic amino acids and pages 66–87 for basic amino acids; see also the website "amino-acids.com"), incorporated herein by reference, by and available from RSP Amino Acid Analogues, Inc., Worcester, Mass. Examples of non-natural acid amino acids include those derivatives bearing acidic functionality, including carboxyl, phosphate, sulfonate and non-natural tetrazolyl derivatives such as described by Ornstein et al. (1993) and in U.S. Pat. No. 5,331,001, each incorporated herein by reference.

Optionally, in the peptides of general formula I and the specific peptides described above, the Asn residues may be modified to contain an N-glycan and the Ser, Thr and Hyp residues may be modified to contain an O-glyean (e.g., g-N, g-S, g-T and g-Hyp). In accordance with the present invention, a glycan shall mean any N—, S—or O— linked mono-, di-, tri-, poly- or oligosaccharide that can be attached to any hydroxy, amino or thiol group of natural or modified amino acids by synthetic or enzymatic methodologies known in the art. The monosaccharides making up the glycan can include D-allose, D-altrose, D-glucose, D-mannose, D-gulose, D-idose, D-galactose, D-talose, D-galactosamine, D-glucosamine, D-N-acetyl-glucosamine (GlcNAc), D-N-acetyl-galactosamine (GalNAc), D-fucose or D-arabinose. These saccharides may be structurally modified, e.g., with one or more O-sulfate, O-phosphate, O-acetyl or acidic groups, such as sialic acid, including combinations thereof. The glycan may also include similar polyhydroxy groups, such as D-penicillamine 2,5 and halogenated derivatives thereof or polypropylene glycol derivatives. The glycosidic linkage is beta and 1–4 or 1–3, preferably 1–3. The linkage between the glycan and the amino acid may be alpha or beta, preferably alpha and is 1-.

Core O-glycans have been described by Van de Steen et al. (1998), incorporated herein by reference. Mucin type O-linked oligosaccharides are attached to Ser or Thr (or other hydroxylated residues of the present peptides) by a GalNAc residue. The monosaccharide building blocks and the linkage attached to this first GalNAc residue define the "core glycans," of which eight have been identified. The type of glycosidic linkage (orientation and connectivities) are defined for each core glycan. Suitable glycans and glycan analogs are described further in U.S. Ser. No. 09/420,797 filed Oct. 19, 1999 and in PCT Application No. PCT/US99/24380 filed Oct. 19, 1999 (PCT Published Application No. WO 00/23092), each incorporated herein by reference. A preferred glycan is Gal(β1→3)GalNAc(α1→).

Optionally, in the peptides of general formula I and the specific peptides described above, pairs of Cys residues may be replaced pairwise with isoteric lactam or ester-thioether replacements, such as Ser/(Glu or Asp), Lys/(Glu or Asp), Cys/(Glu or Asp) or Cys/Ala combinations. Sequential coupling by known methods (Barnay et al., 2000; Hruby et al., 1994; Bitan et al., 1997) allows replacement of native Cys bridges with lactam bridges. Thioether analogs may be readily synthesized using halo-Ala residues commercially available from RSP Amino Acid Analogues.

The peptides of the general formula and the specific peptides disclosed herein contain 8 Cys residues leading to 4 disulfide bridges. Related peptides called Janus faced atrachatoxins (J-ACTXs) have been isolated from the Australian funnel web spider (*Hadronyche versuta*) (King et al., 2000). The peptides of the present invention can be aligned with these peptides as shown below for the I-Superfamily peptides R11.9 and R11.7. The alignment of all of the I-Superfamily peptides is set forth in Tables 2–4 herein.

```
JACTX-Hv1a  TICTGADRPCAA---CCP--CCPGTSCQGPESNGVVYCRNF       (SEQ ID NO:3)

JACTX-Hv1b  TICTGADRPCAA---CCP--CCPGTSCQGPEPNGVSYCRND       (SEQ ID NO:4)

JACTX-Hv1c  AICTGADRPCAA---CCP--CCPGTSCKA-ESNGVSYCRKDEP     (SEQ ID NO:5)

E11.9      GPSFCKADEKPCEYHADCCN--CCLSGICAPSTNWILPGCSTSSFFKI^ (SEQ ID NO:6)

R11.7      GPSFCKADEKPCEYHSDCCN--CCLSGICAPSTNWTLPGCSTSSFFKI^ (SEQ ID NO:7)
```

Based on alignment of the peptides of the present invention with the J-ACTXs, the preferred disulfide bridging is as follows: Cys1-Cys6, Cys2-Cys7, Cys3-Cys-4 and Cys5-Cys8, wherein Cys1 refers to the first Cys residue in the sequence of the I-Superfamily peptides, Cys2 refers to the second Cys residue in the sequence of the I-Superfamily peptides, etc.

The present invention is also directed to the identification of the nucleic acid sequences encoding these peptides and their propeptides and the identication of nucleic acid sequences of additional related 1-conotoxin peptides. Thus, the present invention is directed to nucleic acids coding for the conotoxin peptide precursors (or conotoxin propeptides) set forth in Table 1. The present invention is further directed to the conotoxin propeptides set forth in Table 1.

The present invention is further directed to a method of treating disorders associated with voltage gated ion channel disorders in a subject comprising administering to the subject an effective amount of the pharmaceutical composition comprising a therapeutically effective amount of a 1-conotoxin peptide described herein or a pharmaceutically acceptable salt or solvate thereof. The present invention is also directed to a pharmaceutical composition comprising a therapeutically effective amount of a 1-conotoxin peptide described herein or a pharmaceutically acceptable salt or solvate thereof and a pharmaceutically acceptable carrier.

Another embodiment of the invention contemplates a method of identifying compounds that mimic the therapeutic activity of the instant peptide, comprising the steps of: (a) conducting a biological assay on a test compound to determine the therapeutic activity; and (b) comparing the results obtained from the biological assay of the test compound to the results obtained from the biological assay of the peptide. The peptide is labeled with any conventional label, preferably a radioiodine on an available Tyr. Thus, the invention is also directed to radioiodinated 1-conotoxins.

BRIEF DESCRIPTION OF THE FIGURES

FIG. 1 shows the muscle response as recorded extracellularly for electrical stimulation of the motor nerve of a cutaneus pectoris muscle before and after administration of I-conotoxin R11.19. The peptide was introduced just before the $8^{th}$ trace. The tracings below the $8^{th}$ trace represent controls and the tracings above the $8^{th}$ trace represent experimental. Vertical units are millivolts, horizontal units are milliseconds.

FIG. 2 shows response of motor nerve and muscle to the effect of R11.19 with units the same as in FIG. 1. The bottom three traces represent activity recorded extracellularly from muscle, and the remaining traces are those from motor nerve.

DETAILED DESCRIPTION OF THE PREFERRED EMBODIMENT

The invention relates to relatively short peptides (termed I-conotoxins herein), about 30–50 residues in length, which are naturally available in minute amounts in the venom of the cone snails or analogous to the naturally available peptides, and which preferably include four disulfide bonds. The I-conotoxins are members of the I-Superfamily of conotoxins. The I-conotoxins are useful for treating disorders involving voltage gated ion channels.

The present invention, in another aspect, relates to a pharmaceutical composition comprising an effective amount of an I-conotoxin peptide, a mutein thereof, an analog thereof, an active fragment thereof or pharmaceutically acceptable salts or solvates. Such a pharmaceutical composition has the capability of acting at voltage gated ion channels, and are thus useful for treating a disorder or disease of a living animal body, including a human, which disorder or disease is responsive to the partial or complete blockade of voltage gated ion channels of the central nervous system comprising the step of administering to such a living animal body, including a human, in need thereof a therapeutically effective amount of a pharmaceutical composition of the present invention.

The membranes found at the surface of mammalian cells perform functions of great importance relating to the integrity and activities of cells and tissues. Of particular interest is the study of ion channel biochemistry, physiology, pharmacology and biokinetics. These ion channels, which include sodium (Na), potassium (K) and calcium (Ca) channels are present in all mammalian cells and control a variety of physiological and pharmacological processes.

For example, attention has been focused on the potassium channel, particularly its involvement in normal cellular homeostasis and its possible association with and derangements relating to a variety of disease states and immune responses. Considerable research has been expended and is currently underway in order not only to devise a treatment or prophylaxis against such devastating diseases, but also to study the underlying etiology(ies) such that a better understanding can be gained as to common denominators, if any, that would more directly focus a plan of attack for conquering them. Diseases having a particular association with such channels include autoimmune diseases and other proliferative disorders such as cancers. Autoimmune diseases include rheumatoid arthritis, type-1 diabetes mellitus (insulin dependent), multiple sclerosis, myasthenia gravis, systematic lupus erythematosus, Sjögren's syndrome, mixed connective tissue disease, experimental allergic encephalomyclitis (EAE), to name a few.

Potassium channels comprise a large and diverse group of proteins that, through maintenance of the cellular membrane potential, are fundamental in normal biological function. These channels are vital in controlling the resting membrane potential in excitable cells and can be broadly sub-divided into three classes: voltage-gated $K^+$ channels, $Ca^{2+}$ activated $K^+$ channels and ATP-sensitive $K^+$ channels. Many disorders are associated with abnormal flow of potassium ions through these channels. These disorders include multiple sclerosis, other demyelinating diseases (such as acute disseminated encephalomyelitis, optic neuromyelitis, adrenoleukodystrophy, acute transverse myelitis, progressive multifocal leukoencephalopathy), sub-acute sclerosing panencephalomyelitis (SSPE), metachromatic leukodystrophy, Pelizaeus-Merzbacher disease, spinal cord injury, botulinum toxin poisoning, Huntington's chorea, compression and entrapment neuropathies (such as carpal tunnel syndrome, ulnar nerve palsy), cardiovascular disorders (such as cardiac arrhythmias, congestive heart failure), reactive gliosis, hyperglycemia, immunosuppression, cocaine addiction, cancer, cognitive dysfunction, disorders resulting from defects in neurotransmitter release (such as Eaton-Lambert syndrome), and reversal of the actions of curare and other neuromuscular blocking drugs.

Activators of $K_{ATP}$ channels have therapeutic significance for the treatment of asthma, cardiac ischemia and cerebral ischemia, among others.

Asthma: Asthma is a serious and common condition that effects approximately 12 million people in the United States alone. This disorder is particularly serious in children and it has been estimated that the greatest number of asthma patients are those under the age of 18 (National Health Survey, National Center of Health Statistics, 1989). The disease is characterized by chronic inflammation and hyperresponsiveness of the airway which results in periodic attacks of wheezing and difficulty in breathing. An attack occurs when the airway smooth muscle become inflamed and swells as a result of exposure to a trigger substance. In severe cases, the airway may become blocked or obstructed as a result of the smooth muscle contraction. Further exacerbating the problem is the release of large quantities of mucus which also act to block the airway. Chronic asthmatics are most commonly treated prophylactically with inhaled corticosteroids and acutely with inhaled bronchodilators, usually β-2 agonists. However, chronic treatment with inhaled corticosteroids has an associated risk of immune system impairment, osteoporosis, adrenal gland malfunction and an increased susceptibility to fungal infections (Rakel, 1997). In addition use of β-2 agonists has been reported in some cases to cause adverse reactions including tremor, tachycardia and palpitations and muscle cramps (Rakel, 1997). Therefore, there is great potential in developing anti-asthmatic agents with fewer side-effects.

$K^+$ channel openers have been shown to be effective relaxants of airway smooth muscle reducing hyperactivity induced obstruction of intact airway. In cryopreserved human bronchi (Muller-Schweinitzer and Fozard, 1997) and in the isolated guinea pig tracheal preparation (Lin et al, 1998; Ando et al., 1997; Nielson-Kudsk, 1996; Nagai et al., 1991). $K_{ATP}$ openers produced relaxation whether the muscle was contracted spontaneously or induced by a range of spasmogens. Under these conditions, the $K^+$ channel openers are thought to be acting to produce a $K^+$ ion efflux and consequent membrane hyperpolarization. As a result, voltage-sensitive $Ca^{2+}$ channels would close and intracellular calcium levels would drop, producing muscular relaxation. The development of new and more specific $K_{ATP}$ openers may offer a novel approach both to the prophylactic and symptomatic treatment of asthma.

$K_{ATP}$ channels are present in many tissue types beyond just the target tissue, therefore their activation may result in unwanted side effects. In particular, as $K_{ATP}$ channels are found in vascular smooth muscle, it is possible that in addition to the beneficial anti-asthmatic properties of $K_{ATP}$ openers there could be an associated drop in blood pressure. It is possible that delivering the compound in inhalant form directly to the airway smooth muscle will allow the concentration of the compound to be reduced significantly thereby minimizing adverse reactions.

Cardiac Ischemia: While numerous subtypes of potassium channels in cardiac tissue have not yet been fully characterized, openers of $K_{ATP}$ channels show great promise as cardioprotective agents. The beneficial vasodilatory effects afforded by $K^+$ channel openers in patients with angina pectoris are now well established (Chen et al., 1997; Goldschmidt et al., 1996; Yamabe et al., 1995; Koike et al., 1995). Furthermore, the activation of $K_{ATP}$ channels appears also to be involved in the acute preconditioning of the myocardium following brief ischemic periods, acting to reduce the risk (Pell et al., 1998) and size of the reperfusion infarct (Kouchi et al., 1998).

Direct evidence for the cytoprotective properties of $K_{ATP}$ channels was demonstrated by Jovanovic et al. (1998a). In these studies, the DNA encoding for the Kir6.2/SUR2A (cardiac $K_{ATP}$) channel were transfected in COS-7 monkey cells and the degree of calcium loading monitored. Untransfected cells were demonstrated to be vulnerable to the increases in intracellular calcium seen following hypoxia/reoxygenation. However, the transfection of the cells with the $K_{ATP}$ channel conferred resistance to the potentially damaging effects of the hypoxia-reoxygenation. Thus, the cardiac $K_{ATP}$ channels are likely to play a significant role in protecting the myocardium against reperfusion injury.

Cerebral Ischemia: Although treatment of cerebral ischemia has advanced significantly over the past 30 years, cerebral ischemia (stroke) still remains the third leading cause of death in the United States. More than 500,000 new stroke/ischemia cases are reported each year. Even though initial mortality is high (38%), there are close to three million survivors of stroke in the United States, and yearly cost for rehabilitation of these patients in the United States is close to $17 billion (Rakel, 1997).

The initial cellular effects occur very rapidly (a matter of minutes) after an ischemic episode, whereas the actual cellular destruction does not occur until several hours or days following the infarction. Initial effects include depolarization due to bioenergetic failure, and inactivation of $Na^+$ channels. Voltage-gated calcium channels are activated resulting in a massive rise in intracellular calcium. Further exacerbating the problem is a large transient release of glutamate which itself increases both $Na^+$ and $Ca^{2+}$ influx through ionotropic glutamate receptors. Glutamate also binds to metabotropic receptors, which results in activation of the inositol phosphate pathway. This sets off a cascade of intracellular events, including further release of calcium from intracellular stores. It is now well accepted that this initial overload of intracellular calcium ultimately leads to the delayed cytotoxicity that is seen hours or days later.

Recently it has been reported that dopaminergic neurons exposed to a very short hypoxic challenge will hyperpolarize primarily through an opening of $K_{ATP}$ channels (Guatteo et al., 1998). This stimulatory effect was suggested to be a direct result of the increased metabolic demand and the consequent drop in intracellular ATP levels. Furthermore Jovanovic et al. (1998b) recently reported that cells transfected with DNA encoding for Kir6.2/SUR1 (neuronal $K_{ATP}$) channel showed increased resistance to injury caused through hypoxia-reoxygenation. Therefore, the opening of $K_{ATP}$ channels may serve a vital cytoprotective role during short periods of reduced oxygen in neuronal tissue. Thus, there is great therapeutic potential in developing compounds that not only will act to prevent this calcium influx prophylactically, but will aid in reestablishing the normal resting membrane potential in damaged tissue. Treatment with I-conotoxin peptides of the present invention will act to open $K_{ATP}$ channels, inducing membrane hyperpolarization and indirectly producing closure of the voltage-gated $Ca^{2+}$ channels, thereby preventing or reducing deleterious effects of a massive calcium influx.

The present invention is also directed to the use of I-conopeptides as a local anesthetic for treating pain. The I-conopeptides have long lasting anesthetic activity and are particularly useful for spinal anesthesia, either administered acutely for post-operative pain or via an intrathecal pump for severe chronic pain situations.

The present invention is further directed to the use of I-conopeptides as neuromuscular blockers and for treating neuromuscular disorders. As such, the I-conopeptides are useful for providing relaxation of muscle, for treating benign essential blepharospasm and other forms of focal dystonia and for anti-wrinkle use. Thus, in one aspect, the I-conopeptides are useful as neuromuscular blocking agents in conjunction with surgery or for intubation of the trachea by conventional parenteral administration e.g., intramuscular or intravenous administration in solution. In a second aspect, the I-conopeptides are useful as agents for treating neuromuscular disorders such as myofacial pain syndrome, chronic muscle spasm, dystonias and spasticity.

The primary factor detrimental to neurons in neurological disorders associated with deficient oxygen supply or mitochondrial dysfunction is insufficient ATP production relative to their requirement. As a large part of the energy consumed by brain cells is used for maintenance of the $Na^+$ gradient across the cellular membrane, reduction of energy demand by down-modulation of voltage-gated Na(+)-channels is one strategy for neuroprotection. In addition, preservation of the inward $Na^+$ gradient may be beneficial because it is an essential driving force for vital ion exchanges and transport mechanisms such as $Ca^{2+}$ homeostasis and neurotransmitter uptake. Thus, the I-conopeptides of the present invention are useful as neuroprotectants.

Voltage-gated calcium channels are present in neurons, and in cardiac, smooth, and skeletal muscle and other excitable cells, and are known to play a variety of roles in membrane excitability, muscle contraction, and cellular secretion, such as in synaptic transmission (McCleskey). In neuronal cells, voltage-gated calcium channels have been classified by their electrophysiological as well as by their biochemical (binding) properties. Six classes of physiologically distinct calcium channels have been identified to date, namely the T, L, N, P, Q, and R-type channels.

It is well known that an accumulation of calcium (calcium overload) in the brain is seen after anoxia, ischemia, migraine and other hyperactivity periods of the brain, such as after epileptic convulsions. An uncontrolled high concentration of calcium in the cells of the central nervous system (CNS) is known to cause most of the degenerative changes connected with the above diseases. Compounds which can block the calcium channels of brain cells are therefore useful in the treatment of stroke, anoxia, ischemia, migraine, psychosis, or epilepsy, any other convulsive disorder and in the prevention of the degenerative changes connected with the same.

Compounds blocking the so called I-type calcium channels in the CNS are useful for the treatment of the above disorders by directly blocking the calcium uptake in the CNS. Further, it is well known that the so called N- and P-types of calcium channels, as well as possibly other types of calcium channels, are involved in the regulation of neurotransmitter release. Compounds blocking the N- and/or P-types of calcium channels indirectly and very powerfully prevent calcium overload in the CNS after the hyperactivity periods of the brain as described above by inhibiting the enhanced neurotransmitter release seen after such hyperactivity periods of the CNS, and especially the neurotoxic, enhanced glutamate release after such hyperactivity periods of the CNS. Furthermore, blockers of the N- and/or P-types of calcium channels, as dependent upon the selectivity of the compound in question, inhibit the release of various other neurotransmitters such as aspartate, GABA, glycine, dopamine, serotonin and noradrenaline.

Thus, the pharmaceutical compositions of the present invention are useful as neuroprotectants, anticonvulsants, anxiolytics, analgesics, muscle relaxants or adjuvants to general anesthetics. A "neurological disorder or disease" is a disorder or disease of the nervous system including, but not limited to, global and focal ischemic and hemorrhagic stroke, head trauma, spinal cord injury, hypoxia-induced nerve cell damage as in cardiac arrest or neonatal distress, epilepsy, anxiety, and neurodegenerative disease. In addition, a "neurological disorder or disease" is a disease state and condition in which a neuroprotectant, anticonvulsant, anxiolytic, analgesic, muscle relaxant and/or adjunct in general anesthesia may be indicated, useful, recommended or prescribed. A "neurodegenerative disease" is a disease including, but not limited to, Alzheimer's Disease, Huntington's Disease, Parkinson's Disease, and amyotrophic lateral sclerosis (ALS).

A "neuroprotectant" is a compound capable of preventing the neuronal death associated with a neurological disorder or disease. An "anticonvulsant" is a compound capable of reducing convulsions produced by conditions such as simple partial seizures, complex partial seizures, status epilepticus, and trauma-induced seizures such as occur following head injury, including head surgery. An "anxiolytic" is a compound capable of relieving the feelings of apprehension, uncertainty and fear that are characteristic of anxiety. An "analgesic" is a compound capable of relieving pain by altering perception of nociceptive stimuli without producing anesthesia or loss of consciousness. A "muscle relaxant" is a compound that reduces muscular tension. A "adjunct in general anesthesia" is a compound useful in conjunction with anesthetic agents in producing the loss of ability to perceive pain associated with the loss of consciousness.

The invention relates as well to methods useful for treatment of neurological disorders and diseases, including, but not limited to, global and focal ischemic and hemorrhagic stroke, head trauma, spinal cord injury, hypoxia-induced nerve cell damage such as in cardiac arrest or neonatal distress, epilepsy or other convulsive disorders, movement disorders (such as tardive dyskinesia and acute dystonic reactions), inflammation, anxiety, schizophrenia and neurodegenerative diseases such as Alzheimer's Disease, Huntington's Disease, Parkinson's Disease, and amyotrophic lateral sclerosis (ALS), without undesirable side effects.

Thus, in one embodiment, the invention provides a method of reducing/alleviating/decreasing the perception of pain by a subject or for inducing analgesia, including local, in a subject comprising administering to the subject an effective amount of the pharmaceutical composition comprising a therapeutically effective amount of a I-conotoxin peptide described herein or a pharmaceutically acceptable salt or solvate thereof. The pain maybe acute, persistent, migraine, inflammatory, nociceptive or neuropathic pain.

In a second embodiment, the invention provides a method of treating stroke, head or spinal cord trauma or injury, anoxia, hypoxia-induced nerve cell damage, ischemia, migraine, psychosis, anxiety, schizophrenia, inflammation, movement disorder, epilepsy, any other convulsive disorder or in the prevention of the degenerative changes connected with the same in a subject comprising administering to the subject an effective amount of the pharmaceutical composition comprising a therapeutically effective amount of a I-conotoxin peptide described herein or a pharmaceutically acceptable salt or solvate thereof.

In a third embodiment, the invention provides a method of treating neurodegenerative diseases such as Alzheimer's Disease, Huntington's Disease, Parkinson's Disease, and amyotrophic lateral sclerosis (ALS) in a subject comprising administering to the subject an effective amount of the pharmaceutical composition comprising a therapeutically effective amount of a I-conotoxin peptide described herein or a pharmaceutically acceptable salt or solvate thereof.

In a fourth embodiment, the invention provides a method of treating multiple sclerosis, other demyelinating diseases, SSPE, metachromatic leukodystrophy, Pelizaeus-Merzbacher disease, botulinum toxin poisoning, compression and entrapment neuropathies, cardiovascular disorders, reactive gliosis, hyperglycemia, immunosuppression, cocaine addiction, cancer, cognitive dysfunction, disorders resulting from defects in neurotransmitter release (such as Eaton-Lambert syndrome), and reversal of the actions of curare and other neuromuscular blocking drugs.

In a fifth embodiment, the invention provides a method for providing a neuromuscular block or for treating neuromuscular disorders, such as methods for providing relaxation of muscle, for treating benign essential blepharospasm and other forms of focal dystonia and for anti-wrinkle use. Thus, in one aspect, the I-conopeptides are useful as neuromuscular blocking agents in conjunction with surgery or for intubation of the trachea by conventional parenteral administration e.g., intramuscular or intravenous administration in solution. In a second aspect, the I-conopeptides are useful as agents for treating neuromuscular disorders such as myofacial pain syndrome, chronic muscle spasm, dystonias and spasticity.

In a sixth embodiment, the I-conopeptides of the present invention are also useful to reduce neurotoxic injury associated with conditions of hypoxia, anoxia or ischemia which typically follows stroke, cerebrovascular accident, brain or spinal chord trauma, myocardial infarct, physical trauma, drownings, suffocation, perinatal asphyxia, or hypoglycemic events.

The I-conotoxin peptides described herein are sufficiently small to be chemically synthesized. General chemical syntheses for preparing the foregoing I-conotoxin peptides are described hereinafter. Various ones of the I-conotoxin peptides can also be obtained by isolation and purification from specific Conus species using the technique described in U.S. Pat. No. 4,447,356 (Olivera et al., 1984); U.S. Pat. Nos. 5,514,774; 5,719,264; and 5,591,821, as well as in PCT published application WO 98/03189, the disclosures of which are incorporated herein by reference.

Although the I-conotoxin peptides of the present invention can be obtained by purification from cone snails, because the amounts of I-conotoxin peptides obtainable from individual snails are very small, the desired substantially pure I-conotoxin peptides are best practically obtained in commercially valuable amounts by chemical synthesis using solid-phase strategy. For example, the yield from a single cone snail may be about 10 micrograms or less of I-conotoxin peptide. By "substantially pure" is meant that the peptide is present in the substantial absence of other biological molecules of the same type; it is preferably present in an amount of at least about 85% purity and preferably at least about 95% purity. Chemical synthesis of biologically active I-conotoxin peptides depends of course upon correct determination of the amino acid sequence.

The I-conotoxin peptides can also be produced by recombinant DNA techniques well known in the art. Such techniques are described by Sambrook et al. (1989). A gene of interest (i.e., a gene that encodes a suitable I-conotoxin peptide) can be inserted into a cloning site of a suitable expression vector by using standard techniques. These techniques are well known to those skilled in the art. The expression vector containing the gene of interest may then be used to transfect the desired cell line. Standard transfection techniques such as calcium phosphate co-precipitation, DEAE-dextran transfection or electroporation may be utilized. A wide variety of host/expression vector combinations may be used to express a gene encoding a conotoxin peptide of interest. Such combinations are well known to a skilled artisan. The peptides produced in this manner are isolated, reduced if necessary, and oxidized to form the correct disulfide bonds.

One method of forming disulfide bonds in the I-conotoxin peptides of the present invention is the air oxidation of the linear peptides for prolonged periods under cold room temperatures or at room temperature. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. However, because of the dilution resulting from the presence of other fractions of less biopotency, a somewhat higher dosage may be required.

The peptides are synthesized by a suitable method, such as by exclusively solid-phase techniques, by partial solid-phase techniques, by fragment condensation or by classical solution couplings.

In conventional solution phase peptide synthesis, the peptide chain can be prepared by a series of coupling reactions in which constituent amino acids are added to the growing peptide chain in the desired sequence. Use of various coupling reagents, e.g., dicyclohexylcarbodiimide or diisopropylcarbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise, "Methoden der Organischen Chemie (Houben-Weyl): Synthese von Peptiden," (1974). Techniques of exclusively solid-phase synthesis are set forth in the textbook, "Solid-Phase Peptide Synthesis," (Stewart and Young, 1969), and are exemplified by the disclosure of U.S. Pat. No. 4,105,603 (Vale et al., 1978). The fragment condensation method of synthesis is exemplified in U.S. Pat. No. 3,972,859 (1976). Other available syntheses are exemplified by U.S. Pat. No. 3,842,067 (1974) and U.S. Pat. No. 3,862,925 (1975). The synthesis of peptides containing carboxyglutamic acid residues is exemplified by Rivier et al. (1987), Nishiuchi et al. (1993) and Zhou et al. (1996).

Common to such chemical syntheses is the protection of the labile side chain groups of the various amino acid moieties with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chain protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or param-ethylbenzhydrylamine (MBHA) resin. Preparation of the hydroxymethyl resin is described by Bodansky et al. (1966). Chloromethylated resins are commercially available from Bio Rad Laboratories (Richmond, Calif.) and from Lab. Systems, Inc. The preparation of such a resin is described by Stewart and Young (1969). BHA and MBHA resin supports are commercially available, and are generally used when the desired polypeptide being synthesized has an unsubstituted amide at the C-terminus. Thus, solid resin supports may be any of those known in the art, such as one having the formulae —O—CH$_2$—resin support, —NH BHA resin support, or —NH-MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 (Kornreich et al., 1986) can be used, or should still other groups than the free acid be desired at the C-terminus, it may be preferable to synthesize the peptide using classical methods as set forth in the Houben-Weyl text (1974).

The C-terminal amino acid, protected by Boc or Fmoc and by a side-chain protecting group, if appropriate, can be first coupled to a chloromethylated resin according to the procedure set forth in K. Horiki et al. (1978), using KF in DMF at about 60° C. for 24 hours with stirring, when a peptide having free acid at the C-terminus is to be synthesized. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder & Lubke (1965).

After removal of the α-amino-protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (DCC, DIC, HBTU, HATU, TBTU in the presence of HoBt or HoAt).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke (1965) and Kapoor (1970).

Each protected amino acid or amino acid sequence is introduced into the solid-phase reactor in about a twofold or more excess, and the coupling may be carried out in a medium of dimethylformamide (DMF):CH$_2$Cl$_2$ (1:1) or in DMF or CH$_2$Cl$_2$ alone. In cases where intermediate coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by Kaiser et al. (1970). Coupling reactions can be performed automatically, as on a Beckman 990 automatic synthesizer, using a program such as that reported in Rivier et al. (1978).

After the desired amino acid sequence has been completed, the intermediate peptide can be removed from the resin support by treatment with a reagent, such as liquid hydrogen fluoride or TFA (if using Fmoc chemistry), which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride or TFA for cleaving, one or more scavengers such as anisole, cresol, dimethyl sulfide and methylethyl sulfide are included in the reaction vessel.

Cyclization of the linear peptide is preferably affected, as opposed to cyclizing the peptide while a part of the peptido-resin, to create bonds between Cys residues. To effect such a disulfide cyclizing linkage, fully protected peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the peptide from the above resins or a benzhydrylamine (BHA) resin or a methylbenzhydrylamine (MBHA), can take place at 0° C. with hydrofluoric acid (HF) or TFA, followed by oxidation as described above.

The peptides are also synthesized using an automatic synthesizer. Amino acids are sequentially coupled to an MBHA Rink resin (typically 100 mg of resin) beginning at the C-terminus using an Advanced Chemtech 357 Automatic Peptide Synthesizer. Couplings are carried out using 1,3-diisopropylcarbodimide in N-methylpyrrolidinone (NMP) or by 2-(1 H-benzotriazole-1-yl)-1,1,3,3-tetramethyluronium hexafluorophosphate (HBTU) and diethylisopro-pylethylamine (DIEA). The FMOC protecting group is removed by treatment with a 20% solution of piperidine in dimethylformamide(DMF). Resins are subsequently washed with DMF (twice), followed by methanol and NMP.

On the basis of the amino acid sequence of any of the I-conotoxins described herein, oligonucleotide primers are synthesized and used in 5' and 3' RACE (rapid amplification of cDNA ends) procedures to isolate the gene encoding the precursor proteins. Alternatively, the DNA to be probed is DNA which is isolated and cloned in accordance with conventional techniques using general procedures well known in the art, such as described in Olivera et al. (1996). As is common with conotoxin peptides, the identified DNAs coding for I-conotoxins code for precursor peptides which are translationally modified to yield the I-conotoxin peptides.

Additional conotoxin peptides are identified by cloning by reverse transcription-polymerase chain reaction (RT-PCR) from cone snail venom duct mRNA. The PCR primers are based on the DNA sequences coding for the precursor peptides described herein. RT-PCR of venom duct mRNA produces a product of about 250–300 nucleotides in Conus species that express conotoxin genes. The PCR product is then cloned into a plasmid vector and individual clones are sequenced to determine the sequence of various conotoxin genes. Alternatively, cDNA libraries are prepared from Conus venom duct using conventional techniques. DNA from single clones is amplified by conventional techniques using primers which correspond approximately to the M13 universal priming site and the M13 reverse universal priming site. Clones having a size of approximately 250 nucleotides are sequenced and screened for similarity in sequence to the propeptide described herein. In this manner, conotoxins having the basic structure and activity described herein are cloned from many Conus species.

Muteins, analogs or active fragments, of the foregoing conotoxin peptides are also contemplated here. See, e.g., Hammerland et al. (1992). Derivative muteins, analogs or active fragments of the conotoxin peptides may be synthesized according to known techniques, including conservative amino acid substitutions, such as outlined in U.S. Pat. No. 5,545,723 (see particularly col. 2, line 50-col. 3, line 8); U.S. Pat. No. 5,534,615 (see particularly col. 19, line 45-col. 22, line 33); and U.S. Pat. No. 5,364,769 (see particularly col. 4, line 55-col. 7, line 26), each herein incorporated by reference.

Pharmaceutical compositions containing a compound of the present invention or its pharmaceutically acceptable salts or solvates as the active ingredient can be prepared according to conventional pharmaceutical compounding techniques. See, for example, Remington's Pharmaceutical Sciences, 18th Ed. (1990, Mack Publishing Co., Easton, Pa.). Typically, an analgesic amount of the active ingredient will be admixed with a pharmaceutically acceptable carrier. The carrier may take a wide variety of forms depending on the form of preparation desired for administration, e.g., intravenous, oral or parenteral. The compositions may further contain antioxidizing agents (e.g., to maintain disulfide bridges intact, including among others, lactate buffer and methionine), stabilizing agents, preservatives and the like. For examples of delivery methods, see U.S. Pat. No. 5,844,077.

"Pharmaceutical composition" means physically discrete coherent portions suitable for medical administration. "Pharmaceutical composition in dosage unit form" means physically discrete coherent units suitable for medical administration, each containing a daily dose or a multiple (up to four times) or a sub-multiple (down to a fortieth) of a daily dose of the active compound in association with a carrier and/or enclosed within an envelope. Whether the composition contains a daily dose, or for example, a half, a third or a quarter of a daily dose, will depend on whether the pharmaceutical composition is to be administered once or, for example, twice, three times or four times a day, respectively.

The term "salt", as used herein, denotes acidic and/or basic salts, formed with inorganic or organic acids and/or bases, preferably basic salts. While pharmaceutically acceptable salts are preferred, particularly when employing the compounds of the invention as medicaments, other salts find utility, for example, in processing these compounds, or where non-medicament-type uses are contemplated. Salts of these compounds may be prepared by art-recognized techniques.

Examples of such pharmaceutically acceptable salts include, but are not limited to, inorganic and organic addition salts, such as hydrochloride, sulphates, nitrates or phosphates and acetates, trifluoroacetates, propionates, succinates, benzoates, citrates, tartrates, fumarates, maleates, methane-sulfonates, isothionates, theophylline acetates, salicylates, respectively, or the like. Lower alkyl quaternary ammonium salts and the like are suitable, as well.

As used herein, the term "pharmaceutically acceptable" carrier means a non-toxic, inert solid, semi-solid liquid filler, diluent, encapsulating material, formulation auxiliary of any type, or simply a sterile aqueous medium, such as saline.

Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically acceptable antioxidants include, but are not limited to, water soluble antioxidants such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, alohatocopherol and the like; and the metal chelating agents such as citric acid, ethylenediamine tetraacetic acid (EDTA), sorbitol, tartaric acid, phosphoric acid and the like.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

A variety of administration routes are available. The particular mode selected will depend of course, upon the particular drug selected, the severity of the disease state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, topical, nasal, transdermal or parenteral routes. The term "parenteral" includes subcutaneous, intravenous, epidural, irrigation, intramuscular, release pumps, or infusion.

For example, administration of the active agent according to this invention may be achieved using any suitable delivery means, including:

(a) pump (see, e.g., Lauer & Hatton (1993), Zimm et al. (1984) and Ettinger et al. (1978));

(b), microencapsulation (see, e.g., U.S. Pat. Nos. 4,352,883; 4,353,888; and 5,084,350);

(c) continuous release polymer implants (see, e.g., U.S. Pat. No. 4,883,666);

(d) macroencapsulation (see, e.g., U.S. Pat. Nos. 5,284,761, 5,158,881, 4,976,859 and 4,968,733 and published PCT patent applications WO92/19195, WO 95/05452);

(e) naked or unencapsulated cell grafts to the CNS (see, e.g., U.S. Pat. Nos. 5,082,670 and 5,618,531);

(f) injection, either subcutaneously, intravenously, intraarterially, intramuscularly, or to other suitable site; or (g) oral administration, in capsule, liquid, tablet, pill, or prolonged release formulation.

In one embodiment of this invention, an active agent is delivered directly into the CNS, preferably to the brain ventricles, brain parenchyma, the intrathecal space or other suitable CNS location, most preferably intrathecally.

Alternatively, targeting therapies may be used to deliver the active agent more specifically to certain types of cells, by the use of targeting systems such as antibodies or cell-specific ligands. Targeting may be desirable for a variety of reasons, e.g. if the agent is unacceptably toxic, if it would otherwise require too high a dosage, or if it would not otherwise be able to enter target cells.

The active agents, which are peptides, can also be administered in a cell based delivery system in which a DNA sequence encoding an active agent is introduced into cells designed for implantation in the body of the patient, especially in the spinal cord region. Suitable delivery systems are described in U.S. Pat. No. 5,550,050 and published PCT Application Nos. WO 92/19195, WO 94/25503, WO 95/01203, WO 95/05452, WO 96/02286, WO 96/02646, WO 96/40871, WO 96/40959 and WO 97/12635. Suitable DNA sequences can be prepared synthetically for each active agent on the basis of the developed sequences and the known genetic code.

The active agent is preferably administered in an therapeutically effective amount. By a "therapeutically effective amount" or simply "effective amount" of an active compound is meant a sufficient amount of the compound to treat or alleviate pain or to induce analgesia at a reasonable benefit/risk ratio applicable to any medical treatment. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Parmaceutical Sciences*.

Dosage may be adjusted appropriately to achieve desired drug levels, locally or systemically. Typically the conopeptides of the present invention exhibit their effect at a dosage range from about 0.001 mg/kg to about 250 mg/kg, preferably from about 0.05 mg/kg to about 100 mg/kg of the active ingredient, more preferably from about 0.1 mg/kg to about 75 mg/kg, and most preferably from about 1.0 mg/kg to about 50 mg/kg. A suitable dose can be administered in multiple sub-doses per day. Typically, a dose or sub-dose may contain from about 0.1 mg to about 500 mg of the active ingredient per unit dosage form. A more preferred dosage will contain from about 0.5 mg to about 100 mg of active ingredient per unit dosage form. Dosages are generally initiated at lower levels and increased until desired effects are achieved. In the event that the response in a subject is insufficient at such doses, even higher doses (or effective higher doses by a different, more localized delivery route) may be employed to the extent that patient tolerance permits. Continuous dosing over, for example 24 hours or multiple doses per day are contemplated to achieve appropriate systemic levels of compounds.

Advantageously, the compositions are formulated as dosage units, each unit being adapted to supply a fixed dose of active ingredients. Tablets, coated tablets, capsules, ampoules and suppositories are examples of dosage forms according to the invention.

It is only necessary that the active ingredient constitute an effective amount, i.e., such that a suitable effective dosage will be consistent with the dosage form employed in single or multiple unit doses. The exact individual dosages, as well as daily dosages, are determined according to standard medical principles under the direction of a physician or veterinarian for use humans or animals.

The pharmaceutical compositions will generally contain from about 0.0001 to 99 wt. %, preferably about 0.001 to 50 wt. %, more preferably about 0.01 to 10 wt. % of the active ingredient by weight of the total composition. In addition to the active agent, the pharmaceutical compositions and medicaments can also contain other pharmaceutically active compounds. Examples of other pharmaceutically active compounds include, but are not limited to, analgesic agents, cytokines and therapeutic agents in all of the major areas of clinical medicine. When used with other pharmaceutically active compounds, the conotoxin peptides of the present invention may be delivered in the form of drug cocktails. A cocktail is a mixture of any one of the compounds useful with this invention with another drug or agent. In this embodiment, a common administration vehicle (e.g., pill, tablet, implant, pump, injectable solution, etc.) would contain both the instant composition in combination supplementary potentiating agent. The individual drugs of the cocktail are each administered in therapeutically effective amounts. A therapeutically effective amount will be determined by the parameters described above; but, in any event, is that amount which establishes a level of the drugs in the area of body where the drugs are required for a period of time which is effective in attaining the desired effects.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982; Sambrook et al., 1989; Ausubel et al., 1992; Glover, 1985; Anand, 1992; Guthrie and Fink, 1991; Harlow and Lane, 1988; Jakoby and Pastan, 1979*; Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology,* 6th Edition, Blackwell Scientific Publications, Oxford, 1988; Hogan et al., Manipulating the Mouse Embryo, (Cold Spring Harbor Laboratory Press, Cold Spring Harbor, N.Y., 1986).

EXAMPLES

The present invention is described by reference to the following Examples, which are offered by way of illustration and are not intended to limit the invention in any manner. Standard techniques well known in the art or the techniques specifically described below were utilized.

Example 1

Isolation of I-Conotoxins

Crude venom was extracted from venom ducts (Cruz et al., 1976), and the components were purified as previously described (Cartier et al., 1996). The crude extract from venom ducts was purified by reverse phase liquid chromatography (RPLC) using VYDAC® $C_{18}$ semi-preparative column (10×250 mm). Further purification of bioactive peaks was done on a VYDAC® analytical column (4.6×220 mm). The effluents were monitored at 220 nm. Peaks were collected, and aliquots were assayed for activity. Throughout purification, HPLC fractions were assayed by means of intracerebral ventricular (i.c.v.) injection into mice (Clark et at, 1981).

The amino acid sequence of the purified peptides were determined by standard methods. The purified peptides were reduced and alkylated prior to sequencing by automated Edman degradation on an Applied Biosystems 477A Protein Sequencer with a 120A Analyzer (DNA/Peptide Facility, University of Utah) (Martinez et al., 1995; Shon et al., 1994).

In accordance with this method, peptides U026, GH-015, R11.14 and R11.19 were obtained.

Example 2

Synthesis of Conopeptides

The synthesis of conopeptides, either the mature toxins or the precursor peptides, was separately performed using conventional protection chemistry as described by Cartier et al. (1996).

Briefly, the linear chains were built on Rink amide resin by Fmoc procedures with 2-(1H-benzotriol-1-yl)-1,1,3,3,-tetramethyluronium tetrafluoroborated coupling using an ABI model 430A peptide sythesizer with amino acid derivatives purchased from Bachem (Torrence Calif.). Orthogonal protection was used on cysteines: two cysteines were protected as the stable Cys(S-acetamidomethyl), while the other two cysteines were protected as the acid-labile Cys(S-trityl). After removal of the terminal Fmoc protecting group and cleavage of the peptides from the resins, the released peptides were precipitated by filtering the reaction mixture into −10° C. methyl t-butyl ether, which removed the protecting groups except the Cys(S-acetamidomethyl). The peptides were dissolved in 0.1% TEA and 60% acetonitrile and purified by RPLC on a VYDAC® C$_{18}$ preparative column (22×250 mm) and eluted at a flow rate of 20 mL/min with a gradient of acetonitrile in 0.1% TFA.

The disulfide bridges in the conopeptides were formed as described in Cartier et al. (1996). Briefly, the disulfide bridges between one pair of cystemes were formed by air oxidation which was judged to be complete by analytical RPLC. The monocyclic peptides were purified by RPLC on a VYDAC® C$_{18}$ prepartive column (22×250 mm) and eluted with a gradient of acetonitrile in 0.1% TEA. Removal of S-acetamidomethyl groups and closure of the disulfide bridge between the other pair of cysteines was carried out simultaneously be iodine oxidation. The cyclic peptides were purified by RPLC on a VYDAC® C$_{18}$ prepartive column (22×250 mm) and eluted with a gradient of acetonitrile in 0.1% TFA. HPLC fractions were assayed by means of intracerebral ventricular (i.c.v.) injection into mice (Clark et al., 1981). The most active cyclic peptide is the one having the same disulfide bond arrangement as the native peptide.

Example 3

Isolation of DNA Encoding I-Conotoxins

DNA coding for I-conotoxins was isolated and cloned in accordance with conventional techniques using general procedures well known in the art, such as described in Olivera et al. (1996). Alternatively, cDNA libraries was prepared from Conus venom duct using conventional techniques. DNA from single clones was amplified by conventional techniques using primers which correspond approximately to the M13 universal priming site and the M13 reverse universal priming site. Clones having a size of approximately 300–500 nucleotides were sequenced and screened for similarity in sequence to known I-conotoxins isolated in Example 1. The DNA sequences and encoded propeptide sequences are set forth in Table 1. DNA sequences coding for the mature toxin can also be prepared on the basis of the DNA sequences set forth in these Tables. An alignment of the I-Superfamily conotoxins by type are set forth in Tables 2–4.

TABLE 1

Type I
Name:     GH-015
Species:  radiatus
Isolated: Yes
Cloned:   Yes

DNA Sequence:
TTCGCCAGCTATTTAGGTGACACTATAGAATACTCAAGCTTGCATGCCTGCAGGTCGACTCTAGAGGATC   (SEQ ID NO:8)

CAGGCTTCAGACGAGGACAACCCAGCTATCAGCACTTCGCAGCAGTCGAGGCTTTCAAATCCTAATCATA

GAAGAAGGCAAAAATATCTGCTGGTCAATATGAAGCTGTGCCTGACGTTCCTTCTTGTTCTGATGATTCT

GGCATCAGTGACTGGGCAGAAGTCAAGCAAGCATACACTGAGTCGTGCTGCTAGGGTAAAAAACACAGCC

TGTAAGAAAGACAGAAAGCCATGCTCGTATCATGCAGATTGCTGTAATTGCTGTCTCAGTGGAATCTGTG

CACCAAGCACAAATTGGATTTTACCTGGATGCTCGACGAGTACGTTCACTTGACGCGCTOACTTTCAGCC

AGCTAGGCCATGCCTAGGTCCTCATGCACATTCACATTTGCTGTGAATTGAATTCATGTGCATTAAAGCC

ATTAGGCGTAGAAAGAT

Translation:
MKLCLTFLLVLMTLASVTGEKSSKHTLSRAARVKNRGCKKDRKPCSYHADCCNCCLSGICAPSTNWTLPG   (SEQ ID NO:9)

CSTSTFT

Toxin Sequence:
Gly-Cys-Lys-Lys-Asp-Arg-Lys-Xaa3-Cys-Ser-Xaa5-His-Ala-Asp-Cys-Cys-Asn-   (SEQ ID NO:10)

Cys-Cys-Leu-Ser-Gly-Ile-Cys-Ala-Xaa3-Ser-Thr-Asn-Xaa4-Ile-Leu-Xaa3-

Gly-Cys-Ser-Thr-Ser-Thr-Phe-Thr-

Name:     J029
Species:  radiatus
Isolated: Yes
Cloned:   Yes

DNA Sequence:
CCAGCTATCAGCACTTCGCAGCAGTCGAGGCTTTGAAATCCTAATCATAGAAGAAGGCAAAAATATCTGC   (SEQ ID NO:11)

TGGTCAATATGAAGCTGTGCCTGACGTTCCTTCTTGTTCTGATCATTCTGGCATCAGTGACTGGGGAGAA

GTCAAGCAAGCATACACTGAGTCGTGCTGCTAGGGTAAAAAACAGAGGCCCTAGTTTTTGTAAGGCAGAC

GAAAAGCCATGCGAGTATCATGCAGATTGCTGTAATTGCTGTCTCAGTGGAATCTGTGCACCAAGCACAA

ATTGGATTTTACCTGGATGCTCGACGAGTTCGTTCTTCAAGATCTGACTTTCAGCCAGCTAGGCCATGCC

TAGGTCCTCATGCACATTCACATTTGCTGTGAATTGAATTCATGTGCATTAAAGCCATTAGGCGTAGAAA

TABLE 1-continued

GATGAAAAAA

Translation:
MKLCLTFLLVLMILASVTGEKSSKHTLSRAARVKNRGPSFCKADEKPCEYHADCCNCCLSGICAPSTNWI (SEQ ID NO:12)

LPGCSTSSFFKI

Toxin Sequence:
Gly-Xaa3-Ser-Phe-Cys-Lys-Ala-Asp-Xaa1-Lys-Xaa3-Cys-Xaa1-Xaa5-His-Ala- (SEQ ID NO:13)

Asp-Cys-Cys-Asn-Cys-Cys-Leu-Ser-Gly-Ile-Cys-Ala-Xaa3-Ser-Thr-Asn-Xaa4-

Ile-Leu-Xaa3-Gly-Cys-Ser-Thr-Ser-Ser-Phe-Phe-Lys-Ile-^

Name:     R11.1
Species:  radiatus
Isolated: No
Cloned:   Yes

DNA Sequence:
CGGAATTCCGATCAGCACTTCGCAGCAGTCGAGGCTTTGATATCCTAATCATAGAAGAAGGCAAAAATAT (SEQ ID NO:14)

CTGCTGGTCAATATGAAGCTGTGCCTGACGTTCCTTCTTGTTCTGATGATTCTGGCATCAGTGACTGGGG

AGAAGTTAAGCGAGCAAACACTGCGTCGTGCTGCTAGGAAAAACAAAGGCCATGTTCCATGCGGGAAAGA

CGGAAGGAAATGCGGGTATCATGCAGATTGCTGTAATTGCTGTCTCAGTGGAATCTGTAAACCAAGCACA

AGTTGGACTGGATGCTCGACGAGTACCGTTCGATTGACGCGCTGACTTTCAGCCAGCTAGGCCATGCCTA

GGTCCTCATGCACATTCACATTTGCTGTGAATTGAATTCATGTGCATTAAAGCCATTAGGCGTAGAAAGA

TTAAA

Translation:
MKLCLTFLLVLMILASVTGEKLSEQTLRRAARKNKGHVPCGKDGRKCGYHADCCNCCLSGICKPSTSWTG (SEQ ID NO:15)

CSTSTVRLTR

Toxin Sequence:
Gly-His-Val-Xaa3-Cys-Gly-Lys-Asp-Gly-Arg-Lys-Cys-Gly-Xaa5-His-Ala-Asp- (SEQ. ID NO:16)

Cys-Cys-Asn-Cys-Cys-Leu-Ser-Gly-Ile-Cys-Lys-Xaa3-Ser-Thr-Ser-Xaa4-Thr-

Gly-Cys-Ser-Thr-Ser-Thr-Val-Arg-Leu-Thr-Arg^

Name:     R11.2
Species:  radiatus
Isolated: No
Cloned:   Yes

DNA Sequence:
AATCATAGAAGAAGGCAAAAATATCTGCTGGTCAATATGAAGCTGTGCCTGACGTTCCTTCTTGTTCTGA (SEQ ID NO:17)

TGATTCTGGCATCAGTGACTGGGGAGAAGTTAAGCAAGCATACACTGAGTCATGCTACTAGGAGACCCAA

CAAAGGCGCTGTTCCATGCGGGAAAGACGGAAGGCAATGCAGGAATCATGCAGATTGCTGTAATTGCTGT

CCCATTGGAACCTGTGCACCAAGCACAAATTGGATTTTACCTGGATGCTCGACGGGTCCGTTCATGACGC

GCTGACTTTCAGCCAGCTAGGCCATGCCTAGGTCCTCATGCACATTCACATTTGCTGTGAATTGAATTAA

TGTGCATTAAAGCCATTAGGCGTAGAAAGATGAAA

Translation:
MKLCLTFLLVLMTLASVTGEKLSKHTLSHATRRPNKGAVPCGKDGRQCRNHADCCNCCPIGTCAPSTNWI (SEQ ID NO:18)

LPGCSTGPFMTR

Toxin Sequence:
Gly-Ala-Val-Xaa3-Cys-Gly-Lys-Asp-Gly-Arg-Gln-Cys-Arg-Asn-His-Ala-Asp- (SEQ ID NO:19)

Cys-Cys-Asn-Cys-Cys-Xaa3-Ile-Gly-Thr-Cys-Ala-Xaa3-Ser-Thr-Asn-Xaa4-

Ile-Leu-Xaa3-Gly-Cys-Ser-Thr-Gly-Xaa3-Phe-Met-Thr-Arg-^

Name:     R11.3
Species:  radiatus
Isolated: No

TABLE 1-continued

Cloned: Yes

DNA Sequence:
CAGACGAGGACATCCCAGCTATCAGCACTTCGCAGCAGTCGAGGCTTTGAAATCCTAATCATAGAAGAAG (SEQ ID NO:20)

GCAAAAATATCTGCTGGTCAATATGAAGCTGTGCCTGACGTTCCTTCTTGTTCTGATGATTCTGGCATCA

GTGACTGGGGAGAAGTTAAGCGAGCAAACACTGCGTCGTGCTGCTAGGAAAAACAAAGGCCCTCGATGCT

GGGTCGGCCGTGTCCATTGCACCTATCATAAAGACTGCTGTCCGTCGGTATGTTGTTTCAAGGGAAGGTG

TAAACCACAATCATGGGGATGCTGGTCGGGTCCGACCTAGGCGTGCTGGCCTTGAGGCAGCTAGGCCATG

CCTAGGTCCTCATGCACATTCACATTTGCTGTGAATTGAATTCATGTGCATTAAAGCCATTANGCGTAGA

AAGATTAAAAA

Translation:
MKLCLTFLLVLMILASVTGEKLSEQTLRRAARKNKGPRCWVGRVHCTYHKDCCPSVCCFKGRCKPQSWGC (SEQ ID NO:21)

WSGPT

Toxin Sequence:
Gly-Xaa3-Arg-Cys-Xaa4-Val-Gly-Arg-Val-His-Cys-Thr-Xaa5-His-Lys-Asp- (SEQ ID NO:22)

Cys-Cys-Xaa3-Ser-Val-Cys-Cys-Phe-Lys-Gly-Arg-Cys-Lys-Xaa3-Gln-Ser-

Xaa4-Gly-Cys-Xaa4-Ser-Gly-Xaa3-Thr-^

Name: R11.4
Species: radiatus
Isolated: No
Cloned: Yes

DNA Sequence:
CCCAGCTATCAGCACTCCGCAGGCTTCAGACGAGGACATCCCAGCTATCAGCACTTCGCAGCAGTCGAGG (SEQ ID NO:23)

CTTTGAAATCCTAATCATAGAAGAAGGCAAAAATATCTGCTGGTCAATATGAAGCTGTGCCTGACGTTCC

TTCTTGTTCTGATGATTCTGGCATCAGTGACTGGGGAGAAGTCAAGCAAGCATACACTGAGTCGTGCTGC

TAGGGTAAAAAACAGAGGCCCTAGTTTTTGTAAGGCAGACGAAAAGCCATGCAAGTATCATGCAGATTGC

TGTAACTGCTGTCTCGGTGGAATCTGTAAACCAAGCACAAGTTGGATTGGATGCTCGACGAATGTGTTCT

TGACGCGCTGACTTTCAGCCAGCTAGGCCATGCCTAGGTCCTCATGCACATTCACATTTGCTGTGAATTG

AATTCATGTGCATTAAAGCCATTAGGCGTAGAAAGATGAAAAAA

Translation:
MKLCLTFLLVLMILASVTGEKSSKHTLSRAARVKNRGPSFCKADEKPCKYHADCCNCCLGGTCKPSTSWI (SEQ ID NO:24)

GCSTNVFLTR

Toxin Sequence:
Gly-Xaa3-Ser-Phe-Cys-Lys-Ala-Asp-Xaa1-Lys-Xaa3-Cys-Lys-Xaa5-His-Ala- (SEQ ID NO:25)

Asp-Cys-Cys-Asn-Cys-Cys-Leu-Gly-Gly-Ile-Cys-Lys-Xaa3-Ser-Thr-Ser-Xaa4-

Ile-Gly-Cys-Ser-Thr-Asn-Val-Phe-Leu-Thr-Arg-^

Name: R11.5
Species: radiatus
Isolated: No
Cloned: Yes

DNA Sequence:
CGGAATTCCGCGGAATTCCGCCAGCTATCAGCACTTCGCAGCAGTCGAGGCTTTGAAATCCTAATCATAG (SEQ ID NO:26)

AAGAAGGCAAAAATATCTGCTGGTCAATATGAACCTGTGCCTGACGTTCCTTCTTGTTCTGATGATTCTG

GCATCAGTGACTGGGGAGAAGTTAAGCAAGCATACACTGACTCATGCTGCTAGGAGACCCAACAAAGGCG

CTGTTCCATGCGGGAAAGACGGAAGGCAATGCAGGAATCATGCAGATTGCTGTAATTGCTGTCCCATTGG

AACCTGTGCACCAAGCACAAATTGGATTTTACCTGGATGGTCGACGGGTCAATTCATGACCGCTGACTTT

TAGCCAGCTAGGCCATGCCTAGGTCTTATGCACATTACATTTGCTGGGAATGAATTATTGTGCATTAAAG

TABLE 1-continued

CCATAGGCGTTAAAGATGGAAAAAAA

Translation:
MKLCLTFLLVLMTLASVTGEKLSKHTLSHAARRPNKGAVPCGKDGRQCRNHADCCNCCPIGTCAPSTNWI (SEQ ID NO:27)

LPGCSTGQFMTADF

Toxin Sequence:
Gly-Ala-Val-Xaa3-Cys-Gly-Lys-Asp-Gly-Arg-Gln-Cys-Arg-Asn-His-Ala-Asp- (SEQ ID NO:28)

Cys-Cys-Asn-Cys-Cys-Xaa3-Ile-Gly-Thr-Cys-Ala-Xaa3-Ser-Thr-Asn-Xaa4-

Ile-Leu-Xaa3-Gly-Cys-Ser-Thr-Gly-Gln-Phe-Met-Thr-Ala-Asp-Phe-^

Name: R11.7
Species: radiatus
Isolated: No
Cloned: Yes

DNA Sequence:
CAGACGAGGACAACCCAGCTATCAGCACTTCGCAGCAGTCAGGCTTTGAAATCCTAATCATAGAAGAAGG (SEQ ID NO:29)

CAAAAATATCTGCTGGTCAATATGAAGCTGTGCCTGACGTTCCTTCTTGTTCTGATGATTCTGGCATCAG

TGACTGGGGAGAAGTCAAGCAAGCATACACTGAGTCGTGCTGCTAGGGTAAAAAACAGAGGCCCTAGTTT

TTGTAAGGCAGACGAAAAGCCATGCGAGTATCATTCAGATTGCTGTAATTGCTGTCTCAGTGGAATCTGT

GCACCAAGCACAAATTGGATTTTACCTGGATGCTCGACGAGTTCGTTCTTCAAGATCTGACTTTCAGCCA

GCTAGGCCATGCCTAGGTCCTCATGCACATTCACATTTGCTGTGAATTGAATTCATGTGCATTAAAGCCA

TTAGGCGTAGAAAGATGAAA

Translation:
NKLCLTFLLVLMILASVTGEKSSKHTLSRAARVKNRGPSFCKADEKPCEYHSDCCNCCLSGICAPSTNWI (SEQ ID NO:30)

LPGCSTSSFFKI

Toxin Sequence:
Gly-Xaa3-Ser-Phe-Cys-Lys-Ala-Asp-Xaa1-Lys-Xaa3-Cys-Xaa1-Xaa5-His-Ser- (SEQ ID NO:31)

Asp-Cys-Cys-Asn-Cys-Cys-Leu-Ser-Gly-Ile-Cys-Ala-Xaa3-Ser-Thr-Asn-Xaa4-

Ile-Leu-Xaa3-Gly-Cys-Ser-Thr-Ser-Ser-Phe-Phe-Lys-Ile-^

Name: R11.10
Species: radiatus
Isolated: No
Cloned: Yes

DNA Sequence:
CGAGGACATCCCAGCTATCAGCACTTCGCAGCAGTCGAGGCTTTGAAATCCTAATCATAGAAGAAGGCAA (SEQ ID NO:32)

AAATATCTGCTGGTCAATATGAAGCTGTGCCTGACGTTCCTTCTTGTTCTGATGATTCTGGCATCAGTGA

CTGGGGAGAAGTTAAGCGAGCAAACACTGCGTCGTGCTGCTAGGAAAAACAAAGGCCATGTTCCATGCGG

GAAAGACGGAAGGAAATGCGGGTATCATGCAGATTGCTGTAATTGCTGTCTCAGTGGAATCTGTAAACCA

AGCACAAGTTGGACTGGATGCTCGACGAGTACCGTTCAATTGACGCGCTGACTTTCAGCCAGCTAGGCCA

TGCCTAGGTCCTCATGCACATTCACATTTGCTGTGAATTGAATTCATGTGCATTAAAGCCATTAGGCGTA

GAAAGATGAAAAA

Translation:
MKLCLTFLLVLMILASVTGEKLSEQTLRPAARKNKGHVPCGKDGRKCGYHADCCNCCLSGICKPSTSWTG (SEQ ID NO:33)

CSTSTVQLTR

Toxin Sequence:
Gly-His-Val-Xaa3-Cys-Gly-Lys-Asp-Gly-Arg-Lys-Cys-Gly-Xaa5-His-Ala-Asp- (SEQ ID NO:34)

Cys-Cys-Asn-Cys-Cys-Leu-Ser-Gly-Ile-Cys-Lys-Xaa3-Ser-Thr-Ser-Xaa4-Thr-

Gly-Cys-Ser-Thr-Ser-Thr-Val-Gln-Leu-Thr-Arg-^

Name: R11.11

TABLE 1-continued

Species: radiatus
Isolated: No
Cloned: Yes

DNA Sequence:
CAGACGAGGACATCCCAGCTATCAGCACTTCGCAGCAGTCGAGGCTTTGAAATCCTAATCATAGAAGAAG (SEQ ID NO:35)

GCAAAAATATCTGCTGGTCAATATGAAGCTGTGCCTGACGTTCCTTCTTGTTCTGATGATTCTGGCATCC

GTGACTGGGGAGAAGTCAAGCAAGCATACACTGAGTCGTGCTGCTAGGGTAAAAAACAAAGGCCATGTTT

CATGCGGGAAAGACGGAAGGGCATGCGATTATCATGCAGATTGCTGTAACTGCTGTCTCGGTGGAATCTG

TAAACCAAGCACAAGTTGGATTGGATGCTCGACGAATGTGTTCTTGACGCGCTGACTTTCAGCCAGCTAG

GCCATGCCTAGGTCCTCATGCACATTCACATTTGCTGTGAATTGAATTCATGTGCATTAAAGCCATTAGG

CGTAGAAAGATGAAAAAA

Translation:
MKLCLTFLLVLMILASVTGEKSSKHTLSRAARVKNKGHVSCGKDGRACDYHADCCNCCLGGICKPSTSWI (SEQ ID NO:36)

GCSTNVFLTR

Toxin Sequence:
Gly-His-Val-Ser-Cys-Gly-Lys-Asp-Gly-Arg-Ala-Cys-Asp-Xaa5-His-Ala-Asp- (SEQ ID NO:37)

Cys-Cys-Asn-Cys-Cys-Leu-Gly-Gly-Ile-Cys-Lys-Xaa3-Ser-Thr-Ser-Xaa4-Ile-

Gly-Cys-Ser-Thr-Asn-Val-Phe-Leu-Thr-Arg-^

Name: R11.12
Species: radiatus
Isolated: No
Cloned: Yes

DNA Sequence:
CAGCTATCAACACTTCgCAGCAgTCGAGGCTTTGAAATcCTAATCATAGAAGAAGGCAAAAATATCTGCT (SEQ ID NO:38)

GGTCAATATGAAGCTGTGCCTGACGTTCCTTCTTGTTCTGATGATTCTGGCATCAGTGACTGGGGAGAAG

TTAAGCGAGCAAACACTGCGTCgtGCTGCTAGGAAAAACAAAGGCCATGTTCCATGCGGGAAAGACCGAA

GGAAATGCGGGtATCATGCAGATTGCTGtAATTGCTGtCTCAGTGGAATCTGTAAACCAAGCACAAGTTG

GACTGGATGCTCGACGAGTACGTTTTTATTGACGCGCTGACTTTCAGCCAgCTAGGCCATGCCTAGGTCC

TCATGCaCATTCACATTTGCTGTGAATTGAATTCATGTGCATTAAAGCCATTTGGCGTaGAAAGATGAAA

AAA

Translation:
MKLCLTFLLVLMILASVTGEKLSEQTLRRAARKNKGHVPCGKDRRKCGYHADCCNCCLSGICKPSTSWTG (SEQ ID NO:39)

CSTSTFLLTR

Toxin Sequence:
Gly-His-Val-Xaa3-Cys-Gly-Lys-Asp-Arg-Arg-Lys-Cys-Gly-Xaa5-His-Ala-Asp- (SEQ ID NO:40)

Cys-Cys-Asn-Cys-Cys-Leu-Ser-Gly-Ile-Cys-Lys-Xaa3-Ser-Thr-Ser-Xaa4-Thr-

Gly-Cys-Ser-Thr-Ser-Thr-Phe-Leu-Leu-Thr-Arg-^

Name: R11.13
Species: radiatus
Isolated: No
Cloned: Yes

DNA Sequence:
GGCTTCAGACGAGGACATCCCAGCTATCAGCACTTCGCAGCAGTCGAGGCTTTGAAATCCTAATCATAGA (SEQ ID NO:41)

AGAAGGCAAAAATATCTGCTGGTCAATATGAAGCTGTGCCTGACGTTCCTTCTTGTTCTGATGATTCTGG

CATCAGTGACTGGGGAGAAGTTAAGCGAGCAAACACTGCGTCGTGCTGCTAGGAAAAACAAAGGCCATGT

TCCATGCGGGAAAGACGGAAGGAAATGCGGGTATCATGCAGATTGCTGTAATTGCTGTCTCAGTGGAATC

TGTAAACCAAGCACAAGTTGGACTGGATGCTCGACGAGTACGTTTTTATTGACGCGCTGACTTTCAGCCA

TABLE 1-continued

```
GCTAGGCCATCCCTAGGTCCTCATGCACATTCACATTTGCTGTGAATTGAATTCATGTGCATTAAAGCCA

TTAGGCGTAGAAAGATGAAAAAA

Translation:
MKLCLTFLLVLMILASVTGEKLSEQTLRRAARKNKGHVPCGKDGRKCGYHADCCNCCLSGICKPSTSWTG    (SEQ ID NO:42)

CSTSTFLLTR

Toxin Sequence:
Gly-His-Val-Xaa3-Cys-Gly-Lys-Asp-Gly-Arg-Lys-Cys-Gly-Xaa5-His-Ala-Asp-    (SEQ ID NO:43)

Cys-Cys-Asn-Cys-Cys-Leu-Ser-Gly-Ile-Cys-Lys-Xaa3-Ser-Thr-Ser-Xaa4-Thr-

Gly-Cys-Ser-Thr-Ser-Thr-Phe-Leu-Leu-Thr-Arg-^

Name:      R11.14
Species:   radiatus
Isolated:  Yes
Cloned:    Yes

DNA Sequence:
GCTTCAGACGAGGACAACCCAGCTATCAGCACTTCGCAGCAGTCGAGGCTTTGAAATCCTAATCATAGAA   (SEQ ID NO:44)

GAAGGCAAAAATATCTGCTGGTCAATATGAAGCTGTGCCTGACGTTCCTTCTTGTTCTGATGATTCTGGC

ATCAGTGACTGGGGAGAAGTCAAGCAAGCATACACTGAGTCGTGCTGCTAGGGTAAAAAACAGAGGCCCT

AGTTTTTGTAAGGCAAACGGAAAGCCATGCTCGTATCATGCAGATTGCTGTAATTGCTGTCTCAGTGGAA

TCTGTAAACCAAGCACAAATGTGATTTTACCTGGATGCTCGACGAGTTCGTTCTTCAGGATCTGACTTTC

AGCCACCTAGGCCATGCCTAGGTTCTCATGCACATTCACATTTGCTGTGAATTGAATTCATGTGCATTAA

AGCCATTAGGCGTAGAAAGATGAAAAAAAAA

Translation:
MKLCLTFLLVLMTLASVTGEKSSKHTLSRAARVKNRGPSFCKANGKPCSYHADCCNCCLSGICKPSTNVI   (SEQ ID NO:45)

LPGCSTSSFFRT

Toxin Sequence:
Gly-Xaa3-Ser-Phe-Cys-Lys-Ala-Asn-Gly-Lys-Xaa3-Cys-Ser-Xaa5-His-Ala-      (SEQ ID NO:46)

Asp-Cys-Cys-Asn-Cys-Cys-Leu-Ser-Gly-Ile-Cys-Lys-Xaa3-Ser-Thr-Asn-Val-

Ile-Leu-Xaa3-Gly-Cys-Ser-Thr-Ser-Ser-Phe-Phe-Arg-Ile-^

Name:      R11.15
Species:   radiatus
Isolated:  No
Cloned:    Yes

DNA Sequence:
CAGCTATCAGCACTTCGCAGCAGTCGAGGCTTTGAAATCCTAATCATAGAAGAAGGCAAAAATATCTGCT   (SEQ ID NO:47)

GGTCAATATGAAGCTGTGCCTGACGTTCCTTCTTGTTCTGATGATTCTGGCATCAGTGACTGGGGAGAAG

TTAAGCGAGCAAACACTGCGTCGTGCTGCTAGGAAAAACAAAGGCCATGTTCCATGCGGGAAAGACGGAA

GGAAATGCGGGTATCATGCAGATTGCTGTAATTGCTGTCTCAGTGGAATCTGTAAACCAAGCACAAGTTG

GACTGGATGCTCGACGAGTACGTTCAATTGACGCGCTGACTTTCAGCCAGCTAGGCCATGCCTAGGTCCT

CATGCACATTCACATTTGCTGTGAATTGAATTCATGTGCATTAAAGCCATTAGGCGTAAAAGATGAAAAA

AAAAA

Translation:
MKLCLTFLLVLMILASVTGEKLSEQTLRRAARKNKGHVPCGKDGRKCGYHADCCNCCLSGTCKPSTSWTG   (SEQ ID NO:48)

CSTSTFN

Toxin Sequence:
Gly-His-Val-Xaa3-Cys-Gly-Lys-Asp-Gly-Arg-Lys-Cys-Gly-Xaa5-His-Ala-Asp-   (SEQ ID NO:49)

Cys-Cys-Asn-Cys-Cys-Leu-Ser-Gly-Ile-Cys-Lys-Xaa3-Ser-Thr-Ser-Xaa4-Thr-
```

TABLE 1-continued

Gly-Cys-Ser-Thr-Ser-Thr-Phe-Asn-^

Name:     R11.16
Species:  radiatus
Isolated: No
Cloned:   Yes

DNA Sequence:
GCTTCAGACGAGGACATCCCAGCTATCAGCACTTCGCAGCAGTCGAGGCTTTGAAATCCTAATCATAGAA   (SEQ ID NO:50)

GAAGGCAAAAATATCTGCTGCTCAATATGAAGCTGTGCCTGACGTTCCTTCTTGTTCTGATGATTCTGCC

ATcAGTGACTGGGGAGAAGTCAAGCAAGCATACACTGAGTCgTGCTGcTAGGGTAAAAAACAAAGGCCAT

GTTCCATGCGGGAAAGACGGAAGGAAATGCGGGTATCATACACATTGCTGTAATTGCTGTCTCAGTGGAA

TCTGTAAACCAAGCACAAGTTTGATTGGATGCTCGACGAGTTCGTTCACTTGACGCGCTGACTTTCAGCC

AGCTAGGCCATGCCTAGGTCCTCATGCACATTCACATTTGCTGTGAATTGAATTCATGTGCATTAAAGCC

ATTAGGCGTAGAAAGATT

Translation:
MKLCLTFLLVLMILASVTGEKSSKHTLSRAARVKNKGHVPCGKDGRKCGYHTHCCNCCLSGICKPSTSLI   (SEQ ID NO:51)

GCSTSSFT

Toxin Sequence:
Gly-His-Val-Xaa3-Cys-Gly-Lys-Asp-Gly-Arg-Lys-Cys-Gly-Xaa5-His-Thr-His-   (SEQ ID NO:52)

Cys-Cys-Asn-Cys-Cys-Leu-Ser-Gly-Ile-Cys-Lys-Xaa3-Ser-Thr-Ser-Leu-Ile

Gly-Cys-Ser-Thr-Ser-Ser-Phe-Thr-^

Name:     R11.17
Species:  radiatus
Isolated: No
Cloned:   Yes

DNA Sequence:
GATCCCCAAGCTATTTAGGTGACACTATAGAATACTCAAGCTTGCATGCCTGCAGGTCGACTCTAGAGGA   (SEQ ID NO:53)

TCCCAGCTATCAGCACTTCGCAGCAGTCGAGGCTTTGAAATCCTAATCATAGAAGAAGGCAAAAATATCT

GCTGGTCAATATGAAGCTGTGCCTGACGTTCCTTCTTGTTCTGATGATTCTGGCATCAGTGACTGGGGAG

AAGTCAAGCAAGCATACACTGAGTCGTGCTGCTAGGGTAAAAAACAGAGGCCCTAGTTTTTGTAAGGCAA

ACGGAAAGCCATGCTCGTATCATGCAGATTGCTGTAATTGCTGTCTCAGTGGAATCTGTGCACCAAGCAC

AAATTGGATTTTACCTGGATCCTCGACCAGTTCGTTCTTCAAGATCTCACTTTCAGCCAgCTAGGCCATG

CCTAgGTCCTCATGCACATTCACATTTGCTGTGAATTGAATTCATGTGCATTAAAGCCATTAgGCGTAGA

AAGATGAA

Translation:
MKLCLTFLLVLMILASVTGEKSSKHTLSRAARVKNRGPSFCKANGKPCSYHADCCNCCLSGICAPSTNWT   (SEQ ID NO:54)

LPGCSTSSFFKI

Toxin Sequence:
Gly-Xaa3-Ser-Phe-Cys-Lys-Ala-Asn-Gly-Lys-Xaa3-Cys-Ser-Xaa5-His-Ala-   (SEQ ID NO:55)

Asp-Cys-Cys-Asn-Cys-Cys-Leu-Ser-Gly-Ile-Cys-Ala-Xaa3-Ser-Thr-Asn-Xaa4-

Ile-Leu-Xaa3-Gly-Cys-Ser-Thr-Ser-Ser-Phe-Phe-Lys-Ile-^

Name:     R11.18
Species:  radiatus
Isolated: No
Cloned:   Yes

DNA Sequence:
CCCAGCTATCAGCACTTCGCAGCAGTCGAGGCTTTGAAATCCTAATCATAGAAGAAGGCAAAAATATCTG   (SEQ ID NO:56)

CTGGTCAATATGAAGCTGTGCCTGACGTTCCTTCTTGTTCTGATGATTCTGGCATCAGTGACTGGGGAGA

AGTCAAGCAAGCATACACTGAGTCGTGCTGCTAGGGTAAAAAACAAAGGCGCTGTTCCATGCGGGAAAGA

TABLE 1-continued

```
CGGAAGGCAATGCAGGAATCATGCAGATTGCTGTAATTGCTGTCCCTTTGGAACCTGTGCACCAAGCACA

AATCGGATTTTACCTGGATGCTCGACGGGTATGTTCTTGACGCGCTGACTTTCAGCCAGCTAGGCCATGC

CTAGGTCCTCATGCACATTCACATTTGCTGTGAATTGAATTCATGTGCATTAAACCCATTAGGCGTA
```

Translation:
MKLCLTFLLVLMTLASVTGEKSSKHTLSRAARVKNKGAVPCGKDGRQCRNHADCCNCCPFGTCAPSTNRI   (SEQ ID NO:57)

LPGCSTGMFLTR

Toxin Sequence:
Gly-Ala-Val-Xaa3-Cys-Gly-Lys-Asp-Gly-Arg-Gln-Cys-Arg-Asn-His-Ala-Asp-   (SEQ ID NO:58)

Cys-Cys-Asn-Cys-Cys-Xaa3-Phe-Gly-Thr-Cys-Ala-Xaa3-Ser-Thr-Asn-Arg-Ile-

Ile-Leu-Xaa3-Gly-Cys-Ser-Thr-Ser-Ser-Phe-Phe-Lys-Ile-^

Name:     J029 [011P]
Species:  radiatus
Isolated: Yes
Cloned:   Yes

Toxin Sequence:
Gly-Xaa3-Ser-Phe-Cys-Lys-Ala-Asp-Xaa1-Lys-Xaa3-Cys-Xaa1-Xaa5-His-Ala-   (SEQ ID NO:59)

Asp-Cys-Cys-Asn-Cys-Cys-Leu-Ser-Gly-Ile-Cys-Ala-Xaa3-Ser-Thr-Asn-Xaa4-

Ile-Leu-Xaa3-Gly-Cys-Ser-Thr-Ser-Ser-Phe-Phe-Lys-Ile-^

Name:     R11.19
Species:  radiatus
Isolated: Yes
Cloned:   No

Toxin Sequence:
Xaa2-Cys-Lys-Thr-Asn-Lys-Met-Ser-Cys-Ser-Leu-His-Xaa1-Xaa1-Cys-Cys-   (SEQ ID NO:60)

Arg-Phe-Arg-Cys-Cys-Phe-His-Gly-Lys-Cys-Gln-Thr-Ser-Val-Phe-Gly-Cys

Xaa4-Val-Asp-Xaa3-^

Name:     Ca11.1
Species:  caracteristicus
Isolated: No
Cloned:   Yes

DNA Sequence:
```
CCAGCTATCAGCACTTCGCAGCAGTCGAGGCTTTAAAATCCTAATCGTAGAAGAAGGCAAAACCATCTGG   (SEQ ID NO:61)

TGGTCAGTATGAAGCTGTGTGTGACGTTTCTTCTTGTTCTGGTGATTCTGCCATCGGTGACCGGGGAGAA

GTCTAGCGAGCGTACACGGATTGGTGCTGTTCTGAAAGGCCATTGGTGCGGATACCCAGGAGAACGCGGA

TGCCGATATCATAGCCAATGCTGTGGGACATGTGTTGTTACGACCGCAAGTGTGTTGCGACTGCTATGC

CATGTGACTTTCCCTACTAGTGCGATGGACCTAGGCGTGCTGGCCTTGTGGCAGACTCGCTCAGTATGCC

TGACCTGTCCAAGTGAAACGAGCGGACACGATCGTCGTATTCCTTTGCCAAGAGCTAGCTAGGCCATGCC

TAGG
```

Translation:
MKLCVTFLLVLVILPSVTGEKSSERTRIGAVLKGHWCGYPCERGCRYHSQCCGDMCCYDRKCVATAMPCD   (SEQ ID NO:62)

FPY

Toxin Sequence:
Gly-His-Xaa4-Cys-Gly-Xaa5-Xaa3-Gly-Xaa1-Arg-Gly-Cys-Arg-Xaa5-His-Ser-   (SEQ ID NO:63)

Gln-Cys-Cys-Gly-Asp-Met-Cys-Cys-Xaa5-Asp-Arg-Lys-Cys-Val-Ala-Thr-Ala-

Met-Xaa3-Cys-Asp-Phe-Xaa3-Xaa5^

Name:     M11.9
Species:  magus
Isolated: No
Cloned:   Yes

TABLE 1-continued

DNA Sequence:
CCGCTATCAGCACTTCGCAGCAGTCGAGGCTTTGAAATCCTAATCATAGAAGAGGGCAAAAATATCTGCT (SEQ ID NO:64)

GGTCAATATGAAGCTGTGCCTGACGTTCCTTCTTGTTCTGATGATTCTGGCATCAGTGACTGGGGAGAAG

TCAAGCAAGCATACACTGAGTCGTGCTGCTAGGGTAAAAAACAGAGGCTGTAAGAAAGACAGAAAGCCAT

GCTCGTATCATGCAGATTGCTGTAATTGCTGTCTCAGTGGGATCTGTGCACCAAGCACAAATTGGATTTT

ACCTGCATGCTCGACGAGTACGTTCACTTGACGCGCTGACTTTCAGCCAGCTAGGCCATGCCTAGG

Translation:
MKLCLTFLLVLMILASVTGEKSSKHTLSRAARVKNRGCKKDRKPCSYHADCCNCCLSGTCAPSTNWILPG (SEQ ID NO:65)

CSTSTFT

Toxin Sequence:
Gly-Cys-Lys-Lys-Asp-Arg-Lys-Xaa3-Cys-Ser-Xaa5-His-Ala-Asp-Cys-Cys-Asn- (SEQ ID NO:66)

Cys-Cys-Leu-Ser-Gly-Ile-Cys-Ala-Xaa3-Ser-Thr-Asn-Xaa4-Ile-Leu-Xaa3-

Gly-Cys-Ser-Thr-Ser-Thr-Phe-Thr-^

Name:      M11.13
Species:   magus
Isolated:  No
Cloned:    Yes

DNA Sequence:
CCGCTATCAGCACTTCGCAGCAGTCGAGGCTTTGAAATCCTAGTCATAGAAGAAGGCAAAAATATCTGCT (SEQ ID NO:67)

GGTCAATATGAAGCTGTGCCTGACGTTCCTTCTTGTTCTGATCATTCTGGCATCCGTGACTGGGGAGAAG

TCAAGCAAGCATACACTGAGTCGTGCTGCTAGGGTAAAAAACAAAGGCCATGTTTCATGCGGGAAAGACG

GAAGGGCATGCGATTATCATGCAGATTGCTGTAACTGCTGTCTCGGTGGAATCTGTAAACCAAGCACAAG

TTGGATTGGATGCTCGACGAATGTGTTCTTGACGCGCTGACTTTCAGCCAGCTAGGCCATGCCTAGG

Translation:
MKLCLTFLLVLMILASVTGEKSSKHTLSRAARVKNKGHVSCGKDGPACDYHADCCNCCLGGICKPSTSWI (SEQ ID NO:68)

GCSTNVFLTR

Toxin Sequence:
Gly-His-Val-Ser-Cys-Gly-Lys-Asp-Gly-Arg-Ala-Cys-Asp-Xaa5-His-Ala-Asp- (SEQ ID NO:69)

Cys-Cys-Asn-Cys-Cys-Leu-Gly-Gly-Ile-Cys-Lys-Xaa3-Ser-Thr-Ser-Xaa4-Ile-

Gly-Cys-Ser-Thr-Asn-Val-Phe-Leu-Thr-Arg-^

Name:      S11.5
Species:   striatus
Isolated:  No
Cloned:    Yes

DNA Sequence:
CCGCTATCAGCACTTCGCAGCAGTCGAGGCTTTGAAATCCTAATCATAGAAGAAGGCAAAAATATCTGCT (SEQ ID NO:70)

GGTCAATATGAAGCTGTGCCTGACGTTCCTTCTTGTTCTGATGATTCTGGCATCAGTGACTGGGGAGAAG

TCAAGCAAGCATACACTGAGTCGTGCTGCTAGCGTAAAAAACAGAGGCCCTAGTTTTTGTAAGGCAAACG

GAAAGCCATGCTCGTATCATGCAGATTGCTGTAATTGCTGTCTCAGTGGAATCTGTAAACCAAGCACAAA

TGTGATTTTACCTGGATGCTCGACGAGTTCCTTCTTCAGGATCTGACTTTCAGCCAGCTAGGCCATGCCT

AGG

Translation:
MKLCLTFLLVLMILASVTGEKSSKHTLSRAARVKNRGPSFCKANGKPCSYHADCCNCCLSGICKPSTNVT (SEQ ID NO:71)

LPGCSTSSFFRI

Toxin Sequence:
Gly-Xaa3-Ser-Phe-Cys-Lys-Ala-Asn-Gly-Lys-Xaa3-Cys-Ser-Xaa5-His-Ala- (SEQ ID NO:72)

Asp-Cys-Cys-Asn-Cys-Cys-Leu-Ser-Gly-Ile-Cys-Lys-Xaa3-Ser-Thr-Asn-Val-

TABLE 1-continued

Ile-Leu-Xaa3-Gly-Cys-Ser-Thr-Ser-Ser-Phe-Phe-Arg-Ile-^

Name: S11.1
Species: striatus
Isolated: No
Cloned: Yes

DNA Sequence:
CCAGCTATCAGCACTTCGCAGCAGTCGAGGCTTTAAAATCCTAATCGTAGAAGAAGGCAAAAACATCTGG (SEQ ID NO:73)

TGGTCAGTATGAAGCTGTGTGTGACGTTTCTTCTTGTTCTGGTGATTCTGCCATCAGTAACTGGGGAGGA

GTCTAGCGAGCGTACACTGAGTGGTGCTACTCTGACAGGCGATCGGGGAACGTGCTCATTCTTAGGACAA

GGATGCGGAGATCATTCCGACTGCTGTTGGAACATGTGTTGTGCCAGCGAAATGTGCGTTGTGACTCTCC

TTCAATGTAAATGATTTCCCTTCTAGGGCGATGGACCTAGGCGTGCTGGCCTAGCGGTAGACTCGCTCAG

TATGCCTGATCTGTCTGAGTGAAACGACCTGACACGATCCGTCGTATTCCTTTGCCAAGAGCCAGCTAGG

CCATGCCTAGG

Translation:
MKLCVTFLLVLVILPSVTGEESSERTLSGATLTGDRGTCSFLGQGCGDHSDCCWNMCCASEMCVVTLLQC (SEQ ID NO:74)

K

Toxin Sequence:
Gly-Thr-Cys-Ser-Phe-Leu-Gly-Gln-Gly-Cys-Gly-Asp-His-Ser-Asp-Cys-Cys- (SEQ ID NO:75)

Xaa4-Asn-Met-Cys-Cys-Ala-Ser-Xaa1-Met-Cys-Val-Val-Thr-Leu-Leu-Gln-Cys-

Lys-^

Name: S11.2
Species: striatus
Isolated: No
Cloned: Yes

DNA Sequence:
CCAGCTATCACCACTTCGCAGCAGTCGAGGCTTTGAAATCCTAATCATAGAAGAAGGCAAAAATATCTGC (SEQ ID NO:76)

TGGTCAATATGAAGCTGTGCCTGACGTTCCTTCTTGTTCTGATGATTCTGGCATCAGTGACTGGGGAGAA

GTCAAGCAAGCATACACTGAGTCGTGCTGCTAGGGTAAAAAACAGAGGCTGTAAGAAAGACAGAAAGCCA

TGCTCGTATCAGGCAGATTGCTGTAATTGCTGTCCCATTGGAACCTGTGCACCAAGCACAAATTGGATTT

TACCTGGATGCTCGACGGGTCCGTTCATGGCGCGCTGACTTTCAGCCAGCTAGGCCATGCCTAGG

Translation:
MKLGLTFLLVLMILASVTGEKSSKHTLSRAARVKNRGCKKDRKPCSYQADCCNCCPIGTCAPSTNWTLPG (SEQ ID NO:77)

CSTGPFMAR

Toxin Sequence:
Gly-Cys-Lys-Lys-Asp-Arg-Lys-Xaa3-Cys-Ser-Xaa5-Gln-Ala-Asp-Cys-Cys-Asn- (SEQ ID NO:78)

Cys-Cys-Xaa3-Ile-Gly-Thr-Cys-Ala-Xaa3-Ser-Thr-Asn-Xaa4-Ile-Leu-Xaa3-

Gly-Cys-Ser-Thr-Gly-Xaa3-Phe-Met-Ala-Arg-^

Name: S11.3
Species: striatus
Isolated: No
Cloned: Yes

DNA Sequence:
CCAGCTATCAGCACTTCGCAGCAGTCGAGGCTTTGAAATCCTAATCATAGAAGAAGGCAAAAATATCTGC (SEQ ID NO:79)

TGGTCAATATGAAGCTGTGCCTGACGTTCCTTCTTGTTCTGATGATTCTGGCATCAGTGACTGGGGAGAA

GTCAAGCAAGCATACACTGGGTCGTGCTGCTAGGGTAAAAAACAGAGGCCCTAGTTTTTGTAAGGCAGAC

GAAAAGCQATGCAAGTATCATGCAGATTGCTGTAACTGCTGTCTCGGTGGAATCTGTAAACCAAGCACAA

GTTGGATTGGATGCTCGACGAATGTGTTCTTGACGCGCTGACTTTCAGCCAGCTAGGCCATGCCTAGG

TABLE 1-continued

Translation:
MKLCLTFLLVLMILASVTGEKSSKHTLGRAARVKNRGPSFCKADEKPCKYHADCCNCCLGGICKPSTSWI (SEQ ID NO:80)

GCSTNVFLTR

Toxin Sequence:
Gly-Xaa3-Ser-Phe-Cys-Lys-Ala-Asp-Xaa1-Lys-Xaa3-Cys-Lys-Xaa5-His-Ala- (SEQ ID NO:81)

Asp-Cys-Cys-Asn-Cys-Cys-Leu-Gly-Gly-Ile-Cys-Lys-Xaa3-Ser-Thr-Ser-Xaa4-

Ile-Gly-Cys-Ser-Thr-Asn-Val-Phe-Leu-Thr-Arg-

Name: S11.4
Species: striatus
Isolated: No
Cloned: Yes

DNA Sequence:
CCGCTATCAGCACTTCGCAGCAGTCGAGGCTTTGAAATCCTAATCATAGAAGAAGGCAAAAATATCTGCT (SEQ ID NO:82)

GGTCAATATGAAGCTGTGCCTGACGTTCCTTCTTGTTCTGATGATTCTGGCATCAGTGACTGGGGAGAAG

TCAAGCAAGCATACACTGAGTCGTGCTGCTAGGGTAAAAAACAGAGGCCCTAGTTTTTGTAAGGCAGACG

AAAAGCCATGCAAGTATCATGCAGGTTGCTGTAACTGCTGTCTCGGTGGAATCTGTAAACCAAGCACAAG

TTGGATTGGATCCTCGACGAATGTGTTCTTGACGCGCTGACTTTCAGCCAGCTAGGCCATGCCTAGG

Translation:
MKLCLTFLLVLMILASVTGEKSSKHTLSRAARVKNRGPSFCKADEKPCKYHAGCCNCCLGGICKPSTSWI (SEQ ID NO:83)

GCSTNVFLTR

Toxin Sequence:
Gly-Xaa3-Ser-Phe-Cys-Lys-Ala-Asp-Xaa1-Lys-Xaa3-Cys-Lys-Xaa5-His-Ala- (SEQ ID NO:84)

Gly-Cys-Cys-Asn-Cys-Cys-Leu-Gly-Gly-Ile-Cys-Lys-Xaa3-Ser-Thr-Ser-Xaa4-

Ile-Gly-Cys-Ser-Thr-Asn-Val-Phe-Leu-Thr-Arg-

Name: Ca11.2
Species: caracteristicus
Isolated: No
Cloned: Yes

DNA Sequence:
CCAGCTATCAGCACTTCGCAGCAGTCGACGCTTTAAAATCCTAATCGTAGAAGAAGGCAAAACCATCTGG (SEQ ID NO:85)

TGGTCAGTATGAAGCTGTGTGTGACGTTTCTTCTTGTTCTGGTGATTCTGCCATCGGTGACGGGGGAGAA

GTCTAGCGAGCGTACACGGATTGGTGCTGTTCTGAAAGGCCATTGGTGCGGATACCTAGGAGAACGCGGA

TGCCGATATCATAGCCAATGCTGTGGGGACATGTGTTGTTACGACCGCAAGTGTGTTGTGACTGCTATGC

CATGTGACTTTCCCTACTAGTGCGATGGACCTAGGCGTGCCGGCCTTGTGGCAGACTCGCTCAGTATGCC

TGATCTGTCCAAGTGAAACGACCGGACACGATCGTCGTATTCCTTTGCCAAGAGCCAGCTAGGCCATGCC

TAGG

Translation:
MKLCVTFLLVLVILPSVTGEKSSERTRIGAVLKGHWCGYLGERGCRYHSQCCGDMCCYDRKCVVTAMPCD (SEQ ID NO:86)

EPY

Toxin Sequence:
Gly-His-Xaa4-Cys-Gly-Xaa5-Leu-Gly-Xaa1-Arg-Gly-Cys-Arg-Xaa5-His-Ser- (SEQ ID NO:87)

Gln-Cys-Cys-Gly-Asp-Met-Cys-Cys-Xaa5-Asp-Arg-Lys-Cys-Val-Val-Thr-Ala-

Met-Xaa3-Cys-Asp-Phe-Xaa3-Xaa5-

Name: Ca11.3
Species: caracteristicus
Isolated: No
Cloned: Yes

DNA Sequence:
CCAGCTATCAGCACTTCGCAGCAGTCGAGGCTTTAAAATCCTAATCGTAGAAGAAGGCAAAACCATCTGG (SEQ ID NO:88)

TABLE 1-continued

```
TGGTCAGTATGAAGCTGTGTGTGACGTTTCTTCTTGTTCTGGTGATTCTGCCATCGGTCACCGGGGAGAA

GTCTAGCGAGCGTACACGGATTGGTGCTGTTCTGAAAGGCCATTGGTGCGGATACCCAGGAGAACGCGCA

TGCCGATATCATAGCCAATGCTGTGGGGACATGTGTTGTTACGACCGCAAGTGTGTTGTGACTGCTATGC

CATGTGACTTTCCCTACTAGTGCGATGGACCTAGGCGTGCTGGCCTTGTGGCAGACTCGCTCAGTATGCC

TGATCTGTCCAAGTGAAACGACCGGACACGATCGTCGTATTCCTTTGCCAAGAGCCAGCTAGGCCATGCC

TAGG
```

Translation:
MKLCVTFLLVLVILPSVTGEKSSERTRIGAVLKGHWCGYPGERGCRYHSQCCGDMCCYDRKCVVTAMPCD (SEQ ID NO:89)

FPY

Toxin Sequence:
Gly-His-Xaa4-Cys-Gly-Xaa5-Xaa3-Gly-Xaa1-Arg-Gly-Cys-Arg-Xaa5-His-Ser- (SEQ ID NO:90)

Gln-Cys-Cys-Gly-Asp-Met-Cys-Cys-Xaa5-Asp-Arg-Lys-Cys-Val-Val-Thr-Ala-

Met-Xaa3-Cys-Asp-Phe-Xaa3-Xaa5-^

Name: Ca11.4
Species: caracteristicus
Isolated: No
Cloned: Yes

DNA Sequence:
CCAGCTATCAGCACTTCGCAGCAGTCGAGGCTTTAAAATCCTAATCGTAGAAGAAGGCAAAACCATCTGG (SEQ ID NO:91)

```
TGGTCAGTATGAAGCTGTGTGTGACGTTTCTTCTTGTTCTGGTGATTCTGCCATCGGTGACCGGGGAGAA

GTCTAGCGAGCGTACACGGATTGGTGCTGTTCTGAAAGGCCATTGGTGCGGATACCTAGGAGAACGCGGA

TGCCGATATCATAGCCAATGCTGTGGGGACATGTGTTGTTACGACCGCAAGTGTGCTGTGACTGCTATGC

CATGTGACTTTCCCTACTAGTGCGATGGACCTAGGCGTGCTGGCCTTGTGGCAGACTCGCTCAGTATGCC

TGATCTGTCCAAGTGAAACGACCGGACACGATCGTCGTATTCCTTTGCCAAGAGCCACCTAGGCCATGCC

TAGG
```

Translation:
MKLCVTFLLVLVILPSVTGEKSSERTRIGAVLKGHWCGYLGERGCRYHSQCCGDMCCYDRKCAVTAMPCD (SEQ ID NO:92)

FPY

Toxin Sequence:
Gly-His-Xaa4-Cys-Gly-Xaa5-Leu-Gly-Xaa1-Arg-Gly-Cys-Arg-Xaa5-His-Ser- (SEQ ID NO:93)

Gln-Cys-Cys-Gly-Asp-Met-Cys-Cys-Xaa5-Asp-Arg-Lys-Cys-Ala-Val-Thr-Ala-

Met-Xaa3-Cys-Asp-Phe-Xaa3-Xaa5-^

Name: Ca11.5
Species: caracteristicus
Isolated: No
Cloned: Yes

DNA Sequence:
CCGCTATCAGCACTTCGCAGCAGTCGAGGCTTTAAAATCCTAATCATAGAAGAAGGCAAAACCATCTGGT (SEQ ID NO:94)

```
GGTCAGTATGAAGCTGTGTGTGACGTTTCTTCTTGTTCTGGTGATTCTGCCATCGGTGACCGGGGAGAAG

TCTAGCGAGCGTACACGGATTGGTGCTGTTCTGAAAGGCCATTGGTGCGGATACCCAGGAGAACGCGGAT

GCCGATATCATAGCCAATGCTGTGGGGACATGTGTTGTTACGACCGCATGTGTGTTGTGACTGCTATGCC

ATGTGACTTTCCCTACTAGTGCGATGGACCTAGGCGTGCTGGCCTTGTGGCAGACTCGCTCAGTATGCCT

GATCTGTCCAAGTGAAACGACCGGACACGATCGTCGTATTCCTTTGCCAAGAGCCAGCTAGGCCATGCCT

AGG
```

Translation:
MKLCVTFLLVLVTLPSVTGEKSSERTRIGAVLKGHWCGYPGERGCRYHSQCCGDMCCYDRMCVVTAMPCD (SEQ ID NO:95)

TABLE 1-continued

FPY

Toxin Sequence:
Gly-His-Xaa4-Cys-Gly-Xaa5-Xaa3-Gly-Xaa1-Arg-Gly-Cys-Arg-Xaa5-His-Ser- (SEQ ID NO:96)

Gln-Cys-Cys-Gly-Asp-Met-Cys-Cys-Xaa5-Asp-Arg-Met-Cys-Val-Val-Thr-Ala-

Met-Xaa3-Cys-Asp-Phe-Xaa3-Xaa5-^

Name:     Ca11.6
Species:  caracteristicus
Isolated: No
Cloned:   Yes

DNA Sequence:
CCAGCTATAGCACTTCGCAGCAGNCGAGGCTTTAAAATCCTAATCATAGAAGAAGGCAAAACCATCTGGT (SEQ ID NO:97)

GGTCAGTATGAAGCTGTGTGTGACGTTTCTTCTTGTTCTGGTGATTCTGCCATCGGTGACCGGGGAGAAG

TCTAGCGAGCGTACACGGATTGGTGCTGTTCTGAAAGGCCATTGGTGCGGATACCTAGGAGAACGCGGAT

GCCGATATCATGGCCAATGCTGTGGGACATGTGTTGTTACGACCGCAAGTGTGTTGTGACTGCTATGCC

ATGTGACTTTCCCTACTAGTGCGATGGACCTAGGCGTGCTGGCCTTGTGGCAGACTCGCTCAGTATGCCT

GATCTGTCCAAGCGAAACGACCGGACACGATCGTCGTATTCCTTTGCCAAGAGCCAGCTAGGCCATGCCT

AGG

Translation:
MKLCVTFLLVLVTLPSVTGEKSSERTRIGAVLKGHWCGYLGERGCRYHGQCCGDMCCYDRKCVVTXAPCD (SEQ ID NO:98)

EPY

Toxin Sequence:
Gly-His-Xaa4-Cys-Gly-Xaa5-Leu-Gly-Xaa1-Arg-Gly-Cys-Arg-Xaa5-His-Gly- (SEQ ID NO:99)

Gln-Cys-Cys-Gly-Asp-Met-Cys-Cys-Xaa5-Asp-Arg-Lys-Cys-Val-Val-Thr-Ala-

Met-Xaa3-Cys-Asp-Phe-Xaa3-Xaa5-^

Name:     Ca11.7
Species:  caracteristicus
Isolated: No
Cloned:   Yes

DNA Sequence:
CCGCTATCAGCACTTCGCAGCAGTCGAGGCTTTGAAATCCTAATCATAGAAGAAGGCAAAAATATCTGCT (SEQ ID NO:100)

GGTCAATATGAAGCTGTGCCTGACGTTCCTTCTTGTTCTGATGATTCTGGCATCAGTGACTGGGGTGAGG

TCAAGCAAGCATACACTGAGTCGTGCTGCTAGGGTAAAAAACAGAGGCCCTAGTTTTTGTAAGGCAAACG

GAAAGCCATGCTCGTATCATGCAGATTGCTGTAATTGCTGTCTCAGTGGAATCTGTGAACCAAGCACAAA

TGTGATTTTACCTGGATGCTCGACGAGTTCGTTCTTCAGGATCTGACTTTCAGCCAGCTAGGCCATGCCT

AGG

Translation:
MKLCLTFLLVLMILASVTGVRSSKHTLSRAARVKNRGPSFCKANGKPCSYHADCCNCCLSGICEPSTNVI (SEQ ID NO:101)

LPGCSTSSFFRI

Toxin Sequence:
Gly-Xaa3-Ser-Phe-Cys-Lys-Ala-Asn-Gly-Lys-Xaa3-Cys-Ser-Xaa5-His-Ala- (SEQ ID NO:102)

Asp-Cys-Cys-Asn-Cys-Cys-Leu-Ser-Gly-Ile-Cys-Xaa1-Xaa3-Ser-Thr-Asn-Val-

Ile-Leu-Xaa3-Gly-Cys-Ser-Thr-Ser-Ser-Phe-Phe-Arg-Ile-^

Name:     M11.1
Species:  magus
Isolated: No
Cloned:   Yes

DNA Sequence:
CCGCTATCAGCACTTCGCAGCAGTCGAGGCTTTGAAGTCCTAATCATAGAAGAAGGCAAAAATATCTGCT (SEQ ID NO:103)

TABLE 1-continued

```
GGTCAATATGAAGCTGTGCCTGACGTTCCTTCTTGTTCTGATGATTCTGGCATCAGTGACTGGGGAGAAG

TTGAGCAAGCATACACTGAGTCATGCTGCTAGGAGACCCAACAAAGGCGCTGTTCCATGCGGGAAAGACG

GAAGGCAATGCAGGAATCATGCAGATTGCTGTAATTGCTGTCCCATTGGAACCTGTGCACCAAGCACAAA

TTGGATTTTACCTGGATGCTCGACGGGTCAATTCATGACGCGCTGACTTTCAGCCAGCTAGGCCATGCCT

AGG

Translation:
MKLCLTFLLVLMILASVTGEKLSKHTLSHAARRPNKGAVPCGKDGRQCRNHADCCNCCPIGTCAPSTNWI    (SEQ ID NO:104)

LPGCSTGQFMTR

Toxin Sequence:
Gly-Ala-Val-Xaa3-Cys-Gly-Lys-Asp-Gly-Arg-Gln-Cys-Arg-Asn-His-Ala-Asp-     (SEQ ID NO:105)

Cys-Cys-Asn-Cys-Cys-Xaa3-Ile-GlY-Thr-CYS-Ala-Xaa3-Ser-Thr-Asn-Xaa4-

Ile-Leu-Xaa3-Gly-Cys-Ser-Thr-Gly-Gln-Phe-Met-Thr-Arg-^

Name:      M11.2
Species:   magus
Isolated:  No
Cloned:    Yes

DNA Sequence:
CCAGCTATCAGCACTTCGCAGCAGNNGAGGCTTTAAAATCCTAATCGTAGAAGAAGGCAAAAACATCTGG    (SEQ ID NO:106)

TGTCAGTATGAAGCTGTGTGTGACGTTTCTTCTTGTTCTGGTGATTCTGCCATCAGTAACTGGGGAGAAG

TCTAGCGAGCGTACACTGAGTGGTGCTGCTCTGAGAGGCGATCGGAGAACGTGCTCAAACAAAGGACAAC

AATGCGGAGATGATTCCGACTGCTGTTGGCATTTGTGTTGTGTGAACAACAAGTGCGCTCACTTGATCCT

ATTATGTAACTTATAGTGCGATGGACCTAGGCGTGCTGGCCTAGCAGCCGACTCGCTCAGTATGCCTGAT

CTGTCCGAGTGACCTGACACGATCCGTCGTATTCCTTTGCCAAGAGCCAGCTAGGCCATGCCTAGG

Translation:
MKLCVTFLLVLVILPSVTGEKSSERTLSGAALRGDRRTCSNKGQQCGDDSDCCWHLCCVNNKCAHLILLC    (SEQ ID NO:107)

NL

Toxin Sequence:
Thr-Cys-Ser-Asn-Lys-Gly-Gln-Gln-Cys-Gly-Asp-Asp-Ser-Asp-Cys-Cys-Xaa4-    (SEQ ID NO:108)

His-Leu-Cys-Cys-Val-Asn-Asn-Lys-Cys-Ala-His-Leu-Ile-Leu-Leu-Cys-Asn-

Leu-^

Name:      M11.3
Species:   magus
Isolated:  No
Cloned:    Yes

DNA Sequence:
CCAGCTATCAGCACTTCGCAGCAGTCGAGGNTTTGAAATCCTAATCATAGAAGAAGGCAAAAATATCTGC    (SEQ ID NO:109)

TGGTCAATATGAAGCTGTGCCTGACGTTCCTTCTTGTTCTGATGATTCTGGCATCAGTGACTGGGGAGAA

GTCAAGCAAGcATACACTGAGTCGTGCTGCCAGGGTAAAAAACAGAGGCCCgAGTTTTTGTAAGGCAGAC

GAAAAGCCATGCGAGTATCATGCAGATTGCTGTAATTGCTGTCTCAGTGGAATCTGTGCACCAAGCACAA

ATTGGATTTTACCTGGATGCTCGACGAGTTCGTTCTTCGAGATCTGACTTTCAGCCAGCTAGGCCATGCC

TAGG

Translation:
MKLCLTFLLVLMILASVTGEKSSKHTLSRAARVKNRGPSFCKADEKPCEYHADCCNCCLSGICAPSTNWI    (SEQ ID NO:110)

LPGCSTSSFFET

Toxin Sequence:
Gly-Xaa3-Ser-Phe-Cys-Lys-Ala-Asp-Xaa1-Lys-Xaa3-Cys-Xaa1-Xaa5-His-Ala-    (SEQ ID NO:111)
```

TABLE 1-continued

Asp-Cys-Cys-Asn-Cys-Cys-Leu-Ser-Gly-Ile-Cys-Ala-Xaa3-Ser-Thr-Asn-Xaa4-

Ile-Leu-Xaa3-Gly-Cys-Ser-Thr-Ser-Ser-Phe-Phe-Xaa1-Ile-^

Name: M11.4
Species: magus
Isolated: No
Cloned: Yes

DNA Sequence:
CCGCTATCAGCACTTCGCAGCAGTCGAGGCTTTGAAATCCTAATCATAGAAGAAGGCAAAAATATCTGCT (SEQ ID NO:112)

GGTCAATATGAGGCTGTGCCTGACGTTCCTTCTTGTTCTGATGATTCTGCCATCAGTGACTGGGGAGAAG

TCAAGCAAGCATACACTGAGTCGTGCTGCTAGGGTAAAAAACAGAGGCCCTAGTTTTTGTAAGGCAGACG

AAAAGCCATGCGAGTATCATGCAGATTGCTGTAATTGCTGTCTCAGTGGAATCTGTGCACCAAGCACAAA

TTGGATTTTACCTGGATGCTCGACGAGTTCGTTCTTCAAGACCTGACTTTCAGCTAGCTAGGCCATGCCT

AGG

Translation:
MRLCLTFLLVLMILASVTGEKSSKHTLSRAARVKNRGPSFCKADEKPCEYHADCCNCCLSGTCAPSTNWI (SEQ ID NO:113)

LPGCSTSSFFKT

Toxin Sequence:
Gly-Xaa3-Ser-Phe-Cys-Lys-Ala-Asp-Xaa1-Lys-Xaa3-Cys-Xaa1-Xaa5-His-Ala- (SEQ ID NO:114)

Asp-Cys-Cys-Asn-Cys-Cys-Leu-Ser-Gly-Ile-Cys-Ala-Xaa3-Ser-Thr-Asn-Xaa4-

Ile-Leu-Xaa3-Gly-Cys-Ser-Thr-Ser-Ser-Phe-Phe-Lys-Thr-^

Name: M11.5
Species: mnagus
Isolated: No
Cloned: Yes

DNA Sequence:
CCAGCTATCAGCACTTCGCAGCAGTCGAGGCTTTGATATCCTAATCATAGAAGAAGGCAAAAATATCTGC (SEQ ID NO:115)

TGGTCAATATGAAGCTGTGCCTGACGTTCCTTCTTGTTCTGATGATTCTGGCATCAGTGACTGGGGAGAA

GTTAAGCGAGCAAACACTGCGTCGTGCTGCTAGGAAAAACAAAGGCCATGTTCCATGCGGGAAAGACGGA

AGGAAATGCGGGTATCATGCAGATTGCTGTAATTGCTGTCTCAGTGGAATCTGTAAACCAAGCACAAGTT

GGACTGGATGCTCGACGAGTACGTTCGATTGACGCGCTGACTTTCAGCTAGCTAGGCCATGCCTAGG

Translation:
MKLCLTFLLVLMILASVTGEKLSEQTLRRAARKNKGHVPCGKDGRKCGYHADCCNCCLSGICKPSTSWTG (SEQ ID NO:116)

CSTSTFD

Toxin Sequence:
Gly-His-Val-Xaa3-Cys-Gly-Lys-Asp-Gly-Arg-Lys-Cys-Gly-Xaa5-His-Ala-Asp- (SEQ ID NO:117)

Cys-Cys-Asn-Cys-Cys-Leu-Ser-Gly-Ile-Cys-Lys-Xaa3-Ser-Thr-Ser-Xaa4-Thr-

Gly-Cys-Ser-Thr-Ser-Thr-Phe-Asp-^

Name: M11.6
Species: magus
Isolated: No
Cloned: Yes

DNA Sequence:
CCAGCTATCAGCACTTCGCAGCAGTCGAGGCTTTAAAATCCTAATCGTAGAAGAAGGCAAAAACATCTGG (SEQ ID NO:118)

TGGTCAGTATGAAGCTGTGTGTGACGTTTCTTCTTGTTCTGGTGATTCTGCCATCAGTAACTGGGGAGGA

GTCTAGCGAGCGTACACTGAGTGGTGCTACTCTGACAGGCGATCGGGGAATGTGCTCACTCTTAGGACAA

CGATGCGGAGATCATTCCGACTGCTGTTGGGACATGTGTTGTGCCAGCGAAATGTGCGTTGTGACTTTCC

TTCCATGTAAATGATTTCCCTACTAGGGCGATGGACCTAGGCGTGCTGGCCTAGCGGTAGACTCGCTCAG

TATGCCTGATCTGTCTGAGTGAAACGACCTGACACGATCCGTCGTATTCCTTTGCCAAGAGCCAGCTAGG

TABLE 1-continued

```
CCATGCCTAGG

Translation:
MKLCVTFLLVLVILPSVTGEESSERTLSGATLTGDRGMCSLLGQRCGDHSDCCWDMCCASEMCVVTFLPC    (SEQ ID NO:119)

K

Toxin Sequence:
Gly-Met-Cys-Ser-Leu-Leu-Gly-Gln-Arg-Cys-Gly-Asp-His-Ser-Asp-Cys-Cys-      (SEQ ID NO:120)

Xaa4-Asp-Met-Cys-Cys-Ala-Ser-Xaa1-Met-Cys-Val-Val-Thr-Phe-Leu-Xaa3-

Cys-Lys-

Name:      M11.7
Species:   magus
Isolated:  No
Cloned:    Yes

DNA Sequence:
CCAGCTATCAGCACTTCGCAGCAGTCGNGGNTTTGAAATCCTAATCATAGAAGAAGGCAAAAATATCTGC    (SEQ ID NO:121)

TGGTCAATATGAAGCTGTGCCTGACGTTCCTTCTTGTTCTGATGATTCTGGCATCAGTGACTGGGGAGAA

GTCAAGCAAGCATACACTGAGTCGTGCTGCTAGGGTAAAAAACAGAGGCCCTAGTTTTTGTAAGGCAAAC

GGAAAGCCATGCTCGTATCATGCAGATTGCTGTAATTGCTGTCTCAGTGGAATCTGTAAACCAAGCACAA

ATGTGATTTTACCTGGATGCTCGACGAGTTCGCTCTTCAGGATCTGACTTTCAGCTAGCTAGGCCATGCC

TAGG

Translation:
MKLCLTFLLVLMILASVTGEKSSKHTLSRAARVKNRGPSFCKANGKPCSYHADCCNCCLSGICKPSTNVI    (SEQ ID NO:122)

LPGCSTSSLFRI

Toxin Sequence:
Gly-Xaa3-Ser-Phe-Cys-Lys-Ala-Asn-Gly-Lys-Xaa3-Cys-Ser-Xaa5-His-Ala-       (SEQ ID NO:123)

Asp-Cys-Cys-Asn-Cys-Cys-Leu-Ser-Gly-Ile-Cys-Lys-Xaa3-Ser-Thr-Asn-Val-

Ile-Leu-Xaa3-Gly-Cys-Ser-Thr-Ser-Ser-Leu-Phe-Arg-Ile-

Name:      M11.8
Species:   magus
Isolated:  No
Cloned:    Yes

DNA Sequence:
CCGCTATCAGCACTTCGCAGCAGTCGAGGCTTTAAAATCCTAATCGTAGAAGAAGGCAAAAACATCTGGT    (SEQ ID NO:124)

GGTCAGTATGAAGCTGTGTGTGACGTTTCTTCTTGTTCTGGTGATTCTGCCATCAGTAACTGGGGTGAAG

TCTAGCGAGCGTACACTGAGTGGTGCTGCTCTGAGAGGCGATCGGGGAACGTGCTCAGGCAGAGGACAAG

AATGCAAACATGATTCCGACTGCTGTGGGCATTTGTGTTGTGCCGGCATAACGTGCCAATTCACTTACAT

TCCATGTAAATGATTTCCCTACTAGTGCGATGGACCTAGGCGTGCTGGCCTAGCGGTAGACTCGCTCAGT

ATGCCTGATCTGTCCGAGTGAAACGACCTGACATGATCCCTCGTATTCCTTTGCCAAGAGCCAGCTAGGC

CATGCCTAGG

Translation:
MKLCVTFLLVLVILPSVTGVKSSERTLSGAALRGDRGTCSGRGQECKHDSDCCGHLCCAGITCQFTYIPC    (SEQ ID NO:125)

K

Toxin Sequence:
Gly-Thr-Cys-Ser-Gly-Arg-Gly-Gln-Xaa1-Cys-Lys-His-Asp-Ser-Asp-Cys-Cys-     (SEQ ID NO:126)

Gly-His-Leu-Cys-Cys-Ala-Gly-Ile-Thr-Cys-Gln-Phe-Thr-Xaa5-Ile-Xaa3-Cys-

Lys-

Name:      Ca11.8
```

TABLE 1-continued

Species: caracteristicus
Isolated: No
Cloned: Yes

DNA Sequence:
CCGCTATCAGCACTTCGCAGCAGTCGAGGCTTTGAAATCCTAATCATAGAAGAAGGCAAAAATATCTGCT (SEQ ID NO:127)

GGTCAATATGAAGCTGTGCCTGACCTTCCTTCTTGTTCTGATGATTCTGGCATCAGTGACTGGGGAGAAG

TCAAGCAAGCATACACTGAGTCGTGCTGCTAGGGTAAAAAACAGAGGCCCTAGTTTTTGTAAGGCAGACG

AAAGCCATGCGAGTATCATGCAGATTGCTGTAATTGCTTTCTCAGTGGAATCTGTGCACCAAGCACAAAA

TTGGATTTTACCTGGATGCTCGACGAGTTCGTTCTTCAAGATCTGACTTTCAGCCAGCTAGGCCATGCCT

AGG

Translation:
MKLCLTFLLVLMILASVTGEKSSKHTLSRAARVKNRGPSFCKADEKPCEYHADCCNCFLSGICAPSTNWI (SEQ ID NO:128)

LPGCSTSSFFKT

Toxin Sequence:
Gly-Xaa3-Ser-Phe-Cys-Lys-Ala-Asp-Xaa1-Lys-Xaa3-Cys-Xaa1-Xaa5-His-Ala- (SEQ ID NO:129)

Asp-Cys-Cys-Asn-Cys-Phe-Leu-Ser-Gly-Ile-Cys-Ala-Xaa3-Ser-Thr-Asn-Xaa4-

Ile-Leu-Xaa3-Gly-Cys-Ser-Thr-Ser-Ser-Phe-Phe-Lys-Ile-^

Name: Ca11.9
Species: caracteristicus
Isolated: No
Cloned: Yes

DNA Sequence:
CCAGCTATCAGCACTTCGCAGCAGTCGAGGCTTTGAAATCCTAATCATAGAAGAAGGCAAAAATATCTGC (SEQ ID NO:130)

TGGTCAATATGAAGCTGTGCCTGACGTTCCTTCTTGTTCTGATGATTCTGGCATCAGTGACTGGGGAGAA

GTCAAGCAAGCATACACTGAGTCGTGCTGCTAGGGTAAAAAACAGAGGCCCTAGTTTTTGTAAGGCAGAC

GAAAAGCCATGCAAGTATCATGCAGATTGCTGTAACTGCTGTCTCGGTGGAATCTGTAAACCAAGCACAA

GTTGGATTGGATGCTCGACGAATGTGTTCCTGACGCGCTGACTTTCAGCCAGCTAGGCCATGCCTAGG

Translation:
MKLCLTFLLVLMILASVTGEKSSKHTLSRAARVKNRGPSFCKADEKPCKYHADCCNCCLGGTCKPSTSWI (SEQ ID NO:131)

GCSTNVFLTR

Toxin Sequence:
Gly-Xaa3-Ser-Phe-Cys-Lys-Ala-Asp-Xaa1-Lys-Xaa3-Cys-Lys-Xaa5-His-Ala- (SEQ ID NO:132)

Asp-Cys-Cys-Asn-Cys-Cys-Leu-Gly-Gly-Ile-Cys-Lys-Xaa3-Ser-Thr-Ser-Xaa4-

Ile-Gly-Cys-Ser-Thr-Asn-Val-Phe-Leu-Thr-Arg-^

Name: Ca11.10
Species: caracteristicus
Isolated: No
Cloned: Yes

DNA Sequence:
CCGCTATCAGCACTTCGCAGCAGTCGAGGCTTTGAAATCCTAATCATAGAAGAAGGCAAAAATATCTGCT (SEQ ID NO:133)

GGTCAATATGAAGCTGTGCCTGACGTTCCTTCTTGTTCTGATGATTCTGGCATCAGTGACTGGGGAGAAG

TCAAGCAAGCATACACTGAGTCGTGCTGCTAGGGTAAAAAACAGAGGCCCTAGTTTTTGTAAGGCAGACG

AAAAGCCATGCAAGTATCATGCAGATTGCTGTAACTGCTGTCTCGGTGGAATCTGTAAACCAAGCACAAG

TTGGATTGGATGCTCGACGAATGTGTTCTTGACGCGCTGACTTTCAGCCAGCTAGGCCATGCCTAGG

Translation:
MKLCLTFLLVLMILASVTGEKSSKHTLSRAARVKNRGPSFCKADEKPCKYHADCCNCCLGGTCKPSTSWT (SEQ ID NO:134)

GCSTNVFLTR

Toxin Sequence:

TABLE 1-continued

Gly-Xaa3-Ser-Phe-Cys-Lys-Ala-Asp-Xaa1-Lys-Xaa3-Cys-Lys-Xaa5-His-Ala- (SEQ ID NO:135)

Asp-Cys-Cys-Asn-Cys-Cys-Leu-Gly-Gly-Ile-Cys-Lys-Xaa3-Ser-Thr-Ser-Xaa4-

Ile-Gly-Cys-Ser-Thr-Asn-Val-Phe-Leu-Thr-Arg-^

Name:     Ca11.11
Species:  caracteristicus
Isolated: No
Cloned:   Yes

DNA Sequence:
CCAGCTATCAGCACTTCGCAGCAGTCGAGGNTTTGAAATCCTAATCATAGAAGAAGGCAAAAATATCTGC (SEQ ID NO:136)

TGGTCAATATGAAGCTGTGCCTGACGTTCCTTCTTGTTCTGATGATTCTGGCATCCGTGACTGGGGAGAA

GTTAAGCGAGCAAACACTGCGCCGTGCTGCTAGGAAAAACAAAGGCCCTCGATGCTGGGTCGGCCGTGTC

CATTGCACCTATCATAAAGACTGCTGTCCGTCGGTATGTTGTTTCAAGGGAAGGTGTAAACCACAATCAT

GGGGATGCTGGTCGGGTCCGACCTAGGCGTGCTGGCCTTGAGGCAGCTAGGCCATGCCTAGG

Translation:
MKLCLTFLLVLMILASVTGEKLSEQTLRRAARKNKGPRCWVGRVHCTYHKDCCPSVCCFKGRCKPQSWGC (SEQ ID NO:137)

WSGPT

Toxin Sequence:
Gly-Xaa3-Arg-Cys-Xaa4-Val-Gly-Arg-Val-His-Cys-Thr-Xaa3-His-Lys-Asp- (SEQ ID NO:138)

Cys-Cys-Xaa3-Ser-Val-Cys-Cys-Phe-Lys-Gly-Arg-Cys-Lys-Xaa3-Gln-Ser-

Xaa4-Gly-Cys-Xaa4-Ser-Gly-Xaa4-Thr-^

Name:     Ca11.12
Species:  caracteristicus
Isolated: No
Cloned:   Yes

DNA Sequence:
CCAGCTATCAGCACTTCGCAGCAGNNGAGGCTTTGAAATCCTAATCATAGAAGAAGGCAAAAATATCTGC (SEQ ID NO:139)

TGGTCAATATGAAGCTGTGCCTGACGTTCCTTCTTGTTCTGATGATTCTGGCATCAGTGACTGGGGAGAA

GTCAAGCAAGCATACACTGAGTCGTGCTGCTAGGGTAAAAAACAGAGGCCCTAGTTTTTGTAAGGCAGAC

GAAAAGCCATGCGAGTATCATGCAGATTGCTGTAATTGCTGTCTCAGTGGAATCTGTGCACCAAGCACAA

ATTGGATTTTACCTGGATGCTCGACGAGTTCGTTCTTCAAGATCTGACTTTCAGCCAGCTAGGCCATGCC

TAGG

Translation:
MKLCLTFLLVLMILASVTGEKSSKHTLSRAARVKNRGPSFCKADEKPCEYHADCCNCCLSGICAPSTNWI (SEQ ID NO:140)

LPGCSTSSFFKI

Toxin Sequence:
Gly-Xaa3-Ser-Phe-Cys-Lys-Ala-Asp-Xaa1-Lys-Xaa3-Cys-Xaa1-Xaa5-His-Ala- (SEQ ID NO:141)

Asp-Cys-Cys-Asn-Cys-Cys-Leu-Ser-Gly-Ile-Cys-Ala-Xaa3-Ser-Thr-Asn-Xaa4-

Ile-Leu-Xaa3-Gly-Cys-Ser-Thr-Ser-Ser-Phe-Phe-Lys-Ile-^

Name:     Ca11.14
Species:  caracteristicus
Isolated: No
Cloned:   Yes

DNA Sequence:
CCAGCTATCAGCACTTCGCAGCAGTCGAGGCTTTGAAATCCTAATCATAGAAGAAGGCAAAAATATCTGC (SEQ ID NO:142)

TGGTCAATATGAAGCTGTGCCTGACGTTCCTTCTTGTTCTGATGATTCTGGCATCAGTGACTGGGGAGAA

GTCAAGCAAGCATACACTGAGTCGTGCTGCTAGGGTAAAAAACAGAGGCCCTAGTTTTTGTAAGGCAAAC

GGAAAGCCATGCTCGTATCATGCAGATTGCTGTAATTGCTGTCTCAGTGGAATCTGTAAACCAAGCACAA

ATGTGATTTTACCTGGATGCTCGACGAGTTCGTTCTTCAGGATCTGACTTTCAGCCAGCTAGGCCATGCC

TABLE 1-continued

TAGG

Translation:
MKLCLTFLLVLMTLASVTGEKSSKHTLSRAARVKNRGPSFCKANGKPCSYHADCCNCCLSGICKPSTNVI   (SEQ ID NO:143)

LPGCSTSSFFRT

Toxin Sequence:
Gly-Xaa3-Ser-Phe-Cys-Lys-Ala-Asn-Gly-Lys-Xaa3-Cys-Ser-Xaa5-His-Ala-   (SEQ ID NO:144)

Asp-Cys-Cys-Asn-Cys-Cys-Leu-Ser-Gly-Ile-Cys-Lys-Xaa3-Ser-Thr-Asn-Val-

Ile-Leu-Xaa3-Gly-Cys-Ser-Thr-Ser-Ser-Phe-Phe-Arg-Ile-^

Name:      S11.6
Species:   striatus
Isolated:  No
Cloned:    Yes

DNA Sequence:
CCGCTATCAGCACTTCGCAGCAGTCGAGGCTTTGAAATCCTAATCATAGAAGAGGGCAAAAATATCTGCT   (SEQ ID NO:145)

GGTCAATATGAAGCTGTGCCTGACOTTCCTTCTTGTTCTGATGATTCTGGCATCAGTGACTGGGGAGAAG

TCAAGCAAGCATACACTGAGTCGTGCTGCTAGGGTAAAAAACAGAGGCCCTAGTTTTTGTAAGGCAGACG

AAAAGCCATGCGACTATCATGCAGATTGCTGTAATTGCTGTCTCAGCGGAATCTGTGCACCAAGCACAAA

TTGGATTTTACCTGGATGCTCGACGAGTTCGTTCTTCAAGATCTGACTTTCAGCTAGCTAGGCCATGCCT

AGG

Translation:
MKLCLTFLLVLMILASVTGEKSSKHTLSRAARVKNRGPSFCKADEKPCEYRADCCNCCLSGICAPSTNWI   (SEQ ID NO:146)

LPGCSTSSFFKI

Toxin Sequence:
Gly-Xaa3-Ser-Phe-Cys-Lys-Ala-Asp-Xaa1-Lys-Xaa3-Cys-Xaa1-Xaa5-His-Ala-   (SEQ ID NO:147)

Asp-Cys-Cys-Asn-Cys-Cys-Leu-Ser-Gly-Ile-Cys-Ala-Xaa3-Ser-Thr-Asn-Xaa4-

Ile-Leu-Xaa3-Gly-Cys-Ser-Thr-Ser-Ser-Phe-Phe-Lys-Ile-^

Name:      S11.7
Species:   striatus
Isolated:  No
Cloned:    Yes

DNA Sequence:
CCAGCTATCAGCACTTCGCAGCAGTCGAGGCTTTGAAATCCTAATCATAGAAGAAGGCAAAAATATCTGC   (SEQ ID NO:148)

TGGTCAATATGAAGCTGTGCCTGGCGTTCCTTCTTGTTCTGATGATTCTGGCATCAGTGACTGGGGAGAA

GTCAAGCAAGCATACACTGAGTCGTGCTGCTAGGGTAAAAAACAGAGGCTGTAAGAAAGACAGAAAGCCA

TGCTCGTATCATGCAGATTGCTGTAATTGCTGTCTCAGTGGAATCTGTGCACCAAGCACAAATTGGATTT

TACCTGGATGCTCGACGAGTACGTTCACTTGACGCGCTGACTTTCAGCCAGCTAGGCCATGCCTAGG

Translation:
MKLCLAFLLVLMILASVTGEKSSKHTLSRAARVKNRGCKKDRKPCSYHADCCNCCLSGTCAPSTNWILPG   (SEQ ID NO:149)

CSTSTFT

Toxin Sequence:
Gly-Cys-Lys-Lys-Asp-Arg-Lys-Xaa3-Cys-Ser-Xaa5-His-Ala-Asp-Cys-Cys-Asn-   (SEQ ID NO:150)

Cys-Cys-Leu-Ser-Gly-Ile-Cys-Ala-Xaa3-Ser-Thr-Asn-Xaa4-Ile-Leu-Xaa3-

Gly-Cys-Ser-Thr-Ser-Thr-Phe-Thr-^

Name:      S11.8
Species:   striatus
Isolated:  No
Cloned:    Yes

DNA Sequence:

TABLE 1-continued

CCGCTATCACCACTTCGCAGCAGTCGAGGCTTTAAAATCCTAATCGTAGAAGAAGGCAAAAATATCTGCT (SEQ ID NO:151)

GGTCAATATGAAGCTGTGCCTGACGTTCCTTCTTGTTCTGATGATTCTGGCATCAGTGACTGGGGAGAAG

TCAAGCAAGCATACACTGAGTCGTGCTGCTAGGGTAAAAAACAGAGGCCCTAGTTTTTGTAAGGCAGACG

AAAAGCCATGCAAGTATCATGCAGATTGCTGTAACTGCTGTCTCGGTGGAATCTGTAAACCAAGCACAAG

TTGGATTGGATGCTCGACGAATGTGTTCTTGACGCGCTGACTTTCAGCCAGCTAGGCCATGCCTAGG

Translation:
MKLCLTFLLVLMILASVTGEKSSKHTLSRAARVKNRGPSFCKADEKPCKYHADCCNCCLGGICKPSTSWT (SEQ ID NO:152)

GCSTNVFLTR

Toxin Sequence:
Gly-Xaa3-Ser-Phe-Cys-Lys-Ala-Asp-Xaa1-Lys-Xaa3-Cys-Lys-Xaa5-His-Ala- (SEQ ID NO:153)

Asp-Cys-Cys-Asn-Cys-Cys-Leu-Gly-Gly-Ile-Cys-Lys-Xaa3-Ser-Thr-Ser-Xaa4-

Ile-Gly-Cys-Ser-Thr-Asn-Val-Phe-Leu-Thr-Arg-^

Name:      Bt11.1
Species:   betulinus
Isolated:  No
Cloned:    Yes

DNA Sequence:
CCAGCTATCAGCACTTCGCAGCAGTCGAGGCTTTAAAATCCTAATCGTAGAAGAAGGGAAACATATCTGG (SEQ ID NO:154)

TGGTCAGTATGAAGCTGTGTGTGGCGTTTCTTCTTGTTCTGGTGATTCTGCCATCGGTGATTGGGGGGAA

GCCTAGCGAGCGTACACTGAGTGGTGCTACTCGGAGAGGCGATCGGAGAATGTGCTTATCCCTAGGACAA

AGATGCGAACGTCATTCCAACTGCTGTGGCTATCTGTGTTGTTTCTACGACAAGTGTGTTGTGACTGCCA

TAGGGTGTGGCCACTACTAGTGCGATCGACCTAGGCGCGCTGCCCTCTGGCAGACTCGCTCAGTATGCC

TGATCTGTCCAAGTGACACGACCTGACACGATCGTCGTATTCCTTTGCCAAGAGTCAGCTAGGCCATGCC

TAGG

Translation:
MKLCVAFLLVLVILPSVTGGKPSERTLSGATRRGDRRMCLSLGQRCERHSNCCGYLCCFYDKCVVTAIGC (SEQ ID NO:155)

GRY

Toxin Sequence:
Met-Cys-Leu-Ser-Leu-Gly-Gln-Arg-Cys-Xaa1-Arg-His-Ser-Asn-Cys-Cys-Gly- (SEQ ID NO:156)

Xaa5-Leu-Cys-Cys-Phe-Xaa5-Asp-Lys-Cys-Val-Val-Thr-Ala-Ile-Gly-Cys-Gly-

His-Xaa5-^

Name:      Bt11.2
Species:   betulinus
Isolated:  No
Cloned:    Yes

DNA Sequence:
CCGCTATCAGCACTTCGCAGCAGTCGAGGCTTTAAAATCCTAATCGTAGAAGAAGGGAAACATATCTGGT (SEQ ID NO:157)

GGTCAGTATGAAGCTGTGTGTGGCGTTTCTTCTTGTTCTGGTGATTCTGCCATCGGTGATTGGGGGGAAG

CCTAGCGAGCGTACACTGAGTGGTGCTACTCGGAGAGGCGATCGGAGAATGTGCTCATTCCTAGGACAAA

GATGCGAACGTCATTTCAACTGCTGTGGCGACCTGTGTTGTTTCGACGACATGTGTCTTGTGGCTGCCAT

AGGGTGTGGCTACTAATAATGCGATGGACCTAGGCGCGCTGGCTCTGTGGCAGGCTCGTTCAGTATGCCT

GATCTGTCCAAGTGACACGACCTGACACGATCGTCGTATTTCTTTGCCAAGAGCCAGCTAGGCCATGCCT

AGG

Translation:
MKLCVAFLLVLVILPSVTGGKPSERTLSGATRRGDRRMCSFLGQRCERHFNCCGDLCCFDDMCLVAAIGC (SEQ ID NO:158)

GY

TABLE 1-continued

Toxin Sequence:
Met-Cys-Ser-Phe-Leu-Gly-Gln-Arg-Cys-Xaa1-Arg-His-Phe-Asn-Cys-Cys-Gly-   (SEQ ID NO:159)

Asp-Leu-Cys-Cys-Phe-Asp-Asp-Met-Cys-Leu-Val-Ala-Ala-Ile-Gly-Cys-Gly-

Xaa5-^

Name:      Bt11.3
Species:   betulinus
Isolated:  No
Cloned:    Yes

DNA Sequence:
CCAGCTATCAGCACTTCGCAGCAGNNGAGGCTTTAAAATCCTAATCGTAGAAGAAGGGAAACATATCTGG   (SEQ ID NO:160)

TGGTCAGTATGAAGCTGTGTGTGGCGTTTCTTCTTGTTCTGGTGATTCTGCCATCGGTGATTGGGGGAA

GCCTAGCGAGCGTACACTGAGTGGTGCTACTCGGAGAGGCGATCGGAGAATCTGCTCATTCCTAGGATGC

GAACGTCATTTCAACTGCTGTGGCGATCTGTGTTGTTTCGACGACATGTGTGTTGTGACTGCCATAGGGT

GTGGCCACTAGTAGTGCGACGGACCTAGGCGCGCTGGCCCTGTGGCAGACTCGCTCAGTATGCCTGATCT

GTCCAAGTGACACGACCTGACACGATCGTCGTATTCCTTTGCCAAGAGTTAGCTAGGCCATGCCTAGG

Translation:
MKLCVAFLLVLVILPSVIGGKPSERTLSGATRRGDRRICSFLGCERHFNCCGDLCCFDDMCVVTATGCGH   (SEQ ID NO:161)

Toxin Sequence:
Ile-Cys-Ser-Phe-Leu-Gly-Cys-Xaa1-Arg-His-Phe-Asn-Cys-Cys-Gly-Asp-Leu-   (SEQ ID NO:162)

Cys-Cys-Phe-Asp-Asp-Met-Cys-Val-Val-Thr-Ala-Ile-Gly-Cys-Gly-His-^

Name:      Bt11.4
Species:   betulinus
Isolated:  No
Cloned:    Yes

DNA Sequence:
CCAGCTATCAGCACTTCGCAGCAGTCGAGGCTTTAAAATCCTAATCGTAGAAGAAGGGAAACATATCTGG   (SEQ ID NO:163)

TGGTCAGTATGAAGCTGTGTGTGGCGTTTCTTCTTGTTCTGGTGATTCTGCCATCGGTGATTGGGGGAA

GCCTAGCGAGCGTACACTCAGTGGTGCTACTCGGAGAGGCGATCGGAGAATGtGCTTATCCCTAGGACAA

CGATGCGGACGTCATTCCAACTGCTGTGGCTATCTGTGTTGTTTCTACGACAAGTGTGTTGTGACTGCCA

TAGGGTGTGGCCACTACTAGTGCGATGGACCTAGGTGCGCTGGCCCTGTGGCAGACTCGCTCAGTATGCC

TGATCTGTCCAAGTGACACGACCTGACACGATCGTCGTATTCCTTTGCCAAGAGTCAGCTAGGCCATGCC

TAGG

Translation:
MKLCVAFLLVLVILPSVTGGKPSERTLSGATRRGDRRMCLSLGQRCGRHSNCCGYLCCFYDKCVVTAIGC   (SEQ ID NO:164)

GHY

Toxin Sequence:
Met-Cys-Leu-Ser-Leu-Gly-Gln-Arg-Cys-Gly-Arg-His-Ser-Asn-Cys-Cys-Gly-   (SEQ ID NO:165)

Xaa5-Leu-Cys-Cys-Phe-Xaa5-Asp-Lys-Cys-Val-Val-Thr-Ala-Ile-Gly-Cys-Gly-

His-Xaa5-^

Name:      Bt11.5
Species:   betulinus
Isolated:  No
Cloned:    Yes

DNA Sequence:
CCAGCTATCAGCACTTCGCAGCAGTCGAGGCTTTAAAATCCTAATCGTAGAAGAAGGGAAACATATCTGG   (SEQ ID NO:166)

TGGTCAGTATGAAGCTGTGTGTGGCGTTTCTTCTTGTTCTGGTGATTCTGCCATCGGTGATTGGGGGAA

GCCTAGCGAGCGTACACTGAGTGGTGCTACTCCGAGAGGCGATCGGAGAATGTGCCTATCCCTAGGACAA

AGATGCGAACGTCATTCCGACTGCTGTGGCTATCTGTGTtGTTTCTACGACAAGTGTGTTGTGACTGCCA

TABLE 1-continued

```
TAGGGTGTGGCCACTACTAGTGCGATGGACCTAGGCGCGCTGGCCCTGTGGCAGACTCGCTCAGTATGCC

TGATCTGTCCAAGTGACACGACCTGACACGGTCGTCGTATTCCTTTGCCAAGAGTCAGCTAGGCCATGCC

TAGG

Translation:
MKLCVAFLLVLVTLPSVTGGKPSERTLSGATRRGDRRNCLSLGQRCERHSDCCGYLCCFYDKCVVTAIGC  (SEQ ID NO:167)

GHY

Toxin Sequence:
Met-Cys-Leu-Ser-Leu-Gly-Gln-Arg-Cys-Xaa1-Arg-His-Ser-Asp-Cys-Cys-Gly-  (SEQ ID NO:168)

Xaa5-Leu-Cys-Cys-Phe-Xaa5-Asp-Lys-Cys-Val-Val-Thr-Ala-Ile-Gly-Cys-Gly-

His-Xaa5-^

Name:      Bt11.6
Species:   betulinus
Isolated:  No
Cloned:    Yes

DNA Sequence:
CCAGCTATCAGCACTTCGCAGCAGTCGAGGCTTTGAAATCCTAATCATAGAAGAAGGCAAAAATATCTGC  (SEQ ID NO:169)

TGGTCAATATGAAGCTGTGCCTGACGTTCCTTCTTGTTCTGATGATTCTGGCATCAGTGACTGGGGAGAA

GTCAAGCAAGCATACACTGAGTCGTGCTGCTAGGGTAAAAAACAAAGGCCATGTTCCATGCGGGAAAGAC

GGAAGGAAATGCGGGTATCATACACATTGCTGTAATTGCTGTCTCAGTGGAATCTGTAAACCAAGCACAA

GTTTGATTGGATGCTCGACGAGTTCGTTCACTTGACGCGCTGACTTTCAGCCAGCTAGGCCATGCCTAGG

Translation:
MKLCLTFLLVLMILASVTGEKSSKHTLSPAARVKNKGHVPCGKDGRKCGYHTHCCNCCLSGICKPSTSLI  (SEQ ID NO:170)

GCSTSSFT

Toxin Sequence:
Gly-His-Val-Xaa3-Cys-Gly-Lys-Asp-Gly-Arg-Lys-Cys-Gly-Xaa5-His-Thr-His-  (SEQ ID NO:171)

Cys-Cys-Asn-Cys-Cys-Leu-Ser-Gly-Ile-Cys-Lys-Xaa3-Ser-Thr-Ser-Leu-Ile-

Gly-Cys-Ser-Thr-Ser-Ser-Phe-Thr-^

Name:      Bt11.7
Species:   betulinus
Isolated:  No
Cloned:    Yes

DNA Sequence:
CCAGCTATCAGCACTTCGCAGCAGTCGAGGCTTTAAAATCCTAATCGTAGAAGAAGGGAAACATATCTGG  (SEQ ID NO:172)

TGGTCAGTATGAAGCTGTGTGTGGCGTTTCTTCTTGTTCTGGTGATTCTGCCATCGGTGATTGGGGGGAA

GCCTAGCGAGCGTACACTGAGTGGTGCTACTCGGAGAGGCGATCGGAGAATGTGCTTATCCCTAGGACAA

AGATGCGAACGTCATTCCAACTGCTGTGGCTATCTGTGTTGCTTCTACGACAAGTGTGTTGTGACTGCCG

TAGGGTGTGGCCACTACTAGTGCGATGGACCTAGGCGCGCTGGCCCTGTGGCAGACTCGCTCAGTATGCC

TGATCTGTCCAAGTGACACGACCTGACACGATCGTCGTATTCCTTTGCCAAGAGTCAGCTAGGCCAGCCT

AGG

Translation:
MKLCVAFLLVLVILPSVIGGKPSERTLSGATRRGDRRMCLSLGQRCERHSNCCGYLCCFYDKCVVTAVGC  (SEQ ID NO:173)

GRY

Toxin Sequence:
Met-Cys-Leu-Ser-Leu-Gly-Gly-Arg-Cys-Xaa1-Arg-His-Ser-Asn-Cys-Cys-Gly-  (SEQ ID NO:174)

Xaa5-Leu-Cys-Cys-Phe-Xaa5-Asp-Lys-Cys-Val-Val-Thr-Ala-Val-Gly-Cys-Gly-

His-Xaa5-^

Name:      Bt11.8
```

TABLE 1-continued

Species: betulinus
Isolated: No
Cloned: Yes

DNA Sequence:
CAGGCTTTAAAATCCTAATCGTAGAAGAAGGGAAACATATCTGGTGGTAGTATGAAGCTGTGTGTGGCGT (SEQ ID NO:175)

TTCTTCTTGTTCTGGTGATTCTGCCATCGGTGATTGGGGGAAGCCTAACGAGCGTACACTGAGTGGTGC

TACTCGGAGAGGCGATCGGAGAATGTGCTTATCCCTAGGACAAAGATGCGAACGTCATTCCAACTGCTGT

GGCTATCTGTGTTGCTTCTACGACAAGTGTGTTATGACTGCCATAGGGTGTGGCCACTACTAGTGCGATG

GACCTACGCGCTGGCCCTGTGGCAGACTCGCTCAGTATGCCTGATCTGTCCAAGTGACACGACCTGAC

ACGATCGTCGTATTCCTTTGACAAGAGTAACGCTAGGCCATGCCTAGG

Translation:
MKLCVAFLLVLVILPSVTGGKPNERTLSGATRRGDRRNCLSLGQRCERHSNCCGYLCCFYDKCVMTAIGC (SEQ ID NO:176)

GHY

Toxin Sequence:
Met-Cys-Leu-Ser-Leu-Gly-Gln-Arg-Cys-Xaa1-Arg-His-Ser-Asn-Cys-Cys-Gly- (SEQ ID NO:177)

Xaa5-Leu-Cys-Cys-Phe-Xaa5-Asp-Lys-Cys-Val-Met-Thr-Ala-Ile-Gly-Cys-Gly-

His-Xaa5-^

Name: Fi11.1
Species: figulinus
Isolated: No
Cloned: Yes

DNA Sequence:
CCAGCTATCAGCACTTCGCAGCAGTCOAGGCTTTGAAATCCTAATCATAGAAGAAGGCAAAAATATCTGC (SEQ ID NO:178)

TGGTCAATATGAAGCTGTGCCTGACGTTCCTTCTTGTTCTGATGATTCTGGCATCAGTGACTGGGGAGAA

GTCAAGCAAGCATACACTGAGTCGTGCTGCTAGGGTAAAAAGCAAAGGCCATGTTTCATGCGGGAAAGAC

GGAAGGCCATGCGATTATCATGCAGATTCCTGTAACTGCTGTCTCGGTGGAATCTGTAAACCAAGCACAA

GTTGGATTGGATGCTCOACGAATGTGTTCTTGACGCGCTGACTTTCAOCTAGCTAGGCCATGCCTAGG

Translation:
MKLCLTFLLVLMILASVTGEKSSKHTLSRAARVKSKGHVSCGKDGRACDYHADCCNCCLGGICKPSTSWI (SEQ ID NO:179)

GCSTNVFLTR
Toxin Sequence:

Gly-His-Val-Ser-Gys-Gly-Lys-Asp-Gly-Arg-Ala-Cys-Asp-Xaa5-His-Ala-Asp- (SEQ ID NO:180)

Cys-Cys-Asn-Cys-Cys-Leu-Gly-Gly-Ile-Cys-Lys-Xaa3-Ser-Thr-Ser-Xaa4-Ile-

Gly-Cys-Ser-Thr-Asn-Val-Phe-Leu-Thr-Arg-^

Name: Fi11.2
Species: figulinus
Isolated: No
Cloned: Yes

DNA Sequence:
CCGCTATCAGCACTTCGCAGCAGTCGAGGCTTTGAAATCCTAATCATAGAAGAAGGCAAAAATATCTACT (SEQ ID NO:181)

GGTCAATATGAAGCTGTGCCTGACGTTCCTTCTTGTTCTGATGATTCTGGCATCAGCGACTGGGGAGAAG

TCAAGCAAGCATACACTGAGTCGTGCTGCTAGGGTAAAAAACAGAGGCCCTAGTTTTTGTAAGGCAGACG

AAAAGCCATGCGAGTATCATGCAGATTGCTGTAATTGCTGTCTCAGTGGAATCTGTGCACCAAGCACAAA

TTGGATTTTACCTGGATGCTCGACGAGTTCGTTCTTCAAGATCTGACTTTCAGCCAGCTAGGCCATGCCT

AGG

Translation:
MKLCLTFLLVLMILASATGEKSSKHTLSRAARVKNRGPSFCKADEKPCEYHADCCNCCLSGICAPSTNWT (SEQ ID NO:182)

LPGCSTSSFFKI

TABLE 1-continued

```
Toxin Sequence:
Gly-Xaa3-Ser-Phe-Cys-Lys-Ala-Asp-Xaa1-Lys-Xaa3-Cys-Xaa1-Xaa5-His-Ala-    (SEQ ID NO:183)

Asp-Cys-Cys-Asn-Cys-Cys-Leu-Ser-Gly-Ile-Cys-Ala-Xaa3-Ser-Thr-Asn-Xaa4-

Ile-Leu-Xaa3-Gly-Cys-Ser-Thr-Ser-Ser-Phe-Phe-Lys-Ile-^

Name:      Fi11.3
Species:   figulinus
Isolated:  No
Cloned:    Yes

DNA Sequence:
CCAGCTATCAGCACTTCGCAGCAGTCGAGGCTTTGAAATCCTAATCATAGAAGAAGGCAAAAATATCTGC    (SEQ ID NO:184)

TGGGCAATATGAAGCTGTGCCTGACGTTCCTTCTTGTTCTGATGATTCTGGCATCAGTGACTGGGGAGAA

CTCAACCAAGCATACACTGAGTCGTGCTGCTAGGGTAAAAAACAGAGGCCCTAGTTTTTGTAAGCCAGAC

GAAAAGCCATGCGAGTATCATGCAGATTGCTGTAATTGCTGTCTCAGTGGAATCTGTGCACCAAGCACAA

ATTGGATTTTACCTGGATGCTCGACGAGTTCGTTCTTCAAGATCCGACTTTCGGCCAGCTAGGCCATGCC

TAGG

Translation:
MKLCLTFLLVLMILASVTGEKSSKHTLSRAARVKNRGPSFCKADEKPCEYHADCCNCCLSCICAPSTNWT    (SEQ ID NO:185)

LPGCSTSSFFKIRLSAS

Toxin Sequence:
Gly-Xaa3-Ser-Phe-Cys-Lys-Ala-Asp-Xaa1-Lys-Xaa3-Cys-Xaa1-Xaa5-His-Ala     (SEQ ID NO:186)

Asp-Cys-Cys-Asn-Cys-Cys-Leu-Ser-Gly-Ile-Cys-Ala-Xaa3-Ser-Thr-Asn-Xaa4-

Ile-Leu-Xaa3-Gly-Cys-Ser-Thr-Ser-Ser-Phe-Phe-Lys-Ile-Arg-Leu-Ser-Ala-

Ser-^

Name:      Fi11.4
Species:   figulinus
Isolated:  No
Cloned:    Yes

DNA Sequence:
CCAGCTATCAGCACTTCGCAGCAGTCGAGGCTTTGAAATCCTAATCATAGAAGAAGGCAAAAATATCTGC    (SEQ ID NO:187)

TGGTCAATATCAAGCTGTGCCTGACGTTCCTTCTTGTTCTGATGATTCTCCCATCAGTGACTGGCGAGAA

GTCAAGCAAGCATACACTGAGTCGTGCTGCTAGGGTAAAAAACAAAGGCCCTCGATGCTGGGTCGGCCGT

GTCCATTGCACCTATCATAAAGACTGCTGTCCGTCGGTATGTTGCTTCAAGGGAAGGTGTAAACCACAAT

CATGCCGATGCTGGTCGGGTCCCACCTAGGCGTGCTCGCCTTGAGGCAGCTAGGCCATGCCTAGG

Translation:
MKLCLTFLLVLMILASVTGEKSSKHTLSRAARVKNKGPRCWVGRVHCTYHKDCCPSVCCFKGRCKPQSWG    (SEQ ID NO:188)

CWSGPT

Toxin Sequence:
Gly-Xaa3-Arg-Cys-Xaa4-Val-Gly-Arg-Val-His-Cys-Thr-Xaa5-His-Lys-Asp-      (SEQ ID NO:189)

Cys-Cys-Xaa3-Ser-Val-Cys-Cys-Phe-Lys-Gly-Arg-Cys-Lys-Xaa3-Gln-Ser-

Xaa4-Gly-Cys-Xaa4-Ser-Gly-Xaa3-Thr-^

Name:      Fi11.5
Species:   figulinus
Isolated:  No
Cloned:    Yes

DNA Sequence:
CCGCTATCAGCACTTCGCAGCAGTCGAGGCTTTGAAATCCTAATCATAGAAGAAGGCAAAAATATCTGCT    (SEQ ID NO:190)

GGTCAATATGAAGCTGTGCCTGACGTTCCTTCTTGTTCTGATGATTCTGGCATCAGTGACTGGGGAGAAG

TCAAGCAAGCATACACTGAGTCGTGCTGCTAGGGTAAAAAACAGAGGCTGTAAGAAAGACAGAAAGCCAT
```

TABLE 1-continued

GCTCGTATCATGCAGATTGCTGTAATTGCTGTCTCAGTGGAATCTGTGCACCAAGCACAAATTGGATTTT

ACCTGGATGCTCGACGAGTACGTTCACTTGACGCGCTGACTTTCAGCCAGCTAGGCCATGCCTAGG

Translation:
MKLCLTFLLVLMILASVTGEKSSKHTLSRAARVKNRGCKKDRKPCSYHADCCNCCLSGICAPSTNWILPG (SEQ ID NO:191)

CSTSTFT

Toxin Sequence:
Gly-Cys-Lys-Lys-Asp-Arg-Lys-Xaa3-Cys-Ser-Xaa5-His-Ala-Asp-Cys-Cys-Asn- (SEQ ID NO:192)

Cys-Cys-Leu-Ser-Gly-Ile-Cys-Ala-Xaa3-Ser-Thr-Asn-Xaa4-Ile-Leu-Xaa3-

Gly-Cys-Ser-Thr-Ser-Thr-Phe-Thr-^

Name:      Fi11.6
Species:   figulinus
Isolated:  No
Cloned:    Yes

DNA Sequence:
CCAGCTATCANCACTTCGCAGCNGNCGAGGCTTTGAAGTCCTAATCATAGAAGAAGGCAAAAATATCTGC (SEQ ID NO:193)

TGGTCAATATGAAGCTGTGCCTGACGTTCCTTCTTGTTCTGATGATTCTGGCATCAGTGACTGGGGAGAA

GTCAAGCAAGCATACACTGAGTCGTGCTGCTAGGGTAAAAAACAGAGGCTGTAAGAAAGACAGAAAGCCA

TGCTCGTATCATGCAGATTGCTGTAATTGCTGTCTCAGTGGAATCTGTGCACCAAGCACAAATTGGATTT

TACCTGGATGCTCGACGAGTTCGTTCTTCAAGATCTGACTTTCAGCCAGCTAGGCCATGCCTAGG

Translation:
MKLCLTFLLVLMILASVTGEKSSKHTLSPAARVKNRGCKKDRKPCSYHADCCNCCLSGICAPSTNWILPG (SEQ ID NO:194)

CSTSSFFKI

Toxin Sequence:
Gly-Cys-Lys-Lys-Asp-Arg-Lys-Xaa3-Cys-Ser-Xaa5-His-Ala-Asp-Cys-Cys-Asn- (SEQ ID NO:195)

Cys-Cys-Leu-Ser-Gly-Ile-Cys-Ala-Xaa3-Ser-Thr-Asn--Xaa4-Ile-Leu-Xaa3-

Gly-Cys-Ser-Thr-Ser-Ser-Phe-Phe-Lys-Ile-^

Name:      Fi11.7
Species:   figulinus
Isolated:  No
Cloned:    Yes

DNA Sequence:
CCGCTATCAGCACTTCGCAGCAGNCGAGGCTTTGAAGTCCTAATCATAGAAGAAGGCAAAAATATCTGCT (SEQ ID NO:196)

GGTCAATATGAAGCTGTGCCTGACGTTCCTTCTTGTTCTGATGATTCTGGCATCAGTGACTGgGgAGAAG

TCAAGCAAGCATACACTGAGTCGTGCTGCTAGGGTAAAAAACAGAGGCCCTAGTTCTTGTAAGGCAGACG

AAGAGCCATGCGAGTATCATGCAGATTGCTGTAATTGCTGTCTCAGTGGAATCTGTGCACCAAGCACAAA

TTGGATTTTACCTGGATGCTCGACGAGTTCGTTCTTCAAGATCTGACTTTCAGCCAGCTAGGCCATGCCT

AGG

Translation:
MKLCLTFLLVLMILASVTGEKSSKHTLSRAARVKNRGPSSCKADEEPCEYHADCCNCCLSGICAPSTNWI (SEQ ID NO:197)

LPGCSTSSFFKI

Toxin Sequence:
Gly-Xaa3-Ser-Ser-Cys-Lys-Ala-Asp-Xaa1-Xaa1-Xaa3-Cys-Xaa1-Xaa5-His-Ala- (SEQ ID NO:198)

Asp-Cys-Cys-Asn-Cys-Cys-Leu-Ser-Gly-Ile-Cys-Ala-Xaa3-Ser-Thr-Asn-Xaa4-

Ile-Leu-Xaa3-Gly-Cys-Ser-Thr-Ser-Ser-Phe-Phe-Lys-Ile-^

Name:      L11.1
Species:   lynceus
Isolated:  No
Cloned:    Yes

TABLE 1-continued

```
DNA Sequence:
CCAGCTATCAGCACTTCGCAGCAGTCGAGGCTTTGAAATCCTAATCATAGAAGAAGGCAAAAATATCTGC    (SEQ ID NO:199)

TGGTCAATATGAAGCTGTGTGTGACGTTCCTTCTTGTTCTGATGATTCTGCCATCGGTGACTGGGGAGAA

GTCTAGCAAGCGTACACTGAATGGTGCTCTTCTGAAACGCAATTGGAGCTGGTGCTTCAACGCTGGAGTA

AAATGCGACAATCATTCCGACTGCTGTGAGGATACCTGTTGTTACGATAACACCTGTGTTGTGGCTGTCG

CGGCGTGCTAGGTGCGATGGACCTAGGCGAGCTGGCCTTGAGCTAGCTAGGCCATGCCTAGG

Translation:
MKLCVTFLLVLMILPSVTGEKSSKRTLNGALLKRNWSWCFNAGVKCDNHSDCCEDTCCYDNTCVVAVAAC    (SEQ ID NO:200)

Toxin Sequence:
Asn-Xaa4-Ser-Xaa4-Cys-Phe-Asn-Ala-Gly-Val-Lys-Cys-Asn-Asn-His-Ser-Asp-    (SEQ ID NO:201)

Cys-Cys-Xaa1-Asp-Thr-Cys-Cys-Xaa5-Asp-Asn-Thr-Cys-Val-Val-Ala-Val-Ala-

Ala-Cys-^

Name:       L11.2
Species:    lynceus
Isolated:   No
Cloned:     Yes

DNA Sequence:
CCAGCTATCAGCACTTCGCAGCAGTCGAGGCTTTGAAATCCTAATCATAGAAGAAGGTAAAAATATCTGC    (SEQ ID NO:202)

TGGTCAGTATGAAGCTGAGTGTGACGTTCCTTCTTATTCTGATGATTCCGCCATCGGTGACTGGGGAAAA

GTCAAGCAAGCATACACTGAGTCGTGCTCTTCTGACAGCTATCGCGCTGGAAGAAGCACTGAAAAAGA

TGCTACTTCAATGGAGCACCATGCGACAGACATGAAGAGTGCTGTACGTGGCAAAGATGTTGTTTTTCGC

AAAGGTGTGGCACAGCTACCTTTGGATGCTGGGTGGATCCGTACTAGGCGTGCTGGCCTTGAGCCAGCTA

GGCCATGCCTAGG

Translation:
MKLSVTFLLILMIPPSVTGEKSSKHTLSRALLTGYRAGRSTEKRCYFNGAPCDRHEECCTWQRCCFSQRC    (SEQ ID NO:203)

GTATFGCWVDPY

Toxin Sequence:
Cys-Xaa5-Phe-Asn-Gly-Ala-Xaa3-Cys-Asp-Arg-His-Xaa1-Xaa1-Cys-Cys-Thr-    (SEQ ID NO:204)

Xaa4-Gln-Arg-Cys-Cys-Phe-Ser-Gln-Arg-Cys-Gly-Thr-Ala-Thr-Phe-Gly-Cys-

Xaa4-Val-Asp-Xaa3-Xaa5-^

Name:       L11.3
Species:    lynceus
Isolated:   No
Cloned:     Yes

DNA Sequence:
CCAGCTATCAGCACTTCGCAGCAGTCGAGGCTTTGAAATCCTAATCATAGAAGAAGGCAAAAATATCTGC    (SEQ ID NO:205)

TGGTCAATATGAAGCTGTGTGTGACGTTCCTTCTTGTTCTGATGATTCTGCCATCGGTGACTGGGGAGAA

GTCTAGCAAGCGTACACTGAATGGTGCTCTTCTGAAACGCAATTGGAGCTGGTGCTTCAACGCTGGAGTA

GAATGCGACAATCATTCCGACTGCTGTGAGGATACCTGTTGTTACGATAACACCTGTGTTGTGGCTGTCG

CGGCGTGCTAGGTGCGATGGACCTAGGCGAGCTGGCCTTGAGCTAGCTAGGCCATGCCTAGG

Translation:
MKLCVTFLLVLNILPSVTGEKSSKRTLNGALLKRNWSWCFNAGVECDNHSDCCEDTCCYDNTCVVAVAAC    (SEQ ID NO:206)

Toxin Sequence:
Asn-Xaa4-Ser-Xaa4-Cys-Phe-Asn-Ala-Gly-Val-Xaa1-Cys-Asp-Asn-His-Ser-    (SEQ ID NO:207)

Asp-Cys-Cys-Xaa1-Asp-Thr-Cys-Cys-Xaa5-Asp-Asn-Thr-Cys-Val-Val-Ala-Val-

Ala-Ala-Cys-^

Name:       L11.4
```

TABLE 1-continued

Species: lynceus
Isolated: No
Cloned: Yes

DNA Sequence:
CCAGCTATCAGCACTTCGCAGCAGTCGAGGCTTTGAAATCCTAATCATAGAAGAAGGCAAAAATATCTGC (SEQ ID NO:208)

TGGCACGCCAATATGAAGCTGTGTGTGACGTTCCTTCTTGTTCTGATGATTCTGCCATCGGTGACTGGGG

AGAAGTCTAGCAAGCGTACACTGAATGGTGCTCTTCTGAAACGCAATTGGAGCTGGTGCTTCAACGCTGG

AGTAAAATGCGACAATCATTCCGACTGCTGTGCTGATACCTGTTGTTACGATAACACCTGTGTTGTGGCT

GTCGCGGCGTGCTAGGTGCGATGGACCTAGGCGAGCTGGCCTTGAGCTAGCTAGGCCATGCCTAGG

Translation:
MKLCVTFLLVLMILPSVTGEKSSKRTLNGALLKRNWSWCFNAGVKCDNHSDCCADTCCYDNTCVVAVAAC (SEQ ID NO:209)

Toxin Sequence:
Asn-Xaa4-Ser-Xaa4-Cys-Phe-Asn-Ala-Gly-Val-Lys-Cys-Asp-Asn-His-Ser-Asp- (SEQ ID NO:210)

Cys-Cys-Ala-Asp-Thr-Cys-Cys-Xaa5-Asp-Asn-Thr-Cys-Val-Val-Ala-Val-Ala-

Ala-Cys-^

Name: L11.5
Species: lynceus
Isolated: No
Cloned: Yes

DNA Sequence:
CCAGCTATCAGCACTTCGCAGCAGTCGACGCTTTGAAATCCTAATCATAGAAGAAGGCAAAAATATCTGC (SEQ ID NO:211)

TGGTCAATATGAAGCTGTGTGTCACGTTCCTTCTTGTTCTGATGACTCTGCCATCGCTGACTCGGGAGAA

GTCTAGCATGCGTACACTGAATCGTCTTCTGAAACCCAATTGGAGTTGGTGCTCAGGCTCTGGAGAAGGA

TGCGACTATCATTCCGAGTGCTGTGGGGAGAGATGTTGTATCGAAAGCATGTGTATTGGGGATGGCGTGG

CGTGCTGGCCTTGAGCCAGCTAGGCCATGCCTAGG

Translation:
MKLCVTELLVLMTLPSVTGEKSSMRTLNRLLKRNWSWCSGSGEGCDYHSECCGERCCIESMCTGDGVACW (SEQ ID NO:212)

P

Toxin Sequence:
Asn-Xaa4-Ser-Xaa4-Cys-Ser-Gly-Ser-Gly-Xaa1-Gly-Cys-Asp-Xaa5-His-Ser- (SEQ ID NO:213)

Xaa1-Cys-Cys-Gly-Xaa1-Arg-Cys-Cys-Ile-Xaa1-Ser-Met-Cys-Ile-Gly-Asp-

Gly-Val-Ala-Cys-Xaa4-Xaa3-^

Name: L11.6
Species: lynceus
Isolated: No
Cloned: Yes

DNA Sequence:
CCAGCTATCAGCACTTCGCAGCAGTCGAGGCTTTGAAATCCTAATCATAGAAGAAGGCAAAAATATCTGC (SEQ ID NO:214)

TGGTCAATATGAAGCTGTGTGTGACGTTCCTTCTTGTTCTGATGATTCTGCCATCGGTGACTGGGGAGAA

GTCTAGCAAGCGTACACTGAATGGTGCTCTTCTGAAACGCAATTGGAGCTGGTGCTTCAACGCTGGAGTA

AAATGCGACAATCATTCCGACTGCTGTGAGGATACCTGTTGTTACGATAGCACCTGTGTTGTGGCTGTCG

CGGCGTGCTAGGTGCGATGGACCTAGGCGAGCCGGCCTTGAGCTAGCTAGGCCATGCCTAGG

Translation:
MKLCVTFLLVLMILPSVTGEKSSKRTLNGALLKRNWSWCFNAGVKCDNHSDCCEDTCCYDSTCVVAVAAC (SEQ ID NO:215)

Toxin Sequence:
Asn-Xaa4-Ser-Xaa4-Cys-Phe-Asn-Ala-Gly-Val-Lys-Cys-Asp-Asn-His-Ser-Asp- (SEQ ID NO:216)

Cys-Cys-Xaa1-Asp-Thr-Cys-Cys-Xaa5-Asp-Ser-Thr-Cys-Val-Val-Ala-Val-Ala-

Ala-Cys-^

TABLE 1-continued

```
Name:      br11a
Species:   brunneus
Isolated:  Yes
Cloned:    No

Toxin Sequence:
Cys-Gly-Xaa5-Val-Gly-Gln-Ala-Cys-Asp-Asp-Asp-Ser-Asp-Cys-Cys-Gly-Ser-    (SEQ ID NO:217)

Ile-Cys-Cys-Val-Ala-Gly-Xaa1-Cys-Val-Ile-Thr-Gly-Arg-Arg-Cys-#

Name:      Em11.1
Species:   emaciatus
Isolated:  No
Cloned:    Yes

DNA Sequence:
GCTATCAGCACTTCGCAGCAGTCGAGGCTTTAAAATCCTGATCGTAGAAGGCTAAAACAACTGGTGGTCA  (SEQ ID NO:218)

GCATGAAACTGTGTTCGACGTCTCTTCTTATTCTGGTGATTCTGCCATCGGTGACTGGAGAGAAGTCTGG

CAAGCATACACTGAGTGGTGCTGCTCTGAGAGGCAATCGGGGAGCGTGCTCAGACACAGGACAAGGATGC

ATACATCATTTCAACTGCTGTTGGGATTTGTGCTGTTACGGCCGCACGTGTGGTGTGAATGTCATGGGGT

GTCCTCCCTTCTAGTGCGATGGAGCCAGGCGTGCTGGCCTCGTGGCAGACTCGCTCAGTGTGcCTGATCT

GTCCAAGTGGAACGACCTGACATGATCATCGTATTCCTTTGCCAAGAGCAAGCTAGGCCATGCCTAGGT

Translation:
MKLCSTSLLTLVTLPSVTGEKSGKHTLSGAALRGNRGACSDTGQGCIHHFNCCWDLCCYGRTCGVNVMGC  (SEQ ID NO:219)

PPF

Toxin Sequence:
Gly-Ala-Cys-Ser-Asp-Thr-Gly-Gln-Gly-Cys-Ile-His-His-Phe-Asn-Cys-Cys-    (SEQ ID NO:220)

Xaa4-Asp-Leu-Cys-Cys-Xaa5-Gly-Arg-Thr-Cys-Gly-Val-Asn-Val-Met-Gly-Cys-

Xaa3-Xaa3-Phe-

Name:      Em11.2
Species:   emaciatus
Isolated:  No
Cloned:    Yes

DNA Sequence:
GCTATCAGCACTTCGCAGCAGTCGAGGCTTTAAAATCCTGATCGTAGAAGGCTAAAACAACTGGTGGTCA  (SEQ ID NO:221)

GCATGAAACTGTGTTTGAGGTTTCTTCTTATTCTGGTGATTCTGCCATCGGTGACTGGAGAGAAGTCTGG

CAAGCATACACTGAGTGGTGCTGCTCTGAGAGGCGATCGGGGAGCGTGCTCAGACACAGGACAAGGATGC

ATACATCATTCCAACTGCTGTTGGGATTTGTGCTGTTACGGCCGCACGTGTGGTGTGAATGTCATCGGGT

GTCCTCCCTTCTAGTGCGATGGAGCCAGGCGTGCTGGCCTCGTGGCAGACTCGCTCAGTGTGCCTGATCT

GTCCAAGTGGAACGACCTGACATGATCATCGTATTCCTTTGCCAAGAGCCAGCTAGGCCATGCCTAGGT

Translation:
MKLCLTFLLTLVILPSVTGEKSGKHTLSGAALRGDRGACSDTGQGCTHHSNCCWDLCCYGRTCGVNVMGC  (SEQ ID NO:222)

PPF

Toxin Sequence:
Gly-Ala-Cys-Ser-Asp-Thr-Gly-Gln-Gly-Cys-Ile-His-His-Ser-Asn-Cys-Cys-    (SEQ ID NO:223)

Xaa4-Asp-Leu-Cys-Cys-Xaa5-Gly-Arg-Thr-Cys-Gly-Val-Asn-Val-Met-Gly-Cys-

Xaa3-Xaa3-Phe-

Name:      Em11.3
Species:   entaciatus
Isolated:  No
Cloned:    Yes

DNA Sequence:
GCTATCAGCACTTCGCAGCAGTCGAGGCTTTAAAATCCTGCTCGTAGAAGAAGGCAAAAACATCTGGTGG  (SEQ ID NO:224)

TCAGTATGGAGCTGTGTGTGGCGTTTCTTCTTATTCTGGTGATTCTGCCATCGGTGACTGGGGAGAAGTC
```

TABLE 1-continued

```
TAGCAAGCGTACACTGAGTGGTGCTGCTCTGAGAGGCGATCGGGGAACGTGCTCAGGCATAGGACAAGGA

TGCATACATCATTTGAACTGCTGTTGGGATATGTGCTGTTACGGCCACACGTGTGTTGTGAATATCATAG

GGTGTCCTCCACACTAGTGCGATGGGGCTAGGCGTGCTGGCCTCGTGGCGGACTCGCTCACTATGCCTGA

TCTGTCCAAGTGAAACGACCAGATGACATGATCGTCGTATTCCTTTGCCAGGAGCCAGCTAGGCCATGCC

TAGGT

Translation:
MELCVAFLLTLVILPSVTGEKSSKRTLSGAALRGDRGTCSGIGQGCIHHLNCCWDMCCYGHTCVVNIIGC   (SEQ ID NO:225)

PPH

Toxin Sequence:
Gly-Thr-Cys-Ser-Gly-Ile-Gly-Gln-Gly-Cys-Ile-His-His-Leu-Asn-Cys-Cys-   (SEQ ID NO:226)

Xaa4-Asp-Met-Cys-Cys-Xaa5-Gly-His-Thr-Cys-Val-Val-Asn-Ile-Ile-Gly-Cys-

Xaa3-Xaa3-His-^

Name:      Em11.4
Species:   emaciatus
Isolated:  No
Cloned:    Yes

DNA Sequence:
GCTATCAGCACTTCGCAGCACTCGAGGCTTTAAAATCCTGATCGTAGAAGAAGGCTAAAACAACTGGTGG   (SEQ ID NO:227)

TCAGCATGAAACTGTGTTTGACGTTTCTTCTTATTCTGGTGGTTCTGCCATCGGTGACTGGAGAGAAGTC

TGGCAAGCATACACTGAGTGGTGCTGCTCTGAGAGGCGATCGGGGAGCGTGCTCAGACACAGGACAAGGA

TGCATACATCATTCCGACTGCTGTTGGGATTTGTGCTGTTACGGCCGCACGTGTGGTGTGAATGTCATGG

GGTGTCCTCCCTTCTAGTGCGATGGAGCCAGGCGTGCTGGCCTCGTGGCAGACTCGCTCAGTGTGCCTGA

TCTGTCCAAGTGGAACGACCTGACATGATCATCGTATTCCTTTGCCAAGAGCCAGCTAGGCCATGCCTAG

GT

Translation:
MKLCLTFLLTLVVLPSVTGEKSGKHTLSGAALRGDRGACSDTGQGCIHHSDCCWDLCCYGRTCGVNVMGC   (SEQ ID NO:228)

PPF

Toxin Sequence:
Gly-Ala-Cys-Ser-Asp-Thr-Gly-Gln-Gly-Cys-Ile-His-His-Ser-Asp-Cys-Cys-   (SEQ ID NO:229)

Xaa4-Asp-Leu-Cys-Cys-Xaa5-Gly-Arg-Thr-Cys-Gly-Val-Asn-Val-Met-Gly-Cys-

Xaa3-Xaa3-Phe-^

Type II
Name:      U026
Species:   episcopatus
Isolated:  Yes
Cloned:    No

Toxin Sequence:
Cys-Ile-Arg-Xaa1-Asp-Ala-Xaa3-Cys-Ser-Phe-Ser-Ala-His-Cys-Cys-Gly-Arg-   (SEQ ID NO:230)

Asn-Cys-Cys-Arg-Gly-Xaa5-Cys-Xaa1-Arg-Xaa3-Cys-Arg-Xaa4-Ile-#

Name:      Em11.5
Species:   emaciatus
Isolated:  No
Cloned:    Yes

DNA Sequence:
ATGATGTTTCGTGTGACGTCAGTCAGCTGTTTCCTGCTGGTCATCGTTTGTCTGAACTTGATTGTGCTTA   (SEQ ID NO:231)

CCAATGCCTGCCTCCATGAAACGTCGCCCTGCAGACGTAGTTTCCAATGCTGTCACGGAATTTGCTGTTT

TCGGAGATGCAGTAATTCGTGTCGATTTGGAAAGAGGGCGACATTCCAAGAATTCATTCTACATCGCTGA

TATGTTGCCCAGAGGTCTGCTGCTTCTCGT
```

TABLE 1-continued

Translation:
MMFRVTSVSCFLLVIVCLNLIVLTNACLHETSPCRRSFQCCHGICCFRRCSNSCRFGKRATFQEFILHR (SEQ ID NO:232)

Toxin Sequence:
Cys-Leu-His-Xaa1-Thr-Ser-Xaa3-Cys-Arg-Arg-Ser-Phe-Gln-Cys-Cys-His-Gly- (SEQ ID NO:233)

Ile-Cys-Cys-Phe-Arg-Arg-Cys-Ser-Asn-Ser-Cys-Arg-Phe-<u>Gly-Lys-Arg-Ala-</u>

<u>Thr-Phe-Gln-Xaa1-Phe-Ile-Leu-His-Arg-</u>[1]

Name:     Em11.6
Species:  emaciatus
Isolated: No
Cloned:   Yes

DNA Sequence:
ATGATGTTTCGTGTGACGTCACTCAGCTGTTTCCTCCTGGTCATCGCTTGTCTGAACTTGGTTGTGCTTA (SEQ ID NO:234)

CCAATGCCTGCCTCCGTGACGGACAGTCCTGCAGATATCATTCCGATTGCTGTAGATACTCTTGCTGTTG

GGCGTATTGCGATCAGAAGTGTCTAATTATTGGAAAGAGGGCGACATTCCAAGAACTCATCCTACATCGT

TGAAATGTTGCCCAGAGGTCTGCTGCTTCTCGT

Translation:
MMFRVTSVSCFLLVIACLNLVVLTNACLRDGQSCRYHSDCCRYSCCWGYCDQKCLIIGKRATFQELILHR (SEQ ID NO:235)

Toxin Sequence:
Cys-Leu-Arg-Asp-Gly-Gln-Ser-Cys-Arg-Xaa5-His-Ser-Asp-Cys-Cys-Arg-Xaa5- (SEQ ID NO:236)

Ser-Cys-Cys-Xaa4-Gly-Xaa5-Cys-Asp-Gln-Lys-Cys-Leu-Ile-Ile-<u>Gly-Lys-Arg-</u>

<u>Ala-Thr-Phe-Gln-Xaa1-Leu-Ile-Leu-His-Arg-</u>[1]

Name:     Em11.7
Species:  emaciatus
Isolated: No
Cloned:   Yes

DNA Sequence:
ATGATGTTTCGTGTGACGTCAGTCGGCTGTTTCCTGCTGGTCATCGTTTGTCTGAACTTGGTTGTGCTTA (SEQ ID NO:237)

CCAATGCCTGCCGCCGTGAAGGATCGTCCTGCAGACGTTCTTACCAGTGCTGTCGTAAGAGTTGCTGTAT

TGGGGAGTGCGAATTTCCGTGTCGATGGGTTGGAAAGAGGGCAACATTCCGAGAACTCATCCTACATCAT

TGAAATGTTGCCCAGAGGTCTGCTGCTTCTCGT

Translation:
MMFRVTSVGCFLLVIVCLNLVVLTNACRREGSSCRRSYQCCRKSCCIGECEFPCRWVGKPATFRELTLHH (SEQ ID NO:238)

Toxin Sequence:
Cys-Arg-Arg-Xaa1-Gly-Ser-Ser-Cys-Arg-Arg-Ser-Xaa5-Gln-Cys-Cys-Arg-Lys- (SEQ ID NO:239)

Ser-Cys-Cys-Ile-Gly-Xaa1-Cys-Xaa1-Phe-Xaa3-Cys-Arg-Xaa4-Val-<u>Gly-Lys-</u>

<u>Arg-Ala-Thr-Phe-Arg-Xaa1-Leu-Ile-Leu-His-His-</u>[1]

Name:     Em11.8
Species:  emaciatus
Isolated: No
Cloned:   Yes

DNA Sequence:
ATGATGTTTCGTGTGACGTCAGTCAGCTGTTTCCTACTGGTCATCGTTTGTCTGAACTTGATTGTGCTTA (SEQ ID NO:240)

TCAATGCCTGCTACCAAGATGAAACGCCCTGCAGAGGTAGTATCTTCTGCTGTCGCAAAAAATGCTGTAT

AGGGACATGCAGATTTCCGTGTTACGTTAAATTAGAGAGGGCGACTTTCCAAGAACTCATCCTACAACCT

TGAAACGTTGCCCAGAGGTCTGCTGCTTCTCGT

Translation:
MMFRVTSVSCFLLVIVCLNLTVLINACYQDETPCRGSIFCCRKKCCTGTCRFPCYVKLERATFQELILQP (SEQ ID NO:241)

Toxin Sequence:
Cys-Xaa5-Gln-Asp-Xaa1-Thr-Xaa3-Cys-Arg-Gly-Ser-Ile-Phe-Cys-Cys-Arg- (SEQ ID NO:242)

TABLE 1-continued

Lys-Lys-Cys-Cys-Ile-Gly-Thr-Cys-Arg-Phe-Xaa3-Cys-Xaa5-Val-Lys-Leu-

Xaa1-Arg-Ala-Thr-Phe-Gln-Xaa1-Leu-Ile-Leu-Gln-Xaa3-^

Name:     Em11.9
Species:  emnaciatus
Isolated: No
Cloned:   Yes

DNA Sequence:
ATGATGTTTCGTGTGACGTCAGTCAGCTGTTTCCTGCTGGTCATCGCTTGTCTGAACCTGGTTGTGCTTA    (SEQ ID NO:243)

CCAATGCCTGCCTCCGTGACGGACAGTCCTGCGGATATGATTCCGATTGCTGTAGATACTCTTGCTGTTG

GGGGTATTGCGATCTTACGTGTCTAATTATTGGAAAGAGGGCGACATTCCAAGAACTCATCCTACATCGT

TGAAATGTTGCCCAGAGGTCTGCTGCTTCTCGT

Translation:
MMFRVTSVSCFLLVIACLNLVVLTNACLRDGQSCGYDSDCCRYSCCWGYCDLTCLIIGKRATFQELILHR    (SEQ ID NO:244)

Toxin Sequence:
Cys-Leu-Arg-Asp-Gly-Gln-Ser-Cys-Gly-Xaa5-Asp-Ser-Asp-Cys-Cys-Arg-Xaa5-    (SEQ ID NO:245)

Ser-Cys-Cys-Xaa4-Gly-Xaa5-Cys-Asp-Leu-Thr-Cys-Leu-Ile-Ile-Gly-Lys-Arg-

Ala-Thr-Phe-Gln-Xaa1-Leu-Ile-Leu-His-Arg-^1

Name:     Em11.10
Species:  emaciatus
Isolated: No
Cloned:   Yes

DNA Sequence:
ATGATGTTTCGTGTGACGTCAGTCAGCTGTTTCCTGCTGGTCATCGCTTGTCTGAACTCGTTTCAGGTTG    (SEQ ID NO:246)

TGCTTACCAGCCGCTGCTTCCCTCCAGGAATATACTGCACACCCTATCTCCCCTGCTGTTGGGGAATTTG

CTGTGGGACGTGCAGAAATGTGTGTCATTTGAGGATTGGAAAGAGGGCGACATTCCAAGAATGAATTCAT

TCTACATCGTTTATATGTTGCCCAGAGGTCTGCTCCTTCTCGT

Translation:
MMFRVTSVSCFLLVIACLNSFQVVLTSRCFPPGIYCTPYLPCCWGICCGTCRNVCHLRIGKRATFQE       (SEQ ID NO:247)

Toxin Sequence:
Cys-Phe-Xaa3-Xaa3-Gly-Ile-Xaa5-Cys-Thr-Xaa3-Xaa5-Leu-Xaa3-Cys-Cys-         (SEQ ID NO:248)

Xaa4-Gly-Ile-Cys-Cys-Gly-Thr-Cys-Arg-Asn-Val-Cys-His-Leu-Arg-Ile-Gly-

Lys-Arg-Ala-Thr-Phe-Gln-Xaa1-^1

Name:     Em11.11
Species:  emaciatus
Isolated: No
Cloned:   Yes

DNA Sequence:
ATGATGTTTCGTGTGACGTCAGTCAGCTGTTTCCTACTGGTCATCGTTTGTCTGAACTTGATTGTGCTTA    (SEQ ID NO:249)

TCAATGCCTGCTACCAAGATGAAACGCCCTGCAGAGGTAGTACCTTCTGCTGTCGCAAAAAATGCTGTAT

AGGGACATGCAGATTTCCGTGTTACGTTAAATTAGAGAGGGCGACTTTCCAAGAACTCATCCTACAACCT

TGAAACGTTGCCCAGAGGTCTGCTGCTTCTCGT

Translation:
MMFRVTSVSCFLLVIVCLNLIVLTNACYQDETPCRGSTFCCRKKCCTGTCRFPCYVKLEPATFQELILQP    (SEQ ID NO:250)

Toxin Sequence:
Cys-Xaa5-Gln-Asp-Xaa1-Thr-Xaa3-Cys-Arg-Gly-Ser-Thr-Phe-Cys-Cys-Arg-        (SEQ ID NO:251)

Lys-Lys-Cys-Cys-Ile-Gly-Thr-Cys-Arg-Phe-Xaa3-Cys-Xaa5-Val-Lys-Leu-

Xaa1-Arg-Ala-Thr-Phe-Gln-Xaa1-Leu-Gln-Xaa3-^

Name:     Em11.12

TABLE 1-continued

```
Species:    emaciatus
Isolated:   No
Cloned:     Yes

DNA Sequence:
ATGATGTTTCGTGTGACGTCAGTCAGCTGTTTCCTGCTCGTCATCGCTTGTCTGAACTTGGTTGTGCTTA    (SEQ ID NO:252)

CCAATGCCTGCCTCCGTGACGGACAGTCCTGCGGATATCATTCCGATTGCTGTAGATAGTCTTGCTGTTG

GGGGTATTGCGATCAGAAGTGTCTAATTATTGGAAAGAGGGCGACATTCCAAGAACTCATCCTACATCCT

TGAAATGTTGCCCAGAGGTCTGCTGCTTCTCGT

Translation:
MMFRVTSVSCFLLVTACLNLVVLTNACLRDGQSCGYHSDCCRYSCCWGYCDQKCLIIGKRATFQELILHP    (SEQ ID NO:253)

Toxin Sequence:
Cys-Leu-Arg-Asp-Gly-Gln-Ser-Cys-Gly-Xaa5-His-Ser-Asp-Cys-Cys-Arg-Xaa5-    (SEQ ID NO:254)

Ser-Cys-Cys-Xaa4-Gly-Xaa5-Cys-Asp-Gln-Lys-Cys-Leu-Ile-Ile-Gly-Lys-Arg-

Ala-Thr-Phe-Gln-Xaa1-Leu-Ile-Leu-His-Xaa3-^1

Name:       Vr11.1
Species:    virgo
Isolated:   No
Cloned:     Yes

DNA Sequence:
ATGATGTTTCGTGTGACGTCAGTCAGCTGTTTCCTGCTGGTCATCGCTTGTCTGAACTTGGTTGTGCTTA    (SEQ ID NO:255)

CCAATGCCTGCCTTCGTGACGGACAGTCCTGCGGATATGATTCCGATTGCTGTAGATACTCTTGCTGTTG

GGGGTATTGCGATCTTACGTGTCTAATTATTGGAAAGAGGGCGACATTCCAAGAACTCATCCTACATCGT

TGAAATGTTGCCCAGAGGTCTGCTGCTTCTCGT

Translation:
MMFRVTSVSCFLLVIACLNLVVLTNACLRDGQSCGYDSDCCRYSCCWGYCDLTCLTIGKPATFQELILHR    (SEQ ID NO:256)

Toxin Sequence:
Cys-Leu-Arg-Asp-Gly-Gln-Ser-Cys-Gly-Xaa5-Asp-Ser-Asp-Cys-Cys-Arg-Xaa5-    (SEQ ID NO:257)

Ser-Cys-Cys-Xaa4-Gly-Xaa5-Cys-Asp-Leu-Thr-Cys-Leu-Ile-Ile-Gly-Lys-Arg-

Ala-Thr-Phe-Gln-Xaa1-Leu-Ile-Leu-His-Arg-^1

Name:       Vr11.2
Species:    virgo
Isolated:   No
Cloned:     Yes

DNA Sequence:
ATGATGTTTCGTGTGACGTCAGTCGGCTGTTTCCTGCTGGCCATCGTTTGTCTGAACTTGATTGTGCTTA    (SEQ ID NO:258)

CCAATGCCTGCCTCCATGAAACGTCGCCCTGCAGACGTAGTTTCCAATGCTGTCACGGAATTTGCTGTTT

TCGGAGATGCAGTAATTCGTGTCGATTTGGAAAGAGGGCGACATTCCAAGAATTCATTCTACATCGCTGA

TATGTTGCCCAGAGGTCTGCTGCTTCTCGt

Translation:
MMFRVTSVGCFLLAIVCLNLIVLTNACLHETSPCRRSFQCCHGICCFRRCSNSCRFGKRATFQEFILHR    (SEQ ID NO:259)

Toxin Sequence:
Cys-Leu-His-Xaa1-Thr-Ser-Xaa3-Cys-Arg-Arg-Ser-Phe-Gln-Cys-Cys-His-Gly-    (SEQ ID NO:260)

Ile-Cys-Cys-Phe-Arg-Arg-Cys-Ser-Asn-Ser-Cys-Arg-Phe-Gly-Lys-Arg-Ala-

Thr-Phe-Gln-Xaa1-Phe-Ile-Leu-His-Arg-^1

Name:       Vr11.3
Species:    Virgo
Isolated:   No
Cloned:     Yes

DNA Sequence:
ATGATGTTTCGTGTGACGTCAGTCAGCTGTTTCCTGCTGGTCATCGCTTGTCTGAACTTGGTTGTGCTTA    (SEQ ID NO:261)
```

TABLE 1-continued

```
CCAATGCCTGCCTCCGTGACGGACAGTCCTGCGGATATCATTCCGATTGCTGTAGGTACTCTTGCTGTTG

GGGGTATTGCGATCAGAAGTGTCThATTATTGGAAAGAGGGCGACATTCCAAGAACTCATCCTACATCGT

TGAAATGTTGCCCAGAGGTCTGCTGCTTCTCGT
```

Translation:
MMFRVTSVSCFLLVIACLNLVVLTNACLRDGQSCGYHSDCCRYSCCWGYCDQKCLIIGKRATFQELILHR (SEQ ID NO:262)

Toxin Sequence:
Cys-Leu-Arg-Asp-Gly-Gln-Ser-Cys-Gly-Xaa5-His-Ser-Asp-Cys-Cys-Arg-Xaa5- (SEQ ID NO:263)

Ser-Cys-Cys-Xaa4-Gly-Xaa5-Cys-Asp-Gln-Lys-Cys-Leu-Ile-Ile-<u>Gly-Lys-Arg-</u>

<u>Ala-Thr-Phe-Gln-Xaa1-Leu-Ile-Leu-His-Arg-</u>[1]

Name: Vr11.4
Species: Virgo
Isolated: No
Cloned: Yes

DNA Sequence:
ATGATGTTTCGTGTGACGTCAGTCAGCTGTTTCCTGCTGGTCATCGTTTGTCTGAACTTGGTTGTGCTTA (SEQ ID NO:264)

CCAATGCCTGCCTCCATGAAACGCCGCCCTGCAGACGTAGTTTCCAATGCTGTCACGGAAATTGCTGTTT

TCGGAGATGCAGTAATTCGTGTCGATTTGGAAAGAGGGCGACATTCCAAGAATTCATTCTACATcGCTGA

TATGTTGCCCAGAGGTCTGCTGCTTCTCGT

Translation:
MMFRVTSVSCFLLVTVCLNLVVLTNACLHETPPCRRSFQCCHGNCCFRRCSNSCRFGKRATEQEFTLHR (SEQ ID NO:265)

Toxin Sequence:
Cys-Leu-His-Xaa1-Thr-Xaa3-Xaa3-Cys-Arg-Arg-Ser-Phe-Gln-Cys-Cys-His- (SEQ ID NO:266)

Gly-Asn-Cys-Cys-Phe-Arg-Arg-Cys-Ser-Asn-Ser-Cys-Arg-Phe-<u>Gly-Lys-Arg-</u>

<u>Ala-Thr-Phe-Gln-Xaa1-Phe-Ile-Leu-His-Arg-</u>[1]

Name: Vr11.5
Species: Virgo
Isolated: No
Cloned: Yes

DNA Sequence:
ATGATGTTTCGTGTGACGTCAGTCGGCTGTTTCCTGCTGGTCATCGTTTGTCTGAACTTGGTTGTGCTTA (SEQ ID NO:267)

CCAATGCCTGCCTCCATGAAACGTCGCCCTGCGGACGTAGTTTCCAATGCTGTCACGGAATTTGTTGTTT

TCGGAGATGCAGTAATTCGTGTCCATTTGGAAAGAGGGCGACATTCCAAGAATTCATTCTACATCGCTGA

TATGTTGCCCAGAGGTCTGCTGCTTCTCGT

Translation:
MMFRVTSVGCFLLVIVCLNLVVLTNACLHETSPCGRSFQCCHGTCCFRRCSNSCRFGKRATFQEFILHR (SEQ ID NO:268)

Toxin Sequence:
Cys-Leu-His-Xaa1-Thr-Ser-Xaa3-Cys-Gly-Arg-Ser-Phe-Gln-Cys-Cys-His-Gly- (SEQ ID NO:269)

Ile-Cys-Cys-Phe-Arg-Arg-Cys-Ser-Asn-Ser-Cys-Arg-Phe-<u>Gly-Lys-Arg-Ala-</u>

<u>Thr-Phe-Gln-Xaa1-Phe-Ile-Leu-His-Arg-</u>[1]

Name: Vr11.6
Species: Virgo
Isolated: No
Cloned: Yes

DNA Sequence:
ATGATGTTTCGTGTGACGTCAGTCAGCTGTTTCCTGCTGGTCATCGTTTGTCTGAACTTGGTTGTGCTTA (SEQ ID NO:270)

CCAATGCCTGCCTCTATGAAACGTCGCCCTGCAGACGTAGTTTCCAATGCTGTCACGGAATTTGCTGTTT

TCGGAGATGCAGTAATTCGTGTCGATTTGGAAAGAGGGCGACATTCCAAGAATTCATTCTACATCGCTGA

TATGTTGCCCAGAGGTCTGCTGCTTCTCGT

TABLE 1-continued

Translation:
MMFRVTSVSCFLLVIVCLNLVVLTNACLYETSPCRRSFQCCHGICCFRRCSNSCRFGKPATFQEFILHR    (SEQ ID NO:271)

Toxin Sequence:
Cys-Leu-Xaa5-Xaa1-Thr-Ser-Xaa3-Cys-Arg-Arg-Ser-Phe-Gln-Cys-Cys-His-    (SEQ ID NO:272)

Gly-Ile-Cys-Cys-Phe-Arg-Arg-Cys-Ser-Asn-Ser-Cys-Arg-Phe-<u>Gly-Lys-Arg-</u>

<u>Ala-Thr-Phe-Gln-Xaa1-Phe-Ile-Leu-His-Arg-</u>^1

Name: Vr11.7
Species: virgo
Isolated: No
Cloned: Yes

DNA Sequence:
ATGATGTTTCGTGTGACGTCAGTCGGCTGTTTCCTGCTGGTCATCGCTTGTCTGAACTTGTTTCAGGTTG    (SEQ ID NO:273)

TGCTTACCAGACGCTGCTTCCCTCTAGGAACGTTCTGCTCAAGATATCTCCCCTGCTGTAGTGGAATGTG

CTGTTCTGGGTGGTGCACACGAAGGTGTGCCCCAAGGTTTGGAAAGAGGGCGACATTCCAAGAATGAATT

CATTCTACATCGTTGATATGTTGCCCAGAGGTCTGCTGCTTCTCGT

Translation:
MMFRVTSVGCFLLVTACLNLFQVVLTRRCFPLGTFCSRYLPCCSGMCCSGWCTRRCAPRFGKRATFQE    (SEQ ID NO:274)

Toxin Sequence:
Cys-Phe-Xaa3-Leu-Gly-Thr-Phe-Cys-Ser-Arg-XaaB-Leu-Xaa3-Cys-Cys-Ser-    (SEQ ID NO:275)

Gly-Met-Cys-Cys-Ser-Gly-Xaa4-Cys-Thr-Arg-Arg-Cys-Ala-Xaa3-Arg-Phe-<u>Gly-</u>

<u>Lys-Arg-Ala-Thr-Phe-Gln-Xaa1-</u>^1

Name: Fi11.8
Species: figulinus
Isolated: No
Cloned: Yes

DNA Sequence:
ATGATGTTTCGTGTGACGTCAGTCGGCTGTTTCCTGCTGGTCATCGTTTTTCTGAACTTGGTTGTGCTTA    (SEQ ID NO:276)

CCGATGCCTGTCACCATGAAGGATTGCCCTGCACAAGTGATGACGGTTGCTGTGGCATGGAATGCTGCGG

CGGGGTTTGCTCATCACATTGTGGAAACGGGAGGCGACGCCAAGTTCCGTTGAAATCATTTGGCCAACGT

TGATATGTTTGACCAGAGGTCTGCTGCTTCTCGT

Translation:
MMFRVTSVGCFLLVIVFLNLVVLTDACHHECLPCTSDDGCCGMECCGGVCSSHCGNGRRRQVPLKSFGQR    (SEQ ID NO:277)

Toxin sequence:
Cys-His-His-Xaa1-Gly-Leu-Xaa3-Cys-Thr-Ser-Asp-Asp-Gly-Cys-Cys-Gly-Met-    (SEQ ID NO:278)

Xaa1-Cys-Cys-Gly-Gly-Val-Cys-Ser-Ser-His-Cys-Gly-Asn-<u>Gly-Arg-Arg-Arg-</u>

<u>Gln-Val-Xaa3-Leu-Lys-Ser-Phe-Gly-Gln-Arg-</u>^1

Name: Fi11.8A
Species: figulinus
Isolated: No
Cloned: Yes

DNA Sequence:
ATGATGTTTCGTGTGACGTCAGTCGGCTGTTTCCTGCTGGTCATCGTTTTTCTGAACTTGGTTGTGCTTA    (SEQ TD NO:279)

CCGATGCCTGTCACCATGAAGGATTGCCCTGCACAAGTGATGACGGTTGCTGTGGCATGGAATGCTGCGG

CGGGGTTTGCTCATCACATTGTGGAAACGCGAGGCGACGCCGAGTTCCGTTGAAATCATTTGGCCAACGT

TGATATCTTTGACCAGAGGTCTCCTGCTTCTCGT

Translation:
MMFRVTSVGCFLLVTVFLNLVVLTDACHHEGLPCTSDDGCCGMECCGGVCSSHCGNGRRRRVPLKSFGQR    (SEQ ID NO:280)

Toxin sequence:
Cys-His-His-Xaa1-Gly-Leu-Xaa3-Cys-Thr-Ser-Asp-Asp-Gly-Cys-Cys-Gly-Met-    (SEQ ID NO:281)

TABLE 1-continued

Xaa1-Cys-Cys-Gly-Gly-Val-Cys-Ser-Ser-His-Cys-Gly-Asn-<u>Gly-Arg-Arg-Arg-</u>

<u>Arg-Val-Xaa3-Leu-Lys-Ser-Phe-Gly-Gln-Arg-</u>^1

Name: Fi11.8B
Species: figulinus
Isolated: No
Cloned: Yes

DNA Sequence:
ATGATGTTTCGTGTGACGTCAGTCGGCTGTTTCCTGCTGGTCATCGTTTTTCTGAACTTGOTTGTGCTTA (SEQ ID NO:282)

CCGATGCCTGTCACCATGAAGGATTGCCCTGCACAAGTGATGACGGTTGCTGTGGCATGGAATGCTGCGG

CGGGGTTTGCTCATCACATTGTGGAAACGGGGGCGACGCCGAGTTCCGTTGAAATCATTTGGCCAACGT

TGATATGTTTGACCAGAGGTCTGCTGCTTCTCGT

Translation:
MMFRVTSVGCFLLVTVFLNLVVLTDACHHEGLPCTSDDGCCGMECCGGVCSSHCGNGGRRRVPLKSFGQR (SEQ ID NO:283)

Toxin sequence:
Cys-His-His-Xaa1-Gly-Leu-Xaa3-Cys-Thr-Ser-Asp-Asp-Gly-Cys-Cys-Gly-Met- (SEQ ID NO:284)

Xaa1-Cys-Cys-Gly-Gly-Val-Cys-Ser-Ser-His-Cys-Gly-Asn-Gly-<u>Gly-Arg-Arg-</u>

<u>Arg-Val-Xaa3-Leu-Lys-Ser-Phe-Gly-Gln-Arg-</u>^1

Name: Fi11.9
Species: figulinus
Isolated: No
Cloned: Yes

DNA Sequence:
ATGATGTTTCGTGTGACGTCAGTCGGCTGTTTCCTGCTGGTCATCGTTTTTCTGAACTTGATTGTGCCTT (SEQ ID NO:285)

CCAGTTCCTGCCGCGCTGAAGGAGTGCGCTGCGAATTTGATTCCCAATGCTGTGAATCTGAATGCTGTAT

GGGGAGTTGCGCAAATCCGTGTCGAATTCCTGGGAAGAGGGCGAGACTCTTTCGACAACGTTGATATGTT

GCCCAGAGGTCTGCTGCTTCTCGT

Translation:
MMFRVTSVGCFLLVIVFLNLIVPSSSCRAEGVRCEFDSQCCESECCMGSCANPCRIPGKRARLFRQR (SEQ ID NO:286)

Toxin sequence:
Cys-Arg-Ala-Xaa1-Gly-Val-Arg-Cys-Xaa1-Phe-Asp-Ser-Gln-Cys-Cys-Xaa1- (SEQ ID NO:287)

Ser-Xaa1-Cys-Cys-Met-Gly-Ser-Cys-Ala-Asn-Xaa3-Cys-Arg-Ile-Xaa3-Gly-

Lys-Arg-Ala-Arg-Leu-Phe-Arg-Gln-Arg-^1

Name: Fi11.10
Species: figulinus
Isolated: No
Cloned: Yes

DNA Sequence:
ATGATGTTTCGTGTGACGTCAGTCGGCTGTTTCCTGCTGGTCATCGTTTTTCTGAACTTGGTTGTGCCTA (SEQ ID NO:288)

CCAGTGCCTGCCGCGCTGAAGGAGTGTACTGCGAATATGGTTCCCAATGCTGTCTATCTCAATGCTGTAT

GGCGAGTTGCGCAAATCCGTGTCGCCATCCTGGAAAGAGGGCGAGACTCCAAGAATTCTTTCGACAACGT

TGATACGTTGCCCAGAGGTCTGCTGCTTCTCGT

Translation:
MMFRVTSVGCFLLVIVFLNLVVPTSACRAEGVYCEYGSQCCLSQCGMASCANPCRHPGKRARLQEFFRQR (SEQ ID NO:289)

Toxin sequence:
Cys-Arg-Ala-Xaa1-Gly-Val-Xaa5-Cys-Xaa1-Xaa5-Gly-Ser-Gln-Cys-Cys-Leu- (SEQ ID NO:290)

Ser-Gln-Cys-Cys-Met-Ala-Ser-Cys-Ala-Asn-Xaa3-Cys-Arg-His-Xaa3-<u>Gly-Lys-</u>

<u>Arg-Ala-Arg-Leu-Gln-Xaa1-Phe-Phe-Arg-Gln-Arg-</u>^1

Name: Fi11.10A

TABLE 1-continued

```
Species:    figulinus
Isolated:   No
Cloned:     Yes

DNA Sequence:
ATGATGTTTCGTGTGACGTCAGTCGGCTGTTTCCTGCTGGTCATCGTTTTTCTGAACTTGGTTGTGCCTA    (SEQ ID NO:291)

CCAGTGCCTGCCGCGCTGAAGGAGTGTACTGCGAATATGGTTCCCAATGCTGTCTATCTCAATGCTGTAT

GGCGAGTTGCGCAAATCCGTGTCGCCATCCTGGAAAGAGCGCGAGACTCCAAGAATTCTTTCGACGACGT

TGATACGTTGCCCAGAGGTCTGCTGCTTCTCGT

Translation:
MMFRVTSVGCFLLVIVFLNLVVPTSACRAEGVYCEYGSQCCLSQCCMASCANPCRHPGKRARLQEFFRRR    (SEQ ID NO:292)

Toxin sequence:
Cys-Arg-Ala-Xaa1-Gly-Val-Xaa5-Cys-Xaa1-Xaa5-Gly-Ser-Gln-Cys-Cys-Leu-     (SEQ ID NO:293)

Ser-Gln-Cys-Cys-Met-Ala-Ser-Cys-Ala-Asn-Xaa3-Cys-Arg-His-Xaa3-Gly-Lys-

Arg-Ala-Arg-Leu-Gln-Xaa1-Phe-Phe-Arg-Arg-Arg-^1

Name:       Fi11.11
Species:    figulinus
Isolated:   No
Cloned:     Yes

DNA Sequence:
ATGATGTTTCGTGTGACGTCAGTCGGCTGTTTCCTGCTGGTCATCGTTTTTCTGAACTTGGTTGTGCTTA    (SEQ ID NO:294)

CCGATGCCTGTCACCATGAAGGATTGCCCTGCACAAGTGGTGACGGTTGCTGTGGCATGGAATGCTGCGG

CGGGGTTTGCTCATCACATTGTGGAAACGGGAGGCGACGCCAAGTTCCGTTGAAATCATTTGGCCAACGT

TGATATGTTTGACCAGAGGTCTGCTGCTTCTCGT

Translation:
MMFRVTSVGCFLLVIVFLNLVVLTDACHHEGLPCTSGDGCCGMECCGGVCSSHCGNGRRRQVPLKSFGQR    (SEQ ID NO:295)

Toxin sequence:
Cys-His-His-Xaa1-Gly-Leu-Xaa3-Cys-Thr-Ser-Gly-Asp-Gly-Cys-Cys-Gly-Met-    (SEQ ID NO:296)

Xaa1-Cys-Cys-Gly-Gly-Val-Cys-Ser-Ser-His-Cys-Gly-Asn-Gly-Arg-Arg-Arg-

Gln-Val-Xaa3-Leu-Lys-Ser-Phe-Gly-Gln-Arg-^1

Name:       Fi11.12
Species:    figulinus
Isolated:   No
Cloned:     Yes

DNA Sequence:
ATGATGTTTCGTGTGACGTCAGTCGGCTGTTTCCTGCTGGTCATCGTTTTTCTGAACTTGGTTGTGCTCA    (SEQ ID NO:297)

CCGATGCCTGTCACCATGAAGGATTGCCCTGCGCAAGTGATGACGGTTGCTGTGGCATGGAATGCTGCGG

CGGGGTTTGCTCATCACATTGTGGAAACGGGAGGCGACGCCGAGTTCCGTTGAAATCATTTGGCCAACGT

TGATATGTTTGACCAGAGGTCTGCTGCTTCTCGT

Translation:
MFRVTSVGCFLLVIVFLNLVVLTDACHHEGLPCASDDGCCGMECCGGVCSSHCGNGRRRRVPLKSFGQR    (SEQ ID NO:298)

Toxin sequence:
Cys-His-His-Xaa1-Gly-Leu-Xaa3-Cys-Ala-Ser-Asp-Asp-Gly-Cys-Cys-Gly-Met-    (SEQ ID NO:299)

Xaa1-Cys-Cys-Gly-Gly-Val-Cys-Ser-Ser-His-Cys-Gly-Asn-Gly-Arg-Arg-Arg-

Arg-Val-Xaa3-Leu-Lys-Ser-Phe-Gly-Gln-Arg-^1

Name:       J029 [O2P; O11P]
Species:    radiatus
Isolated:   Yes
Cloned:     Yes Toxin Sequence:
Gly-Xaa3-Ser-Phe-Cys-Lys-Ala-Asp-Xaa1-Lys-Xaa3-Cys-Xaa1-Xaa5-His-Ala-    (SEQ ID NO:300)
```

TABLE 1-continued

Asp-Cys-Cys-Asn-Cys-Cys-Leu-Ser-Gly-Ile-Cys-Ala-Xaa3-Ser-Thr-Asn-Xaa4-

Ile-Leu-Xaa3-Gly-Cys-Ser-Thr-Ser-Ser-Phe-Phe-Lys-Ile-^

Name:     Au11.1
Species:  aulicus
Isolated: No
Cloned:   Yes

DNA Sequence:
GCTATCAGCACTTCGCAGCAGTCGAGGCTTTAAAATCCTAATCGTAGAAGAAGGCAAAAACATCTGGTCG  (SEQ ID NO:301)

TCAGTATGAAGCTGTGTGTGACGTTTCTTCTTGTTCTGGTGATTCTGCCATCAGTAACTGGGGAGAAGTC

TAGCGAGCGTACACTGAGTGGTGCTACTCTGAGAGGCGATTGGGGAACGTGCTCATGGCCAGGACAAGAA

TGCAAACATGATTCCGACTGCTGTGGGAGTTTCTGTTGTGTCGGCAAAAGGTGCTTACACACTTACTTTC

CATGTAACTTATCTCGCTCCTAGTGCGATGGACCTAGGCGTGCTGGCCTAGCGGTAGACTCGCTCAGTAT

GCCTGATCTGTCCGAGTGAAACGACCTGACGCGATCCGTCGTATTCCTTTGCCAAGAGCCAGCTAGGCCA

TGCCTAGGT

Translation:
MKLCVTFLLVLVILPSVTGEKSSERTLSGATLRGDWGTCSWPGQECKHDSDCCGSFCCVGKRCLHTYFPC  (SEQ ID NO:302)

NLSRS

Toxin Sequence:
Gly-Asp-Xaa4-Gly-Thr-Cys-Ser-Xaa4-Xaa3-Gly-Gln-Xaa1-Cys-Lys-His-Asp-  (SEQ ID NO:303)

Ser-Asp-Cys-Cys-Gly-Ser-Phe-Cys-Cys-Val-Gly-Lys-Arg-Cys-Leu-His-Thr-

Xaa5-Phe-Xaa3-Cys-Asn-Leu-Ser-Arg-Ser-^

Name:     Au1.2
Species:  aulicus
Isolated: No
Cloned:   Yes

DNA Sequence:
GCTATCAGCACTTCGCAGCAGTCGAGGCTTTAAAATCCTAATCGTAGAAGAAGGCAAAAACATCTGGTGG  (SEQ ID NO:304)

TCAGTATGAAGCTGTGTGTGACGTTTCTTCTTGTTCTGGTGATTCTGCCATCAGTAACTGGGGAGAAGTC

TAGCGAGCGCACACTGAGTGGTGCTACTCTGAGAGGCGATTGGGGAACGTGCTCATGGTCAGGACAAGAA

TGCAAACATGTTTCCGACTGCTGTGGGAGTTTCTGTTGTGTCGGCAAAAGGTGCTTACACATTTACTTTC

CATGTAACTTATCTCGCTCCTAGTGCGATGGACCTAGGCGTGCTGGCCTAGTGGTAGACTCGCTCAGTAT

GCCTGATCTGTCCGAGTGAAACGACCTGACGCGATCCGTCGTATTCCTTTGCCAAGAGCCAGCTAGGCCA

TGCCTAGGT

Translation:
MKLCVTFLLVLVILPSVTGEKSSERTLSGATLRGDWGTCSWSGQECKHVSDCCGSFCCVGKRCLHIYFPC  (SEQ ID NO:305)

NLSRS

Toxin Sequence:
Gly-Asp-Xaa4-Gly-Thr-Cys-Ser-Xaa4-Ser-Gly-Gln-Xaa1-Cys-Lys-His-Val-  (SEQ ID NO:306)

Ser-Asp-Cys-Cys-Gly-Ser-Phe-Cys-Cys-Val-Gly-Lys-Arg-Cys-Leu-His-Ile-

Xaa5-Phe-Xaa3-Cys-Asn-Leu-Ser-Arg-Ser-^

Name:     Au11.3
Species:  aulicus
Isolated: No
Cloned:   Yes

DNA Sequence:
GCTATCAGCACTTCGCAGCAGTCGAGGCTTTAAAATCCTAATCGTAGAAGAAGGCAAAAACATCTGGTGG  (SEQ ID NO:307)

TCAGTATGAAGCTGTGTGTGACGTTTCTTCTTGTTCTGGTGATTCTGCCATCAGTAACTGGGGAGAAGTC

TABLE 1-continued

```
TAGCGAGCGTACACTGAGTGGTGCTACTCTGAGAGGCGATTGGGGAACGTGCTCATGGTCAGGACAAGAA

TGCAAACATGATTCCGACTGCTGTGGGAGTTTCTGTTGTGTCGGCAAAAGGTGCTTACACATTTACTTTC

CATGTAACTTATCTCGCCCCTAGTGCGATGGACCTAGGCGTGCTGGCCTAGTGGTAGACTCGCTCAGTAT

GCCTGATCTGTCCGAGTGAAACGACCTGACGCGATCCGTCCTATTCCTTTGCCAAGAGCCAGCTAGGCCA

TGCCTAGGT

Translation:
MKLCVTFLLVLVILPSVTGEKSSERTLSGATLRGDWGTCSWSGQECKHDSDCCGSFCCVGKRCLHIYFPC    (SEQ ID NO:308)

NLSRP

Toxin Sequence:
Gly-Asp-Xaa4-Gly-Thr-Cys-Ser-Xaa4-Ser-Gly-Gln-Xaa1-Cys-Lys-His-Asp-   (SEQ ID NO:309)

Ser-Asp-Cys-Cys-Gly-Ser-Phe-Cys-Cys-Val-Gly-Lys-Arg-Cys-Leu-His-Ile-

Xaa5-Phe-Xaa3-Cys-Asn-Leu-Ser-Arg-Xaa3-

Name:      Au11.4
Species:   aulicus
Isolated:  No
Cloned:    Yes

DNA Sequence:
GCTATCAGCACTTCGCAGCAGTCGAGGCTTTAAAATCCTAATCGTAGAAGAAGGCAAAAACATCTGGTGG   (SEQ ID NO:310)

TCAGTATGAAGCTGTGTGTGACGTTTCTTCTTGTTCTGGTGATTCTGCCATCAGTAACTGGGGAGAAGTC

TAGCGAGCGTACACTGAGTGGTGCTACTCTGAGAGCCGATTGGGGAACGTGCTCATGGTCAGGACAAGAA

TGCAAACATGATTCCGACTGCTGTGGGAGTTTCTGTTGTGTCGGCAAAAGGTGCTTACACATTTACTTTC

CATGTAACTTATCTCGCTCCTAGTGCGATGGACCTAGGCGTGCTGGCCTAGTGGTAGACTCGCTCAGTAT

GCCTGATCTGTCCGAGTGAAACGACCTGACGCGATCCGTCGTATTCCTTTGCCAAGAGCCAGCTAGGCCA

TGCCTAGGT

Translation:
MKLCVTFLLVLVILPSVTGEKSSERTLSGATLRGDWGTCSWSGQECKHDSDCCGSFCCVGKRCLHIYFPC    (SEQ ID NO:311)

NLSRS

Toxin Sequence:
Gly-Asp-Xaa4-Gly-Thr-Cys-Ser-Xaa4-Ser-Gly-Gln-Xaa1-Cys-Lys-His-Asp-   (SEQ ID NO:312)

Ser-Asp-Cys-Cys-Gly-Ser-Phe-Cys-Cys-Val-Gly-Lys-Arg-Cys-Leu-His-Ile-

Xaa5-Phe-Xaa3-Cys-Asn-Leu-Ser-Arg-Ser-

Name:      Au11.5
Species:   aulidus
Isolated:  No
Cloned:    Yes

DNA Sequence:
GCTATCAGCACTTCGCAGCAGTCGAGGNTTTAAAATCCTAATCGTAGAAGAAGGCAAAAACATCTGGTGG   (SEQ ID NO:313)

TCAGTATGAAGCTGTGTGTGACGTTTCTTCTTGTTCTGGTGATTCTGCCATCAGTAACTGGGGAGAAGTC

TAGCGAGCGTACACTGAGTGGTGCTACTCTGAGAGGCGATGGGGGAACGTGCTCATGGCCAGGACAAGAA

TGCAAACATGATTCCGACTGCTGTGGGAGTTTCTGTTGTGTCGGCAAAAGGTGCTTACACACTTACTTTC

CATGTAACTTATCTCGCTCCTAGTGCGATGGACCTAGGCGTGCTGGCCTAGCGGTAGACTCGCTCAGTAT

GCCTGATCTGTCCGAGTGAAACGACCTGACGCGATCCGTCGTATTCCTTTGCCAAGAGCCAGCTAGGCCA

TGCCTAGGT

Translation:
MKLCVTFLLVLVILPSVTGEKSSERTLSGATLRGDGGTCSWPGQECKHDSDCCGSFCCVGKRCLHTYFPC    (SEQ ID NO:314)

NLSRS
```

TABLE 1-continued

```
Toxin Sequence:
Gly-Asp-Gly-Gly-Thr-Cys-Ser-Xaa4-Xaa3-Gly-Gln-Xaa1-Cys-Lys-His-Asp-     (SEQ ID NO:315)

Ser-Asp-Cys-Cys-Gly-Ser-Phe-Cys-Cys-Val-Gly-Lys-Arg-Cys-Leu-His-Thr-

Xaa5-Phe-Xaa3-Cys-Asn-Leu-Ser-Arg-Ser-^

Name:       Au11.6
Species:    aulicus
Isolated:   No
Cloned:     Yes

DNA Sequence:
GCTATCAGCACTTCGCAGCAGTCGAGGCTTTAAAATCCTAATCGTAGAAGAAGGCAAAAACATCTGGTGG  (SEQ ID NO:316)

TCAGTATGAAGCTGTGTGTGACGTTTCTTCTTGTTCTGGTGATTCTGCCATCAGTAACTGGGGAGAAGTC

TAGCGAGCGTACACTGAGTGGTGCTACTCTGAGAGGCGATTGGGGAACGTGCTCATGGCCAGGACAAGAA

TGCGAACATGATTCCGACTGCTGCGGGAGTTTCTGTTGTGTCGGCAGAAGGTGCTTACACATTTACTTTC

CATGTAACTTATCTCGCTCCTAGTGCGATGGACCTAGGCGTGCTGGCCTAGTGGTAGACTCGCTCAGTAT

GCCTGATCTGTCCGAGTCAAACGACCTGACGCGATCCGTCGTATTTCTTTGCCAAGAGCCAGCTAGGCCA

TGCCTAGGT

Translation:
MKLCVTFLLVLVTLPSVTGEKSSERTLSGATLRGDWGTCSWPGQECEHDSDCCGSFCCVGRRCLHIYFPC  (SEQ ID NO:317)

NLSRS

Toxin Sequence:
Gly-Asp-Xaa4-Gly-Thr-Cys-Ser-Xaa4-Xaa3-Gly-Gln-Xaa1-Cys-Xaa1-His-Asp-   (SEQ ID NO:318)

Ser-Asp-Cys-Cys-Gly-Ser-Phe-Cys-Cys-Val-Gly-Arg-Arg-Cys-Leu-His-Ile-

Xaa5-Phe-Xaa3-Cys-Asn-Leu-Ser-Arg-Ser-^

Name:       Ep11.1
Species:    episcopatus
Isolated:   No
Cloned:     Yes

DNA Sequence:
GCTATCAGCACTTCGCAGCAGTCGAGGCTTTAAAATCCAAATCGTAGAAGAAGGCAAAAACGTCTGGTGA  (SEQ ID NO:319)

CAGTATGAAGCTGTGTGTGACGTTTCTTCTTATTCTGGTGATTCTGCCATCGGTAACTGGGGAGAAGTCT

AGCAAGCGTACACTGAGTGGTGCTGCTCTGAGAGGCGATTGGGGAATGTOCTCAGGCATAGGACAAGGAT

GCGGACAAGATTCCAACTGCTGTGGGGATATGTGCTGTTATGGCCAAATATGCGCTATGACTTTCGCGGC

ATGTGGTCCCTAACTTCTTTCCCTTCTAGTGCGATGGACCTAGGCGTGCTGGCCTAGCGGCCGACTCGCT

CAGTATGCCTGATCTGTCCGAGTGAAACGACCTGACACGATCCGTCGTATTCCTTTGCCAAGAGCCAGTT

AGGCCATGCCTAGGT

Translation:
MKLCVTFLLILVILPSVTGEKSSKRTLSGAALRGDWGMCSGIGQGCGQDSNCCGDMCCYGQICAMTFAAC  (SEQ ID NO:320)

GP

Toxin Sequence:
Gly-Asp-Xaa4-Gly-Met-Cys-Ser-Gly-Ile-Gly-Gln-Gly-Cys-Gln-Asp-Ser-       (SEQ ID NO:321)

Asn-Cys-Cys-Gly-Asp-Met-Cys-Cys-Xaa5-Gly-Ile-Cys-Ala-Met-Thr-Phe-

Ala-Ala-Cys-Gly-Xaa3-^

Name:       Ep11.2
Species:    episcopatus
Isolated:   No
Cloned:     Yes

DNA Sequence:
GCTATCAGCACTTCGCAGCAGTCGAGGCTTTAAAATCCTAATCGTAGAAGAAGGCAAAAACGTCTGGTGT  (SEQ ID NO:322)
```

TABLE 1-continued

```
CAGTATGAAGCTGTGTGTGACGTTTCTTCTTATTCTOGTGATTCTGCCATCAGTAACTGGGGAGAAGTCT

AGCAAGCGTACACTGAGTGGTGCTGCTCTGAGAGGCGATCGGGGAATGTGCTCTCGCATAGGACAAGGAT

GCGGACAAGATTCCGACTGCTGTGGGGATATGTGCTGTTACGGCCAAATATGCGCTATGACTTTCGCGGC

ATGTGGTCCCTAACTTCTTTCCCTTCTAGTGCGATGGACCTAGGCGTGCTGGCCTAGCGGCCGACACGCT

CAGTATGCCTGATCTGTCCGAGTGAAACGACCTGACACGATCCGTCGTATTCCTTTGCCAAGAGCCAGCT

AGGCCATGCCTAGGT

Translation:
MKLCVTFLLILVTLPSVTGEKSSKRTLSGAALRGDRGMCSRTGQGCGQDSDCCGDMCCYGQICAMTFAAC    (SEQ ID NO:323)

GP

Toxin Sequence:
Gly-Met-Cys-Ser-Arg-Ile-Gly-Gln-Gly-Cys-Gly-Gln-Asp-Ser-Asp-Cys-Cys-    (SEQ ID NO:324)

Gly-Asp-Met-Cys-Cys-Xaa5-Gly-Gln-Ile-Cys-Ala-Met-Thr-Phe-Ala-Ala-Cys-

Gly-Xaa3-^

Name:      Ep11.3
Species:   episcopatus
Isolated:  No
Cloned:    Yes

DNA Sequence:
GCTATCAGCCTTCGCAGCAGTCGAGGCTTTAAAATCCTAATCGTAGAAGAAGGCAAAAACGTCTGGTGTC    (SEQ ID NO:325)

AGTATGAAGCTGTGTGTGACGTTTCTTCTTATTCTGGTGATTCTGCCATCGGTAACTGGGGAGAAGTCTA

GCAAGCGTACACTGAGTGGTGCTGCTCTGAGAGGCGATTGGGGAATGTGCTCAGGCATAGGACAAGGATG

CGGACAAGATTCCGGCTGCTGTGGGGATATGTGCTGTTATGGCCAAATATGCGCTATGACTTTCGCGGCA

TGTGGTCCCTAACTTCTTTCCCTTCTAGTGCGATGGACCTAGGCGTGCTGGCCTAGCGGCCGACTCGCTC

AGTATGCCTGATCTGTCCGAGTGAAACGACCTGACACGATCCGTCGTATTCCTTTGCCAAGAGCCAGCTA

GGCCATGCCTAGGT

Translation:
MKLCVTFLLILVILPSVTGEKSSKRTLSGAALRGDWGMCSGIGQGCGQDSGCCGDMCCYGQICAMTFAAC    (SEQ ID NO:326)

GP

Toxin Sequence:
Gly-Asp-Xaa4-Gly-Met-Cys-Ser-Gly-Ile-Gly-Gln-Gly-Cys-Gly-Gln-Asp-Ser-    (SEQ ID NO:327)

Gly-Cys-Cys-Gly-Asp-Met-Cys-Cys-Xaa5-Gly-Gln-Ile-Cys-Ala-Met-Thr-Phe-

Ala-Ala-Cys-Gly-Xaa3-^

Name:      Ep11.4
Species:   episcopatus
Isolated:  No
Cloned:    Yes

DNA Sequence:
GCTATCAGCACTTCGCAGCAGTCGAGGCTTTAAAATCCAAATCGTAGAAGAAGGCAAAAACGTCTGGTGA    (SEQ ID NO:328)

CAGTATGAAGCTGTGTGTGACGTTTCTTCTTATTCTGGTGATTCTGCCATCGGTAACTGGGGAGAAGTCT

AGCAAGCGTACACTGAGTGGTGCTGCTCTAAGAGGCGATTGGGGAATGTGCTCAGGCATAGGACAAGGAT

GCGGACAAGATTCCAACTGCTGTGGGGATAAGTCCTGTTATGGCCAAATATGCGCTATGACTTTCGCGGC

ATGTGGTCCCTAACTTCTTTCCCTTCTAGTGCGATGGACCTAGGCGTGCTGGCCTAGCGGCCGACTCGCC

CAGTATGCCTGATCTGTCCGAGTGAAACGACCTGACACGATCCGTCGTATTCCTTTGCCAAGAGCCAGCT

AGGCCATGCCTAGGT

Translation:
MKLCVTFLLILVILPSVTGEKSSKRTLSGAALRGDWGMCSGTGQGCGQDSNCCGDKCCYGQTCAMTFAAC    (SEQ ID NO:329)
```

TABLE 1-continued

GP

Toxin Sequence:
Gly-Asp-Xaa4-Gly-Met-Cys-Ser-Gly-Ile-Gly-Gln-Gly-Cys-Gly-Gln-Asp-Ser- (SEQ ID NO:330)

Asn-Cys-Cys-Gly-Asp-Lys-Cys-Cys-Xaa5-Gly-Gln-Ile-Cys-Ala-Met-Thr-Phe-

Ala-Ala-Cys-Gly-Xaa3-^

Name:      Ep11.5
Species:   episcopatus
Isolated:  No
Cloned:    Yes

DNA Sequence:
GCTATAGCACTTCGCAGCAGTCGAGGCTTTAAAATCCAAATCGTAGAAGAGGGCAAAAACGTCTGGTGTC (SEQ ID NO:331)

AGTATGAAGCTGTGTGTGACGTTTCTTCTTATTCTGGTGATTCTGCCATCAGTAACTGGGGAGAAGTCTA

GCAAGCGTACACTGAGTCGTGCTGCTCTGAGAGGCGATCGGGGAATGTGCTCTCGCATAGGACAAGGATG

CGGACAAGATTCCAACTGCTGTGGGGATATGTGCTGTTATGGCCAAATATGCGCTATGACTTTCGCGGCA

TGTGGTCCCTAACTTCTTTCCCTTCTAGTGCGATGGACCTAGGCGTGCTGGCCTAGCGGCCGACTCGCTC

AGTATGCCTGATCTGTCCGAGTGAAACGACCTGACACGATCCGTCGTATTCCTTTGCCAAGAGCAAGCTA

GGCCATGCCTAGGT

Translation:
MKLCVTFLLILVILPSVTGEKSSKRTLSGAALRGDRGMCSRIGQGCGQDSNCCGDMCCYGQICAMTFAAC (SEQ ID NO:332)

GP

Toxin Sequence:
Gly-Met-Cys-Ser-Arg-Ile-Gly-Gln-Gly-Cys-Gly-Gln-Asp-Ser-Asn-Cys-Cys- (SEQ ID NO:333)

Gly-Asp-Met-Cys-Cys-Xaa5-Gly-Gln-Ile-Cys-Ala-Met-Thr-Phe-Ala-Ala-Cys-

Gly-Xaa3-^

Name:      Ep11.G
Species:   episcopatus
Isolated:  No
Cloned:    Yes

DNA Sequence:
CAGTATGAAGCTGTGTGTGTCGTTTCTTCTTATTCTGGTGATTCTGCCATCGGTAACTGGGGAGAAGTCT (SEQ ID NO:334)

CAGTATGAAGCTGTGTGTGTCGTTTCTTCTTATTCTGGTGATTCTGCCATCGGTAACTGGGGAGAAGTCT

AGCAAGCGTACACTGAGTGGTGCTGCTCTGAGAGGCGATCGGGGAATGTGCTCAGGCATAGGACAAGGAT

GCGGACAAGATTCCGGCTGCTGTGGGGATATGTGCTGTTATGGCCAAATATGCGCTATGACTTTCGCGGC

ATGTGGTCCCTAACTTCTTTCCCTTCTAGTGCGATGGACCTAGGCGTGCTGGCCTAGCGGCCGACTCGCT

CAGTATGCCTGATCTGTCCGAGTGAAACGACCTGACACGATCCGTCGTATTCCTTTGCCAAGAGCCAGCT

AGGCCATGCCTAGGT

Translation:
MKLCVSFLLILVILPSVTGEKSSKRTLSGAALRGDRGMCSGTGQGCGQDSGCCGDMCCYGQICAMTFAAC (SEQ ID NO:335)

GP

Toxin Sequence:
Gly-Met-Cys-Ser-Gly-Ile-Gly-Gln-Gly-Cys-Gly-Gln-Asp-Ser-Gly-Cys-Cys- (SEQ ID NO:336)

Gly-Asp-Met-Cys-Cys-Xaa5-Gly-Gln-Ile-Cys-Ala-Met-Thr-Phe-Ala-Ala-Cys-

Gly-Xaa3-^

Name:      Ep11.7
Species:   episcopatus
Isolated:  No
Cloned:    Yes

DNA Sequence:

TABLE 1-continued

```
GCTATCAGCACTTCGCAGCAGTCGAGGCTTTAAAATCCTAATCGTAGAAGAAGGCAAAAACGTCTGGTGT    (SEQ ID NO:337)

CACTATGAAGCTGTGTGTGACGTTTCTTCTTATTCTGGTGATTCTGCCATCAGTAACTGGGGAGAAGTCT

AGCAAGCGTACACTGAGTGGTGCTGCTCTGAGAGGCGATCGGGGAATGTGCTCTCGCATAGGACAAGGAT

GCGGACAAGATTCCGACTGCTGTGGGATATGTGCTGTCACGGCCAAATATGCGCTATGACTTTCGCGGC

ATGTGGTCCCTAACTTCCTTCCCTTCTAGTGCGATGGACCTAGGCGTGCTGGCCTAGCGGCCGACACGCT

CAGTATGCCTGATCTGCCCGAGTGAAACGACCTGACACGATCCGTCGTATTCCTTTGCCAAGAGCCAGCT

AGGCCATGCCTAGGT

Translation:
MKLCVTFLLILVILPSVTGEKSSKRTLSGAALRGDRGMCSRIGQGCGQDSDCCGDMCCHGQICAMTFAAC   (SEQ ID NO:338)

GP

Toxin Sequence:
Gly-Met-Cys-Ser-Arg-Ile-Gly-Gln-Gly-Cys-Gly-Gln-Asp-Ser-Asp-Cys-Cys-     (SEQ ID NO:339)

Gly-Asp-Met-Cys-Cys-His-Gly-Gln-Ile-Cys-Ala-Met-Thr-Phe-Ala-Ala-Cys-

Gly-Xaa3-^

Name:      Ep11.8
Species:   episcopatus
Isolated:  No
Cloned:    Yes

DNA Sequence:
GCTATCAGCACTTCGCAGCAGTCGAGGCTTTAAAATCCAAATCGTAGAAGAAGGCAAAAACGTCTGGTGA    (SEQ ID NO:340)

CAGTATGAAGCTGTGTGTGACGTTTCTTCTTATTCTGGTGATTCTGCCATCGGTAACTGGGGAGAAGTCT

AGCAAGCGTACACTGAGTGGTGCTGCTCTGAGAGGCGATTGGGGAATGTGCTCAGGCATAGGACAAGGAT

GCGCACAAGATTCCAACTGCTGTGGGATATGTGCTGTCATGGCCAAATATGCGCTATGACTTTCGCGGC

ATGTGGTCCCTAACTTCTTTCCCTTCTAGTGCGATGGACCTAGGCGTGCTGGCCTAGCGGCCGACTCGCT

CAGTATGCCTGATCTGTCCGAGTGAAACGACCTGACACGATCCGTCGTATTCCTTTGCCAAGAGCAAGCT

AGGCCATGCCTAGGT

Translation:
MKLCVTFLLILVILPSVTGEKSSKRTLSGAALRGDWGMCSGIGQGCGQDSNCCGDMCCHGQICANTFAAC   (SEQ ID NO:341)

GP
Toxin Sequence:
Gly-Asp-Xaa4-Gly-Met-Cys-Ser-Gly-Ile-Gly-Gln-Gly-Cys-Gly-Gln-Asp-Ser-    (SEQ ID NO:342)

Asn-Cys-Cys-Gly-Asp-Met-Cys-Cys-His-Gly-Gln-Ile-Cys-Ala-Met-Thr-Phe-

Ala-Ala-Cys-Gly-Xaa3-^

Name:      Sx11.1
Species:   striolatus
Isolated:  No
Cloned:    Yes

DNA Sequence:
ATGATGTTTCGTGTGACGTCAGTCAGCTGTTTCTTGCTGGTCATTGTTCTTCTGAACTTGGTTGTGCTTA    (SEQ ID NO:343)

CCGATGCCTGTCACCATGAAGGGTTGCCCTGCTCAAGTGATGACGGTTGCTGTGGCATGGAATGCTGCAA

TGGGGTTTGCTCATCAAGTTGTGGAAACGGGAGGCGACGCCAAGTTCCGTTGAAATCATTTGGCCAACGT

CGATATGTTTGACCAGAGGTCTGCTGCTTCTCGT

Translation:
MMFRVTSVSCFLLVIVLLNLVVLTDACHHEGLPCSSDDGCCGMECCNGVCSSSCGNGRRRQVPLKSFGQR   (SEQ ID NO:344)

RYV

Toxin Sequence:
Cys-His-His-Xaa1-Gly-Leu-Xaa3-Cys-Ser-Ser-Asp-Asp-Gly-Cys-Cys-Gly-Met-   (SEQ ID NO:345)
```

TABLE 1-continued

Xaa1-Cys-Cys-Asn-Gly-Val-Cys-Ser-Ser-Ser-Cys-Gly-Asn-#

Name:      Sx11.3
Species:   striolatus
Isolated:  No
Cloned:    Yes

DNA Sequence:
ATGATGTTTCGTGTGACGTCAGTCCTGCTGGTCATCGTTCTTCTGAATTTGGTTGTGCTTACCAATGCCT   (SEQ ID NO:346)

GCCACATGGATTGCTCAAAGATGACTTGCTGTAGCGGTATATGCTGTTTTTACTGCGGACGTCCTATGTG

TCCTGGCACTAGGAGGGCGCTACTCCAAAGATTAGTGGGACATCAACGTTGATATGTTGCCCAGAGGTCT

GCTGCTTCTCGT

Translation:
MMFRVTSVLLVIVLLNLVVLTNACHMDCSKMTCCSGICCFYCGRPMCPQTRRALLQRLVGHQR   (SEQ ID NO:347)

Toxin Sequence:
Cys-His-Met-Asp-Cys-Ser-Lys-Met-Thr-Cys-Cys-Ser-Gly-Ile-Cys-Cys-Phe-   (SEQ ID NO:348)

Xaa5-Cys-Gly-Arg-Xaa3-Met-Cys-Xaa3-Gly-Thr-Arg-Arg-Ala-Leu-Leu-Gln-

Arg-Leu-Val-Gly-His-Gln-Arg-^

Name:      Ep11.9
Species:   episcopatus
Isolated:  No
Cloned:    Yes

DNA Sequence:
ATGATGTTTCGTGTGACGTCAGTCGGCTGTTTACTGCTGGTCATCGTTTTCCTGAACTTGGTTGTQCCTA   (SEQ ID NO:349)

CCAATGCCTGCGCTGGTCAAGAAGAGCCCTGCAGTTCACGTAGCGATTGCTGTGGTTCAGTTGGTTGCTG

TTTTGGGCAGTGCGAAAGTCCGTGCCGAATGCCTGGGAAGAGGAAACTCCGACAATTCTTTCGACAACGT

TGATATGTTGCCCAGAGGTCTGCTGCTTCTCGT

Translation:
MMFRVTSVGCLLLVIVFLNLVVPTNACAGQEEPCSSRSDCCGSVGCCFGQCESPCRMPGKRKLRQFFRQR   (SEQ ID NO:350)

Toxin Sequence:
Cys-Ala-Gly-Gln-Xaa1-Xaa1-Xaa3-Cys-Ser-Ser-Arg-Ser-Asp-Cys-Cys-Gly-   (SEQ ID NO:351)

Ser-Val-Gly-Cys-Cys-Phe-Gly-Gln-Cys-Xaa1-Ser-Xaa3-Cys-Arg-Met-Xaa3-#

Name:      Ep11.10
Species:   episcopatus
Isolated:  No
Cloned:    Yes

DNA Sequence:
ATGATGTTTCGTGTGACGTCAGTCGGCTGTTTACTGCTGGCCATCGTTTTCCTGAACTTGGTTGTGCCTA   (SEQ ID NO:352)

CCAATGCCTGCGCTGGTCAAGAAGAGCCCTGCAGTTCACGTGACGATTGCTGTGGTTCAGTTGGTTGCTG

TTTTGGGCAGTGCGAAACTCCGTGCCGAATGCCTGGGAAAAGGAAACTCCGACAATTCTTTCGACAACGT

TGATATGTTGCCCAGAGGTCTGCTGCTTCTCGT

Translation:
MMFRVTSVGCLLLAIVFLNLVVPTNACAGQEEPCSSRDDCCGSVGCCFGQCETPCRMPGKRKLRQFFRQR   (SEQ ID NO:353)

Toxin Sequence:
Cys-Ala-Gly-Gln-Xaa1-Xaa1-Xaa3-Cys-Ser-Ser-Arg-Asp-Asp-Cys-Cys-Gly-   (SEQ ID NO:354)

Ser-Val-Gly-Cys-Cys-Phe-Gly-Gln-Cys-Xaa1-Thr-Xaa3-Cys-Arg-Met-Xaa3-#

Name:      Ep11.11
Species:   episcopatus
Isolated:  No
Cloned:    Yes

DNA Sequence:
ATGATGTTTCGTGTGACGTCAGTCGGCTGTTTCCTGCTGGCCATCGTTTTCCTGAACTTGATTGTGCCTA   (SEQ ID NO:355)

CCAATGCCTGCGCAGGTCAAGAAGAGCCCTGCAGTTCACGTAGTGATTGCTGTGGTTCAGTTGGTTGCTG

TABLE 1-continued

TTTTGGGCAGTGCGAAAGTCCGTGCCGAATGATTGGGAAGAGGAAACTCCGACAATTCTTTCGACAACGT

TGATATGTTGCCCAGAGGTCTGCTGCTTCTCGT

Translation:
MMFRVTSVGCFLLAIVFLNLIVPTNACAGQEEPCSSRSDCCGSVGCCFGQCESPCRMIGKRKLRQFFRQR  (SEQ ID NO:356)

Toxin Sequence:
Cys-Ala-Gly-Gln-Xaa1-Xaa1-Xaa3-Cys-Ser-Ser-Arg-Ser-Asp-Cys-Cys-Gly-  (SEQ ID NO:357)

Ser-Val-Gly-Cys-Cys-Phe-Gly-Gln-Cys-Xaa1-Ser-Xaa3-Cys-Arg-Met-Ile-#

Name:      Ep11.12
Species:   episcopatus
Isolated:  No
Cloned:    Yes

DNA Sequence:
ATGATGTTTCGTGTGACGTCAGTCGGCTGTTTCCTGCTGGTCATCCTTTCTCTGAACTTGGTTGTGCTTA  (SEQ ID NO:350)

CCAATGCCTGCCTTTCTGAAGGATCTCCCTGCAGTATGAGTGGCAGTTGCTGTCACAAGAGTTGCTGTCG

TTCGACTTGCACTTTTCCGTGTCTAATTCCTGGGAAGAGGGCGAAACTCCGAGAATTCTTTCGACAACGT

TGATATGTTGCCCAGAGGTCTGCTGCTTCTCGT

Translation:
MMFRVTSVGCFLLVILSLNLVVLTNACLSEGSPCSMSGSCCHKSCCRSTCTFPCLIPGKRAKLREFFRQR  (SEQ ID NO:359)

Toxin Sequence:
Cys-Leu-Ser-Xaa1-Gly-Ser-Xaa3-Cys-Ser-Met-Ser-Gly-Ser-Cys-Cys-His-Lys-  (SEQ ID NO:360)

Ser-Cys-Cys-Arg-Ser-Thr-Cys-Thr-Phe-Xaa3-Cys-Leu-Ile-Xaa3-#

Name:      Ep11.13
Species:   episcopatus
Isolated:  No
Cloned:    Yes

DNA Sequence:
ATGATGTTTCGTGTGACGTCAGTCGGCTGTTTCCTGCTGGTCATCCTTTCTCTGAACTTGGTTATGCTTA  (SEQ ID NO:361)

CCAATGCCTGCCCTTCTGAAGGATCTCCCTGCAGTATGAGTGGCAGTTGCTGTCACAAGAGTTGCTGTCG

TTCGACTTGCACTTTTCCGTGTCTAATTCCTGGGAAGAGGGCGAAACTCCGAGAATTCTTTCGACAACGT

TGATATGTTGCCCAGAGGTCTGCTGCTTCTCGT

Translation:
MNFRVTSVGCFLLVILSLNLVMLTNACPSEGSPCSMSGSCCHKSCCRSTCTFPCLIPGKRAKLREFFRQR  (SEQ ID NO:362)

Toxin Sequence:
Cys-Xaa3-Ser-Xaa1-Gly-Ser-Xaa3-Cys-Ser-Met-Ser-Gly-Ser-Cys-Cys-His-  (SEQ ID NO:363)

Lys-Ser-Cys-Cys-Arg-Ser-Thr-Cys-Thr-Phe-Xaa3-Cys-Leu-Ile-Xaa3-#

Where:
Xaa1 = Glu or β-Carboxy Glu
Xaa2 = Gln or pyroglu
Xaa3 = Pro or Hydroxy Pro
Xaa4 = Trp or Bromo Trp
Xaa5 = Tyr or $^{125}$I-Tyr or Mono-Todo Tyr or Di-Todo Tyr or O-sulpho-Tyr or O-Phospho-Tyr ^ = Free-carboxyl C-term or Amidated C-term, preferably Free-carboxyl
# = Free-carboxyl C-term or Amidated C-term, preferably Amidated
[1] underlined C-terminus may optionally be processed to remove underlined residues, leaving an amidated C-term.

TABLE 2

Alignment of I-Superfamily Conotoxins - Type I (SEQ ID NO:)

| | | |
|---|---|---|
| br11a | -----CGYVGQA-CDDDSDCCG-SICCVAGECVITGR----RC# | (364) |
| Bt11.1 | ----MCLSLGQR-CERHSNCCG-YLCCFYDKCVVTAI----GCHY^ | (365) |

TABLE 2-continued

Alignment of I-Superfamily Conotoxins - Type I (SEQ ID NO:)

| | | |
|---|---|---|
| Bt11.2 | ----MCSFLGQR-CERHFNCCG-DLCCFDDMCLVAAI----GCGY^ | (366) |
| Bt11.3 | ---I-CSFLG---CERHFNCCG-DLCCFDDMCVVTAI----GCGH^ | (367) |
| Bt11.4 | ----MCLSLGQR-CGRHSNCCG-YLCCFYDKCVVTAI----GCGHY^ | (368) |
| Bt11.5 | ----MCLSLGQR-CERHSDCCG-YLCCFYDKCVVTAI----GCGHY^ | (369) |
| Bt11.6 | G-HVPCG-KDGRKCGYHTHCCN---CCLSGICKPSTSLI--GCSTSSFT^ | (370) |
| Bt11.7 | ----MCLSLGQR-CERHSNCCG-YLCCFYDKCVVTAV----GCGHY^ | (371) |
| Bt11.8 | ----MCLSLGQR-CERHSNCCG-YLCCFYDKCVMTAI----GCGHY^ | (372) |
| Ca11.1 | G--HWCGYPGERGCRYHSQCCG-DMCCYDRKCVATAM----PCDFPY^ | (373) |
| Ca11.10 | G-PSFCK-ADEKPCKYHADCCN---CCLGGICKPSTSWI--GCSTNVFLTR^ | (374) |
| Ca11.11 | G-P-RC-WVGRVHCTYHKDCCP-SVCCFKGRCKPQSW----GCWSGPT^ | (375) |
| Ca11.12 | G-PSFCK-ADEKPCEYHADCCN---CCLSGICAPSTNWILPGCSTSSFFKI^ | (376) |
| Ca11.14 | G-PSFCK-ANGKPCSYHADCCN---CCLSGICKPSTNVILPGCSTSSFFRI^ | (377) |
| Ca11.2 | G--HWCGYLGERGCRYHSQCCG-DMCCYDRKCVVTAM----PCDFPY^ | (378) |
| Ca11.3 | G--HWCGYPGERGCRYHSQCCG-DMCCYDRKCVVTAM----PCDFPY^ | (379) |
| Ca11.4 | G--HWCGYLGERGCRYHSQCCG-DMCCYDRKCAVTAM----PCDFPY^ | (380) |
| Ca11.5 | G--HWCGYPGERGCRYHSQCCG-DMCCYDRMCVVTAM----PCDFPY^ | (381) |
| Ca11.6 | G--HWCGYLGERGCRYHGQCCG-DMCCYDRKCVVTAM----PCDFPY^ | (382) |
| Ca11.7 | G-PSFCK-ANGKPCSYHADCCN---CCLSGICEPSTNVILPGCSTSSFFRI^ | (383) |
| Ca11.8 | G-PSFCK-ADGKPCEYHADCCN---CFLSGICAPSTNWILPGCSTSSFFKI^ | (384) |
| Ca11.9 | G-PSFCK-ADEKPCKYHADCCN---CCLGGICKPSTSWI--GCSTNVFLTR^ | (385) |
| Em11.1 | G--A-CSDTGQG-CIHHFNCCW-DLCCYGRTCGVNVM----GCPPF^ | (386) |
| Em11.2 | G--A-CSDTGQG-CIHHSNCCW-DLCCYGRTCGVNVM----GCPPF^ | (387) |
| Em11.3 | G--T-CSGIGQG-CIHHLNCCW-DMCCYGHTCVVNII----GCPPH^ | (388) |
| Em11.4 | G--A-CSDTGQG-CIHHSDCCW-DLCCYGRTCGVNVM----GCPPF^ | (389) |
| Fi11.1 | G-HVSCG-KDGRACDYHADCCN---CCLGGICKPSTSWI--GCSTNVFLTR^ | (390) |
| Fi11.2 | G-PSFCK-ADEKPCEYHADCCN---CCLSGICAPSTNWILPGCSTSSFFKI^ | (391) |
| Fi11.3 | G-PSFCK-ADEKPCEYHADCCN---CCLSGICAPSTNWILPGCSTSSFFKIRLSAS^ | (392) |
| Fi11.4 | G-P-RC-WVGRVHCTYHKDCCP-SVCCFKGRCKPQSW----GCWSGPT^ | (393) |
| Fi11.5 | G----CK-KDRKPCSYHADCCN---CCLSGICAPSTNWILPGCSTSTFT^ | (394) |
| Fi11.6 | G----CK-KDRKPCSYHADCCN---CCLSGICAPSTNWILPGCSTSSFFKI^ | (395) |
| Fi11.7 | G-PSSCK-ADEEPCEYHADCCN---CCLSGICAPSTNWILPGCSTSSFFKI^ | (396) |
| GH-015 | G----CK-KDRKOCSYHADCCN---CCLSGICAOSTNUILPGCSTSTFT^ | (397) |
| J029 | G-OSFCK-ADEKOCEYHADCCN---CCLSGICAOSTNWILPGCSTSSFFKI^ | (398) |
| J029 [O11P] | G-OSFCK-ADEKPCEYHADCCN---CCLSGICAOSTNWILPGCSTSSFFKI^ | (399) |
| J029 [O2p, O11P] | G-PSFCK-ADEKPCEYHADCCN---CCLSGICAOSTNWILPGCSTSSFFKI^ | (400) |
| L11.1 | -NWSWCFNAGVK-CDNHSDCCE-DTCCYDNTCVVAVA----AC^ | (401) |
| L11.2 | -----C-YFNGAPCDRHEECCTWQRCCFSQRCGTATF----GCWVDPY^ | (402) |
| L11.3 | -NWSWCFNAGVE-CDNHSDCCE-DTCCYDNTCVVAVA----AC^ | (403) |
| L11.4 | -NWSWCFNAGVK-CDNHSDCCA-DTCCYDNTCVVAVA----AC^ | (404) |

TABLE 2-continued

Alignment of I-Superfamily Conotoxins - Type I (SEQ ID NO:)

| | | |
|---|---|---|
| L11.5 | -NWSWCSGSGEG-CDYHSECCG-ERCCIESMCIGDGV----ACWP^ | (405) |
| L11.6 | -NWSWCFNAGVK-CDNHSDCCE-DTCCYDSTCVVAVA----AC^ | (406) |
| M11.1 | G--AVPCG-KDGRQCRNHADCCN---CCPIGTCAPSTNWILPGCSTGQFMTR^ | (407) |
| M11.13 | G-HVSCG-KDGRACDYHADCCN---CCLGGICKPSTSWI--GCSTNVFLTR^ | (408) |
| M11.2 | ---T-CSNKGQQ-CGDDSDCCW-HLCCVNNKCAHLIL----LCNL^ | (409) |
| M11.3 | G-PSFCK-ADEKPCEYHADCCN---CCLSGICAPSTNWILPGCSTSSFFEI^ | (410) |
| M11.4 | G-PSFCK-ADEKPCEYHADCCN---CCLSGICAPSTNWILPGCSTSSFFKT^ | (411) |
| M11.5 | G-HVPCG-KDGRKCGYHADCCN---CCLSGICKPSTSWT--GCSTSTFD^ | (412) |
| M11.6 | G---MCSLLGQR-CGDHSDCCW-DMCCASEMCVVTFL----PCK^ | (413) |
| M11.7 | G-PSFCK-ANGKPCSYHADCCN---CCLSGICKPSTNVILPGCSTSSLFRI^ | (414) |
| M11.8 | G--T-CSGRGQE-CKHDSDCCG-HLCCAGITCQFTYI----PCK^ | (415) |
| M11.9 | G----CK-KDRKPCSYHADCCN---CCLSGICAPSTNWILPGCSTSTFT^ | (416) |
| R11.1 | G-HVPCG-KDGRKCGYHADCCN---CCLSGICKPSTSWT--GCSTSTVRLTR^ | (417) |
| R11.10 | G-HVPCG-KDGRKCGYHADCCN---CCLSGICKPSTSWT--GCSTSTVQLTR^ | (418) |
| R11.11 | G-HVSCG-KDGRACDYHADCCN---CCLGGICKPSTSWI--GCSTNVFLTR^ | (419) |
| R11.12 | G-HVPCG-KDRRKCGYHADCCN---CCLSGICKPSTSWT--GCSTSTFLLTR^ | (420) |
| R11.13 | G-HVPCG-KDGRKCGYHADCCN---CCLSGICKPSTSWT--GCSTSTFLLTR^ | (421) |
| R11.14 | G-OSFCK-ANGKOCSYHADCCN---CCLSGICKOSTNVILPGCSTSSFFRI^ | (422) |
| R11.15 | G-HVPCG-KDGRKCGYHADCCN---CCLSGICKPSTSWT--GCSTSTFN^ | (423) |
| R11.16 | G-HVPCG-KDGRKCGYHTHCCN---CCLSGICKPSTSLI--GCSTSSFT^ | (424) |
| R11.17 | G-PSFCK-ANGKPCSYHADCCN---CCLSGICAPSTNWILPGCSTSSFFKI^ | (425) |
| R11.18 | G-AVPCG-KDGRQCRNHADCCN---CCPFGTCAPSTNRILPGCSTGMFLTR^ | (426) |
| R11.19 | -E---C-KTNKMSCSLHXXCCR-FRCCFHGKCQTSVF----GCUVDP^ | (427) |
| R11.2 | G-AVPCG-KDGRQCRNHADCCN---CCPIGTCAPSTNWILPGCSTGPFMTR^ | (428) |
| R11.3 | G-P-RC-WVGRVHCTYHKDCCP-SVCCFKGRCKPQSW----GCWSGPT^ | (429) |
| R11.4 | G-PSFCK-ADEKPCKYHADCCN---CCLGGICKPSTSWI--GCSTNVFLTR^ | (430) |
| R11.5 | G-AVPCG-KDGRQCRNHADCCN---CCPIGTCAPSTNWILPGCSTGQFMTADF^ | (431) |
| R11.7 | G-PSFCK-ADEKPCEYHSDCCN---CCLSGICAPSTNWILPGCSTSSFFKI^ | (432) |
| S11.1 | G--T-CSFLGQG-CGDHSDCCW-NMCCASEMCVVTLL----QCK^ | (433) |
| S11.2 | G----CK-KDRKPCSYQADCCN---CCPIGTCAPSTNWILPGCSTGPFMAR^ | (434) |
| S11.3 | G-PSFCK-ADEKPCKYHADCCN---CCLGGICKPSTSWI--GCSTNVFLTR^ | (435) |
| S11.4 | G-PSFCK-ADEKPCKYHAGCCN---CCLGGICKPSTSWI--GCSTNVFLTR^ | (436) |
| S11.5 | G-PSFCK-ANGKPCSYHADCCN---CCLSGICKPSTNVILPGCSTSSFFRI^ | (437) |
| S11.6 | G-PSFCK-ADEKPCEYHADCCN---CCLSGICAPSTNWILPGCSTSSFFKI^ | (438) |
| S11.7 | G----CK-KDRKPCSYHADCCN---CCLSGICAPSTNWILPGCSTSTFT^ | (439) |
| S11.8 | G-PSFCK-ADEKPCKYHADCCN---CCLGGICKPSTSWI--GCSTNVFLTR^ | (440) |
| Ep11.2 | GMCSRIGQG-CGQDSDCCG-DMCCYGQICAM----TFAACGP | (441) |
| Ep11.5 | GMCSRIGQG-CGQDSNCCG-DMCCYGQICAM----TFAACGP | (442) |

TABLE 2-continued

| | Alignment of I-Superfamily Conotoxins - Type I (SEQ ID NO:) | |
|---|---|---|
| Ep11.7 | GMCSRIGQG-CGQDSDCCG-DMCCHGQICAM----TFAACGP | (443) |
| Ep11.3 | GDWGMCSGIGQG-CGQDSGCCG-DMCCYGQICAM----TFAACGP | (444) |
| Ep11.6 | GMCSGIGQG-CGQDSGCCG-DMCCYGQICAM----TFAACGP | (445) |
| Ep11.1 | GDWGMCSGIGQG-CGQDSNCCG-DMCCYGQICAM----TFAACGP | (446) |
| Ep11.4 | GDWGMCSGIGQG-CGQDSNCCG-DKCCYGQICAM----TFAACGP | (447) |
| Ep11.8 | GDWGMCSGIGQG-CGQDSNCCG-DMCCHGQICAM----TFAACGP | (448) |
| Au11.3 | GDWGTCSWSGQE-CKHDSDCCG-SFCCVGKRCLH----IYFPCNLSRP | (449) |
| Au11.4 | GDWGTCSWSGQE-CKHDSDCCG-SFCCVGKRCLH----IYFPCNLSRS | (450) |
| Au11.1 | GDWGTCSWPGQE-CKHDSDCCG-SFCCVGKRCLH----TYFPCNLSRS | (451) |
| Au11.2 | GDWGTCSWSGQE-CKHVSDCCG-SFCCVGKRCLH----IYFPCNLSRS | (452) |
| Au11.6 | GDWGTCSWPGQE-CEHDSDCCG-SFCCVGRRCLH----IYFPCNLSRS | (453) |
| Au11.5 | GDGGTCSWPGQE-CKHDSDCCG-SFCCVGKRCLH----TYFPCNLSRS | (454) |

X is Gla, O is Hyp and U is Br-Trp

TABLE 3

| | Alignment of I-Superfamily Conotoxins - Type II | |
|---|---|---|
| U026 | CIRXDAPCSFSAHCCGRN-CCRGYCXR-PCRWI# | (455) |
| Em11.5 | CLHETSPCRRSFQCCHGI-CCFRRCSN-SCRF# | (456) |
| Em11.6 | CLRDGQSCRYHSDCCRYS-CCWGYCDQ-KCLII# | (457) |
| Em11.7 | CRREGSSCRRSYQCCRKS-CCIGECEF-PCRWV# | (458) |
| Em11.8 | CYQDETPCRGSIFCCRKK-CCIGTCRF-PCYVKLERATFQELILQP^ | (459) |
| Em11.9 | CLRDGQSCGYDSDCCRYS-CCWGYCDL-TCLII# | (460) |
| Em11.10 | CFPPGIYCTPYLPCCWGI-CC-GTCRN-VCHLRI# | (461) |
| Em11.11 | CYQDETPCRGSTFCCRKK-CCIGTCRF-PCYVKLERATFQELILQP^ | (462) |
| Em11.12 | CLRDGQSCGYHSDCCRYS-CCWGYCDQ-KCLII# | (463) |
| Vr11.1 | CLRDGQSCGYDSDCCRYS-CCWGYCDL-TCLII# | (464) |
| Vr11.2 | CLHETSPCRRSFQCCHGI-CCFRRCSN-SCRF# | (465) |
| Vr11.3 | CLRDGQSCGYHSDCCRYS-CCWGYCDQ-KCLII# | (466) |
| Vr11.4 | CLHETPPCRRSFQCCHGN-CCFRRCSN-SCRF# | (467) |
| Vr11.5 | CLHETSPCGRSFQCCHGI-CCFRRCSN-SCRF# | (468) |
| Vr11.6 | CLYETSPCRRSFQCCHGI-CCFRRCSN-SCRF# | (469) |
| Vr11.7 | CFPLGTFCSRYLPCCSGM-CCSGWCTR-RCAPRF# | (470) |
| Fi11.8 | CHHEGLPCTSDDGCCG-MECCGGVCSS-HCGN# | (471) |
| Fi11.9 | CRAEGVRCEFDSQCCES-ECCMGSCAN-PCRIP# | (472) |
| Fi11.10 | CRAEGVYCEYGSQCCLS-QCCMASCAN-PCRHP# | (473) |
| Fi11.11 | CHHEGLPCTSGDGCCG-MECCGGVCSS-HCGN# | (474) |
| Fi11.12 | CHHEGLPCASDDGCCG-MECCGGVCSS-HCGN# | (475) |
| Ep11.9 | CAGQEEPCSSRSDCCGSVGCCFGQCESP-CRMP# | (476) |
| Ep11.10 | CAGQEEPCSSRDDCCGSVGCCFGQCETP-CRMP# | (477) |

TABLE 3-continued

Alignment of I-Superfamily Conotoxins - Type II

| | | |
|---|---|---|
| Ep11.11 | CAGQEEPCSSRSDCCGSVGCCFGQCESP-CRMI# | (478) |
| Ep11.12 | CLSEGSPCSMSGSCCHK-SCCRSTCTFP-CLIP# | (479) |
| Ep11.13 | CPSEGSPCSMSGSCCHK-SCCRSTCTFP-CLIP# | (480) |
| Sx11.1 | CHHEGLPCSSDDGCCG-MECCNGVCSS-SCGN# | (481) |
| Sx11.3 | CHMD---CSK-MTCCSGI-CC-FYCGRPMCPGTRRALLQRLVGHQR^ | (482) |

X is Gla

TABLE 4

Alignment of Alternatively Processed I-Superfamily Conotoxins - Type II

| | | |
|---|---|---|
| Em11.5: | CLHETSPCRRSFQCCHGICCFRRCSNSCRF<u>GKRATFQEFILHR</u> | (483) |
| Vr11.2: | CLHETSPCRRSFQCCHGICCFRRCSNSCRF<u>GKRATFQEFILHR</u> | (484) |
| Vr11.4: | CLHET<u>P</u>PCRRSFQCCHG<u>N</u>CCFRRCSNSCRF<u>GKRATFQEFILHR</u> | (485) |
| Vr11.5: | CLHETSPC<u>G</u>RSFQCCHGICCFRRCSNSCRF<u>GKRATFQEFILHR</u> | (486) |
| Vr11.6: | CL<u>Y</u>ETSPCRRSFQCCHGICCFRRCSNSCRF<u>GKRATFQEFILHR</u> | (487) |
| Em11.8: | CYQDETPCRGS<u>I</u>FCCRKKCCIGTCRFPCYV<u>KLERATFQELILQP</u> | (488) |
| Em11.11: | CYQDETPCRGS<u>T</u>FCCRKKCCIGTCRFPCYV<u>KLERATFQELILQP</u> | (489) |
| Em11.6: | CLRDGQSC<u>R</u>YHSDCCRYSCCWGYCDQKCLII<u>GKRATFQELILHR</u> | (490) |
| Em11.9: | CLRDGQSCGYDSDCCRYSCCWGYCD<u>L</u>TCLII<u>GKRATFQELILHR</u> | (491) |
| Vr11.1: | CLRDGQSCGYDSDCCRYSCCWGYCD<u>L</u>TCLII<u>GKRATFQELTLHR</u> | (492) |
| Em11.9A: | CLRDGQSCGYDSDCCRYSCCWGYCD<u>L</u>TCLII<u>GKRATFQELILHP</u> | (493) |
| Em11.12: | CLRDGQSCGYHSDCCRYSCCWGYCDQKCLII<u>GKRATFQELILHP</u> | (494) |
| Vr11.3: | CLRDGQSCGYHSDCCRYSCCWGYCDQKCLII<u>GKRATFQELILHR</u> | (495) |
| Em11.7: | CRREGSSCRRSYQCCRKSCCIGECEFPCRWV<u>GKRATFRELILHH</u> | (496) |
| Em11.10: | CFPPGIYCTPYLPCCWGICC-GTCRNVCHLRI<u>GKRATFQE</u> | (497) |
| Vr11.7: | CFPLGTFCSRYLPCCSGMCCSGWCTRRCAPRF<u>GKRATFQE</u> | (498) |
| Fi11.8: | CHHEGLPCTSDDGCCGMECCGGVCSSHCGN<u>GRRRQVPLKSFGQR</u> | (499) |
| Fi11.8A: | CHHEGLPCTSDDGCCGMECCGGVCSSHCGN<u>GRRRRVPLKSFGQR</u> | (500) |
| Fi11.8B: | CHEEGLPCTSDDGCCGMECCGGVCSSHCGN<u>GGRRRVPLKSFGQR</u> | (501) |
| Fi11.11: | CHHEGLPCTS<u>G</u>DGCCGMECCGGVCSSHCGN<u>GRRRQVPLKSFGQR</u> | (502) |
| Fi11.12: | CHHEGLPC<u>A</u>SDDGCCGMECCGGVCSSHCGN<u>GRRRRVPLKSFGQR</u> | (503) |
| Fi11.9: | CRAEGVRCEFDSQCCESECCMGSCANPCRIP<u>GKRARLFRQR</u> | (504) |
| Fi11.10: | CRAEGVYCEYGSQCCLSQCCMASCANPCRHP<u>GKRARLQEFFRQR</u> | (505) |
| Fi11.10A: | CRAEGVYCEYGSQCCLSQCCMASCANPCRHP<u>GKRARLQEFFRRR</u> | (506) |

Example 4

Biological Activity of I-Conotoxins

The biological activity of I-conotoxin peptides were tested in mice and goldfish as exemplified by R11.19. Briefly, approximately 0.5–1.0 nmol of R11.19 was injected i.c. into 13–15 day-old mice weighing approximately 6 g. Shortly after injection, the mice began running and jumping in short duration immediately followed by convulsion with back legs kicking, copius urination, coma and death. The other conotoxins describe herein also produced death in mice at higher doses.

Approximately 0.1 nmol of R11.19 was injected into goldfish weighing aproximately 1 g. Shortly after injection, the goldfish began gasping (gills opening widely), followed by swimming backward or in circular and/or vertical motion, imbalanced swimming (body tilting), lying almost flat near the bottom and death.

Example 5

Effect of I-Conotoxins on Skeletal Neomuscular Junction

The motor nerve of a cutaneus pectoris muscle of frog was electrically stimulated every minute while the muscle's response was recorded extracellularly. Traces were acquired sequentially from bottom to top and aare shown in FIGS. 1 and 2. The peptide (1 μM) was introduced just before the $8^{th}$ trace from the bottom was acquired in FIG. 1. Thus, traces below the $8^{th}$ trace are control responses, and those above the 8th trace are those in the presence of peptide. The control biphasic response is that of a muscle action potential initiated in the middle of the muscle (i.e. at the neuromuscular junction). The repetitive responses induced by the peptide have a similar shape as the control response, indicating that these (repetitive) responses are also initiated at the neuromuscular junction.

Figure 2:
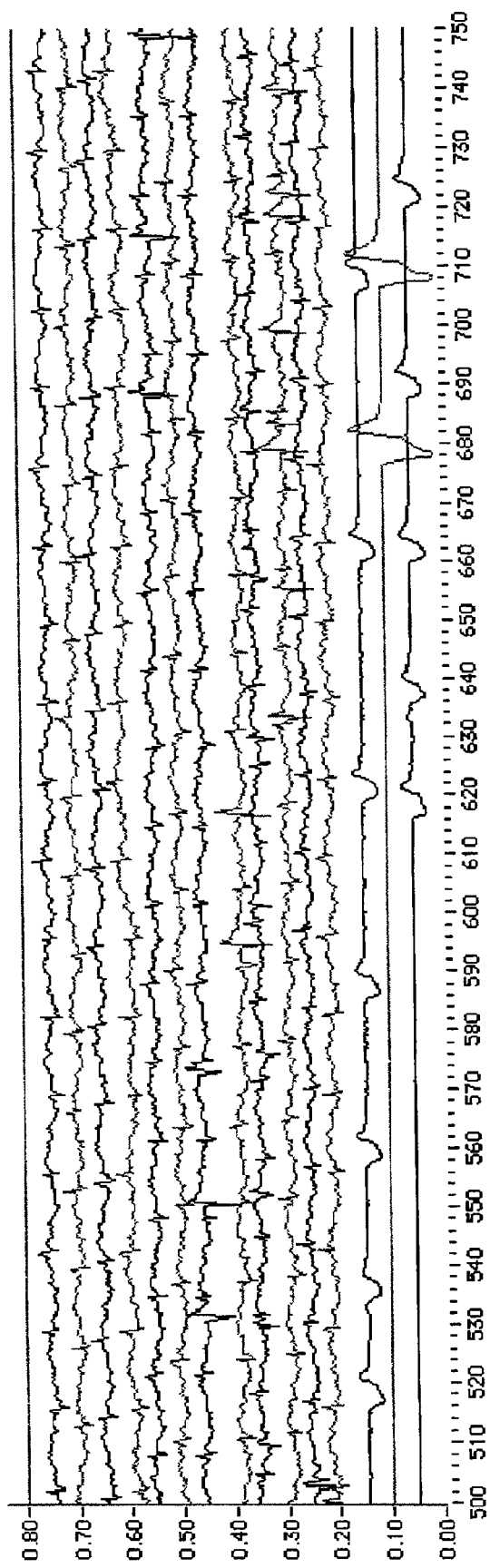

Extracellular recording shows that I-conotoxin R11.19 from *C. radiatus* produces repetitive action potentials in motor nerve. It is thought that the peptide exerts its action by blocking potassium channels in the presynaptic nerve terminal. Hyperactivity of the nerve is evident by recording from the neuromuscular junction (FIGS. 1 & 2) and the motor nerve itself (FIG. 2).

Example 6

Effect of I-Conotoxins in a Pain Model

Analgesic activity of A-conotoxins is also tested in pain models as follows.

Persistent Pain (Formalin Test).

Intrathecal (i.t.) drug injections are performed as described by Hylden and Wilcox (1980). A I-conotoxin, e.g., R11.14, or vehicle is administered in a volume of 5 μl. Fifteen minutes after the i.t. injection, the right hindpaw is injected with 20 μl of 5% formalin. Animals are placed in clear plexiglass cylinders backed by mirrors to facilitate observation. Animals are closely observed for 2 minutes per 5 minute period, and the amount of time the animal spent licking the injected paw is recorded in this manner for a total of 45–50 minutes. Results are expressed as licking time in seconds per five minutes. At the end of the experiment, all animals are placed on an accelerating rotorod and the latency to first fall was recorded. R11.14 is found to be active in this model which is predictive of efficacy for treating neuropathic pain.

Acute Pain (Tail-flick).

A I-conotoxin, e.g., R11.14, or saline is administered intrathecally (i.t.) according to the method of Hylden and Wilcox (1980) in a constant volume of 5 $\mu$l. Mice are gently wrapped in a towel with the tail exposed. At various time-points following the i.t. injection, the tail is dipped in a water bath maintained at 54 C. and the time to a vigorous tail withdrawal is recorded. If there is no withdrawal by 8 seconds, the tail is removed to avoid tissue damage.

Neuropathic Pain.

The partial sciatic nerve ligation model is used to assess the efficacy of I-conotoxin R11.14 in neuropathic pain. Nerve injury is produced according to the methods of Malmberg and Basbaum (1998). Animals are anesthetized with a ketamine/xylazine solution, the sciatic nerve is exposed and tightly ligated with 8-0 silk suture around ⅓ to ½ of the nerve. In sham-operated mice the nerve is exposed, but not ligated. Animals are allowed to recover for at least 1 week before testing is performed. On the testing day, mice are placed in plexiglass cylinders on a wire mesh frame and allowed to habituate for at least 60 minutes. Mechanical allodynia is assessed with calibrated von Frey filaments using the up-down method as described by Chaplan et al. (1994), and the 50% withdrawal threshold is calculated. Animals that did not respond to any of the filaments in the series are assigned a maximal value of 3.6 grams, which is the filament that typically lifted the hindlimb without bending, and corresponds to approximately ⅒ the animal's body weight.

The data obtained demonstrate that I-conotoxins have potent analgesic properties in three commonly used models of pain: acute, persistent/inflammatory and neuropathic pain models.

Example 7

Calcium-channel Antagonist Activity: Inhibition of Ionic Currents

Ionic currents through calcium channels are examined in cells that are voltage-clamped by a single patch-clamp electrode. These whole-cell patch-clamp studies are performed mainly on N1E115 mouse neuroblastoma cells, although a variety of cell types, including human neuroblastoma cell line IMR-32, are also examined.

Most measurements are obtained using a bath saline that allowed examination of the calcium currents in the absence of other ionic currents. These solutions contained 80 mM NMDG (as a sodium replacement), 30 mM TEAC1 (to block potassium currents), 10 mM $BaCl_2$ (as a charge-carrier through the calcium channels), and 10 mM HEPES at pH 7.3. Some solutions also contained 2 mM quinidine (to block potassium currents) and 3 $\mu$M tetrodotoxin (to block sodium currents). Normal bath saline is (mM): 140 NaCl, 10 glucose, 3 KCl, 2 $CaCl_2$, 1 $MgCl_2$, 10 mM HEPES pH 7.3. Intracellular solutions contained (mM): 150 CsCl, 0.5 $CaCl_2$, 5 EGTA, 5 $MgCl_2$, 2 $K_2$ATP at pH 7.3–7.4. Bath saline and all internal solutions are filtered before use.

Pipets are made from Corning 7052 glass (Garner Glass Company, Claremont, Calif. 91711), coated with SYLGARD™ silicone adjuvant (Dow Corning, Midland, Mich. 48640) and fire-polished before use. Bubble numbers are typically 5 to 6, with pipet resistances typically 2–5 MOhms. Coming 8161, Kimble, and other glasses are also used without noticeable effect on the calcium currents observed.

Recordings are carried out at room temperature with an Axopatch 1-C amplifier (Axon Instruments, Foster City, Calif. 94404) and analyzed with pCLAMP software (Axon Instruments). Data are filtered at 1000 Hz for a typical sampling rate of 0.1 kHz; in all cases data are filtered at a frequency at most ⅕ of the sampling rate to avoid biasing. Data are collected on-line by the software. Analysis is performed on-screen with print-out via a Hewlett-Packard LaserJet Printer (Hewlett-Packard, Palo Alto, Calif. 94306).

The typical experiment is conducted as follows: after seal formation followed by series resistance compensation and capacitative transient cancellation, a voltage clamp protocol is performed wherein the cell potential is stepped from the holding potential (typically −100 mV) to test potentials that ranged from −60 mV to +20 mV in 10 mV increments. The cell is held at the holding potential for 5 seconds between pulses. Protocols starting from other holding potentials usually covered the same range of test potentials. I-conotoxins are found to have calcium channel blocking activity in such cell lines.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

Ando, T. et al. (1997). *Clin. Exp. Allergy.* 27:706–713.
Barnay, G. et al. (2000). *J. Med. Chem.*
Bitan, G. et al. (1997). *J. Peptide Res.* 49:421–426.
Bodansky et al. (1966). *Chem. Ind.* 38:1597–98.
Cartier, G. E. et al. (1996). *J. Biol. Chem.* 271:7522–7528.
Chaplan, S. R. et al. (1994). *J. Neurosci. Methods* 53:55–63.
Chen, J. W. et al. (1997) *Am. J. Cardiol.* 80: 32–38.
Clark, C. et al. (1981). *Toxicon* 19:691–699.
Craig, A. G. et al. (1999). *J. Biol. Chem.* 274:13752–13759.
Craik, D. J. et al. (1991). *Toxicon* 39:43–60.
Cruz, L. J. at al. (1976). *Verliger* 18:302–308.
Ettinger, L. J. et al. (1978). *Cancer* 41:1270–1273.
Goldschmidt, M. et al. (1996). *J. Clin. Pharmacol.* 36:559–572.
Guatteo, E. et al. (1998). *J. Neurophysiol.* 79:1239–1245.
Hammerland et al. (1992). *Eur. J. Pharmacol.* 226:239–244.
Heading, C. (1999). *Curr. Opin. CPNS Invest. Drugs* 1:153–166
Horiki, K. et al. (1978). *Chemistry Letters* 165–68.
Hubry, V. et al. (1994). *Reactive Polymers* 22:231–241.
Hylden, J. L. K. and Wilcox, G. (1980). *Eur. J. Pharmacol.* 67:313–316.
Jovanovic, A. et al. (1998a). *Circulation* 98:1548–1555.
Jovanovic, A. et al. (1998b). *Lab. Invest.* 78:1101–1107.
Kaiser et al. (1970). *Anal. Biochem.* 34:595.
King, G. F. et al. (2000). *Nature Structural Biology* 17:505–513.
Kapoor (1970). *J. Pharm. Sci.* 59:1–27.
Koike, A. et al. (1995). *Am J. Cardiol.* 76:449–452.
Kornreich, W. D. et al. (1986). U.S. Pat. No. 4,569,967.
Kouchi, I. et al. (1998). *Am. J. Physiol.* 274(4/2); H1106-H1112.
Lin, C. et al. (1998). *Pharmacology* 57(6); 314–322.
Luer, M. S. & Hatton, J. (1993). *Annals Pharmcotherapy* 27:912–921.
Martinez, J. S. et al. (1995). *Biochem.* 34:14519–14526.
McCleskey, E. W. et al. (1987). *Proc. Natl. Acad. Sci. USA* 84:4327–31.
Malmberg, A. B et al. (1998). *Pain* 76:215–222.
McIntosh, J. M. et al. (1998). *Methods Enzymol.* 294:605–624.
*The Merck Manual of Diagnosis and Therapy*, 16th Ed. (Merck Research Laboratories, Rahway, N.J., 1992).
*Methoden der Organischen Chemie (Houben-Weyl): Synthese von Peptiden*, E. Wunsch (Ed.), Georg Thieme Verlag, Stuttgart, Ger. (1974).
Muller-Shweinitzer, E. and Fozard, J. R.(1997). *Br. J. Pharmacol.* 120(7):1241–1248.
Nagai, H. et al. (1991). *Japan J. Pharmacol.* 56(1):13–21.
Neilson-Kudsk, J. E. (1996). *Dan. Med. Bull.* 43(5):429–447.
Nishiuchi, Y. et al. (1993). *Int. J. Pept. Protein Res.* 42:533–538.
Nowak, L. et al. (1984). *Nature* 307:462–465.
Olivera, B. M. et al. (1984). U.S. Pat. No. 4,447,356.
Olivera, B. M. et al. (1985). *Science* 230:1338–1343.
Olivera, B. M. et al. (1996). U.S. Pat. No. 5,514,774.
Ornstein, et al. (1993). *Biorganic Medicinal Chemistry Letters* 3:43–48.
Pell, T. J. et al. (1998). *Am. J. Physiol.* 275(5 pt 2):H542–547.
Rakel, R. E. (1997). Conn's current therapy.
*Remington's Pharmaceutical Sciences,* 18th Ed. (1990, Mack Publishing Co., Easton, Pa.).
Rivier, J. R. et al. (1978). *Biopolymers* 17:1927–38.
Rivier, J. R. et al. (1987). *Biochem.* 26:8508–8512.
Sambrook, J. et al. (1989). *Molecular Cloning: A Laboratory Manual,* 2nd Ed., Cold Spring Harbor Laboratory, Cold Spring Harbor, N.Y.
Schroder & Lubke (1965). *The Peptides* 1:72–75, Academic Press, N.Y.
Shon, K.-J. et al. (1994). *Biochemistry* 33:11420–11425.
Stewart and Young, *Solid-Phase Peptide Synthesis*, Freeman & Co., San Francisco, Calif. (1969).
Vale et al. (1978). U.S. Pat. No. 4,105,603.
Van de Steen, P. et al. (1998). *Critical Rev. in Biochem. and Mol. Biol.* 33:151–208.
Yamabe H. et al. (1995). *Cardiovasc. Drugs Ther.* 9(6):755–761.
Zhou L. M., et al. (1996). *J. Neurochem.* 66:620–628.
Zimm, S. et al. (1984). *Cancer Res.* 44:1698–1701.
U.S. Pat. No. 3,842,067.
U.S. Pat. No. 3,862,925.
U.S. Pat. No. 3,972,859.
U.S. Pat. No. 4,352,883.
U.S. Pat. No. 4,353,888.
U.S. Pat. No. 4,883,666.
U.S. Pat. No. 4,968,733.
U.S. Pat. No. 4.976,859.
U.S. Pat. No. 5,082,670.
U.S. Pat. No. 5,084,350.
U.S. Pat. No. 5,158,884.
U.S. Pat. No. 5,284,761.
U.S. Pat. No. 5,364,769.
U.S. Pat. No. 5,514,774.
U.S. Pat. No. 5,531,001.
U.S. Pat. No. 5,534,615.
U.S. Pat. No. 5,545,723.
U.S. Pat. No. 5,550,050.
U.S. Pat. No. 5,591,821.
U.S. Pat. No. 5,618,531.
U.S. Pat. No. 5,719,264.
U.S. Pat. No. 5,844,077.
U.S. Pat. No. 5,859,186.
PCT Published Application WO 92/19195.
PCT Published Application WO 94/25503.
PCT Published Application WO 95/01203.
PCT Published Application WO 95/05452.
PCT Published Application WO 96/02286.
PCT Published Application WO 96/02646.
PCT Published Application WO 96/11698.
PCT Published Application WO 96/40871.
PCT Published Application WO 96/40959.
PCT Published Application WO 97/12635.
PCT Published Application WO 98/03189.
PCT Published Application WO 00/23092.

What is claimed is:

1. A substantially pure I-conotoxin peptide having the generic formula I: $Xaa_1$-$Xaa_2$-$Xaa_3$-$Xaa_4$-Cys-$Xaa_5$-$Xaa_6$-$Xaa_7$-$Xaa_8$-$Xaa_9$-$Xaa_{10}$-Cys-$Xaa_{11}$-$Xaa_{12}$-$Xaa_{13}$-$Xaa_{14}$-$Xaa_{15}$-Cys-Cys-$Xaa_{16}$-$Xaa_{17}$-$Xaa_{18}$-Cys-Cys-$Xaa_{19}$-$Xaa_{20}$-Gly-$Xaa_{21}$-Cys-$Xaa_{22}$-$Xaa_{23}$-$Xaa_{24}$-$Xaa_{25}$-$Xaa_{26}$-$Xaa_{27}$-$Xaa_{28}$-$Xaa_{29}$-$Xaa_{30}$-$Xaa_{31}$-Cys-$Xaa_{32}$-$Xaa_{33}$-$Xaa_{34}$-$Xaa_{35}$-$Xaa_{36}$-$Xaa_{37}$-$Xaa_{38}$-$Xaa_{39}$-$Xaa_{40}$-$Xaa_{41}$ (SEQ ID NO: 1), wherein $Xaa_1$ is des-$Xaa_1$ or Gly;

$Xaa_2$ is des-$Xaa_2$, Pro, hydroxy-Pro (Hyp), Ala, His or Gly;

$Xaa_3$ is des-$Xaa_3$, Ser, Val, Pro, Hyp, Thr, g-Ser, g-Thr, g-Hyp or any non-natural hydroxylated amino acid;

$Xaa_4$ is des-$Xaa_4$, Gly, Glu, γ-carboxy-Glu (Gla), Phe, Pro, Hyp, Arg, Lys, ornithine, homo-Lys, homoarginine, nor-Lys, N-methyl-Lys, N,N'-dimethyl-Lys, N,N',N"-trimethyl-Lys or any non-natural basic amino acid;

$Xaa_5$ is an aliphatic amino acid bearing linear or branched saturated hydrocarbon chains selected from the group consisting of Leu (D or L), Ile and Val or non-natural derivatives of the aliphatic amino acid, Lys, Arg, ornithine, homo-Lys, homoarginine, nor-Lys, N-methyl-Lys, N,N'-dimethyl-Lys, N,N',N"-trimethyl-Lys, any non-natural basic amino acid, Gly, Trp (D or L), neo-Trp, halo-Trp (D or L), or any aromatic non-natural amino acid;

$Xaa_6$ is Lys, Arg, ornithine, homo-Lys, homoarginine, nor-Lys, N-methyl-Lys, N,N'-dimethyl-Lys, N,N',N"-trimethyl-Lys, any non-natural basic amino acid, Ala, an aliphatic amino acid bearing linear or branched saturated hydrocarbon chains selected from the group consisting of Leu (D or L), Ile and Val or non-natural derivatives of the aliphatic amino acid, Thr, Ser, g-Thr or g-Ser; $Xaa_7$ is Gly, Asp, Glu, Gla, Asn, Gln or any non-natural acidic amino acid;

$Xaa_8$ is Gly, Lys, Arg, ornithine, homo-Lys, homoarginine, nor-Lys, N-methyl-Lys, N,N'-dimethyl-Lys, N,N',N"-trimethyl-Lys, any non-natural basic amino acid, Asp, Glu, Gla, Asn, Gln or any non-natural acidic amino acid;

$Xaa_9$ is Ala, Val, Met, Lys, Arg, ornithine, homo-Lys, homoarginine, nor-Lys, N-methyl-Lys, N,N'-dimethyl-Lys, N,N',N"-trimethyl-Lys or any non-natural basic amino acid;

$Xaa_{10}$ is Ala, His, Ser, Thr, Pro, Hyp, g-Ser, g-Thr, g-Hyp, any non-natural hydroxylated amino acid, Asp, Glu, Gla, Asn, Gln, any non-natural acidic amino acid, Lys, Arg, ornithine, homo-Lys, homoarginine, nor-Lys, N-methyl-Lys, N,N'-dimethyl-Lys, N,N',N"-trimethyl-Lys or any non-natural basic amino acid;

$Xaa_{11}$ is Gly, Ser, Thr, g-Ser, g-Thr, Asp, Glu, Gla, any non-natural acidic amino acid, Lys, Arg, ornithine, homo-Lys, homoarginine, nor-Lys, N-methyl-Lys, N,N'-dimethyl-Lys, N,N',N"-trimethyl-Lys or any non-natural basic amino acid;

$Xaa_{12}$ is Asn, Phe, Tyr, meta-Tyr, ortho-Tyr, nor-Tyr, mono-halo-Tyr, di-halo-Tyr, O-sulpho-Tyr, O-phospho-Tyr, nitro-Tyr, any non-natural aromatic amino acid, Gln or Leu (D or L);

$Xaa_{13}$ is Ser, Thr, g-Ser, g-Thr or His;

$Xaa_{14}$ is Ala, Gla, Ser, Thr, g-Ser, g-Thr, His, Lys, Arg, ornithine, homo-Lys, homoarginine, nor-Lys, N-methyl-Lys, N,N'-dimethyl-Lys, N,N',N"-trimethyl-Lys or any non-natural basic amino acid;

$Xaa_{15}$ is Asp, Glu, His or Gla; $Xaa_{16}$ is des-$Xaa_{16}$, Gly, His, Ser, Pro, Hyp, Thr, g-Ser, g-Thr, g-Hyp, any non-natural hyrdroxylated amino acid, Lys, Arg, ornithine, homo-Lys, homoarginine, nor-Lys, N-methyl-Lys, N,N'-dimethyl-Lys, N,N',N"-trimethyl-Lys or any non-natural basic amino acid;

$Xaa_{17}$ is des-$Xaa_{17}$, His, Ser, Thr, g-Ser, g-Thr, Lys, Arg, ornithine, homo-Lys, homoarginine, nor-Lys, N-methyl-Lys, N,N'-dimethyl-Lys, N,N',N"-trimethyl-Lys, any non-natural basic amino acid, Phe, Tyr, meta-Tyr, ortho-Tyr, nor-Tyr, mono-halo-Tyr, di-halo-Tyr, O-sulpho-Tyr,O-phospho-Tyr, nitro-Tyr or any non-natural aromatic amino acid;

$Xaa_{18}$ is Val, Asn, Lys, Arg, ornithine, homo-Lys, homoarginine, nor-Lys, N-methyl-Lys, N,N'-dimethyl-Lys, N,N',N"-trimethyl-Lys or any non-natural basic amino acid;

$Xaa_{19}$ is des-$Xaa_{19}$, Leu (D or L), Pro, Hyp, Phe, Tyr, meta-Tyr, ortho-Tyr, nor-Tyr, mono-halo-Tyr, di-halo-Tyr, O-sulpho-Tyr, O-phospho-Tyr, nitro-Tyr or any non-natural aromatic amino acid;

$Xaa_{20}$ is Gly, Ile, Ser, Thr, g-Ser, g-Thr, His, Lys, Arg, ornithine, homo-Lys, homoarginine, nor-Lys, N-methyl-Lys, N,N'-dimethyl-Lys, N,N',N"-trimethyl-Lys, any non-natural basic amino acid, Phe, Tyr, meta-Tyr, ortho-Tyr, nor-Tyr, mono-halo-Tyr, di-halo-Tyr, O-sulpho-Tyr, O-phospho-Tyr, nitro-Tyr or any non-natural aromatic amino acid;

$Xaa_{21}$ is Ser, Thr, g-Ser, g-Thr, an aliphatic amino acids bearing linear or branched saturated hydrocarbon chains such as Leu (D or L), Ile and Val and non-natural derivatives of the aliphatic amino acid, Lys, Arg, ornithine, homo-Lys, homoarginine, nor-Lys, N-methyl-Lys, N,N'-dimethyl-Lys, N,N',N"-trimethyl-Lys, any non-natural basic amino acid, Phe, Tyr, meta-Tyr, ortho-Tyr, nor-Tyr, mono-halo-Tyr, di-halo-Tyr, O-sulpho-Tyr, O-phospho-Tyr, nitro-Tyr or any non-natural aromatic amino acid;

$Xaa_{22}$ is Ala, Gln, Gla, Lys, Arg, ornithine, homo-Lys, homoarginine, nor-Lys, N-methyl-Lys, N,N'-dimethyl-Lys, N,N',N"-trimethyl-Lys or any non-natural basic amino acid;

$Xaa_{23}$ is Ser, Pro, Hyp, Thr, g-Ser, g-Thr, g-Hyp, any non-natural hyrdroxylated amino acid, Lys, Arg, ornithine, homo-Lys, homoarginine, nor-Lys, N-methyl-Lys, N,N'-dimethyl-Lys, N,N',N"-trimethyl-Lys or any non-natural basic amino acid;

$Xaa_{24}$ is Gln, Ser, Pro, Hyp, Thr, g-Ser, g-Thr, g-Hyp or any non-natural hyrdroxylated amino acid;

$Xaa_{25}$ is des-$Xaa_{25}$, Ser, Thr, g-Ser or g-Thr;

$Xaa_{26}$ is des-$Xaa_{26}$, Asn, Gln, Ser, Thr, g-Asn, g-Ser or g-Thr;

$Xaa_{27}$ is des-$Xaa_{27}$, Val, Gla, Trp (D or L), neo-Trp, halo-Trp (D or L), any aromatic non-natural amino acid, Lys, Arg, ornithine, homo-Lys, homoarginine, nor-Lys, N-methyl-Lys, N,N'-dimethyl-Lys, N,N',N"-trimethyl-Lys or any non-natural basic amino acid;

$Xaa_{28}$ is des-$Xaa_{28}$, an aliphatic amino acids bearing linear or branched saturated hydrocarbon chains selected from the group consisting of Leu (D or L), Ile and Val and non-natural derivatives of the aliphatic amino acid;

$Xaa_{29}$ is des-$Xaa_{29}$, an aliphatic amino acids bearing linear or branched saturated hydrocarbon chains selected from the group consisting of Leu (D or L), Ile and Val and non-natural derivatives of the aliphatic amino acid; $Xaa_{30}$ is des-$Xaa_{30}$, Ile, Ser, Pro, Hyp, Thr, g-Ser, g-Thr, g-Hyp, any non-natural hydroxylated amino acid, Phe, Tyr, meta-Tyr, ortho-Tyr, nor-Tyr, mono-halo-Tyr, di-halo-Tyr, O-sulpho-Tyr, O-phospho-Tyr, nitro-Tyr or any non-natural aromatic amino acid;

$Xaa_{31}$ is des-$Xaa_{31}$ or Gly;

$Xaa_{32}$ is Ser, Thr, g-Ser, g-Thr, Trp (D or L), neo-Trp, halo-Trp (D or L), any aromatic non-natural amino acid, Lys, Arg, ornithine, homo-Lys, homoarginine, nor-Lys, N-methyl-Lys, N,N'-dimethyl-Lys, N,N',N"-trimethyl-Lys or any non-natural basic amino acid; $Xaa_{33}$ is Val, Ser, Thr, g-Ser, g-Thr, Tip (D or L), neo-Trp, halo-Trp (D or L) or any aromatic non-natural amino acid;

$Xaa_{34}$ is Gly, Ile, Asp, Glu, Gla, Asn, Ser, Thr, g-Asn, g-Ser or g-Thr;

Xaa$_{35}$ is des-Xaa$_{35}$, Val, Met, Gln, Pro, Hyp, Ser, Thr, g-Ser, g-Thr, g-Hyp or any non-natural hydroxylated amino acid;

Xaa$_{36}$ is des-Xaa$_{36}$, Val, Thr, Ser, g-Thr, g-Ser, Phe, Tyr, meta-Tyr, ortho-Tyr, nor-Tyr, mono-halo-Tyr, di-halo-Tyr, O-sulpho-Tyr, O-phospho-Tyr, nitro-Tyr or any non-natural aromatic amino acid;

Xaa$_{37}$ is des-Xaa$_{37}$, Gln, Asn, Thr, Ser, g-Ser, g-Ser, g-Asn, Met, Leu, Phe, Tyr, meta-Tyr, ortho-Tyr, nor-Tyr, mono-halo-Tyr, di-halo-Tyr, O-sulpho-Tyr, O-phospho-Tyr, nitro-Tyr, any non-natural aromatic amino acid, Lys, Arg, ornithine, homo-Lys, homoarginine, nor-Lys, N-methyl-Lys, N,N'-dimethyl-Lys, N,N',N''-trimethyl-Lys or any non-natural basic amino acid; Xaa$_{38}$ is des-Xaa$_{38}$, Leu, Ser, Thr, g-Ser, g-Thr, Lys, Arg, ornithine, homo-Lys, homoarginine, nor-Lys, N-methyl-Lys, N,N'-dimethyl-Lys, N,N',N''-trimethyl-Lys or any non-natural basic amino acid;

Xaa$_{39}$ is des-Xaa$_{39}$, Ile, Ala, Thr, Ser, g-Ser, g-Thr, Lys, Arg, ornithine, homo-Lys, homoarginine, nor-Lys, N-methyl-Lys, N,N'-dimethyl-Lys, N,N',N''-trimethyl-Lys or any non-natural basic amino acid;

Xaa$_{40}$ is des-Xaa$_{40}$, Asp, Lys, Arg, ornithine, homo-Lys, homoarginine, nor-Lys, N-methyl-Lys, N,N'-dimethyl-Lys, N,N',N''-trimethyl-Lys or any non-natural basic amino acid; and Xaa$_{41}$ is des-Xaa$_{41}$, Phe, Tyr, meta-Tyr, ortho-Tyr, nor-Tyr, mono-halo-Tyr, di-halo-Tyr, O-sulpho-Tyr, O-phospho-Tyr, nitro-Tyr or any non-natural aromatic amino acid, with the proviso that the peptide is not J029 (SEQ ID NO:2).

2. A pharmaceutical composition comprising a I-conotoxin peptide of claim 1 or a pharmaceutically acceptable salt or solvate thereof and a pharmaceutically acceptable carrier.

3. The substantially pure I-conotoxin peptide which comprises the amino acid sequence Gly-Xaa3-Ser-Phe-Cys-Lys-Ala-Asn-Gly-Lys-Xaa3-Cys-Ser-Xaa5-His-Ala-Asp-Cys-Cys-Asn-Cys-Cys-Leu-Ser-Gly-Ile-Cys-Lys-Xaa3-Ser-Thr-Asn-Val-Ile-Leu-Xaa3-Gly-Cys-Ser-Thr-Ser-Ser-Phe-Phe-Arg-Ile (SEQ IDNO:46), wherein Xaa3 is Pro or hydroxy-Pro, Xaa5 is Tyr, $^{125}$I-Tyr, mono-iodo-Tyr, di-iodo-Tyr, O-suipho-Tyr or O-phospho-Tyr and the C-terminus is a free carboxyl or is amidated.

4. The substantially pure I-conotoxin peptide of claim 3 wherein Xaa3 at residues 2, 11 and 29 are hydroxy-Pro, Xaa3 at residue 36 is Pro, Xaa5 is Tyr, and the C-terminus is amidated.

5. The substantially pure I-conotoxin protein precursor which comprises the amino acid sequence MKLCLTFLLVLMILASVTGEKSSKHTLSRAARVKN-RGPSFCKANGKPCSYHADCCNCCL SGICKPST-NVILPGCSTSSFFRI (SEQ ID NO:45).

6. A pharmaceutical composition comprising a I-conotoxin peptide of claim 3 or a pharmaceutically acceptable salt or solvate thereof and a pharmaceutically acceptable carrier.

7. A pharmaceutical composition comprising a I-conotoxin peptide of claim 4 or a pharmaceutically acceptable salt or solvate thereof and a pharmaceutically acceptable carrier.

* * * * *